United States Patent
Schaeper et al.

(10) Patent No.: US 11,820,971 B2
(45) Date of Patent: Nov. 21, 2023

(54) NUCLEIC ACIDS FOR INHIBITING EXPRESSION OF PROS1 IN A CELL

(71) Applicants: UNIVERSITÄT BERN, Bern (CH); SILENCE THERAPEUTICS GMBH, Berlin (DE)

(72) Inventors: Ute Schaeper, Berlin (DE); Sibylle Dames, Berlin (DE); Eliot Morrison, Berlin (DE); Raja Prince Eladnani, Bern (CH); Anne Angelillo-Scherrer, Fribourg (CH)

(73) Assignees: UNIVERSITÄT BERN, Bern (CH); SILENCE THERAPEUTICS GMBH, Berlin (DE)

( * ) Notice: Subject to any disclaimer, the term of this patent is extended or adjusted under 35 U.S.C. 154(b) by 0 days.

(21) Appl. No.: 17/872,003

(22) Filed: Jul. 25, 2022

(65) Prior Publication Data
US 2023/0019513 A1    Jan. 19, 2023

Related U.S. Application Data

(63) Continuation of application No. 17/524,323, filed on Nov. 11, 2021, which is a continuation of application No. PCT/EP2021/080302, filed on Nov. 2, 2021.

(30) Foreign Application Priority Data

Nov. 4, 2020  (EP) ..................... 20205642
Mar. 18, 2021  (EP) ..................... 21163570

(51) Int. Cl.
C07H 21/04   (2006.01)
C12N 15/113  (2010.01)
A61P 7/04    (2006.01)

(52) U.S. Cl.
CPC ............. *C12N 15/113* (2013.01); *A61P 7/04* (2018.01); *C12N 2310/14* (2013.01); *C12N 2310/315* (2013.01); *C12N 2310/322* (2013.01); *C12N 2310/351* (2013.01); *C12N 2320/30* (2013.01)

(58) Field of Classification Search
None
See application file for complete search history.

(56) References Cited

FOREIGN PATENT DOCUMENTS

| WO | 2017174657 | 10/2017 |
|----|------------|---------|
| WO | 2018185241 | 4/2018  |
| WO | 2019086117 | 5/2019  |
| WO | 2019092280 | 5/2019  |
| WO | 2020/225301 | 11/2020 |

OTHER PUBLICATIONS

Ning Peng et al, "Role of protein S in castration-resistant prostate cancer-like cells", Endocrine-Related Cancer, Aug. 1, 2016 (Aug. 1, 2016), vol. 23, No. 8, p. 595-607.
Mohd Firdaus Che Mat et al, "Silencing of PROS1 induces apoptosis and inhibits migration and invasion of glioblastoma multiforme cells", International Journal of Oncology,vol. 49, No. 6, Nov. 3, 2016 (Nov. 3, 2016), p. 2359-2366.
Raja Prince et al, "Targeting anticoagulant protein S to improve hemostasis in hemophilia", Blood,vol. 131, No. 12, Mar. 22, 2018 (Mar. 22, 2018), p. 1360-1371.
Heestermans Marco et al, "Oligonucleotides targeting coagulation factor mRNAs: use in thrombosis and hemophilia research and therapy", Thrombosis Journal, Mar. 7, 2017 (Mar. 7, 2017), vol. 15, No. 1.
Prakash Thazha P et al, "Synergistic effect of phosphorothioate, 5'-vinylphosphonate and GalNAc modifications for enhancing activity of synthetic siRNA", Bioorganic & Medicinal Chemistry Letters, Elsevier, Amsterdam, NL,vol. 26, No. 12, Apr. 27, 2016.

*Primary Examiner* — Kimberly Chong
(74) *Attorney, Agent, or Firm* — JMB Davis Ben-David

(57) ABSTRACT

The invention relates to nucleic acid products that interfere with or inhibit PROS1 gene expression. It further relates to therapeutic uses of PROS1 inhibition for the treatment of bleeding disorders.

19 Claims, 26 Drawing Sheets

Specification includes a Sequence Listing.

A

B

NUCLEIC ACIDS FOR INHIBITING EXPRESSION OF PROS1 IN A CELL

CROSS-REFERENCE TO RELATED APPLICATIONS

This is a Continuation of U.S. patent application Ser. No. 17/524,323, filed on Nov. 11, 2021, which is a Continuation of International Patent Application No. PCT/EP2021/080302, filed on Nov. 2, 2021, which claims the benefit of European Patent Application No. 20205642.0, filed on Nov. 4, 2020, and European Patent Application No. 21163570.1, filed on Mar. 18, 2021. The contents of the foregoing patent applications are incorporated by reference herein in their entirety.

FIELD OF THE INVENTION

The invention relates to nucleic acid products that interfere with or inhibit PROS1 (Protein S) gene expression. It further relates to therapeutic uses of PROS1 inhibition for the treatment of bleeding disorders.

BACKGROUND

Double-stranded RNAs (dsRNA) able to bind through complementary base pairing to expressed mRNAs have been shown to block gene expression (Fire et al., 1998, Nature. 1998 Feb. 19; 391(6669):806-11 and Elbashir et al., 2001, Nature. 2001 May 24; 411(6836):494-8) by a mechanism that has been termed "RNA interference (RNAi)". Short dsRNAs direct gene specific, post transcriptional silencing in many organisms, including vertebrates, and have become a useful tool for studying gene function. RNAi is mediated by the RNA induced silencing complex (RISC), a sequence specific, multi component nuclease that degrades messenger RNAs having sufficient complementary or homology to the silencing trigger loaded into the RISC complex. Interfering RNAs such as siRNAs, antisense RNAs, and micro RNAs, are oligonucleotides that prevent the formation of proteins by gene silencing, i.e., inhibiting gene translation of the protein through degradation of mRNA molecules. Gene silencing agents are becoming increasingly important for therapeutic applications in medicine.

According to Watts and Corey in the Journal of Pathology (2012; Vol 226, p 365-379), there are algorithms that can be used to design nucleic acid silencing triggers, but all of these have severe limitations. It may take various experimental methods to identify potent siRNAs, as algorithms do not take into account factors such as tertiary structure of the target mRNA or the involvement of RNA binding proteins. Therefore, the discovery of a potent nucleic acid silencing trigger with minimal off-target effects is a complex process. For the pharmaceutical development of these highly charged molecules, it is necessary that they can be synthesised economically, distributed to target tissues, enter cells and function within acceptable limits of toxicity.

Haemophilia A and haemophilia B are the most common bleeding disorders and they are caused by deficiencies of procoagulant Factor VIII (FVIII) or Factor IX (FVIX), respectively (Weyand and Pipe, 2019). The severity of haemophilia is classified according to the residual endogenous factor level (Balkaransingh and Young 2017). Patients with severe haemophilia often suffer from spontaneous bleeding within musculoskeletal system, such as hemarthrosis. This can result in disability at a young age if left untreated.

Haemostasis is tightly regulated by an interplay of pro- and anti-coagulant factors to control excess bleeding episodes and prevent thrombotic events. Blood coagulation is activated in response to damage to the vascular wall, where FVIIa binds to the exposed tissue factor and the FVIIa tissue factor complex then efficiently activates FX. FXa and FVa then form the prothrombinase complex that generates thrombin. In addition, the FVIIa-tissue factor complex activates FIX, which together with its cofactor FVIIa activates FX. The efficiency of coagulation is determined by the amount of FXa and thrombin generated, with thrombin being a multifunctional enzyme that cleaves fibrinogen to fibrin and activates platelets. In tissues with low tissue factor level, e.g. the joints and muscles, insufficient amounts of FXa are generated from FVIa-TF. Thus, amplification provided by the FIXa-FVIIIa complex is crucial for efficient haemostasis (Dahlbäck 2018).

In contrast to clotting factors, like FVIII and FIX, Protein S is an anti-coagulant as it acts as cofactor for activated Protein C and tissue factor pathway inhibitor (TFPI). In the absence of Protein S, TFPIα is a poor inhibitor of FXa. Likewise, without Protein S, APC is inefficient at inhibiting FVa and FVIIIa. As a consequence, loss of function mutations of Protein S cause uncontrolled coagulation in mice and in humans. Despite this, the inventors have surprisingly found that reducing the expression of Protein S with a nucleic acid could be a useful treatment for bleeding disorders such as haemophilia.

Current haemophilia treatments include treatment with replacement factors either on demand or in the setting of prophylactic therapy to prevent bleeds and preserve healthy joints. However, replacement therapy can be compromised by the development of alloantibodies to FVIII and FIX. These occur in ~25 to 40% of patients with severe haemophilia. Such patients require treatment with bypassing agents and immune tolerance induction to eradicate inhibitors (Weyand and Pipe 2019).

There is therefore a clear need in the art for new ways of treating bleeding disorders such as haemophilia. The invention addresses this need.

SUMMARY OF THE INVENTION

One aspect of the invention is a double-stranded nucleic acid for inhibiting expression of PROS1, wherein the nucleic acid comprises a first strand and a second strand, wherein the first strand sequence comprises a sequence of at least 15 nucleotides differing by no more than 3 nucleotides from any one of the sequences selected from SEQ ID NO: 187, 189, 191, 193, 195, 197, 199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49.

One aspect relates to a double-stranded nucleic acid that is capable of inhibiting expression of PROS1, particularly in a cell, for use as a medicament or in associated diagnostic or therapeutic methods, wherein the nucleic acid particularly comprises or consists of a first strand and a second strand and particularly wherein the first strand comprises a sequence sufficiently complementary to a PROS1 mRNA so as to mediate RNA interference.

One aspect relates to a composition comprising a nucleic acid as disclosed herein and a solvent (particularly water) and/or a delivery vehicle and/or a physiologically acceptable excipient and/or a carrier and/or a salt and/or a diluent and/or a buffer and/or a preservative.

One aspect relates to a composition comprising a nucleic acid as disclosed herein and a further therapeutic agent selected from e.g., an oligonucleotide, a small molecule, a monoclonal antibody, a polyclonal antibody and a peptide.

One aspect relates to a nucleic acid or composition disclosed herein for use as a medicament or in associated methods.

One aspect relates to a nucleic acid or a composition comprising it as disclosed herein for use in the prevention, decrease of the risk of suffering from, or treatment of a bleeding disorder.

One aspect relates to the use of a nucleic acid or a composition comprising it as disclosed herein in the prevention, decrease of the risk of suffering from, or treatment of a bleeding disorder. The bleeding disorder is particularly a blood coagulation deficiency disorder. A blood coagulation deficiency disorder can be a disorder that is associated with prolonged bleeding episodes and/or with reduced thrombin and/or with a deficiency in clot formation. The bleeding disorder is particularly haemophilia, inherited haemophilia, haemophilia A, haemophilia B, haemophilia C, von Willebrand disease, von Willebrand syndrome, afibrinogenemia, hypofibrinogenemia, parahaemophilia, hemarthrosis (AH), a deficiency in a clotting factor, an inherited deficiency in factor II, V, VII, X and/or XI, a combined deficiency in factor V and VIII, acquired haemophilia, an acquired deficiency in coagulation factors and an acquired bleeding disorder. More particularly, it is haemophilia, particularly haemophilia A or B, most particularly haemophilia A.

One aspect relates to a method of preventing, decreasing the risk of suffering from, or treating a blood disorder comprising administering a pharmaceutically effective dose or amount of a nucleic acid or a composition comprising it as disclosed herein to an individual in need of treatment, particularly wherein the nucleic acid or composition is administered to the subject subcutaneously, intravenously or by oral, rectal, pulmonary, intramuscular or intraperitoneal administration.

BRIEF DESCRIPTION OF THE DESCRIBED SEQUENCES

The nucleic and/or amino acid sequences provided herewith are shown using standard letter abbreviations for nucleotide bases, and three letter code for amino acids, as defined in 37 CFR 1.831 through 37 CFR 1.835. Only one strand of each nucleic acid sequence is shown, but the complementary strand is understood as included by any reference to the displayed strand. The Sequence Listing is submitted as an XML file named 95083_316_2001_seqlist, created Aug. 11, 2022, about 328 KB, which is incorporated by reference herein.

DETAILED DESCRIPTION OF THE INVENTION

The present invention relates to a nucleic acid which is double-stranded and which comprises a sequence homologous to and/or complementary to a portion of an expressed RNA transcript of PROS1, and compositions thereof. These nucleic acids, or conjugates, or compositions thereof, may be used in the treatment and prevention of a bleeding disorder.

A first aspect of the invention is a double-stranded nucleic acid for inhibiting expression of PROS1, particularly in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 187,189,191, 193, 195, 197,199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49. These nucleic acids among others have the advantage of being active in various species that are relevant for pre-clinical and clinical development and/or of having few relevant off-target effects. Having few relevant off-target effects means that a nucleic acid specifically inhibits the intended target and does not significantly inhibit other genes or inhibits only one or few other genes at a therapeutically acceptable level.

Particularly, the first strand sequence comprises, or essentially consists of, a sequence of at least 16, more particularly at least 17, yet more particularly at least 18 and most particularly all 19 nucleotides differing by no more than 3 nucleotides, particularly by no more than 2 nucleotides, more particularly by no more than 1 nucleotide, and most particularly not differing by any nucleotide from any one of the sequences selected from SEQ ID NO: 187, 189, 191, 193, 195, 197, 199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49.

Particularly, the first strand sequence of the nucleic acid consists of one of the sequences selected from SEQ ID NO: 187, 189, 191, 193, 195, 197, 199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49. The sequence may however be modified by a number of nucleic acid modifications that do not change the identity of the nucleotide. For example, modifications of the backbone or sugar residues of the nucleic acid do not change the identity of the nucleotide because the base itself remains the same as in the reference sequence.

A nucleic acid that comprises a sequence according to a reference sequence herein means that the nucleic acid comprises a sequence of contiguous nucleotides in the order as defined in the reference sequence.

When reference is made herein to a sequence comprising or consisting of a number of nucleotides that are not shown to be modified in that sequence, the reference also encompasses the same nucleotide sequence in which one, several, such as two, three, four, five, six, seven or more, including all, nucleotides are modified by modifications such as 2'-OMe, 2'-F, are linked to a ligand or a linker, have a 3' end or 5' end modification or any other modification. It also encompasses sequences in which two or more nucleotides are linked to each other by the natural phosphodiester linkage or by any other linkage such as a phosphorothioate or a phosphorodithioate linkage.

A double-stranded nucleic acid is a nucleic acid in which the first strand and the second strand hybridise to each other over at least part of their lengths and are therefore capable of forming a duplex region under physiological conditions, such as in PBS at 37° C. at a concentration of 1 μM of each strand. The first and second strand are particularly able to hybridise to each other and therefore to form a duplex region over a region of at least 15 nucleotides, particularly 16, 17, 18 or 19 nucleotides. This duplex region comprises nucleotide base parings between the two strands, particularly based on Watson-Crick base pairing and/or wobble base pairing (such as GU base pairing). All the nucleotides of the two strands within a duplex region do not have to base pair to each other to form a duplex region. A certain number of mismatches, deletions or insertions between the nucleotide sequences of the two strands are acceptable. Overhangs on either end of the first or second strand or unpaired nucleotides at either end of the double-stranded nucleic acid are also possible. The double-stranded nucleic acid is particularly a stable double-stranded nucleic acid under physiological conditions, and particularly has a melting temperature (Tm) of 45° C. or more, 50° C. or more, 55° C. or more, 60° C. or more, 65° C. or more, 70° C. or more, 75° C. or more, 80° C. or more, or 85° C. or more, for example in PBS at a concentration of 1 µM of each strand.

The first strand and the second strand are particularly capable of forming a duplex region (i.e., are complementary to each other) over i) at least a portion of their lengths, particularly over at least 15 nucleotides of both of their lengths, ii) over the entire length of the first strand, iii) over the entire length of the second strand or iv) over the entire length of both the first and the second strand. Strands being complementary to each other over a certain length means that the strands are able to base pair to each other, either via Watson-Crick or wobble base pairing, over that length. Each nucleotide of the length does not necessarily have to be able to base pair with its counterpart in the other strand over the entire given length as long as a stable double-stranded nucleotide under physiological conditions can be formed. It is however preferred, in certain embodiments, if each nucleotide of the length can base pair with its counterpart in the other strand over the entire given length.

A certain number of mismatches, deletions or insertions between the first strand and the target sequence, or between the first strand and the second strand can be tolerated in the context of the siRNA and even have the potential in certain cases to increase RNA interference (e.g., inhibition) activity.

The inhibition activity of the nucleic acids according to the present invention relies on the formation of a duplex region between all or a portion of the first strand and a portion of a target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence; however, the first strand must be able to form a duplex structure with both the second strand and the target sequence, at least under physiological conditions.

The complementarity between the first strand and the target sequence may be perfect (i.e., 100% identity with no nucleotide mismatches or insertions or deletions in the first strand as compared to the target sequence).

The complementarity between the first strand and the target sequence may not be perfect. The complementarity may be from about 70% to about 100%. More specifically, the complementarity may be at least 70%, 80%, 85%, 90% or 95% and intermediate values.

The identity between the first strand and the complementary sequence of the target sequence may range from about 75% to about 100%. More specifically, the complementarity may be at least 75%, 80%, 85%, 90% or 95% and intermediate values, provided a nucleic acid is capable of reducing or inhibiting the expression of PROS1.

A nucleic acid having less than 100% complementarity between the first strand and the target sequence may be able to reduce the expression of PROS1 to the same level as a nucleic acid having perfect complementarity between the first strand and target sequence. Alternatively, it may be able to reduce expression of PROS1 to a level that is 15%, 20%, 25%, 30%, 35%, 40%, 45%, 50%, 55%, 60%, 65%, 70%, 75%, 80%, 85%, 90%, 95%, 98%, 99% or 100% of the level of reduction achieved by the nucleic acid with perfect complementarity.

In one aspect, a nucleic acid of the present disclosure is a nucleic acid wherein (a) the first strand sequence comprises a sequence differing by no more than 3 nucleotides from any one of the first strand sequences of Table 1 and optionally wherein the second strand sequence comprises a sequence differing by no more than 3 nucleotides from the second strand sequence in the same line of the table;

(b) the first strand sequence comprises a sequence differing by no more than 2 nucleotides from any one of the first strand sequences of Table 1 and optionally wherein the second strand sequence comprises a sequence differing by no more than 2 nucleotides from the second strand sequence in the same line of the table;

(c) the first strand sequence comprises a sequence differing by no more than 1 nucleotide from any one of the first strand sequences of Table 1 and optionally wherein the second strand sequence comprises a sequence differing by no more than 1 nucleotide from the second strand sequence in the same line of the table;

(d) the first strand sequence comprises a sequence corresponding to nucleotides 2 to 17 from the 5' end of any one of the first strand sequences of Table 1 and optionally wherein the second strand sequence comprises a sequence corresponding to nucleotides 2 to 17 from the 5' end of the second strand sequence in the same line of the table;

(e) the first strand sequence comprises a sequence corresponding to nucleotides 2 to 18 from the 5' end of any one of the first strand sequences of Table 1 and optionally wherein the second strand sequence comprises a sequence corresponding to nucleotides 2 to 18 from the 5' end of the second strand sequence in the same line of the table;

(f) the first strand sequence comprises a sequence corresponding to nucleotides 2 to 19 from the 5' end of any one of the first strand sequences of Table 1 and optionally wherein the second strand sequence comprises a sequence corresponding to nucleotides 2 to 19 from the 5' end of the second strand sequence in the same line of the table;

(g) the first strand sequence comprises a sequence corresponding to nucleotides 2 to 19 from the 5' end of any one of the first strand sequences of Table 1 and optionally wherein the second strand sequence comprises a sequence corresponding to nucleotides 1 to 18 from the 5' end of the second strand sequence in the same line of the table;

(h) the first strand sequence comprises a sequence of any one of the first strand sequences of Table 1 and optionally wherein the second strand sequence comprises a sequence of the second strand sequence in the same line of the table; or (i) the first strand sequence consists of any one of the first strand sequences of Table 1 and optionally wherein the second strand sequence consists of the sequence of the second strand sequence in the same line of the table;

wherein Table 1 is:

TABLE 1

| First strand sequence (SEQ ID NO:) | Second strand sequence (SEQ ID NO:) |
|---|---|
| 187 | 188 |
| 189 | 190 |
| 191 | 192 |
| 193 | 194 |
| 195 | 196 |
| 197 | 198 |
| 199 | 200 |
| 201 | 202 |
| 203 | 204 |
| 205 | 206 |
| 207 | 208 |
| 209 | 210 |
| 211 | 212 |
| 213 | 214 |
| 215 | 216 |
| 217 | 218 |
| 219 | 220 |
| 221 | 222 |
| 223 | 224 |
| 225 | 226 |
| 227 | 228 |
| 229 | 230 |
| 231 | 232 |
| 255 | 200 |
| 19 | 20 |
| 15 | 16 |
| 1 | 2 |
| 3 | 4 |
| 5 | 6 |
| 7 | 8 |
| 9 | 10 |
| 11 | 12 |
| 13 | 14 |
| 17 | 18 |
| 21 | 22 |
| 23 | 24 |
| 25 | 26 |
| 27 | 28 |
| 29 | 30 |
| 31 | 32 |
| 33 | 34 |
| 35 | 36 |
| 37 | 38 |
| 39 | 40 |
| 41 | 42 |
| 43 | 44 |
| 45 | 46 |
| 47 | 48 |
| 49 | 42 |
| 122 | 135 |
| 122 | 107 |
| 123 | 136 |
| 123 | 109 |

In one aspect, the nucleic acid is a nucleic acid wherein:

(a) the first strand sequence comprises the sequence of SEQ ID NO: 209 and optionally wherein the second strand sequence comprises the sequence of SEQ ID NO: 210;

(b) the first strand sequence comprises the sequence of SEQ ID NO: 229 and optionally wherein the second strand sequence comprises the sequence of SEQ ID NO: 230;

(c) the first strand sequence comprises the sequence of SEQ ID NO: 199 and optionally wherein the second strand sequence comprises the sequence of SEQ ID NO: 200; or (d) the first strand sequence comprises the sequence of SEQ ID NO: 203 and optionally wherein the second strand sequence comprises the sequence of SEQ ID NO: 204.

In one aspect, if the 5'-most nucleotide of the first strand is a nucleotide other than A or U, this nucleotide is replaced by an A or U. Particularly, if the 5'-most nucleotide of the first strand is a nucleotide other than a U, this nucleotide is replaced by U, and more particularly by U with a 5' (E)-vinylphosphonate, in the sequence.

In one aspect, there is a mismatch between the first nucleotide at the 5' end of the first strand and the corresponding nucleotide (the nucleotide with which it would form a base pair if there was no mismatch) in the second strand. For example, the 5' nucleotide of the first strand may be U and the corresponding nucleotide in the second strand may be any nucleotide other than A. In this case, the two nucleotides are unable to form a classical Watson-Crick base pair and there is a mismatch between the two nucleotides.

When a nucleic acid of the invention does not comprise the entire sequence of a reference first strand and/or second strand sequence as for example given in Table 1, or one or both strands differ from the corresponding reference sequence by one, two or three nucleotides, this nucleic acid particularly retains at least 30%, more particularly at least 50%, more particularly at least 70%, more particularly at least 80%, even more particularly at least 90%, yet more particularly at least 95% and most particularly 100% of the PROS1 inhibition activity compared to the inhibition activity of the corresponding nucleic acid that comprises the entire first strand and second strand reference sequences in a comparable experiment.

In one aspect, the nucleic acid is a nucleic acid wherein the first strand sequence comprises, or particularly consists of, the sequence of SEQ ID NO: 209 and optionally wherein the second strand sequence comprises, or particularly consists of, a sequence of at least 15, particularly at least 16, more particularly at least 17, yet more particularly at least 18 and most particularly all nucleotides of the sequence of SEQ ID NO: 210; or wherein the first strand sequence comprises, or particularly consists of, the sequence of SEQ ID NO: 229 and optionally wherein the second strand sequence comprises, or particularly consists of, a sequence of at least 15, particularly at least 16, more particularly at least 17, yet more particularly at least 18 and most particularly all nucleotides of the sequence of SEQ ID NO: 230; or wherein the first strand sequence comprises, or particularly consists of, the sequence of SEQ ID NO: 199 and optionally wherein the second strand sequence comprises, or particularly consists of, a sequence of at least 15, particularly at least 16, more particularly at least 17, yet more particularly at least 18 and most particularly all nucleotides of the sequence of SEQ ID NO: 200; or wherein the first strand sequence comprises, or particularly consists of, the sequence of SEQ ID NO: 203 and optionally wherein the second strand sequence comprises, or particularly consists of, a sequence of at least 15, particularly at least 16, more particularly at least 17, yet more particularly at least 18 and most particularly all nucleotides of the sequence of SEQ ID NO: 204.

In one aspect, the nucleic acid is a double-stranded nucleic acid for inhibiting expression of PROS1, particularly in a cell, wherein the nucleic acid comprises a first nucleic acid strand and a second nucleic acid strand, wherein the first strand is capable of hybridising under physiological conditions to a nucleic acid of a sequence selected from SEQ ID NO: 188, 190, 192, 194, 196, 198, 200, 202, 204, 206, 208, 210, 212, 214, 216, 218, 220, 222, 224, 226, 228, 230, 232, 20, 16, 2, 4, 6, 8, 10, 12, 14, 18, 22, 24, 26, 28, 30, 32, 34, 36, 38, 40, 42, 44, 46, 48 and 50; and wherein the second strand is capable of hybridising under physiological conditions to the first strand to form a duplex region.

Nucleic acids that are capable of hybridising under physiological conditions are nucleic acids that are capable of forming base pairs, particularly Watson-Crick or wobble base-pairs, between at least a portion of the opposed nucleotides in the strands so as to form at least a duplex region. Such a double-stranded nucleic acid is particularly a stable double-stranded nucleic acid under physiological conditions (for example in PBS at 37° C. at a concentration of 1 µM of each strand), meaning that under such conditions, the two strands stay hybridised to each other. The Tm of the double-stranded nucleotide is particularly 45° C. or more, particularly 50° C. or more and more particularly 55° C. or more.

One aspect of the present invention relates to a nucleic acid for inhibiting expression of PROS1, particularly in a cell, wherein the nucleic acid comprises a first sequence of at least 15, particularly at least 16, more particularly at least 17, yet more particularly at least 18 and most particularly all nucleotides differing by no more than 3 nucleotides, particularly no more than 2 nucleotides, more particularly no more than 1 nucleotide and most particularly not differing by any nucleotide from any of the sequences of Table 4, the first sequence being able to hybridise to a target gene transcript (such as an mRNA) under physiological conditions. Particularly, the nucleic acid further comprises a second sequence of at least 15, particularly, at least 16, more particularly at least 17, yet more particularly at least 18 and most particularly all nucleotides differing by no more than 3 nucleotides, particularly no more than 2 nucleotides, more particularly no more than 1 nucleotide and most particularly not differing by any nucleotide from any of the sequences of Table 4, wherein the second sequence is able to hybridise to the first sequence under physiological conditions and particularly wherein the nucleic acid is an siRNA that is capable of inhibiting PROS1 expression via the RNAi pathway.

One aspect relates to any double-stranded nucleic acid as disclosed in Table 2, provided that the double-stranded nucleic acid is capable of inhibiting expression of PROS1. These nucleic acids are all siRNAs with various nucleotide modifications. Some of them are conjugates comprising GalNAc moieties that can be specifically targeted to cells with GalNAc receptors, such as hepatocytes.

One aspect relates to a double-stranded nucleic acid that is capable of inhibiting expression of PROS1, particularly in a cell, for use as a medicament or in associated diagnostic or therapeutic methods, wherein the nucleic acid particularly comprises or consists of a first strand and a second strand and particularly wherein the first strand comprises a sequence sufficiently complementary to a PROS1 mRNA so as to mediate RNA interference.

The nucleic acids described herein may be capable of inhibiting the expression of PROS1, particularly in a cell. The nucleic acids may be capable of inhibiting PROS1 expression completely, resulting in 0% remaining expression upon treatment with the nucleic acids. The nucleic acids may be capable of partially inhibiting PROS1 expression. Partial inhibition means that PROS1 expression is decreased by 15%, 20%, 30%, 40%, 50%, 60%, 70%, 75%, 80%, 85%, 90%, 95% or more, or intermediate values, as compared to the absence of the nucleic acids under comparable conditions. The level of inhibition may be measured by comparing a treated sample with an untreated sample or with a sample treated with a control, such as for example a siRNA that does not target PROS1. Inhibition may be measured by measuring PROS1 mRNA and/or protein levels or levels of a biomarker or indicator that correlates with Protein S presence or activity. It may be measured in cells that may have been treated in vitro with a nucleic acid described herein. Alternatively, or in addition, inhibition may be measured in cells, such as hepatocytes, or tissue, such as liver tissue, or an organ, such as the liver, or in a body fluid such as blood, serum, lymph or in any other body part or fluid that has been taken from a subject previously treated with a nucleic acid disclosed herein. Particularly, inhibition of PROS1 expression is determined by comparing the PROS1 mRNA level measured in PROS1-expressing cells after 24 or 48 hours in vitro treatment with a double-stranded RNA disclosed herein under ideal conditions (see the examples for appropriate concentrations and conditions) to the PROS1 mRNA level measured in control cells that were untreated or mock treated or treated with a control double-stranded RNA under the same or at least comparable conditions.

One aspect of the present invention relates to a nucleic acid, wherein the first strand and the second strand are present on a single strand of a nucleic acid that loops around so that the first strand and the second strand are able to hybridise to each other and to thereby form a double-stranded nucleic acid with a duplex region.

Particularly, the first strand and the second strand of the nucleic acid are separate strands. The two separate strands are particularly each 17-25 nucleotides in length, more particularly 18-25 nucleotides in length. The two strands may be of the same or different lengths. The first strand may be 17-25 nucleotides in length, particularly it may be 18-24 nucleotides in length, it may be 18, 19, 20, 21, 22, 23 or 24 nucleotides in length. Most particularly, the first strand is 19 nucleotides in length. The second strand may independently be 17-25 nucleotides in length, particularly it may be 18-24 nucleotides in length, it may be 18, 19, 20, 21, 22, 23 or 24 nucleotides in length. More particularly, the second strand is 18 or 19 or 20 nucleotides in length, and most particularly it is 19 nucleotides in length.

Particularly, the first strand and the second strand of the nucleic acid form a duplex region of 17-25 nucleotides in length. More particularly, the duplex region is 18-24 nucleotides in length. The duplex region may be 17, 18, 19, 20, 21, 22, 23, 24 or 25 nucleotides in length. In the most particular embodiment, the duplex region is 18 or 19 nucleotides in length. The duplex region is defined here as the region between and including the 5'-most nucleotide of the first strand that is base paired to a nucleotide of the second strand to the 3'-most nucleotide of the first strand that is base paired to a nucleotide of the second strand. The duplex region may comprise nucleotides in either or both strands that are not base-paired to a nucleotide in the other strand. It may comprise one, two, three or four such nucleotides on the first strand and/or on the second strand. However, particularly, the duplex region consists of 17-25 consecutive nucleotide base pairs. That is to say that it particularly comprises 17-25 consecutive nucleotides on both of the strands that all base pair to a nucleotide in the other strand. More particularly, the duplex region consists of 18 or 19 consecutive nucleotide base pairs, most particularly 18.

In each of the embodiments disclosed herein, the nucleic acid may be blunt ended at both ends; have an overhang at one end and a blunt end at the other end; or have an overhang at both ends.

The nucleic acid may have an overhang at one end and a blunt end at the other end. The nucleic acid may have an overhang at both ends. The nucleic acid may be blunt ended at both ends. The nucleic acid may be blunt ended at the end with the 5' end of the first strand and the 3' end of the second strand or at the 3' end of the first strand and the 5' end of the second strand.

The nucleic acid may comprise an overhang at a 3' or 5' end. The nucleic acid may have a 3' overhang on the first strand. The nucleic acid may have a 3' overhang on the second strand. The nucleic acid may have a 5' overhang on the first strand. The nucleic acid may have a 5' overhang on the second strand. The nucleic acid may have an overhang at both the 5' end and 3' end of the first strand. The nucleic acid may have an overhang at both the 5' end and 3' end of the second strand. The nucleic acid may have a 5' overhang on the first strand and a 3' overhang on the second strand. The nucleic acid may have a 3' overhang on the first strand and a 5' overhang on the second strand. The nucleic acid may have a 3' overhang on the first strand and a 3' overhang on the second strand. The nucleic acid may have a 5' overhang on the first strand and a 5' overhang on the second strand.

An overhang at the 3' end or 5' end of the second strand or the first strand may consist of 1, 2, 3, 4 and 5 nucleotides in length. Optionally, an overhang may consist of 1 or 2 nucleotides, which may or may not be modified.

In one embodiment, the 5' end of the first strand is a single-stranded overhang of one, two or three nucleotides, particularly of one nucleotide.

Particularly, the nucleic acid is an siRNA. siRNAs are short interfering or short silencing RNAs that are able to inhibit the expression of a target gene through the RNA interference (RNAi) pathway. Inhibition occurs through targeted degradation of mRNA transcripts of the target gene after transcription. The siRNA forms part of the RISC complex. The RISC complex specifically targets the target RNA by sequence complementarity of the first (antisense) strand with the target sequence.

Particularly, the nucleic acid is capable of inhibiting PROS1. The inhibition is particularly mediated by the RNA interference (RNAi) mechanism. Particularly, the nucleic acid mediates RNA interference (i.e., it is capable of inhibiting its target) with an efficacy of at least 50% inhibition, more particularly at least 70%, more particularly at least 80%, even more particularly at least 90%, yet more particularly at least 95% and most particularly 100% inhibition. The inhibition efficacy is particularly measured by comparing the PROS1 mRNA level in cells, such as hepatocytes, treated with a PROS1 specific siRNA to the PROS1 mRNA level in cells treated with a control in a comparable experiment. The control can be a treatment with a non-PROS1 targeting siRNA or without a siRNA. The nucleic acid, or at least the first strand of the nucleic acid, is therefore particularly able to be incorporated into the RISC complex. As a result, the nucleic acid, or at least the first strand of the nucleic acid, is therefore able to guide the RISC complex to a specific target RNA with which the nucleic acid, or at least the first strand of the nucleic acid, is at least partially complementary. The RISC complex then specifically cleaves this target RNA and as a result leads to inhibition of the expression of the gene from which the RNA stems.

A particularly preferred embodiment is a nucleic acid wherein the first strand comprises or consists of SEQ ID NO: 233 and the second strand optionally comprises or consists of SEQ ID NO: 256. This nucleic acid can be further conjugated to a ligand. Even more preferred is a nucleic acid wherein the first strand comprises or consists of SEQ ID NO: 233 and the second strand optionally comprises or consists of SEQ ID NO: 234. Most preferred in this case is an siRNA that consists of SEQ ID NO: 233 and SEQ ID NO: 234. One aspect of the invention is EU161.

An alternative particularly preferred embodiment is a nucleic acid wherein the first strand comprises or consists of SEQ ID NO: 237 and the second strand optionally comprises or consists of SEQ ID NO: 257. This nucleic acid can be further conjugated to a ligand. Even more preferred is a nucleic acid wherein the first strand comprises or consists of SEQ ID NO: 237 and the second strand optionally comprises or consists of SEQ ID NO: 238. Most preferred in this case is an siRNA that consists of SEQ ID NO: 237 and SEQ ID NO: 238. One aspect of the invention is EU163.

An alternative particularly preferred embodiment is a nucleic acid wherein the first strand comprises or consists of SEQ ID NO: 251 and the second strand optionally comprises or consists of SEQ ID NO: 258. This nucleic acid can be further conjugated to a ligand. Even more preferred is a nucleic acid wherein the first strand comprises or consists of SEQ ID NO: 251 and the second strand optionally comprises or consists of SEQ ID NO: 252. Most preferred in this case is an siRNA that consists of SEQ ID NO: 251 and SEQ ID NO: 252. One aspect of the invention is EU170.

One aspect of the present invention relates to a Protein S inhibitor such as an siRNA, an antibody, a small molecule, a peptide, a protein or any other agent that reduces the level of Protein S in the blood or blocks its activity, for use in the treatment of a blood disorder, particularly haemophilia. Particularly the Protein S inhibitor is for inhibiting human Protein S and is particularly for use in the treatment of a human subject in need thereof.

Nucleic Acid Modifications

Nucleic acids discussed herein include unmodified RNA as well as RNA which has been modified, e.g., to improve efficacy or stability. Unmodified RNA refers to a molecule in which the components of the nucleic acid, namely sugars, bases, and phosphate moieties, are the same or essentially the same as those which occur in nature, for example as occur naturally in the human body. The term "modified nucleotide" as used herein refers to a nucleotide in which one or more of the components of the nucleotide, namely the sugar, base, and phosphate moiety, is/are different from those which occur in nature. The term "modified nucleotide" also refers in certain cases to molecules that are not nucleotides in the strict sense of the term because they lack, or have a substitute of, an essential component of a nucleotide, such as the sugar, base or phosphate moiety. A nucleic acid comprising such modified nucleotides is still to be understood as being a nucleic acid, even if one or more of the nucleotides of the nucleic acid has been replaced by a modified nucleotide that lacks, or has a substitution of, an essential component of a nucleotide.

Modifications of the nucleic acid of the present invention generally provide a powerful tool in overcoming potential limitations including, but not limited to, in vitro and in vivo stability and bioavailability inherent to native RNA molecules. The nucleic acids according to the invention may be modified by chemical modifications. Modified nucleic acids can also minimise the possibility of inducing interferon activity in humans. Modifications can further enhance the functional delivery of a nucleic acid to a target cell. The modified nucleic acids of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution with or insertion of analogues of nucleic acids or bases.

Throughout the description of the invention, "same or common modification" means the same modification to any nucleotide, be that A, G, C or U modified with a group such as a methyl group (2'-OMe) or a fluoro group (2'-F). For example, 2'-F-dU, 2'-F-dA, 2'-F-dC, 2'-F-dG are all considered to be the same or common modification, as are 2'-OMe-rU, 2'-OMe-rA; 2'-OMe-rC; 2'-OMe-rG. In contrast, a 2'-F modification is a different modification compared to a 2'-OMe modification.

Particularly, at least one nucleotide of the first and/or second strand of the nucleic acid is a modified nucleotide, particularly a non-naturally occurring nucleotide such as particularly a 2'-F modified nucleotide.

A modified nucleotide can be a nucleotide with a modification of the sugar group. The 2' hydroxyl group (OH) can be modified or replaced with a number of different "oxy" or "deoxy" substituents.

Examples of "oxy"-2' hydroxyl group modifications include alkoxy or aryloxy (OR, e.g., R=H, alkyl (such as methyl), cycloalkyl, aryl, aralkyl, heteroaryl or sugar); polyethyleneglycols (PEG), $O(CH_2CH_2O)_nCH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$, alkylamino, dialkylamino, heterocyclyl, arylamino, diaryl amino, heteroaryl amino, or diheteroaryl amino, ethylene diamine or polyamino) and aminoalkoxy, $O(CH_2)_n$AMINE, (e.g., AMINE=$NH_2$, alkylamino, dialkylamino, heterocyclyl, arylamino, diaryl amino, heteroaryl amino, or diheteroaryl amino, ethylene diamine or polyamino).

"Deoxy" modifications include hydrogen, halogen, amino (e.g., $NH_2$, alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$, alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-$OCH_3$, 2'-O-allyl, 2'-C-allyl, and 2'-fluoro.

The sugar group can also contain one or more carbons that possess the opposite stereochemical configuration than that of the corresponding carbon in ribose. Thus, a modified nucleotide may contain a sugar such as arabinose.

Modified nucleotides can also include "abasic" sugars, which lack a nucleobase at C-1'. These abasic sugars can further contain modifications at one or more of the constituent sugar atoms.

The 2' modifications may be used in combination with one or more phosphate internucleoside linker modifications (e.g., phosphorothioate or phosphorodithioate).

One or more nucleotides of a nucleic acid of the present invention may be modified. The nucleic acid may comprise at least one modified nucleotide. The modified nucleotide may be in the first strand. The modified nucleotide may be in the second strand. The modified nucleotide may be in the duplex region. The modified nucleotide may be outside the duplex region, i.e., in a single-stranded region. The modified nucleotide may be on the first strand and may be outside the duplex region. The modified nucleotide may be on the second strand and may be outside the duplex region. The 3'-terminal nucleotide of the first strand may be a modified nucleotide. The 3'-terminal nucleotide of the second strand may be a modified nucleotide. The 5'-terminal nucleotide of the first strand may be a modified nucleotide. The 5'-terminal nucleotide of the second strand may be a modified nucleotide.

A nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, about 24-26 modified nucleotides or about 26-28 modified nucleotides. In each case the nucleic acid comprising said modified nucleotides retains at least 50% of its activity as compared to the same nucleic acid but without said modified nucleotides or vice versa. The nucleic acid may retain 55%, 60%, 65%, 70%, 75%, 80%, 85%, 90%, 95% or 100% and intermediate values of its activity as compared to the same nucleic acid but without said modified nucleotides, or may have more than 100% of the activity of the same nucleic acid without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 3' terminal deoxy thymine (dT) nucleotide, a 2'-O-methyl (2'-OMe) modified nucleotide, a 2' modified nucleotide, a 2' deoxy modified nucleotide, a locked nucleotide, an abasic nucleotide, a 2' amino modified nucleotide, a 2' alkyl modified nucleotide, a 2'-deoxy-2'-fluoro (2'-F) modified nucleotide, a morpholino nucleotide, a phosphoramidate, a non-natural base comprising nucleotide, a nucleotide comprising a 5'-phosphorothioate group, a nucleotide comprising a 5' phosphate or 5' phosphate mimic and a terminal nucleotide linked to a cholesteryl derivative or a dodecanoic acid bisdecylamide group.

The nucleic acid may comprise a nucleotide comprising a modified base, wherein the base is selected from 2-aminoadenosine, 2,6-diaminopurine, inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Many of the modifications described herein and that occur within a nucleic acid will be repeated within a polynucleotide molecule, such as a modification of a base, or a phosphate moiety, or a non-linking O of a phosphate moiety. In some cases, the modification will occur at all of the possible positions/nucleotides in the polynucleotide but in many cases it will not. A modification may only occur at a 3' or 5' terminal position, may only occur in a terminal region, such as at a position on a terminal nucleotide or in the last 2, 3, 4, 5, or 10 nucleotides of a strand. A modification may occur in a double-strand region, a single-strand region, or in both. A modification may occur only in the double-strand region of a nucleic acid of the invention or may only occur in a single-strand region of a nucleic acid of the invention. A phosphorothioate or phosphorodithioate modification at a non-linking O position may only occur at one or both termini, may only occur in a terminal region, e.g., at a position on a terminal nucleotide or in the last 2, 3, 4 or 5 nucleotides of a strand, or may occur in duplex and/or in single-strand regions, particularly at termini. The 5' end and/or 3' end may be phosphorylated.

Stability of a nucleic acid of the invention may be increased by including particular bases in overhangs, or by including modified nucleotides, in single-strand overhangs, e.g., in a 5' or 3' overhang, or in both. Purine nucleotides may be included in overhangs. All or some of the bases in a 3' or 5' overhang may be modified. Modifications can include the use of modifications at the 2' OH group of the ribose sugar, the use of deoxyribonucleotides, instead of ribonucleotides, and modifications in the phosphate group, such as phosphorothioate or phosphorodithioate modifications. Overhangs need not be homologous with the target sequence.

Nucleases can hydrolyse nucleic acid phosphodiester bonds. However, chemical modifications to nucleic acids can confer improved properties, and, can render oligoribonucleotides more stable to nucleases.

Modified nucleic acids, as used herein, can include one or more of:
(i) alteration, e.g., replacement, of one or both of the non-linking phosphate oxygens and/or of one or more of the linking phosphate oxygens (referred to as linking even if at the 5' and 3' terminus of the nucleic acid of the invention);
(ii) alteration, e.g., replacement, of a constituent of the ribose sugar, e.g., of the 2' hydroxyl on the ribose sugar;
(iii) replacement of the phosphate moiety with "dephospho" linkers;
(iv) modification or replacement of a naturally occurring base;
(v) replacement or modification of the ribose-phosphate backbone; and
(vi) modification of the 3' end or 5' end of the first strand and/or the second strand, e.g., removal, modification or replacement of a terminal phosphate group or conjugation of a moiety, e.g., a fluorescently labelled moiety, to either the 3' or 5' end of one or both strands.

The terms replacement, modification and alteration indicate a difference from a naturally occurring molecule.

Specific modifications are discussed in more detail below.

The nucleic acid may comprise one or more nucleotides on the second and/or first strands that are modified. Alternating nucleotides may be modified, to form modified nucleotides.

Alternating as described herein means to occur one after another in a regular way. In other words, alternating means to occur in turn repeatedly. For example, if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

Some representative modified nucleic acid sequences of the present invention are shown in the examples. These examples are meant to be representative and not limiting.

In one aspect of the nucleic acid, at least nucleotides 2 and 14 of the first strand are modified, particularly by a first common modification, the nucleotides being numbered consecutively starting with nucleotide number 1 at the 5' end of the first strand. The first modification is particularly 2'-F.

In one aspect, at least one, several or particularly all the even-numbered nucleotides of the first strand are modified, particularly by a first common modification, the nucleotides being numbered consecutively starting with nucleotide number 1 at the 5' end of the first strand. The first modification is particularly 2'-F.

In one aspect, at least one, several or particularly all the odd-numbered nucleotides of the first strand are modified, the nucleotides being numbered consecutively starting with nucleotide number 1 at the 5' end of the first strand. Particularly, they are modified by a second modification. This second modification is particularly different from the first modification if the nucleic acid also comprises a first modification, for example of nucleotides 2 and 14 or of all the even-numbered nucleotides of the first strand. The first modification is particularly any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-$NH_2$. The second modification is particularly any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is particularly 2'-F and/or the second modification is particularly 2'-OMe.

In the context of this disclosure, the size or volume of a substituent, such as a 2' ribose modification, is particularly measured as the van der Waals volume.

In one aspect, at least one, several or particularly all the nucleotides of the second strand in a position corresponding to an even-numbered nucleotide of the first strand are modified, particularly by a third modification. Particularly in the same nucleic acid nucleotides 2 and 14 or all the even numbered nucleotides of the first strand are modified with a first modification. In addition, or alternatively, the odd-numbered nucleotides of the first strand are modified with a second modification. Particularly, the third modification is different from the first modification and/or the third modification is the same as the second modification. The first modification is particularly any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-$NH_2$. The second and/or third modification is particularly any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first modification is particularly 2'-F and/or the second and/or third modification is/are particularly 2'-OMe. The nucleotides on the first strand are numbered consecutively starting with nucleotide number 1 at the 5' end of the first strand.

A nucleotide of the second strand that is in a position corresponding, for example, to an even-numbered nucleotide of the first strand is a nucleotide of the second strand that is base-paired to an even-numbered nucleotide of the first strand.

In one aspect, at least one, several or particularly all the nucleotides of the second strand in a position corresponding to an odd-numbered nucleotide of the first strand are modified, particularly by a fourth modification. Particularly in the same nucleic acid nucleotides 2 and 14 or all the even numbered nucleotides of the first strand are modified with a first modification. In addition, or alternatively, the odd-numbered nucleotides of the first strand are modified with a second modification. In addition, or alternatively, all the nucleotides of the second strand in a position corresponding to an even-numbered nucleotide of the first strand are modified with a third modification. The fourth modification is particularly different from the second modification and particularly different from the third modification and the fourth modification is particularly the same as the first modification. The first and/or fourth modification is particularly any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second and/or third modification is particularly any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are particularly a 2'-OMe modification and/or the second and/or third modification is/are particularly a 2'-F modification. The nucleotides on the first strand are numbered consecutively starting with nucleotide number 1 at the 5' end of the first strand.

In one aspect of the nucleic acid, the nucleotide/nucleotides of the second strand in a position corresponding to nucleotide 11 or nucleotide 13 or nucleotides 11 and 13 or nucleotides 11-13 of the first strand is/are modified by a fourth modification. Particularly, all the nucleotides of the second strand other than the nucleotide/nucleotides in a position corresponding to nucleotide 11 or nucleotide 13 or nucleotides 11 and 13 or nucleotides 11-13 of the first strand is/are modified by a third modification. Particularly in the same nucleic acid nucleotides 2 and 14 or all the even numbered nucleotides of the first strand are modified with a first modification. In addition, or alternatively, the odd-numbered nucleotides of the first strand are modified with a second modification. The fourth modification is particularly different from the second modification and particularly different from the third modification and the fourth modification is particularly the same as the first modification. The first and/or fourth modification is particularly any 2' ribose modification that is of the same size or smaller in volume than a 2'-OH group, or a locked nucleic acid (LNA), or an unlocked nucleic acid (UNA), or a 2'-Fluoroarabino Nucleic Acid (FANA) modification. A 2' ribose modification that is of the same size or smaller in volume than a 2'-OH group can for example be a 2'-F, 2'-H, 2'-halo, or 2'-NH$_2$. The second and/or third modification is particularly any 2' ribose modification that is larger in volume than a 2'-OH group. A 2' ribose modification that is larger in volume than a 2'-OH group can for example be a 2'-OMe, 2'-O-MOE (2'-O-methoxyethyl), 2'-O-allyl or 2'-O-alkyl, with the proviso that the nucleic is capable of reducing the expression of the target gene to at least the same extent as the same nucleic acid without the modification(s) under comparable conditions. The first and/or the fourth modification is/are particularly a 2'-OMe modification and/or the second and/or third modification is/are particularly a 2'-F modification. The nucleotides on the first strand are numbered consecutively starting with nucleotide number 1 at the 5' end of the first strand.

In one aspect of the nucleic acid, all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and/or fourth modification is/are 2'-F and/or the second and/or third modification is/are 2'-OMe.

In one aspect of the nucleic acid, all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe. In one embodiment in this aspect, the 3' terminal nucleotide of the second strand is an inverted RNA nucleotide (i.e., the nucleotide is linked to the 3' end of the strand through its 3' carbon, rather than through its 5' carbon as would normally be the case). When the 3' terminal nucleotide of the second strand is an inverted RNA nucleotide, the inverted RNA nucleotide is particularly an unmodified nucleotide in the sense that it does not comprise any modifications compared to the natural nucleotide counterpart. Specifically, the inverted RNA nucleotide is particularly a 2'-OH nucleotide. Particularly, in this aspect when the 3' terminal nucleotide of the second strand is an inverted RNA nucleotide, the nucleic acid is blunt-ended at least at the end that comprises the 5' end of the first strand.

One aspect of the present invention is a nucleic acid as disclosed herein for inhibiting expression of the PROS1 gene, particularly in a cell, wherein said first strand includes modified nucleotides or unmodified nucleotides at a plurality of positions in order to facilitate processing of the nucleic acid by RISC.

In one aspect, "facilitate processing by RISC" means that the nucleic acid can be processed by RISC, for example any modification present will permit the nucleic acid to be processed by RISC and particularly, will be beneficial to processing by RISC, suitably such that siRNA activity can take place.

One aspect is a nucleic acid as disclosed herein, wherein the nucleotides at positions 2 and 14 from the 5' end of the first strand are not modified with a 2' OMe modification, and the nucleotide/nucleotides on the second strand which corresponds to position 11 or position 13 or positions 11 and 13 or positions 11, 12 and 13 of the first strand is/are not modified with a 2'-OMe modification (in other words, they are naturally occurring nucleotides or are modified with a modification other than 2'-OMe).

In one aspect, the nucleotide on the second strand which corresponds to position 13 of the first strand is the nucleotide that forms a base pair with position 13 (from the 5' end) of the first strand.

In one aspect, the nucleotide on the second strand which corresponds to position 11 of the first strand is the nucleotide that forms a base pair with position 11 (from the 5' end) of the first strand.

In one aspect, the nucleotide on the second strand which corresponds to position 12 of the first strand is the nucleotide that forms a base pair with position 12 (from the 5' end) of the first strand.

For example, in a 19-mer nucleic acid which is double-stranded and blunt ended, position 13 (from the 5' end) of the first strand would pair with position 7 (from the 5' end) of the second strand. Position 11 (from the 5' end) of the first strand would pair with position 9 (from the 5' end) of the second strand. This nomenclature may be applied to other positions of the second strand.

In one aspect, in the case of a partially complementary first and second strand, the nucleotide on the second strand that "corresponds to" a position on the first strand may not necessarily form a base pair if that position is the position in which there is a mismatch, but the principle of the nomenclature still applies.

One aspect is a nucleic acid as disclosed herein, wherein the nucleotides at positions 2 and 14 from the 5' end of the first strand are not modified with a 2'-OMe modification, and the nucleotides on the second strand which correspond to position 11, or 13, or 11 and 13, or 11-13 of the first strand are modified with a 2'-F modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are not modified with a 2'-OMe modification.

One aspect is a nucleic acid as disclosed herein, wherein the nucleotides at positions 2 and 14 from the 5' end of the first strand are modified with a 2'-F modification, and the nucleotides on the second strand which correspond to position 11, or 13, or 11 and 13, or 11-13 of the first strand are modified with a 2'-F modification.

One aspect is a nucleic acid as disclosed herein wherein greater than 50% of the nucleotides of the first and/or second strand comprise a 2'-OMe modification, such as greater than 55%, 60%, 65%, 70%, 75%, 80%, or 85%, or more, of the first and/or second strand comprise a 2'-OMe modification.

One aspect is a nucleic acid as disclosed herein wherein greater than 50% of the nucleotides of the first and/or second strand comprise a naturally occurring RNA modification, such as wherein greater than 55%, 60%, 65%, 70%, 75%, 80%, or 85% or more of the first and/or second strands comprise such a modification. Suitable naturally occurring modifications include, as well as 2'-OMe, other 2' sugar modifications, in particular a 2'-H modification resulting in a DNA nucleotide.

One aspect is a nucleic acid as disclosed herein comprising no more than 20%, such as no more than 15% such as no more than 10%, of nucleotides which have 2' modifications that are not 2'-OMe modifications on the first and/or second strand.

One aspect is a nucleic acid as disclosed herein, wherein the number of nucleotides in the first and/or second strand with a 2'-modification that is not a 2'-OMe modification is no more than 7, more particularly no more than 5, and most particularly no more than 3.

One aspect is a nucleic acid as disclosed herein comprising no more than 20%, (such as no more than 15% or no more than 10%) of 2'-F modifications on the first and/or second strand.

One aspect is a nucleic acid as disclosed herein, wherein the number of nucleotides in the first and/or second strand with a 2'-F modification is no more than 7, more particularly no more than 5, and most particularly no more than 3.

One aspect is a nucleic acid as disclosed herein, wherein all nucleotides are modified with a 2'-OMe modification except positions 2 and 14 from the 5' end of the first strand and the nucleotides on the second strand which correspond to position 11, or 13, or 11 and 13, or 11-13 of the first strand. Particularly the nucleotides that are not modified with 2'-OMe are modified with fluoro at the 2' position (2'-F modification).

Particularly, all nucleotides of the nucleic acid are modified at the 2' position of the sugar. Particularly, these nucleotides are modified with a 2'-F modification where the modification is not a 2'-OMe modification.

In one aspect the nucleic acid is modified on the first strand with alternating 2'-OMe modifications and 2-F modifications, and positions 2 and 14 (starting from the 5' end) are modified with 2'-F. Particularly the second strand is modified with 2'-F modifications at nucleotides on the second strand which correspond to position 11, or 13, or 11 and 13, or 11-13 of the first strand. Particularly the second strand is modified with 2'-F modifications at positions 11-13 counting from the 3' end starting at the first position of the complementary (double-stranded) region, and the remaining modifications are naturally occurring modifications, particularly 2'-OMe. The complementary region at least in this case starts at the first position of the second strand that has a corresponding nucleotide in the first strand, regardless of whether the two nucleotides are able to base pair to each other.

In one aspect of the nucleic acid, each of the nucleotides of the first strand and of the second strand is a modified nucleotide.

Unless specifically stated otherwise, herein the nucleotides of the first strand are numbered contiguously starting with nucleotide number 1 at the 5' end of the first strand. Nucleotides of the second strand are numbered contiguously starting with nucleotide number 1 at the 3' end of the second strand.

An "odd numbered" nucleotide is a nucleotide numbered with an odd number in a strand in which the nucleotides are numbered contiguously starting either from the indicated end or from the 5' end of the strand if the end from which the nucleotides are numbered is not indicated.

An "even numbered" nucleotide is a nucleotide numbered with an even number in a strand in which the nucleotides are numbered contiguously starting either from the indicated end or from the 5' end of the strand if the end from which the nucleotides are numbered is not indicated.

One or more nucleotides on the first and/or second strand may be modified, to form modified nucleotides. One or more of the odd-numbered nucleotides of the first strand may be modified.

One or more of the even-numbered nucleotides of the first strand may be modified by at least a second modification, wherein the at least second modification is different from the modification on the one or more odd nucleotides. At least one of the one or more modified even numbered-nucleotides may be adjacent to at least one of the one or more modified odd-numbered nucleotides.

A plurality of odd-numbered nucleotides in the first strand may be modified in the nucleic acid of the invention. A plurality of even-numbered nucleotides in the first strand may be modified by a second modification. The first strand may comprise adjacent nucleotides that are modified by a common modification. The first strand may also comprise adjacent nucleotides that are modified by a second different modification (i.e., the first strand may comprise nucleotides that are adjacent to each other and modified by a first modification as well as other nucleotides that are adjacent to each other and modified by a second modification that is different to the first modification).

One or more of the odd-numbered nucleotides of the second strand (wherein the nucleotides are numbered contiguously starting with nucleotide number 1 at the 3' end of the second strand) may be modified by a modification that is different to the modification of the odd-numbered nucleotides on the first strand (wherein the nucleotides are numbered contiguously starting with nucleotide number 1 at the 5' end of the first strand) and/or one or more of the even-numbered nucleotides of the second strand may be modified by the same modification of the odd-numbered nucleotides of the first strand. At least one of the one or more modified even-numbered nucleotides of the second strand may be adjacent to the one or more modified odd-numbered nucleotides. A plurality of odd-numbered nucleotides of the second strand may be modified by a common modification and/or a plurality of even-numbered nucleotides may be modified by the same modification that is present on the first stand odd-numbered nucleotides. A plurality of odd-numbered nucleotides on the second strand may be modified by a modification that is different from the modification of the first strand odd-numbered nucleotides.

The second strand may comprise adjacent nucleotides that are modified by a common modification, which may be a modification that is different from the modification of the odd-numbered nucleotides of the first strand.

In the nucleic acid of the invention, each of the odd-numbered nucleotides in the first strand and each of the even-numbered nucleotides in the second strand may be modified with a common modification and, each of the even-numbered nucleotides may be modified in the first strand with a different modification and each of the odd-numbered nucleotides may be modified in the second strand with the different modification.

The nucleic acid of the invention may have the modified nucleotides of the first strand shifted by at least one nucleotide relative to the unmodified or differently modified nucleotides of the second strand.

One or more or each of the odd numbered-nucleotides may be modified in the first strand and one or more or each of the even-numbered nucleotides may be modified in the second strand. One or more or each of the alternating nucleotides on either or both strands may be modified by a second modification. One or more or each of the even-numbered nucleotides may be modified in the first strand and one or more or each of the even-numbered nucleotides may be modified in the second strand. One or more or each of the alternating nucleotides on either or both strands may be modified by a second modification. One or more or each of the odd-numbered nucleotides may be modified in the first strand and one or more of the odd-numbered nucleotides may be modified in the second strand by a common modification. One or more or each of the alternating nucleotides on either or both strands may be modified by a second modification. One or more or each of the even-numbered nucleotides may be modified in the first strand and one or more or each of the odd-numbered nucleotides may be modified in the second strand by a common modification. One or more or each of the alternating nucleotides on either or both strands may be modified by a second modification.

The nucleic acid of the invention may comprise single- or double-stranded constructs that comprise at least two regions of alternating modifications in one or both of the strands. These alternating regions can comprise up to about 12 nucleotides but particularly comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each of the termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd-numbered nucleotides of the first strand. One or more nucleotides of the second strand may also be modified with the second modification. One or more nucleotides with the second modification may be adjacent to each other and to nucleotides having a modification that is the same as the modification of the odd-numbered nucleotides of the first strand. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 5' end. The second strand may also be conjugated to a ligand at the 5' end.

The nucleic acid of the invention may comprise a first strand comprising adjacent nucleotides that are modified with a common modification. One or more such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of the second strand may also be modified with the second modification. One or more nucleotides with the second modification may be adjacent. The first strand may also comprise phosphorothioate linkages between the two nucleotides at the 3' end and at the 5' end or a phosphorodithioate linkage between the two nucleotides at the 3' end. The second strand may comprise a phosphorothioate or phosphorodithioate linkage between the two nucleotides at the 3' end. The second strand may also be conjugated to a ligand at the 5' end.

The nucleotides numbered from 5' to 3' on the first strand and 3' to 5' on the second strand, 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Nucleotides are numbered for the sake of the nucleic acid of the present invention from 5' to 3' on the first strand and 3' to 5' on the second strand.

The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

The modification and/or modifications may each and individually be selected from the group consisting of 3' terminal deoxy thymine, 2'-OMe, a 2' deoxy modification, a 2' amino modification, a 2' alkyl modification, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

At least one modification may be 2'-OMe and/or at least one modification may be 2'-F. Further modifications as described herein may be present on the first and/or second strand.

The nucleic acid of the invention may comprise an inverted RNA nucleotide at one or several of the strand ends. Such inverted nucleotides provide stability to the nucleic acid. Particularly, the nucleic acid comprises at least an inverted nucleotide at the 3' end of the first and/or the second strand and/or at the 5' end of the second strand. More particularly, the nucleic acid comprises an inverted nucleotide at the 3' end of the second strand. Most particularly, the nucleic acid comprises an inverted RNA nucleotide at the 3' end of the second strand and this nucleotide is particularly an inverted A. An inverted nucleotide is a nucleotide that is linked to the 3' end of a nucleic acid through its 3' carbon, rather than its 5' carbon as would normally be the case or is linked to the 5' end of a nucleic acid through its 5' carbon, rather than its 3' carbon as would normally be the case. The inverted nucleotide is particularly present at an end of a strand not as an overhang but opposite a corresponding nucleotide in the other strand. Accordingly, the nucleic acid is particularly blunt-ended at the end that comprises the inverted RNA nucleotide. An inverted RNA nucleotide being present at the end of a strand particularly means that the last nucleotide at this end of the strand is the inverted RNA nucleotide. A nucleic acid with such a nucleotide is stable and easy to synthesise. The inverted RNA nucleotide is particularly an unmodified nucleotide in the sense that it does not comprise any modifications compared to the natural nucleotide counterpart. Specifically, the inverted RNA nucleotide is particularly a 2'-OH nucleotide.

Nucleic acids of the invention may comprise one or more nucleotides modified at the 2' position with a 2'-H, and therefore having a DNA nucleotide within the nucleic acid. Nucleic acids of the invention may comprise DNA nucleotides at positions 2 and/or 14 of the first strand counting from the 5' end of the first strand. Nucleic acids may comprise DNA nucleotides on the second strand which correspond to position 11, or 13, or 11 and 13, or 11-13 of the first strand.

In one aspect there is no more than one DNA nucleotide per nucleic acid of the invention.

Nucleic acids of the invention may comprise one or more LNA nucleotides. Nucleic acids of the invention may comprise LNA nucleotides at positions 2 and/or 14 of the first strand counting from the 5' end of the first strand. Nucleic acids may comprise LNA on the second strand which correspond to position 11, or 13, or 11 and 13, or 11-13 of the first strand.

Some representative modified nucleic acid sequences of the present invention are shown in the examples. These examples are meant to be representative and not limiting.

Particularly, the nucleic acid may comprise a first modification and a second or further modification which are each and individually selected from the group comprising 2'-OMe modification and 2'-F modification. The nucleic acid may comprise a modification that is 2'-OMe that may be a first modification, and a second modification that is 2'-F. The nucleic acid of the invention may also include a phosphorothioate or phosphorodithioate modification and/or a deoxy modification which may be present in or between the terminal 2 or 3 nucleotides of each or any end of each or both strands.

In one aspect of the nucleic acid, at least one nucleotide of the first and/or second strand is a modified nucleotide, wherein if the first strand comprises at least one modified nucleotide:
  (i) at least one or both of the nucleotides 2 and 14 of the first strand is/are modified by a first modification; and/or
  (ii) at least one, several, or all the even-numbered nucleotides of the first strand is/are modified by a first modification; and/or
  (iii) at least one, several, or all the odd-numbered nucleotides of the first strand is/are modified by a second modification; and/or
  wherein if the second strand comprises at least one modified nucleotide:
  (iv) at least one, several, or all the nucleotides of the second strand in a position corresponding to an even-numbered nucleotide of the first strand is/are modified by a third modification; and/or (v) at least one, several, or all the nucleotides of the second strand in a position corresponding to an odd-numbered nucleotide of the first strand is/are modified by a fourth modification; and/or (vi) at least one, several, or all the nucleotides of the second strand in a position corresponding to nucleotide 11 or nucleotide 13 or nucleotides 11 and 13 or nucleotides 11-13 of the first strand is/are modified by a fourth modification; and/or (vii) at least one, several, or all the nucleotides of the second strand in a position other than the position corresponding to nucleotide 11 or nucleotide 13 or nucleotides 11 and 13 or nucleotides 11-13 of the first strand is/are modified by a third modification;

wherein the nucleotides on the first strand are numbered consecutively starting with nucleotide number 1 at the 5' end of the first strand;

wherein the modifications are particularly at least one of the following:
(a) the first modification is particularly different from the second and from the third modification;
(b) the first modification is particularly the same as the fourth modification;
(c) the second and the third modification are particularly the same modification;
(d) the first modification is particularly a 2'-F modification;
(e) the second modification is particularly a 2'-OMe modification;
(f) the third modification is particularly a 2'-OMe modification; and/or
(g) the fourth modification is particularly a 2'-F modification; and wherein optionally the nucleic acid is conjugated to a ligand.

One aspect is a double-stranded nucleic acid for inhibiting expression of PROS1, particularly in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 187, 189, 191, 193, 195, 197, 199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49, particularly SEQ ID NO: 199, 203, 209 or 229, wherein all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and fourth modification are 2'-F and the second and third modification are 2'-OMe.

One aspect is a double-stranded nucleic acid for inhibiting expression of PROS1, particularly in a cell, wherein the nucleic acid comprises a first strand and a second strand, wherein the first strand sequence comprises a sequence of at least 15 nucleotides differing by no more than 3 nucleotides from any one of the sequences selected from SEQ ID NO: 187, 189, 191, 193, 195, 197, 199, 201, 203, 205, 207, 209, 211, 213, 215, 217, 219, 221, 223, 225, 227, 229, 231, 255, 19, 15, 1, 3, 5, 7, 9, 11, 13, 17, 21, 23, 25, 27, 29, 31, 33, 35, 37, 39, 41, 43, 45, 47 and 49, particularly SEQ ID NO: 199, 203, 209 or 229, wherein all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe.

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5' O, N, S or C group of the sugar. Alternatively, the linker can connect to or replace the terminal atom of a nucleotide surrogate (e.g., PNAs). These spacers or linkers can include e.g., —$(CH_2)_n$—, —$(CH_2)_nN$—, —$(CH_2)_nO$—, —$(CH_2)_nS$—, —$(CH_2CH_2O)_nCH_2CH_2O$— (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing. Suitable modifications include: 5'-monophosphate ((HO)$_2$(O)P—O-5'); 5'-diphosphate ((HO)$_2$(O)P—O—P(HO)(O)—O-5'); 5'-triphosphate ((HO)$_2$(O)P—O—(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)$_2$(S)P—O-5'); 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (alkyl=methyl, ethyl, isopropyl, propyl, etc., e.g., RP(OH)(O)—O-5'-(wherein R is an alkyl), (OH)$_2$(O)P-5'-CH$_2$—), 5' vinylphosphonate, 5'-alkyletherphosphonates (alkylether=methoxymethyl (MeOCH$_2$—), ethoxymethyl, etc., e.g., RP(OH)(O)—O-5'-) (wherein R is an alkylether)).

Certain moieties may be linked to the 5' terminus of the first strand or the second strand. These include abasic ribose moiety, abasic deoxyribose moiety, modifications abasic ribose and abasic deoxyribose moieties including 2'-O alkyl modifications; inverted abasic ribose and abasic deoxyribose moieties and modifications thereof, C6-imino-Pi; a mirror nucleotide including L-DNA and L-RNA; 5'OMe nucleotide; and nucleotide analogues including 4',5'-methylene nucleotide; 1-($\beta$-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

In each sequence described herein, a C-terminal "—OH" moiety may be substituted for a C-terminal "—NH$_2$" moiety, and vice-versa.

The invention also provides a nucleic acid according to any aspect of the invention described herein, wherein the first strand has a terminal 5' (E)-vinylphosphonate nucleotide at its 5' end. This terminal 5' (E)-vinylphosphonate nucleotide is particularly linked to the second nucleotide in the first strand by a phosphodiester linkage.

The first strand of the nucleic acid may comprise formula (I):

(vp)-N$_{(po)}$[N$_{(po)}$]$_n$—      (I)

where '(vp)-' is the 5' (E)-vinylphosphonate, 'N' is a nucleotide, 'po' is a phosphodiester linkage, and n is from 1 to (the total number of nucleotides in the first strand–2), particularly wherein n is from 1 to (the total number of nucleotides in the first strand–3), more particularly wherein n is from 1 to (the total number of nucleotides in the first strand–4).

Particularly, the terminal 5' (E)-vinylphosphonate nucleotide is an RNA nucleotide, particularly a (vp)-U.

A terminal 5' (E)-vinylphosphonate nucleotide is a nucleotide wherein the natural phosphate group at the 5'-end has been replaced with a E-vinylphosphonate, in which the bridging 5'-oxygen atom of the terminal nucleotide of the 5' phosphorylated strand is replaced with a methynyl (—CH=) group:

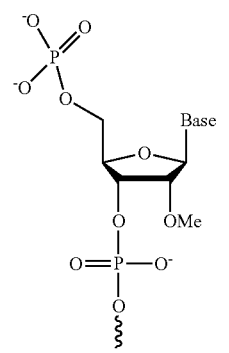

Nucleotides with a natural phosphate at the 5'–end

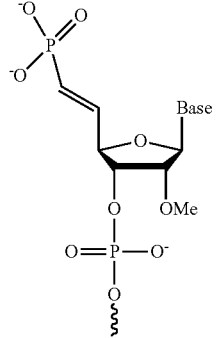

Nucleotide with a E-vinylphosphonate at the 5'–end

A 5' (E)-vinylphosphonate is a 5' phosphate mimic. A biological mimic is a molecule that is capable of carrying out the same function as and is structurally very similar to the original molecule that is being mimicked. In the context of the present invention, 5' (E)-vinylphosphonate mimics the function of a normal 5' phosphate, e.g. enabling efficient RISC loading. In addition, because of its slightly altered structure, 5' (E) vinylphosphonate is capable of stabilizing the 5'-end nucleotide by protecting it from dephosphorylation by enzymes such as phosphatases.

In one aspect, the first strand has a terminal 5' (E)-vinylphosphonate nucleotide at its 5' end, the terminal 5' (E)-vinylphosphonate nucleotide is linked to the second nucleotide in the first strand by a phosphodiester linkage and the first strand comprises a) more than 1 phosphodiester linkage; b) phosphodiester linkages between at least the terminal three 5' nucleotides and/or c) phosphodiester linkages between at least the terminal four 5' nucleotides.

In one aspect, the first strand and/or the second strand of the nucleic acid comprises at least one phosphorothioate (ps) and/or at least one phosphorodithioate (ps2) linkage between two nucleotides.

In one aspect, the first strand and/or the second strand of the nucleic acid comprises more than one phosphorothioate and/or more than one phosphorodithioate linkage.

In one aspect, the first strand and/or the second strand of the nucleic acid comprises a phosphorothioate or phosphorodithioate linkage between the terminal two 3' nucleotides or phosphorothioate or phosphorodithioate linkages between the terminal three 3' nucleotides. Particularly, the linkages between the other nucleotides in the first strand and/or the second strand are phosphodiester linkages.

In one aspect, the first strand and/or the second strand of the nucleic acid comprises a phosphorothioate linkage between the terminal two 5' nucleotides or a phosphorothioate linkages between the terminal three 5' nucleotides.

In one aspect, the nucleic acid of the present invention comprises one or more phosphorothioate or phosphorodithioate modifications on one or more of the terminal ends of the first and/or the second strand. Optionally, each or either end of the first strand may comprise one or two or three phosphorothioate or phosphorodithioate modified nucleotides (internucleoside linkage). Optionally, each or either end of the second strand may comprise one or two or three phosphorothioate or phosphorodithioate modified nucleotides (internucleoside linkage).

In one aspect, the nucleic acid comprises a phosphorothioate linkage between the terminal two or three 3' nucleotides and/or 5' nucleotides of the first and/or the second strand. Particularly, the nucleic acid comprises a phosphorothioate linkage between each of the terminal three 3' nucleotides and the terminal three 5' nucleotides of the first strand and of the second strand. Particularly, all remaining linkages between nucleotides of the first and/or of the second strand are phosphodiester linkages.

In one aspect, the nucleic acid comprises a phosphorodithioate linkage between each of the two, three or four terminal nucleotides at the 3' end of the first strand and/or comprises a phosphorodithioate linkage between each of the two, three or four terminal nucleotides at the 3' end of the second strand and/or a phosphorodithioate linkage between each of the two, three or four terminal nucleotides at the 5' end of the second strand and comprises a linkage other than a phosphorodithioate linkage between the two, three or four terminal nucleotides at the 5' end of the first strand.

In one aspect, the nucleic acid comprises a phosphorothioate linkage between the terminal three 3' nucleotides and the terminal three 5' nucleotides of the first strand and of the second strand. Particularly, all remaining linkages between nucleotides of the first and/or of the second strand are phosphodiester linkages.

In one aspect, the nucleic acid:
(i) has a phosphorothioate linkage between the terminal three 3' nucleotides and the terminal three 5' nucleotides of the first strand;
(ii) is conjugated to a triantennary ligand either on the 3' end nucleotide or on the 5' end nucleotide of the second strand;
(iii) has a phosphorothioate linkage between the terminal three nucleotides of the second strand at the end opposite to the one conjugated to the triantennary ligand; and
(iv) optionally all remaining linkages between nucleotides of the first and/or of the second strand are phosphodiester linkages.

In one aspect, the nucleic acid:
(i) has a terminal 5' (E)-vinylphosphonate nucleotide at the 5' end of the first strand;
(ii) has a phosphorothioate linkage between the terminal three 3' nucleotides on the first and second strand and between the terminal three 5' nucleotides on the second strand or it has a phosphorodithioate linkage between the terminal two 3' nucleotides on the first and second strand and between the terminal two 5' nucleotides on the second strand; and
(iii) optionally all remaining linkages between nucleotides of the first and/or of the second strand are phosphodiester linkages.

The use of a phosphorodithioate linkage in the nucleic acid of the invention reduces the variation in the stereochemistry of a population of nucleic acid molecules compared to molecules comprising a phosphorothioate in that same position. Phosphorothioate linkages introduce chiral centres and it is difficult to control which non-linking oxygen is substituted for sulphur. The use of a phosphorodithioate ensures that no chiral centre exists in that linkage and thus reduces or eliminates any variation in the population of nucleic acid molecules, depending on the number of phosphorodithioate and phosphorothioate linkages used in the nucleic acid molecule.

In one aspect, the nucleic acid comprises a phosphorodithioate linkage between the two terminal nucleotides at the 3' end of the first strand and a phosphorodithioate linkage between the two terminal nucleotides at the 3' end of the second strand and a phosphorodithioate linkage between the two terminal nucleotides at the 5' end of the second strand and comprises a linkage other than a phosphorodithioate linkage between the two, three or four terminal nucleotides at the 5' end of the first strand. Particularly, the first strand has a terminal 5' (E)-vinylphosphonate nucleotide at its 5' end. This terminal 5' (E)-vinylphosphonate nucleotide is particularly linked to the second nucleotide in the first strand by a phosphodiester linkage.

Particularly, all the linkages between the nucleotides of both strands other than the linkage between the two terminal nucleotides at the 3' end of the first strand and the linkages between the two terminal nucleotides at the 3' end and at the 5' end of the second strand are phosphodiester linkages.

In one aspect, the nucleic acid comprises a phosphorothioate linkage between each of the three terminal 3' nucleotides and/or between each of the three terminal 5' nucleotides on the first strand, and/or between each of the three terminal 3' nucleotides and/or between each of the three terminal 5' nucleotides of the second strand when there is no phosphorodithioate linkage present at that end. No phosphorodithioate linkage being present at an end means that the linkage between the two terminal nucleotides, or particularly between the three terminal nucleotides of the nucleic acid end in question are linkages other than phosphorodithioate linkages.

In one aspect, all the linkages of the nucleic acid between the nucleotides of both strands other than the linkage between the two terminal nucleotides at the 3' end of the first strand and the linkages between the two terminal nucleotides at the 3' end and at the 5' end of the second strand are phosphodiester linkages.

Other phosphate linkage modifications are possible.

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

The phosphate groups can also individually be replaced by non-phosphorus containing connectors.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino groups.

The phosphate linker and ribose sugar may be replaced by nuclease resistant nucleotides. Examples include the morpholino, cyclobutyl, pyrrolidine and peptide nucleic acid (PNA) nucleoside surrogates. In certain embodiments, PNA surrogates may be used.

In one aspect, the nucleic acid, which is particularly an siRNA that inhibits expression of PROS1, particularly via RNAi, and particularly in a cell, comprises one or more or all of:
(i) a modified nucleotide;
(ii) a modified nucleotide other than a 2'-OMe modified nucleotide at positions 2 and 14 from the 5' end of the first strand, particularly a 2'-F modified nucleotide;
(iii) each of the odd-numbered nucleotides of the first strand as numbered starting from one at the 5' end of the first strand are 2'-OMe modified nucleotides;
(iv) each of the even-numbered nucleotides of the first strand as numbered starting from one at the 5' end of the first strand are 2'-F modified nucleotides;
(v) the second strand nucleotide corresponding to position 11 and/or 13 or 11-13 of the first strand is modified by a modification other than a 2'-OMe modification, particularly wherein one or both or all of these positions comprise a 2'-F modification;
(vi) an inverted nucleotide, particularly a 3'-3' linkage at the 3' end of the second strand;
(vii) one or more phosphorothioate linkages;
(viii) one or more phosphorodithioate linkages; and/or
(ix) the first strand has a terminal 5' (E)-vinylphosphonate nucleotide at its 5' end, in which case the terminal 5' (E)-vinylphosphonate nucleotide is particularly a uridine and is particularly linked to the second nucleotide in the first strand by a phosphodiester linkage.

All the features of the nucleic acids can be combined with all other aspects of the invention disclosed herein.

Ligands

The nucleic acids of the invention may be conjugated to a ligand. Efficient delivery of oligonucleotides, in particular double-stranded nucleic acids of the invention, to cells in vivo is important and requires specific targeting and substantial protection from the extracellular environment, particularly serum proteins. One method of achieving specific targeting is to conjugate a ligand to the nucleic acid. In some embodiments, the ligand helps in targeting the nucleic acid to a target cell which has a cell surface receptor that binds to and internalises the conjugated ligand. In such embodiments, there is a need to conjugate appropriate ligands for the desired receptor molecules in order for the conjugated molecules to be taken up by the target cells by mechanisms such as different receptor-mediated endocytosis pathways or functionally analogous processes. In other embodiments, a ligand which can mediate internalization of the nucleic acid into a target cell by mechanisms other than receptor mediated endocytosis may alternatively be conjugated to a nucleic acid of the invention for cell or tissue specific targeting.

One example of a conjugate that mediates receptor mediated endocytosis is the asialoglycoprotein receptor complex (ASGP-R) which has high affinity to the GalNAc moiety described herein. The ASGP-R complex is composed of varying ratios of multimers of membrane ASGR1 and ASGR2 receptors, which are highly abundant on hepatocytes. One of the first disclosures of the use of triantennary cluster glycosides as conjugated ligands was in U.S. Pat. No. 5,885,968. Conjugates having three GalNAc ligands and comprising phosphate groups are known and are described in Dubber et al. (Bioconjug. Chem. 2003 January-February; 14(1):239-46.). The ASGP-R complex shows a 50-fold higher affinity for N-Acetyl-D-Galactosamine (GalNAc) than D-Gal.

The ASGP-R complex recognizes specifically terminal β-galactosyl subunits of glycosylated proteins or other oligosaccharides (Weigel, P. H. et. al., Biochim. Biophys. Acta. 2002 Sep. 19; 1572(2-3):341-63) and can be used for delivering a drug to the liver's hepatocytes expressing the receptor complex by covalent coupling of galactose or galactosamine to the drug substance (Ishibashi, S.; et. al., J Biol. Chem. 1994 Nov. 11; 269(45):27803-6). Furthermore, the binding affinity can be significantly increased by the multi-valency effect, which is achieved by the repetition of the targeting moiety (Biessen E A, et al., J Med Chem. 1995 Apr. 28; 38(9):1538-46).

The ASGP-R complex is a mediator for an active uptake of terminal β-galactosyl containing glycoproteins to the cell's endosomes. Thus, the ASGPR is highly suitable for targeted delivery of drug candidates conjugated to such ligands like, e.g., nucleic acids into receptor-expressing cells (Akinc et al., Mol Ther. 2010 July; 18(7):1357-64).

More generally the ligand can comprise a saccharide that is selected to have an affinity for at least one type of receptor on a target cell. In particular, the receptor is on the surface of a mammalian liver cell, for example, the hepatic asialoglycoprotein receptor complex described before (ASGP-R).

The saccharide may be selected from N-acetyl galactosamine, mannose, galactose, glucose, glucosamine and fucose. The saccharide may be N-acetyl galactosamine (GalNAc).

A ligand for use in the present invention may therefore comprise (i) one or more N-acetyl galactosamine (GalNAc) moieties and derivatives thereof, and (ii) a linker, wherein the linker conjugates the GalNAc moieties to a nucleic acid as defined in any preceding aspects. The linker may be a monovalent structure or bivalent or trivalent or tetravalent branched structure. The nucleotides may be modified as defined herein.

The ligand may therefore comprise GalNAc.

In one aspect, the nucleic acid is conjugated to a ligand comprising a compound of formula (II):

$$[S\text{—}X^1\text{—}P\text{—}X^2]_3\text{-}A\text{-}X^3\text{—} \tag{II}$$

wherein:
S represents a saccharide, particularly wherein the saccharide is N-acetyl galactosamine;
$X^1$ represents $C_3$-$C_6$ alkylene or $(\text{—}CH_2\text{—}CH_2\text{—}O)_m$ $(\text{—}CH_2)_2\text{—}$ wherein m is 1, 2, or 3;
P is a phosphate or modified phosphate, particularly a thiophosphate;
$X^2$ is alkylene or an alkylene ether of the formula $(\text{—}CH_2)_n\text{—}O\text{—}CH_2\text{—}$ where n=1-6;
A is a branching unit;
$X^3$ represents a bridging unit;
wherein a nucleic acid according to the present invention is conjugated to $X^3$ via a phosphate or modified phosphate, particularly a thiophosphate.

In formula (II), the branching unit "A" particularly branches into three in order to accommodate three saccharide ligands. The branching unit is particularly covalently attached to the remaining tethered portions of the ligand and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

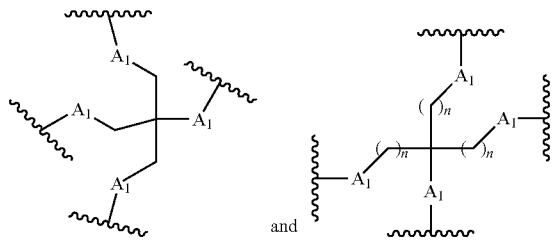

wherein each $A_1$ independently represents O, S, C=O or NH; and each n independently represents an integer from 1 to 20.

The branching unit may have a structure selected from:

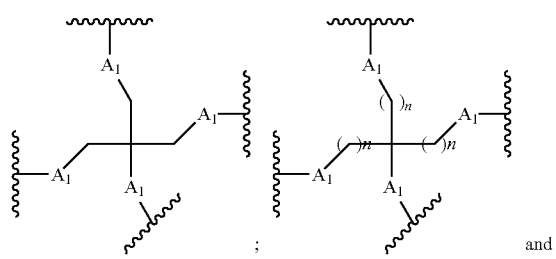

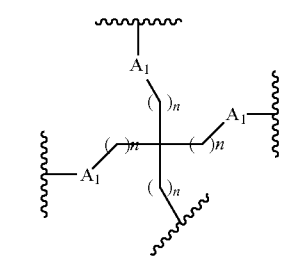

wherein each $A_1$ independently represents O, S, C=O or NH; and each n independently represents an integer from 1 to 20.

The branching unit may have a structure selected from:

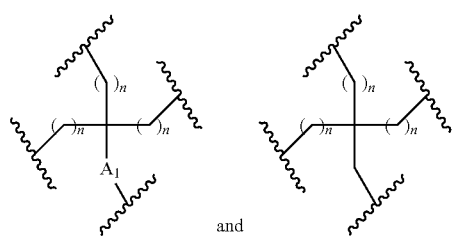

wherein $A_1$ is O, S, C=O or NH; and each n independently represents an integer from 1 to 20. The branching unit may have the structure:

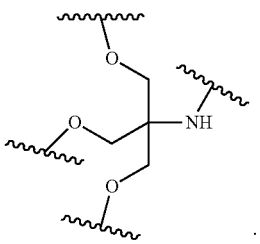 [SMILES: *NC(CO*)(CO*)CO*]

The branching unit may have the structure:

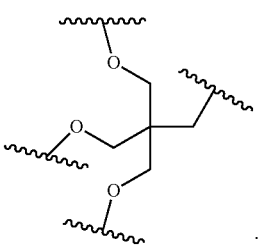 [SMILES: *CC(CO*)(CO*)CO*]

The branching unit may have the structure:

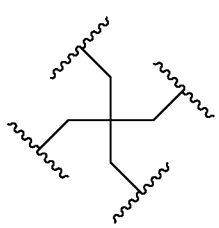

Alternatively, the branching unit A may have a structure selected from:

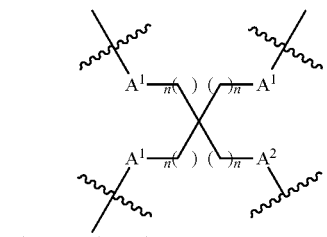

$A^1$ = O, $NR^1$, $C(R^1)_2$     $A^2$ = $NR^2$
n = 1 to 4

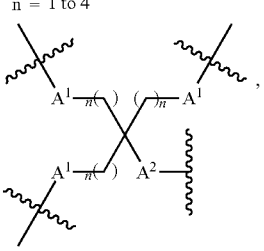

$A^1$ = O, $NR^1$, $C(R^1)_2$     $A^2$ = $NR^2$
n = 1 to 4 wherein:
R1 is hydrogen or C1-C10 alkylene;
and R2 is C1-C10 alkylene.

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$ alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_1$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—O—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

In one aspect, the nucleic acid is conjugated to a ligand comprising a compound of formula (III):

$$[S—X^1—P—X^2]_3\text{-A-}X^3— \quad (III)$$

wherein:
S represents a saccharide, particularly GalNAc;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate, particularly a thiophosphate;
$X^2$ is $C_1$-$C_8$ alkylene;
A is a branching unit selected from:

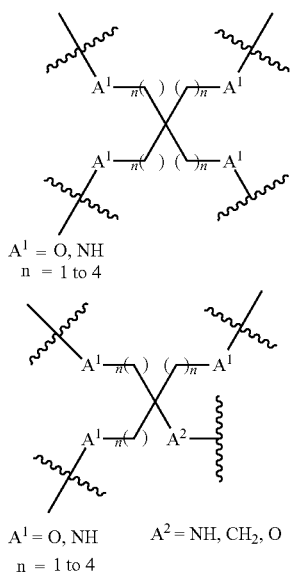

$A^1$ = O, NH
n = 1 to 4

$A^1$ = O, NH    $A^2$ = NH, CH$_2$, O
n = 1 to 4

$X^3$ is a bridging unit;
wherein a nucleic acid according to the present invention is conjugated to $X^3$ via a phosphate or a modified phosphate, particularly a thiophosphate.

The branching unit A may have the structure:

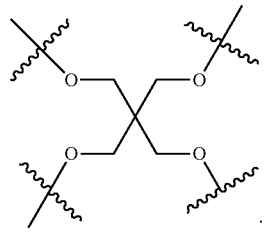 [SMILES: *OCC(CO*)(CO*)CO*]

The branching unit A may have the structure:

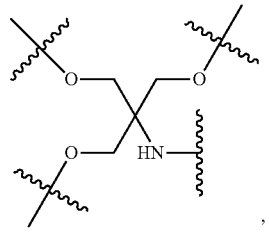

wherein $X^3$ is attached to the nitrogen atom.

$X^3$ may be $C_1$-$C_{20}$ alkylene. Particularly, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

In one aspect, the nucleic acid is conjugated to a ligand comprising a compound of formula (IV):

$$[S—X^1—P—X^2]_3\text{-A-}X^3— \quad (IV)$$

wherein:
S represents a saccharide, particularly GalNAc;
$X^1$ represents $C_3$-$C_6$ alkylene or (—$CH_2$—$CH_2$—O)$_m$(—$CH_2$)$_2$— wherein m is 1, 2, or 3;
P is a phosphate or modified phosphate, particularly a thiophosphate;
$X^2$ is an alkylene ether of formula —$C_3H_6$—O—$CH_2$—;
A is a branching unit;
$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A, and wherein $X^3$ is conjugated to a nucleic acid according to the present invention by a phosphate or modified phosphate, particularly a thiophosphate.

The branching unit may comprise carbon. Particularly, the branching unit is a carbon.

$X^3$ may be selected from the group consisting of —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—. Particularly, $X^3$ is selected from the group consisting of —$CH_2$—O—$C_4H_8$—, —$CH_2$—O—$C_6H_{12}$— and —$CH_2$—O—$C_8H_{16}$.

$X^1$ may be (—$CH_2$—$CH_2$—O)(—$CH_2$)$_2$—. $X^1$ may be (—$CH_2$—$CH_2$—O)$_2$(—$CH_2$)$_2$—. $X^1$ may be (—$CH_2$—$CH_2$—O)$_3$(—$CH_2$)$_2$—. Particularly, $X^1$ is (—$CH_2$—$CH_2$—O)$_2$(—$CH_2$)$_2$—. Alternatively, $X^1$ represents $C_3$-$C_6$ alkylene. $X^1$ may be propylene. $X^1$ may be butylene. $X^1$ may be pentylene. $X^1$ may be hexylene. Particularly the alkyl is a linear alkylene. In particular, $X^1$ may be butylene.

$X^2$ represents an alkylene ether of formula —$C_3H_6$—O—$CH_2$— i.e. $C_3$ alkoxy methylene, or —$CH_2CH_2CH_2OCH_2$—.

For any of the above aspects, when P represents a modified phosphate group, P can be represented by:

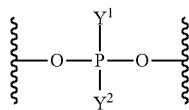

wherein $Y^1$ and $Y^2$ each independently represent =O, =S, —O⁻, —OH, —SH, —BH$_3$, —OCH$_2$CO$_2$, —OCH$_2$CO$_2$R$^x$, —OCH$_2$C(S)OR$^x$, and —OR$^x$, wherein R$^x$ represents $C_1$-$C_6$ alkyl and wherein

indicates attachment to the remainder of the compound.

By modified phosphate it is meant a phosphate group wherein one or more of the non-linking oxygens is replaced. Examples of modified phosphate groups include phosphorothioate, phosphorodithioates, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, $Y^1$ may represent —OH and $Y^2$ may represent =O or =S; or $Y^1$ may represent —O⁻ and $Y^2$ may represent =O or =S;

$Y^1$ may represent =O and $Y^2$ may represent —CH$_3$, —SH, —OR$^x$, or —BH$_3$ $Y^1$ may represent =S and $Y^2$ may represent —CH$_3$, OR$^x$ or —SH.

It will be understood by the skilled person that in certain instances there will be delocalisation between $Y^1$ and $Y^2$.

Particularly, the modified phosphate group is a thiophosphate group. Thiophosphate groups include bithiophosphate (i.e. where $Y^1$ represents =S and $Y^2$ represents —S⁻) and monothiophosphate (i.e. where $Y^1$ represents —O⁻ and $Y^2$ represents =S, or where $Y^1$ represents =O and $Y^2$ represents —S⁻). Particularly, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents OCH$_2$CH$_3$).

The saccharide may be selected to have an affinity for at least one type of receptor on a target cell. In particular, the receptor is on the surface of a mammalian liver cell, for example, the hepatic asialoglycoprotein receptor complex (ASGP-R).

For any of the above or below aspects, the saccharide may be selected from N-acetyl with one or more of galactosamine, mannose, galactose, glucose, glucosamine and fructose. Typically a ligand to be used in the present invention may include N-acetyl galactosamine (GalNAc). Particularly the compounds of the invention may have 3 ligands, which will each particularly include N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Particularly, the compounds of the invention comprise the β-form, 2-(Acetylamino)-2-deoxy-β-D-galactopyranose.

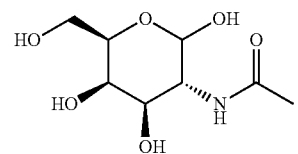

2-(Acetylamino)-2-deoxy-D-galactopyranose

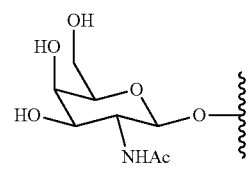 [SMILES: *OC1OC(CO)C(O)C(O)C1NC(C)=O]

2-(Acetylamino)-2-deoxy-β-D-galactopyranose

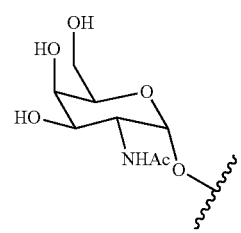 [SMILES: *OC1OC(CO)C(O)C(O)C1NC(C)=O]

2-(Acetylamino)-2-deoxy-α-D-galactopyranose
In one aspect, the nucleic acid is a conjugated nucleic acid, wherein the nucleic acid is conjugated to a triantennary ligand with one of the following structures:
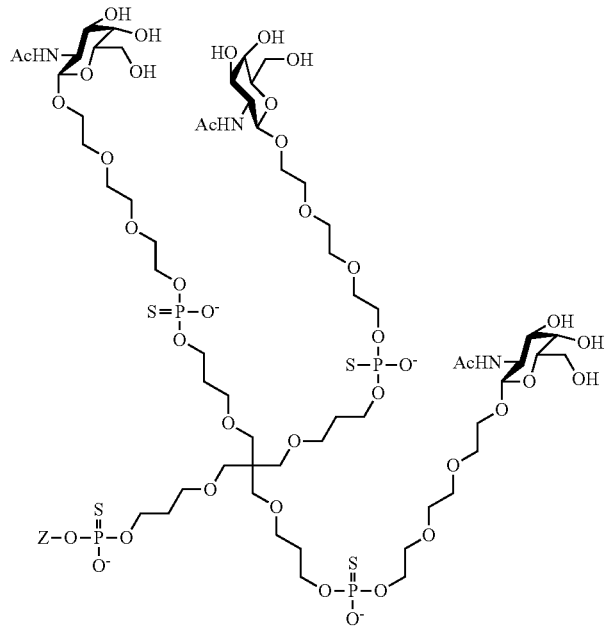
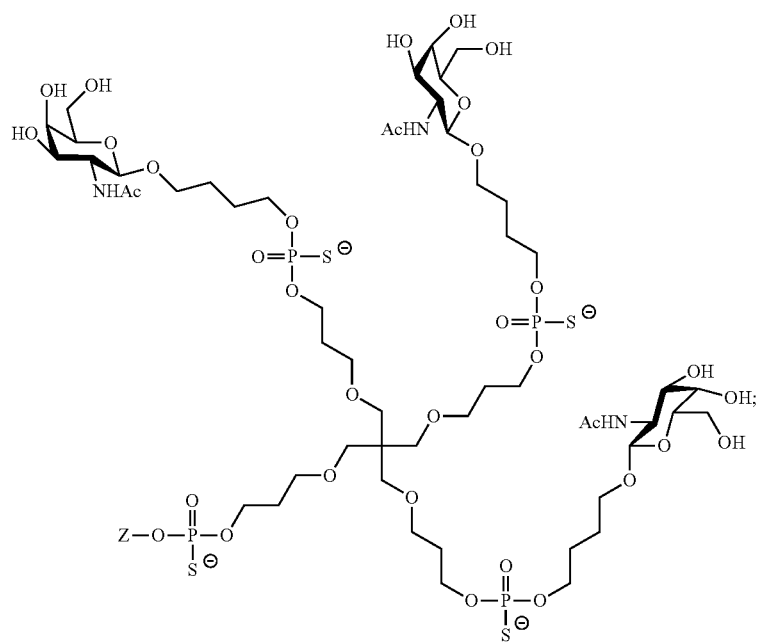

-continued
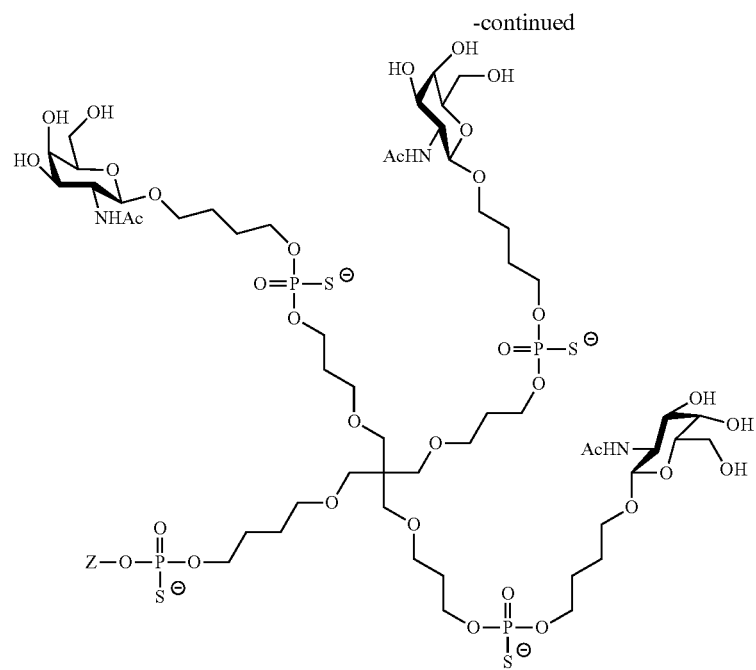
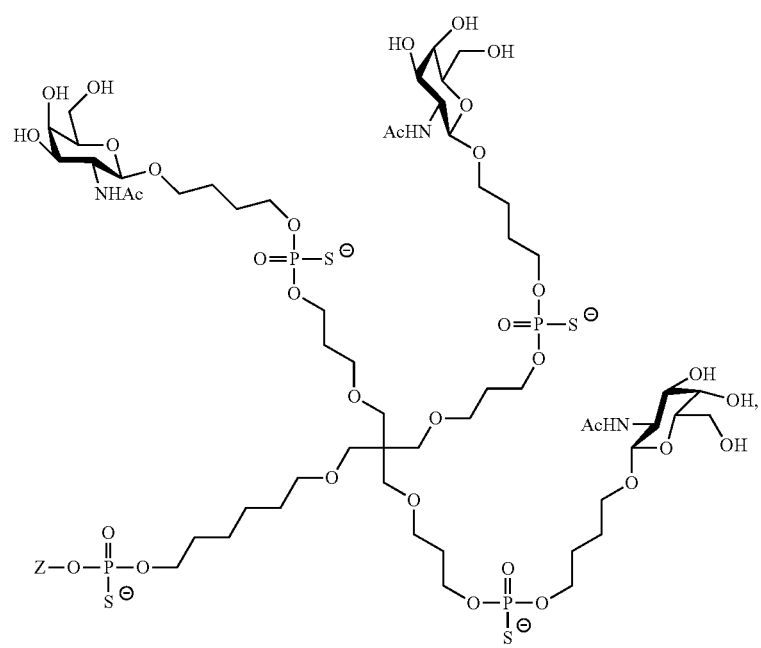

-continued
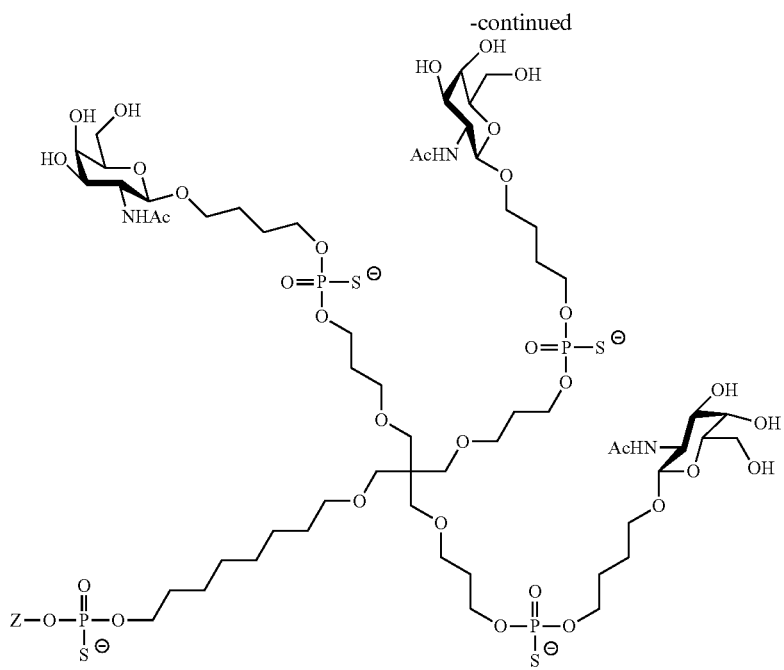
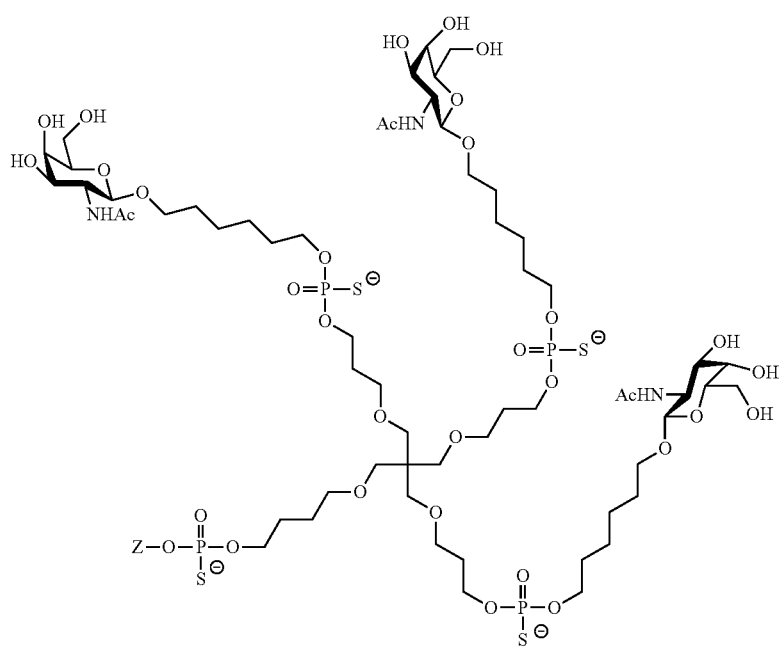

-continued
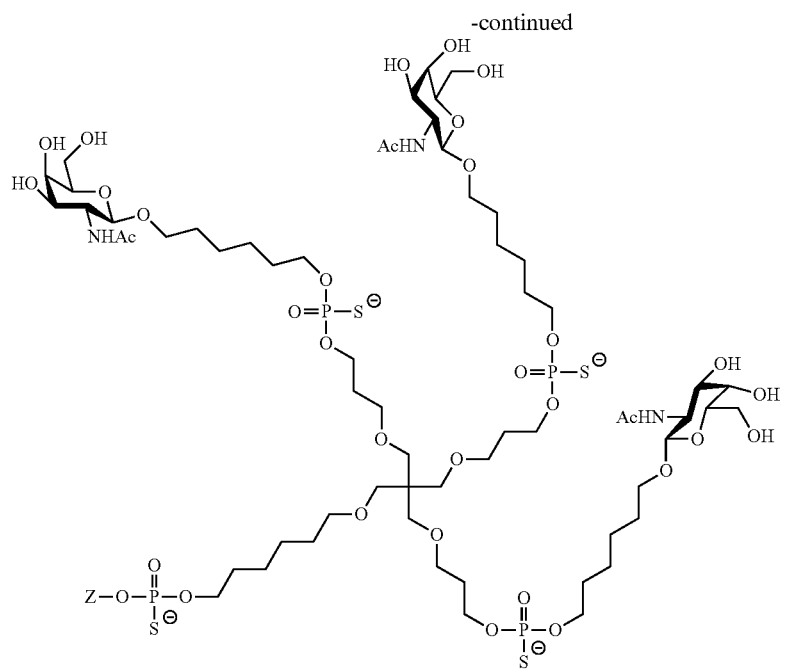
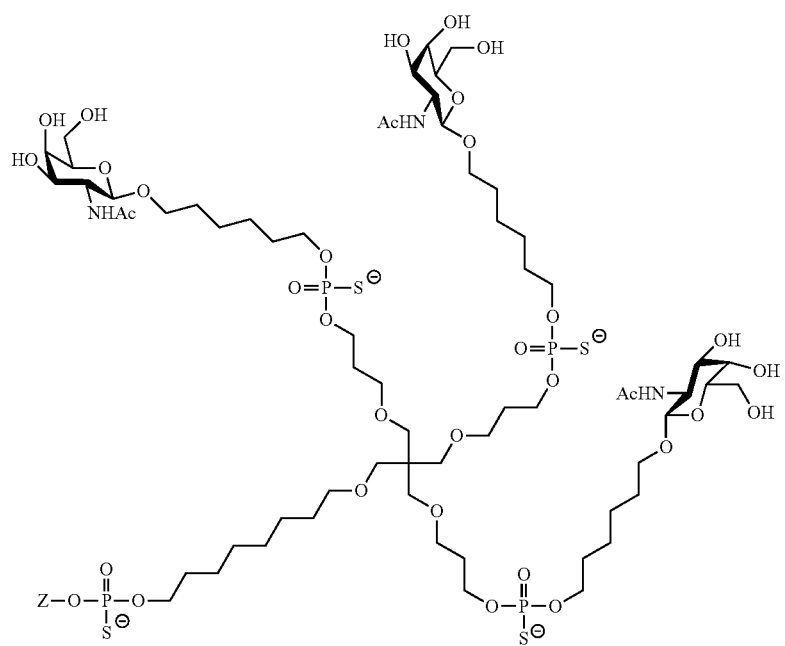

-continued
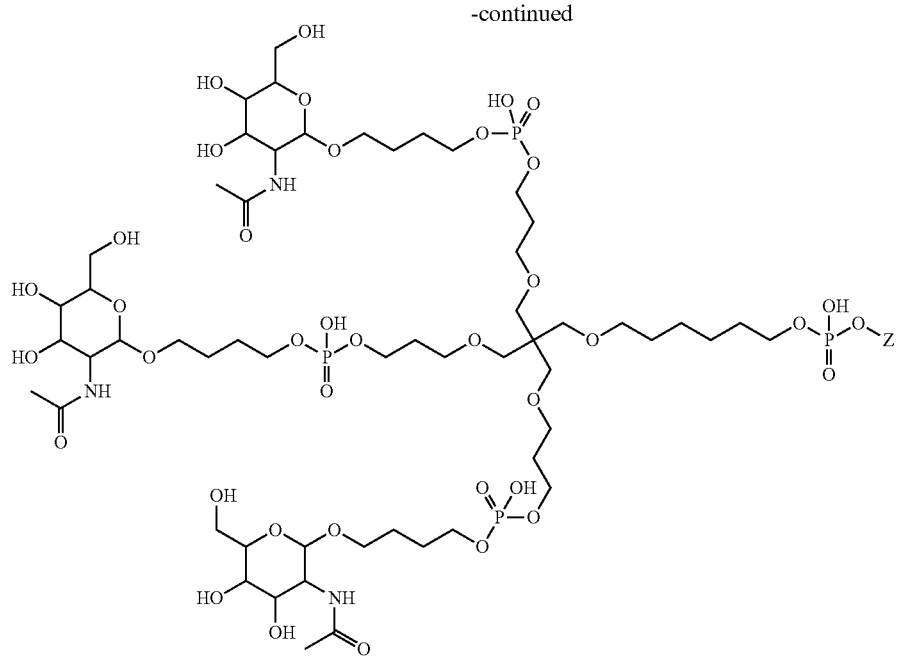
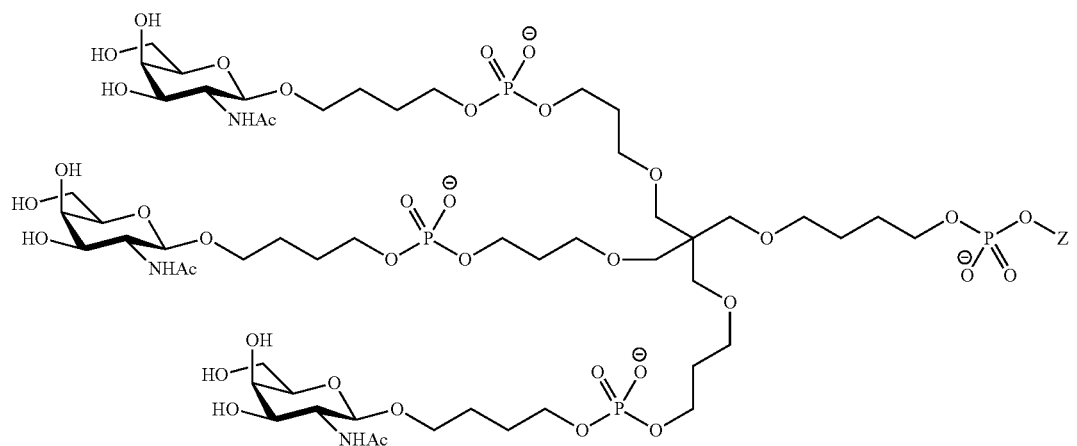
wherein Z is any nucleic acid as defined herein.

Particularly, the nucleic acid is a conjugated nucleic acid, wherein the nucleic acid is conjugated to a triantennary ligand with the following structures:

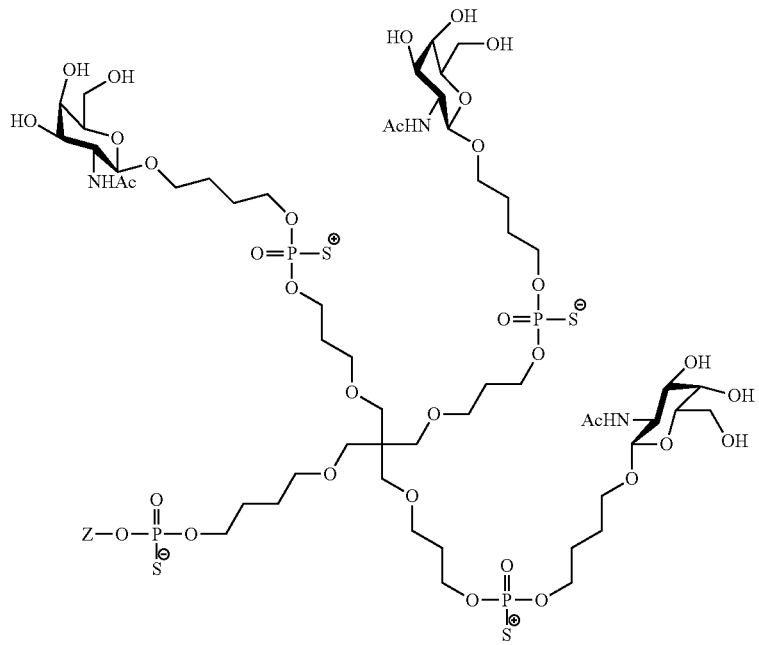

wherein Z is any nucleic acid as defined herein.

A ligand of formula (II), (III) or (IV) or any one of the triantennary ligands disclosed herein can be attached at the 3'-end of the first (antisense) strand and/or at any of the 3' and/or 5' end of the second (sense) strand. The nucleic acid can comprise more than one ligand of formula (II), (III) or (IV) or any one of the triantennary ligands disclosed herein. However, a single ligand of formula (II), (III) or (IV) or any one of the triantennary ligands disclosed herein is preferred because a single such ligand is sufficient for efficient targeting of the nucleic acid to the target cells. Particularly in that case, at least the last two, particularly at least the last three and more particularly at least the last four nucleotides at the end of the nucleic acid to which the ligand is attached are linked by a phosphodiester linkage.

Particularly, the 5'-end of the first (antisense) strand is not attached to a ligand of formula (II), (III) or (IV) or any one of the triantennary ligands disclosed herein, since a ligand in this position can potentially interfere with the biological activity of the nucleic acid.

A nucleic acid with a single ligand of formula (II), (III) or (IV) or any one of the triantennary ligands disclosed herein at the 5' end of a strand is easier and therefore cheaper to synthesise than the same nucleic acid with the same ligand at the 3' end. Particularly therefore, a single ligand of any of formulae (II), (III) or (IV) or any one of the triantennary ligands disclosed herein is covalently attached to (conjugated with) the 5' end of the second strand of the nucleic acid.

In one aspect, the first strand of the nucleic acid is a compound of formula (V):

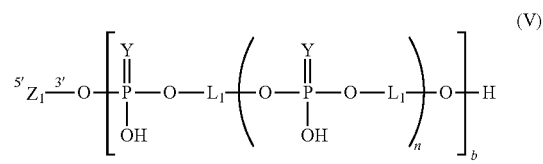

wherein b is particularly 0 or 1; and
the second strand is a compound of formula (VI):

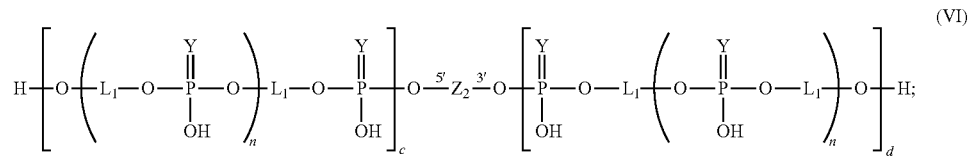

wherein:
c and d are independently particularly 0 or 1;
$Z_1$ and $Z_2$ are respectively the first and second strand of the nucleic acid;

Y is independently O or S;

n is independently 0, 1, 2 or 3; and $L_1$ is a linker to which a ligand is attached, wherein $L_1$ is the same or different in formulae (V) and (VI), and is the same or different within formulae (V) and (VI) when $L_1$ is present more than once within the same formula, wherein $L_1$ is particularly of formula (VII);

and wherein b+c+d is particularly 2 or 3.

Particularly, $L_1$ in formulae (V) and (VI) is of formula (VII):

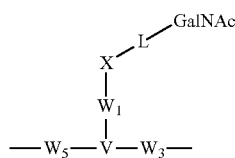
(VII)

wherein:

L is selected from the group comprising, or particularly consisting of:
—$(CH_2)_r$—C(O)—, wherein r=2-12;
—$(CH_2$—$CH_2$—$O)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12; and

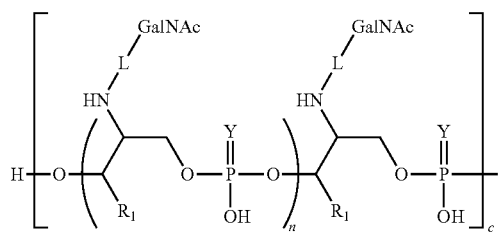

wherein the terminal C(O), if present, is attached to X of formula (VII), or if X is absent, to $W_1$ of formula (VII), or if $W_1$ is absent, to V of formula (VII);

$W_1$, $W_3$ and $W_5$ are individually absent or selected from the group comprising, or particularly consisting of:
—$(CH_2)_r$—, wherein r=1-7;
—$(CH_2)_s$—O—$(CH_2)_s$—, wherein s is independently 0-5;
—$(CH_2)_t$—S—$(CH_2)_t$—, wherein t is independently 0-5;

X is absent or is selected from the group comprising, or particularly consisting of: NH, $NCH_3$ or $NC_2H_5$;

V is selected from the group comprising, or particularly consisting of:
CH, N,

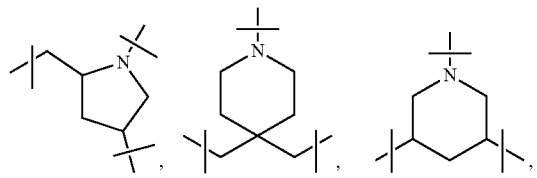

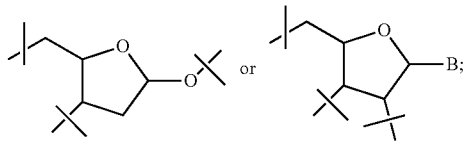

wherein B, if present, is a modified or natural nucleobase.

In one aspect, the first strand is a compound of formula (VIII)

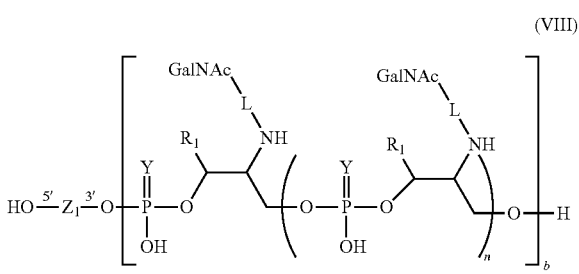
(VIII)

wherein b is particularly 0 or 1; and the second strand is a compound of formula (IX):

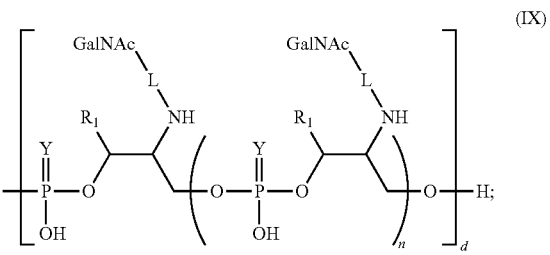
(IX)

wherein c and d are independently particularly 0 or 1;

wherein:

$Z_1$ and $Z_2$ are respectively the first and second strand of the nucleic acid;

Y is independently O or S;

$R_1$ is H or methyl;

n is independently particularly 0, 1, 2 or 3; and

L is the same or different in formulae (VIII) and (IX), and is the same or different within formulae (VIII) and (IX) when L is present more than once within the same formula, and is selected from the group comprising, or particularly consisting of:
—$(CH_2)_r$—C(O)—, wherein r=2-12;
—$(CH_2$—$CH_2$—$O)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12; and wherein the terminal C(O), if present, is attached to the NH group (of the linker, not of the targeting ligand);

and wherein b+c+d is particularly 2 or 3.

In one aspect, the first strand of the nucleic acid is a compound of formula (X):

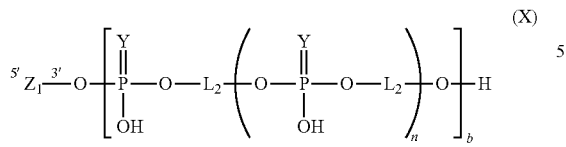

wherein b is particularly 0 or 1; and
the second strand is a compound of formula (XI):

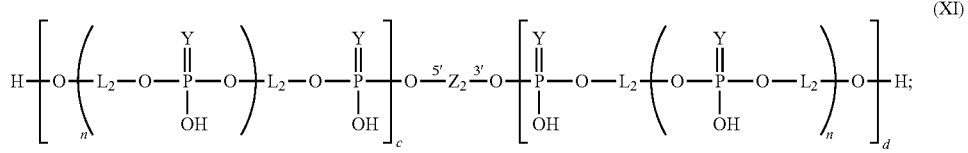

wherein:
c and d are independently particularly 0 or 1;
$Z_1$ and $Z_2$ are respectively the first and second RNA strand of the nucleic;
Y is independently O or S;
n is independently particularly 0, 1, 2 or 3; and
$L_2$ is the same or different in formulae (X) and (XI) and is the same or different in moieties bracketed by b, c and d, and is selected from the group comprising, or particularly consisting of:

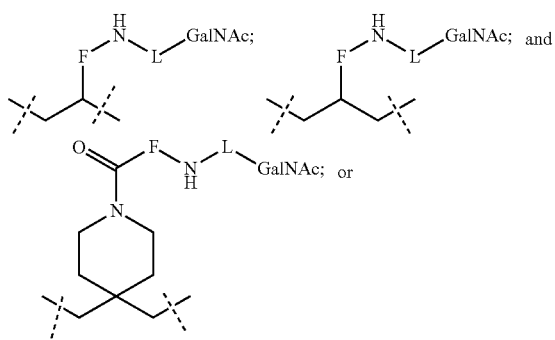

n is 0 and $L_2$ is:

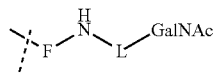

and the terminal OH group is absent such that the following moiety is formed:

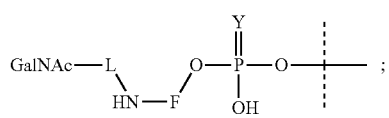

wherein:
F is a saturated branched or unbranched (such as unbranched) $C_{1-8}$alkyl (e.g. $C_{1-6}$alkyl) chain wherein one of the carbon atoms is optionally replaced with an oxygen atom provided that said oxygen atom is separated from another heteroatom (e.g. an O or N atom) by at least 2 carbon atoms;
L is the same or different in formulae (X) and (XI) and is selected from the group comprising, or particularly consisting of:
—$(CH_2)_r$—C(O)—, wherein r=2-12;
—$(CH_2$—$CH_2$—$O)_s$—$CH_2$—C(O)—, wherein s=1-5;
—$(CH_2)_t$—CO—NH—$(CH_2)_t$—NH—C(O)—, wherein t is independently 1-5;
—$(CH_2)_u$—CO—NH—$(CH_2)_u$—C(O)—, wherein u is independently 1-5; and
—$(CH_2)_v$—NH—C(O)—, wherein v is 2-12; and
wherein the terminal C(O), if present, is attached to the NH group (of the linker, not of the targeting ligand);
and wherein b+c+d is particularly 2 or 3.

In one aspect, b is 0, c is 1 and d is 1; b is 1, c is 0 and d is 1; b is 1, c is 1 and d is 0; or b is 1, c is 1 and d is 1 in any of the nucleic acids of formulae (V) and (VI) or (VIII) and (IX) or (X) and (XI). Particularly, b is 0, c is 1 and d is 1; b is 1, c is 0 and d is 1; or b is 1, c is 1 and d is 1. Most particularly, b is 0, c is 1 and d is 1.

In one aspect, Y is O in any of the nucleic acids of formulae (V) and (VI) or (VIII) and (IX) or (X) and (XI). In another aspect, Y is S. In a particular aspect, Y is independently selected from O or S in the different positions in the formulae.

In one aspect, $R_1$ is H or methyl in any of the nucleic acids of formulae (VIII) and (IX). In one aspect, $R_1$ is H. In another aspect, $R_1$ is methyl.

In one aspect, n is 0, 1, 2 or 3 in any of the nucleic acids of formulae (V) and (VI) or (VIII) and (IX) or (X) and (XI). Particularly, n is 0.

Examples of F moieties in any of the nucleic acids of formulae (X) and (XI) include $(CH_2)_{1-6}$ e.g. $(CH_2)_{1-4}$ e.g. $CH_2$, $(CH_2)_4$, $(CH_2)_5$ or $(CH_2)_6$, or $CH_2O(CH_2)_{2-3}$, e.g. $CH_2O(CH_2)CH_3$.

In one aspect, $L_2$ in formulae (X) and (XI) is:

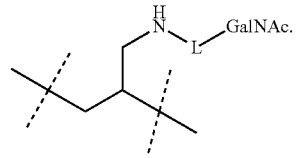

In one aspect, $L_2$ is:

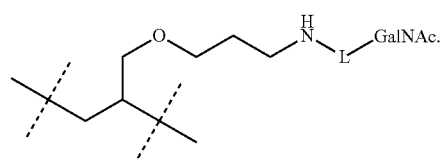

In one aspect, L₂ is:

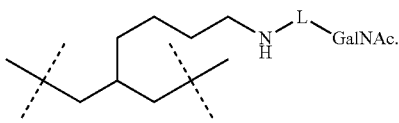

In one aspect, L₂ is:

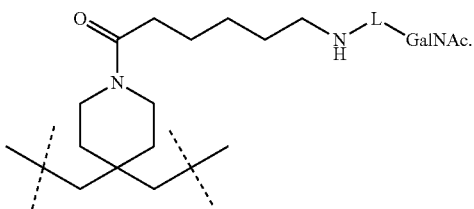

In one aspect, n is 0 and L₂ is:

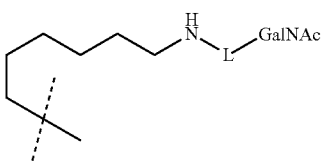

and the terminal OH group is absent such that the following moiety is formed:

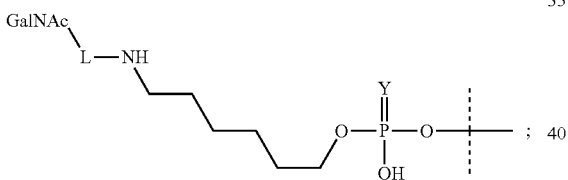

wherein Y is O or S.

In one aspect, L in the nucleic acids of formulae (V) and (VI) or (VIII) and (IX) or (X) and (XI), is selected from the group comprising, or particularly consisting of:
—(CH₂)ᵣ—C(O)—, wherein r=2-12;
—(CH₂—CH₂—O)ₛ—CH₂—C(O)—, wherein s=1-5;
—(CH₂)ₜ—CO—NH—(CH₂)ₜ—NH—C(O)—, wherein t is independently 1-5;
—(CH₂)ᵤ—CO—NH—(CH₂)ᵤ—C(O)—, wherein u is independently 1-5; and
—(CH₂)ᵥ—NH—C(O)—, wherein v is 2-12;
wherein the terminal C(O) is attached to the NH group.

Particularly, L is —(CH₂)ᵣ—C(O)—, wherein r=2-12, more particularly r=2-6 even more particularly, r=4 or 6 e.g. 4.

Particularly, L is:

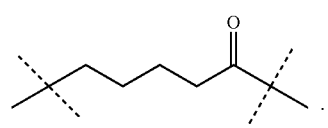

Within the moiety bracketed by b, c and d, L₂ in the nucleic acids of formulae (X) and (XI) is typically the same. Between moieties bracketed by b, c and d, L₂ may be the same or different. In an embodiment, L₂ in the moiety bracketed by c is the same as the L₂ in the moiety bracketed by d. In an embodiment, L₂ in the moiety bracketed by c is not the same as L₂ in the moiety bracketed by d. In an embodiment, the L₂ in the moieties bracketed by b, c and d is the same, for example when the linker moiety is a serinol-derived linker moiety.

Serinol derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

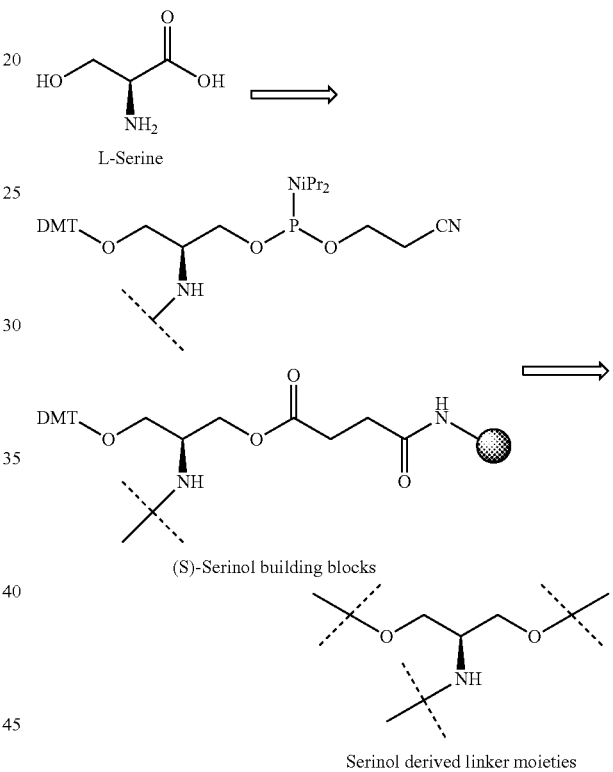

i.e. is based on an (S)-serinol-amidite or (S)-serinol succinate solid supported building block derived from L-serine isomer.

In a particular aspect, the first strand of the nucleic acid is a compound of formula (VIII) and the second strand of the nucleic acid is a compound of formula (IX), wherein:
b is 0;
c and d are 1,
n is 0,
Z₁ and Z₂ are respectively the first and second strand of the nucleic acid,
Y is S,
R₁ is H, and
L is —(CH₂)₄—C(O)—, wherein the terminal C(O) of L is attached to the N atom of the linker (ie not a possible N atom of a targeting ligand).

In another particular aspect, the first strand of the nucleic acid is a compound of formula (V) and the second strand of the nucleic acid is a compound of formula (VI), wherein:

b is 0,
c and d are 1,
n is 0,
$Z_1$ and $Z_2$ are respectively the first and second strand of the nucleic acid,
Y is S,
$L_1$ is of formula (VII), wherein:
  $W_1$ is —$CH_2$—O—$(CH_2)_3$—,
  $W_3$ is —$CH_2$—,
  $W_5$ is absent,
  V is CH,
  X is NH, and
  L is —$(CH_2)_4$—C(O)— wherein the terminal C(O) of L is attached to the N atom of X in formula (VII).

In another particular aspect, the first strand of the nucleic acid is a compound of formula (V) and the second strand of the nucleic acid is a compound of formula (VI), wherein:
b is 0,
c and d are 1,
n is 0,
$Z_1$ and $Z_2$ are respectively the first and second strand of the nucleic acid,
Y is S,
$L_1$ is of formula (VII), wherein:
  $W_1$, $W_3$ and $W_5$ are absent,
  V is,

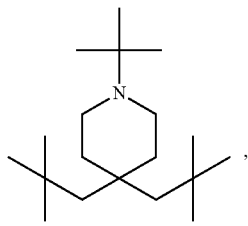 [SMILES: CC(C)(C)CC1(CC(C)(C)C)CCN(C(C)(C)C)CC1]

X is absent, and
L is —$(CH_2)_4$—C(O)—NH—$(CH_2)_5$—C(O)—, wherein the terminal C(O) of L is attached to the N atom of V in formula (VII).

In one aspect, the nucleic acid is conjugated to a triantennary ligand with the following structure:

wherein the nucleic acid is conjugated to the ligand via the phosphate group of the ligand a) to the last nucleotide at the 5' end of the second strand; b) to the last nucleotide at the 3' end of the second strand; or c) to the last nucleotide at the 3' end of the first strand.

In one aspect of the nucleic acid, the cells that are targeted by the nucleic acid with a ligand are hepatocytes.

In any one of the above ligands where GalNAc is present, the GalNAc may be substituted for any other targeting ligand, such as those mentioned herein, in particular mannose, galactose, glucose, glucosamine and fucose.

In one aspect, the nucleic acid is conjugated to a ligand that comprises a lipid, and more particularly, a ligand that comprises a cholesterol.

Compositions, Uses and Methods

The present invention also provides compositions comprising a nucleic acid of the invention. The nucleic acids and compositions may be used as medicaments or as diagnostic agents, alone or in combination with other agents. For example, one or more nucleic acid(s) of the invention can be combined with a delivery vehicle (e.g., liposomes) and/or excipients, such as carriers, diluents. Other agents such as preservatives and stabilizers can also be added. Pharmaceutically acceptable salts or solvates of any of the nucleic acids of the invention are likewise within the scope of the present invention. Methods for the delivery of nucleic acids are known in the art and within the knowledge of the person skilled in the art.

Compositions disclosed herein are particularly pharmaceutical compositions. Such compositions are suitable for administration to a subject.

In one aspect, the composition comprises a nucleic acid disclosed herein, or a pharmaceutically acceptable salt or solvate thereof, and a solvent (particularly water) and/or a delivery vehicle and/or a physiologically acceptable excipient and/or a carrier and/or a salt and/or a diluent and/or a buffer and/or a preservative.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well

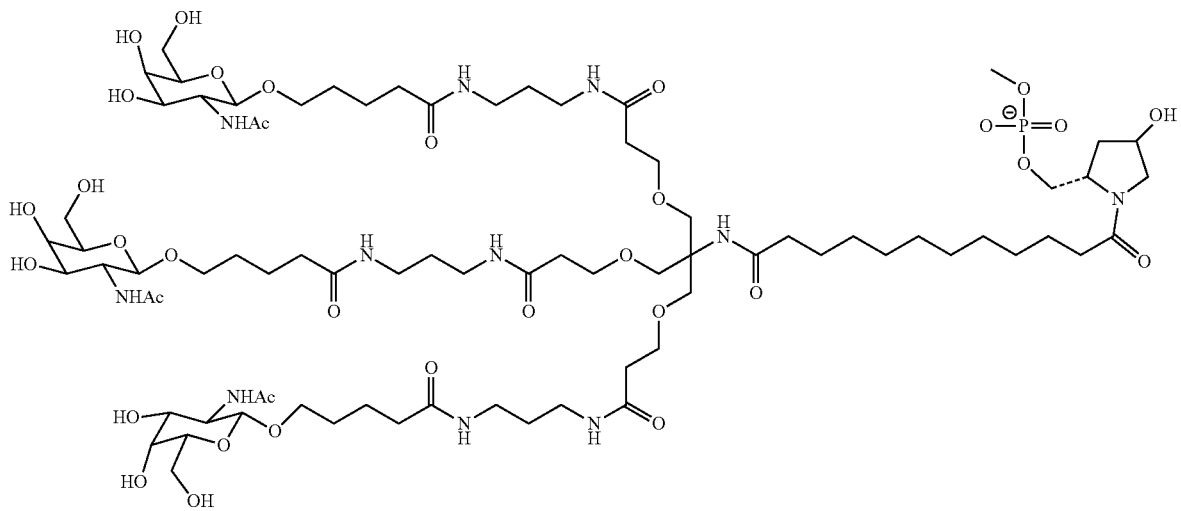

known in the art of pharmacy. Subcutaneous or transdermal modes of administration may be particularly suitable for the compounds described herein.

The therapeutically effective amount of a nucleic acid of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

Nucleic acids of the present invention, or salts thereof, may be formulated as pharmaceutical compositions prepared for storage or administration, which typically comprise a therapeutically effective amount of a nucleic acid of the invention, or a salt thereof, in a pharmaceutically acceptable carrier.

The nucleic acid or conjugated nucleic acid of the present invention can also be administered in combination with other therapeutic compounds, either administered separately or simultaneously, e.g., as a combined unit dose. The invention also includes a composition comprising one or more nucleic acids according to the present invention in a physiologically/pharmaceutically acceptable excipient, such as a stabilizer, preservative, diluent, buffer, and the like.

In one aspect, the composition comprises a nucleic acid disclosed herein and a further therapeutic agent selected from the group comprising an oligonucleotide, a small molecule, a monoclonal antibody, a polyclonal antibody, a peptide and a protein. If the further therapeutic agent is a protein it is particularly FVIII and/or FIX.

In certain embodiments, two or more nucleic acids of the invention with different sequences may be administered simultaneously or sequentially.

In another aspect, the present invention provides a composition, e.g., a pharmaceutical composition, comprising one or a combination of different nucleic acids of the invention and at least one pharmaceutically acceptable carrier.

Dosage levels for the medicament and compositions of the invention can be determined by those skilled in the art by experimentation. In one aspect, a unit dose may contain between about 0.01 mg/kg and about 100 mg/kg body weight of nucleic acid or conjugated nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Alternatively, the dose can be from about 0.5 mg/kg to about 10 mg/kg body weight, or about 0.6 mg/kg to about 8 mg/kg body weight, or about 0.7 mg/kg to about 7 mg/kg body weight, or about 0.8 mg/kg to about 6 mg/kg body weight, or about 0.9 mg/kg to about 5.5 mg/kg body weight, or about 1 mg/kg to about 5 mg/kg body weight, or about 2 mg/kg to about 5 mg/kg body weight, or about 3 mg/kg to about 5 mg/kg body weight, or about 1 mg/kg body weight, or about 3 mg/kg body weight, or about 5 mg/kg body weight, wherein "about" is a deviation of up to 30%, particularly up to 20%, more particularly up to 10%, yet more particularly up to 5% and most particularly 0% from the indicated value. Dosage levels may also be calculated via other parameters such as, e.g., body surface area.

The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of a nucleic acid of the invention alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular nucleic acid or composition employed, the route of administration, the time of administration, the rate of excretion of the particular nucleic acid being employed, the duration of the treatment, other drugs, compounds and/or materials used in combination with the particular compositions employed, the age, sex, weight, condition, general health and prior medical history of the subject or patient being treated, and similar factors well known in the medical arts.

The pharmaceutical composition may be a sterile injectable aqueous suspension or solution, or in a lyophilised form.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

The pharmaceutical compositions and medicaments of the present invention may be administered to a mammalian subject in a pharmaceutically effective dose. The mammal may be selected from a human, a non-human primate, a simian or prosimian, a dog, a cat, a horse, cattle, a pig, a goat, a sheep, a mouse, a rat, a hamster, a hedgehog and a guinea pig, or other species of relevance. On this basis, "PROS1" as used herein denotes nucleic acid or protein in any of the above-mentioned species, if expressed therein naturally or artificially, but particularly this wording denotes human nucleic acids or proteins.

Pharmaceutical compositions of the invention may be administered alone or in combination with one or more other therapeutic or diagnostic agents. A combination therapy may include a nucleic acid of the present invention combined with at least one other therapeutic agent selected based on the particular patient, disease or condition to be treated. Examples of other such agents include, inter alia, a therapeutically active small molecule or polypeptide, a single chain antibody, a classical antibody or fragment thereof, or a nucleic acid molecule which modulates gene expression of one or more additional genes, and similar modulating therapeutics which may complement or otherwise be beneficial in a therapeutic or prophylactic treatment regimen.

Pharmaceutical compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatine.

One aspect of the invention is a nucleic acid or a composition disclosed herein for use as a medicament. The nucleic acid or composition is particularly for use in the prevention, decrease of the risk of suffering from, or treatment of a bleeding disorder.

The present invention provides a nucleic acid for use, alone or in combination with one or more additional therapeutic agents in a pharmaceutical composition, for treatment or prophylaxis of conditions, diseases and disorders responsive to inhibition of PROS1 expression.

One aspect of the invention is the use of a nucleic acid or a composition as disclosed herein in the prevention, decrease of the risk of suffering from, or treatment of a bleeding disorder.

One aspect of the invention is the use of a nucleic acid or a composition as disclosed herein in a method of inhibiting the expression of PROS1 in a cell, preferably in vitro.

One aspect of the invention is a method of inhibiting the expression of PROS1 in a cell, preferably in vitro, comprising a step of administering a nucleic acid or a composition as disclosed herein to cells, preferably in vitro.

Nucleic acids and pharmaceutical compositions of the invention may be used in the treatment of a variety of conditions, disorders or diseases. Treatment with a nucleic acid of the invention particularly leads to in vivo Protein S depletion, particularly in the liver and/or in blood. As such, nucleic acids of the invention, and compositions comprising them, will be useful in methods for treating a variety of pathological disorders in which inhibiting the expression of Protein S may be beneficial, such as, inter alia, bleeding disorders. The present invention provides methods for treating bleeding disorders comprising the step of administering to a subject in need thereof a therapeutically effective amount of a nucleic acid of the invention.

The invention thus provides methods of treatment or prevention of a bleeding disorder, the method comprising the step of administering to a subject (e.g., a patient) in need thereof a therapeutically effective amount of a nucleic acid or pharmaceutical composition comprising a nucleic acid of the invention.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, Pa., 2005.

In certain embodiments, nucleic acids and pharmaceutical compositions of the invention may be used to treat or prevent bleeding disorders.

In certain embodiments, the present invention provides methods for treating a bleeding disorder in a mammalian subject, such as a human, the method comprising the step of administering to a subject in need thereof a therapeutically effective amount of a nucleic acid as disclosed herein.

Administration of a "therapeutically effective dosage" of a nucleic acid of the invention may result in a decrease in severity of disease symptoms, an increase in frequency and duration of disease symptom-free periods, or a prevention of impairment or disability due to the disease affliction.

Nucleic acids of the invention may be beneficial in treating or diagnosing bleeding disorders that may be diagnosed or treated using the methods described herein. Treatment and diagnosis of other bleeding disorders are also considered to fall within the scope of the present invention.

One aspect of the invention is a method of preventing, decreasing the risk of suffering from, or treating a bleeding disorder, comprising administering a pharmaceutically effective dose or amount of a nucleic acid or a composition disclosed herein to an individual in need of treatment, particularly wherein the nucleic acid or composition is administered to the subject subcutaneously, intravenously or by oral, rectal, pulmonary, intramuscular or intraperitoneal administration. Particularly, it is administered subcutaneously.

In certain embodiments, a bleeding disorder is a blood coagulation deficiency disorder. A blood coagulation deficiency disorder can be a disorder that is associated with prolonged bleeding episodes and/or with reduced thrombin and/or with a deficiency in clot formation. The bleeding disorder is particularly haemophilia, inherited haemophilia, haemophilia A, haemophilia B, haemophilia C, von Willebrand disease, von Willebrand syndrome, afibrinogenemia, hypofibrinogenemia, parahaemophilia, hemarthrosis (AH), a deficiency in a clotting factor, an inherited deficiency in factor II, V, VII, X and/or XI, a combined deficiency in factor V and VIII, acquired haemophilia, an acquired deficiency in coagulation factors and an acquired bleeding disorder. More particularly, it is haemophilia or hemarthrosis (AH). More particularly, it is haemophilia, particularly haemophilia A or B, most particularly haemophilia A. Alternatively, it is hemarthrosis. Each such disease, condition, disorder or symptom is envisioned to be a separate embodiment with respect to uses of a pharmaceutical composition according to the invention.

In one embodiment, nucleic acids or compositions of the invention are for use or are used in a method of treatment to:
  a) increase blood clotting; and/or
  b) reduce bleeding.

Particularly, the use of a nucleic acid or composition disclosed herein increases blood clotting in the blood of a subject treated with the nucleic acid or composition to the corresponding level expected in a healthy subject. Alternatively, it increases blood clotting in the blood of the subject treated with the nucleic acid or composition such that the difference between the blood clotting in the blood of the subject before treatment and the corresponding level expected in a healthy subject is at least temporarily reduced by 10%, 20%, 30%, 40%, 50%, 60%, 70%, 80%, 90% or 95%.

Particularly, the use of a nucleic acid or composition disclosed herein reduces bleeding in a subject treated with the nucleic acid or composition to the corresponding level expected in a healthy subject. Alternatively, it decreases bleeding in a subject treated with the nucleic acid or composition such that the difference between the bleeding in a subject before treatment and the corresponding level expected in a healthy subject is at least temporarily reduced by 10%, 20%, 30%, 40%, 50%, 60%, 70%, 80%, 90% or 95%.

It is evident that an appropriate dosage regimen of a nucleic acid or composition is necessary to achieve these outcomes. The skilled person will be able to determine the dosage regimen necessary to achieve these outcomes.

A nucleic acid or compositions disclosed herein may be for use in a regimen comprising treatments once or twice weekly, every week, every two weeks, every three weeks, every four weeks, every five weeks, every six weeks, every seven weeks, every eight weeks, every nine weeks, every ten weeks, every eleven weeks, every twelve weeks, every three months, every four months, every five months, every six months or in regimens with varying dosing frequency such as combinations of the before-mentioned intervals. The nucleic acid or composition may be for use subcutaneously, intravenously or using any other application routes such as oral, rectal, pulmonary, intramuscular or intraperitoneal. Particularly, it is for use subcutaneously.

An exemplary treatment regime is administration once every two weeks, once every three weeks, once every four weeks, once a month, once every two or three months or once every three, four, five or six or more months. Dosages may be selected and readjusted by the skilled health care professional as required to maximize therapeutic benefit for a particular subject, e.g., patient. The nucleic acids will typically be administered on multiple occasions. Intervals between single dosages can be, for example, 2-5 days, weekly, bi-weekly, monthly, every two or three months, every four or five months, every six months, or yearly. Intervals between administrations can also be irregular, based on nucleic acid target gene product levels for example in the blood or liver of the subject or patient.

In cells and/or subjects treated with or receiving a nucleic acid or composition as disclosed herein, the PROS1 expression may be inhibited compared to untreated cells and/or subjects by a range from 15% up to 100% but at least about 30%, 35%, 40%, 45%, 50%, 55%, 60%, 65%, 70%, 75%, 80%, 85%, 90%, 95%, 98%, or 100% or intermediate values. The level of inhibition may allow treatment of a bleeding disorder or may serve to further investigate the functions and physiological roles of the PROS1 gene products. The level of inhibition is preferably measured in the liver or in the blood or in the kidneys, preferably in the blood, of the subject treated with the nucleic acid or composition.

One aspect is the use of a nucleic acid or composition as disclosed herein in the manufacture of a medicament for treating a bleeding disorder such as those as listed above or additional pathologies where inhibition of PROS1 expression is desired. A medicament is a pharmaceutical composition.

Each of the nucleic acids of the invention and pharmaceutically acceptable salts and solvates thereof constitutes an individual embodiment of the invention.

Also included in the invention is a method of treating or preventing a bleeding disorder, such as those listed above, comprising administration of a composition comprising a nucleic acid or composition as described herein, to an individual in need of treatment (to improve such pathologies). The nucleic acid or composition may be administered in a regimen comprising treatments twice every week, once every week, every two weeks, every three weeks, every four weeks, every five weeks, every six weeks, every seven weeks, or every eight to twelve or more weeks or in regimens with varying dosing frequency such as combinations of the before-mentioned intervals. The nucleic acid or conjugated nucleic acid may be for use subcutaneously or intravenously or other application routes such as oral, rectal or intraperitoneal.

A nucleic acid of the invention may be administered by any appropriate administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

The use of a chemical modification pattern of the nucleic acids confers nuclease stability in serum and makes for example subcutaneous application route feasible.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and/or tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a nucleic acid in the required amount in an appropriate solvent with one or a combination of ingredients described above, as required, followed by sterilization microfiltration. Dispersions may be prepared by incorporating the active compound into a sterile vehicle that contains a dispersion medium and optionally other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a nucleic acid of the invention is administered by, e.g., intravenous, cutaneous or subcutaneous injection, the nucleic acid will be in the form of a pyrogen-free, parenterally acceptable aqueous solution. Methods for preparing parenterally acceptable solutions, taking into consideration appropriate pH, isotonicity, stability, and the like, are within the skill in the art. A preferred pharmaceutical composition for intravenous, cutaneous, or subcutaneous injection will contain, in addition to a nucleic acid, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of nucleic acid which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01% to about 99% of nucleic acid, from about 0.1% to about 70%, or from about 1% to about 30% of nucleic acid in combination with a pharmaceutically acceptable carrier.

The nucleic acid may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Dosage regimens may be adjusted to provide the optimum desired response (e.g., a therapeutic response). For example, a dose may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect. The specification for the dosage unit forms of the invention depend on the specific characteristics of the active compound and the particular therapeutic effect(s) to be achieved and the treatment and sensitivity of any individual patient.

The nucleic acid or composition of the present invention can be produced using routine methods in the art including chemical synthesis, such as solid phase chemical synthesis.

Nucleic acids or compositions of the invention may be administered with one or more of a variety of medical devices known in the art. For example, in one embodiment, a nucleic acid of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the nucleic acid or composition of the invention may be formulated to ensure a desired distribution in vivo. To target a therapeutic compound or composition of the invention to a particular in vivo location, they can be formulated, for example, in liposomes which may comprise one or more moieties that are selectively transported into specific cells or organs, thus enhancing targeted drug delivery.

The invention is characterized by high specificity at the molecular and tissue-directed delivery level. The sequences of the nucleic acids of the invention are highly specific for their target, meaning that they do not inhibit the expression of genes that they are not designed to target or only minimally inhibit the expression of genes that they are not designed to target and/or only inhibit the expression of a low number of genes that they are not designed to target. A further level of specificity is achieved when nucleic acids are linked to a ligand that is specifically recognised and internalised by a particular cell type. This is for example the case when a nucleic acid is linked to a ligand comprising GalNAc moieties, which are specifically recognised and internalised by hepatocytes. This leads to the nucleic acid inhibiting the expression of their target only in the cells that are targeted by the ligand to which they are linked. These two levels of specificity potentially confer a better safety profile than the currently available treatments. In certain embodiments, the present invention thus provides nucleic acids of the invention linked to a ligand comprising one or more GalNAc moieties, or comprising one or more other moieties that confer cell-type or tissue-specific internalisation of the nucleic acid thereby conferring additional specificity of target gene knockdown by RNA interference.

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:
  i) a cationic lipid, or a pharmaceutically acceptable salt thereof;
  ii) a steroid;
  iii) a phosphatidylethanolamine phospholipid; and/or
  iv) a PEGylated lipid.

The cationic lipid may be an amino cationic lipid.

The content of the cationic lipid component may be from about 55 mol % to about 65 mol % of the overall lipid content of the composition. In particular, the cationic lipid component is about 59 mol % of the overall lipid content of the composition.

The compositions can further comprise a steroid. The steroid may be cholesterol. The content of the steroid may be from about 26 mol % to about 35 mol % of the overall lipid content of the lipid composition. More particularly, the content of steroid may be about 30 mol % of the overall lipid content of the lipid composition.

The phosphatidylethanolamine phospholipid may be selected from the group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the composition.

The content of the cationic lipid component in the composition may be from about 55 mol % to about 65 mol % of the overall lipid content of the lipid composition, particularly about 59 mol % of the overall lipid content of the lipid composition.

The composition may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary, a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Nucleic acid formulations of the present invention may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerol, polyglycerol, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

Definitions

As used herein, the terms "inhibit", "down-regulate", or "reduce" with respect to gene expression mean that the expression of the gene, or the level of RNA molecules or equivalent RNA molecules encoding one or more proteins or protein subunits (e.g., mRNA), or the activity of one or more proteins or protein subunits, is reduced below that observed either in the absence of the nucleic acid or conjugated nucleic acid of the invention or as compared to that obtained with an siRNA molecule with no known homology to the human transcript (herein termed non-silencing control). Such control may be conjugated and modified in an analogous manner to the molecule of the invention and delivered into the target cell by the same route. The expression after treatment with the nucleic acid of the invention may be reduced to 95%, 90%, 80%, 70%, 60%, 50%, 40%, 30%, 20%, 15%, 10%, 5% or 0% or to intermediate values, or less than that observed in the absence of the nucleic acid or conjugated nucleic acid. The expression may be measured in the cells to which the nucleic acid is applied. Alternatively, especially if the nucleic acid is administered to a subject, the level can be measured in a different group of cells or in a tissue or an organ or in a body fluid such as blood or plasma. The level of inhibition is particularly measured in conditions that have been selected because they show the greatest effect of the nucleic acid on the target mRNA level in cells treated with the nucleic acid in vitro. The level of inhibition may for example be measured after 24 hours or 48 hours of treatment with a nucleic acid at a concentration of between 0.038 nM-10 μM, particularly 1 nM, 10 nM or 100 nM. These conditions may be different for different nucleic acid sequences or for different types of nucleic acids, such as for nucleic acids that are unmodified or modified or conjugated to a ligand or not. Examples of suitable conditions for determining levels of inhibition are described in the examples.

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand; and a second strand, which may also be a passenger strand. The first strand and the second strand may be part of the same polynucleotide molecule that is self-complementary which 'folds' back to form a double-stranded molecule. The nucleic acid may be an siRNA molecule.

The nucleic acid may comprise ribonucleotides, modified ribonucleotides, deoxynucleotides, deoxyribonucleotides, or nucleotide analogues non-nucleotides that are able to mimic nucleotides such that they may 'pair' with the corresponding base on the target sequence or complementary strand. The nucleic acid may further comprise a double-stranded nucleic acid portion or duplex region formed by all or a portion of the first strand (also known in the art as a guide strand) and all or a portion of the second strand (also known in the art as a passenger strand). The duplex region is defined as beginning with the first base pair formed between the first strand and the second strand and ending with the last base pair formed between the first strand and the second strand, inclusive.

By duplex region it is meant the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 nucleotides on each strand are complementary or substantially complementary, such that the "duplex region" consists of 19 base pairs. The remaining base pairs may exist as 5' and 3' overhangs, or as single-stranded regions. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another. The portion of the first strand and second strand that forms at least one duplex region may be fully complementary and is at least partially complementary to each other. Depending on the length of a nucleic acid, a perfect match in terms of base complementarity between the first strand and the second strand is not necessarily required. However, the first and second strands must be able to hybridise under physiological conditions.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, and N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, and ether groups.

An "overhang" as used herein has its normal and customary meaning in the art, i.e. a single-stranded portion of a nucleic acid that extends beyond the terminal nucleotide of a complementary strand in a double-strand nucleic acid. The term "blunt end" includes double-stranded nucleic acid whereby both strands terminate at the same position, regardless of whether the terminal nucleotide(s) are base-paired. The terminal nucleotide of a first strand and a second strand at a blunt end may be base paired. The terminal nucleotide of a first strand and a second strand at a blunt end may not be paired. The terminal two nucleotides of a first strand and a second strand at a blunt end may be base-paired. The terminal two nucleotides of a first strand and a second strand at a blunt end may not be paired.

The term "serinol-derived linker moiety" means the linker moiety comprises the following structure:

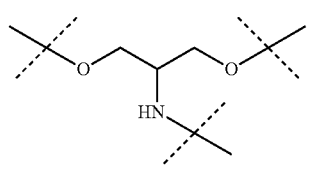

An O atom of said structure typically links to an RNA strand and the N atom typically links to the targeting ligand.

"Protein S" in the context of the present invention relates to human "Vitamin K-dependent protein S" (UniProt ID P07225), encoded by the gene PROS1 (NCBI Gene ID: 5627).

The term "haemophilia" in the context of the present specification relates to a condition in which the body's ability to make blood clots is impaired. Conditions or disorders included under the term "haemophilia" are inherited haemophilia, haemophilia A or B or C, acquired haemophilia, afibrinogenemia, hypofibrinogenemia, parahaemophilia, hemarthrosis (AH), inherited deficiency in factor II, V, VII, X and/or XI, combined deficiency in factor V and VIII, von Willebrand disease, von Willebrand syndrome, acquired deficiency in coagulation factors.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type $N(R^1)(R^2)(R^3)(R^4)^+$, wherein $R^1$, $R^2$, $R^3$ and $R^4$ independently will typically designate hydrogen, optionally substituted C1-6-alkyl groups or optionally substituted C2-6-alkenyl groups. Examples of relevant C1-6-alkyl groups include methyl, ethyl, 1-propyl and 2-propyl groups. Examples of C2-6-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, Pa., USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977). A "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. Exemplary pH buffering agents include phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans. A "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the nucleic acid may be coated in a material or materials intended to protect the compound from the action of acids and other natural inactivating conditions to which the nucleic acid may be exposed when administered to a subject by a particular route of administration.

The term "solvate" in the context of the present invention refers to a complex of defined stoichiometry formed between a solute (in casu, a nucleic acid compound or pharmaceutically acceptable salt thereof according to the invention) and a solvent. The solvent in this connection may, for example, be water or another pharmaceutically acceptable, typically small-molecular organic species, such as, but not limited to, acetic acid or lactic acid. When the solvent in question is water, such a solvate is normally referred to as a hydrate.

The invention will now be described with reference to the following non-limiting Figures and Examples.

EXAMPLES

Example 1—Synthesis of Building Blocks

Figure 1:
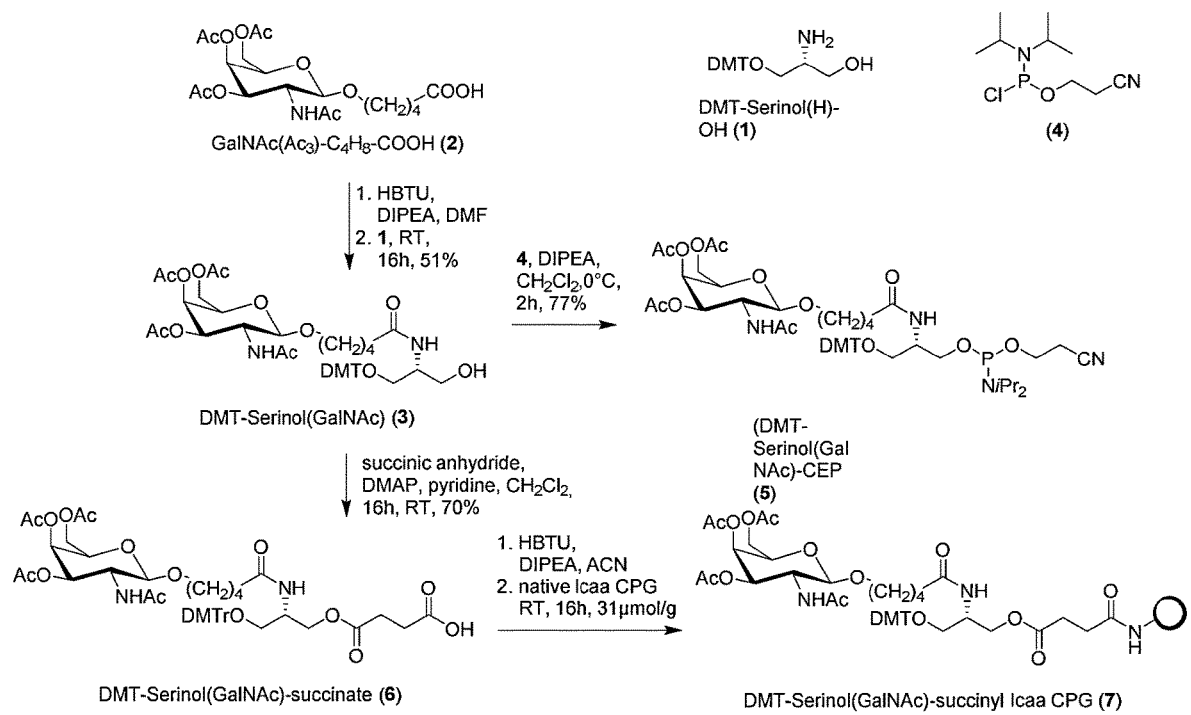
FIG. 1 shows a possible synthesis route to DMT-Serinol (GalNAc)-CEP and CPG.

The synthesis route for DMT-Serinol(GalNAc)-CEP and CPG as described below is outlined in FIG. 1. Starting material DMT-Serinol(H) (1) was made according to literature published methods (Hoevelmann et al. Chem. Sci., 2016, 7, 128-135) from commercially available L-Serine. $GalNAc(Ac_3)$—$C_4H_8$—COOH (2) was prepared according to literature published methods (Nair et al. J. Am. Chem. Soc., 2014, 136 (49), pp 16958-1696), starting from commercially available per-acetylated galactose amine. Phosphitylation reagent 2-Cyanoethyl-N,N-diisopropylchlorophosphor-amidite (4) is commercially available. Synthesis of (vp)-mU-phos was performed as described in Prakash, Nucleic Acids Res. 2015, 43(6), 2993-3011 and Haraszti, Nucleic Acids Res. 2017, 45(13), 7581-7592. Synthesis of the phosphoramidite derivatives of ST43 (ST43-phos) as well as ST23 (ST23-phos) and similar can be performed as described in WO2017/174657.

DMT-Serinol(GalNAc) (3)

HBTU (9.16 g, 24.14 mmol) was added to a stirring solution of $GalNAc(Ac_3)$—$C_4H_8$—COOH (2) (11.4 g, 25.4 mmol) and DIPEA (8.85 ml, 50.8 mmol). After 2 minutes activation time a solution of DMT-Serinol(H) (1) (10 g, 25.4 mmol) in Acetonitrile (anhydrous) (200 ml) was added to the stirring mixture. After 1 h LCMS showed good conversion.

The reaction mixture was concentrated in vacuo. The residue was dissolved up in EtOAc, washed subsequently with water (2×) and brine. The organic layer was dried over $Na_2SO_4$, filtered and concentrated under reduced pressure. The residue was further purified by column chromatography (3% MeOH in $CH_2Cl_2$+1% $Et_3N$, 700 g silica). Product containing fractions were pooled, concentrated and stripped with $CH_2Cl_2$ (2×) to yield to yield 10.6 g (51%) of DMT-Serinol (GalNAc) (3) as an off-white foam.

DMT-Serinol(GalNAc)-CEP (5)

2-Cyanoethyl-N,N-diisopropylchlorophosphoramidite (4) (5.71 ml, 25.6 mmol) was added slowly to a stirring mixture of DMT-Serinol(GalNAc) (3) (15.0 g, 17.0 mmol), DIPEA (14.9 ml, 85 mmol) and 4 Å molecular sieves in Dichloromethane (dry) (150 ml) at 0° C. under argon atmosphere. The reaction mixture was stirred at 0° C. for 1 h. TLC indicated complete conversion. The reaction mixture was filtered and concentrated in vacuo to give a thick oil. The residue was dissolved in Dichloromethane and was further purified by flash chromatography (0-50% acetone in toluene 1% Et3N, 220 g silica). Product containing fractions were pooled and concentrated in vacuo. The resulting oil was stripped with MeCN (2×) to yield 13.5 g (77%) of the colorless DMT-Serinol(GalNAc)-CEP (5) foam.

DMT-Serinol(GalNAc)-succinate (6)

DMAP (1.11 g, 9.11 mmol) was added to a stirring solution of DMT-Serinol(GalNAc) (3) (7.5 g, 9.11 mmol) and succinic anhydride (4.56 g, 45.6 mmol) in a mixture of Dichloromethane (50 ml) and Pyridine (50 ml) under argon atmosphere. After 16 h of stirring the reaction mixture was concentrated in vacuo and the residue was taken up in EtOAc and washed with 5% citric acid (aq). The aqueous layer was extracted with EtOAc. The combined organic layers were washed subsequently with sat $NaHCO_3$ (aq.) and brine, dried over $Na_2SO_4$, filtered and concentrated in vacuo. Further purification was achieved by flash chromatography (0-5% MeOH in $CH_2Cl_2$+1% $Et_3N$, 120 g silica). Product containing fractions were pooled and concentrated in vacuo. The residue was stripped with MeCN (3×) to yield 5.9 g (70%) DMT-Serinol(GalNAc)-succinate (6).

DMT-Serinol(GalNAc)-succinyl-Icaa-CPG (7)

The DMT-Serinol(GalNAc)-succinate (6) (1 eq.) and HBTU (1.1 eq.) were dissolved in $CH_3CN$ (10 ml). Diisopropylethylamine (2 eq.) was added to the solution, and the mixture was swirled for 2 min followed by addition native amino-Icaa-CPG (500 A, 88 μmol/g, 1 eq.). The suspension was gently shaken at room temperature on a wrist-action shaker for 16 h, then filtered and washed with acetonitrile. The solid support was dried under reduced pressure for 2 h. The unreacted amines on the support were capped by stirring with $Ac_2O$/2,6-lutidine/NMI at room temperature (2×15 min). The washing of the support was repeated as above. The solid was dried under vacuum to yield DMT-Serinol (GalNAc)-succinyl-Icaa-CPG (7) (loading: 34 μmol/g, determined by detritylation assay).

Example 2—Oligonucleotide Synthesis

Example compounds were synthesised according to methods described below and known to the person skilled in the art. Assembly of the oligonucleotide chain and linker building blocks was performed by solid phase synthesis applying phosphoramidite methodology.

Downstream cleavage, deprotection and purification followed standard procedures that are known in the art.

Oligonucleotide syntheses was performed on an AKTA oligopilot 10 using commercially available 2'O-Methyl RNA and 2'Fluoro-2'Deoxy RNA base loaded CPG solid support and phosphoramidites (all standard protection, ChemGenes, LinkTech) were used. Synthesis of DMT-(S)-Serinol(GalNAc)-succinyl Icaa CPG (7) and DMT-(S)-Serinol(GalNAc)-CEP (5) are described in example 1.

Ancillary reagents were purchased from EMP Biotech. Synthesis was performed using a 0.1 M solution of the phosphoramidite in dry acetonitrile (<20 ppm $H_2O$) and benzylthiotetrazole (BTT) was used as activator (0.3M in acetonitrile). Coupling time was 10 min. A Cap/OX/Cap or Cap/Thio/Cap cycle was applied (Cap: $Ac_2O$/NMI/Lutidine/Acetonitrile, Oxidizer: 0.05M $I_2$ in pyridine/$H_2O$). Phosphorothioates were introduced using commercially available thiolation reagent 50 mM EDITH in acetonitrile (Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the Serinol(GalNAc) moiety was achieved by use of either base-loaded (S)-DMT-Serinol(GalNAc)-succinyl-Icaa-CPG (7) or a (S)-DMT-Serinol(GalNAc)-CEP (5). Triantennary GalNAc clusters (ST23/ST43) were introduced by successive coupling of the branching trebler amidite derivative (C6XLT-phos) followed by the GalNAc amidite (ST23-phos). Attachment of (vp)-mU moiety was achieved by use of (vp)-mU-phos in the last synthesis cycle. The (vp)-mU-phos does not provide a hydroxy group suitable for further synthesis elongation and therefore, does not possess an DMT-group. Hence coupling of (vp)-mU-phos results in synthesis termination.

For the removal of the methyl esters masking the vinylphosphonate, the CPG carrying the fully assembled oligonucleotide was dried under reduced pressure and transferred into a 20 ml PP syringe reactor for solid phase peptide synthesis equipped with a disc frit (Carl Roth GmbH). The CPG was then brought into contact with a solution of 250 μL TMSBr and 177 μL pyridine in $CH_2Cl_2$ (0.5 ml/μmol solid support bound oligonucleotide) at room temperature and the reactor was sealed with a Luer cap. The reaction vessels were slightly agitated over a period of 2×15 min, the excess reagent discarded, and the residual CPG washed 2× with 10 ml acetonitrile. Further downstream processing did not alter from any other example compound.

The single strands were cleaved off the CPG by 40% aq. methylamine treatment (90 min, RT). The resulting crude oligonucleotide was purified by ion exchange chromatography (Resource Q, 6 ml, GE Healthcare) on a AKTA Pure HPLC System using a sodium chloride gradient. Product containing fractions were pooled, desalted on a size exclusion column (Zetadex, EMP Biotech) and lyophilised until further use.

All final single-stranded products were analysed by AEX-HPLC to prove their purity. Identity of the respective single-stranded products was proved by LC-MS analysis.

Example 3—Double-Strand Formation

Individual single strands were dissolved in a concentration of 60 OD/ml in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double-strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Figure 2:
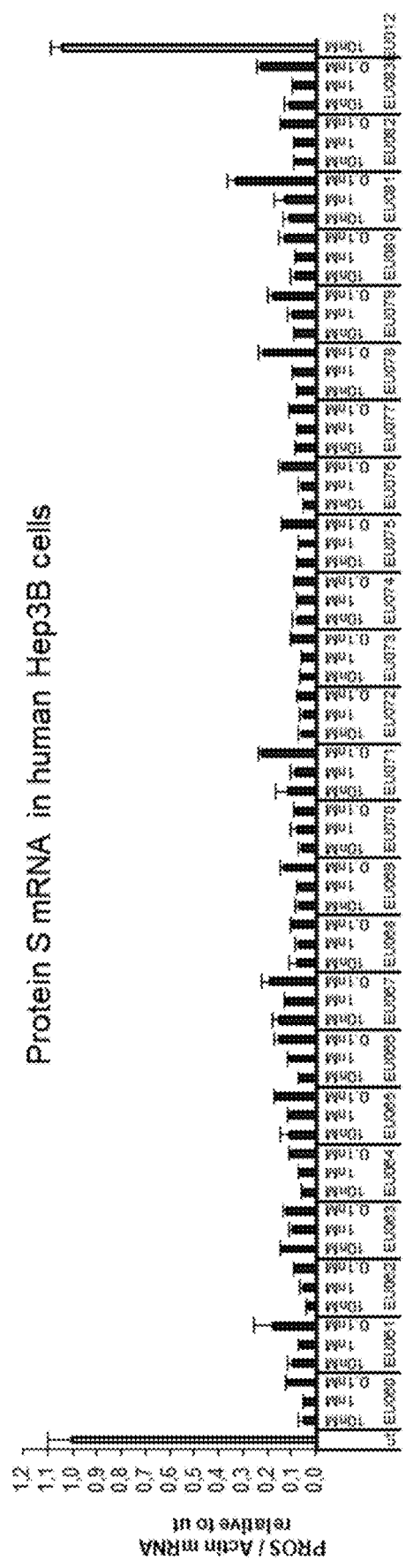
FIG. 2 shows inhibition of the PROS1 mRNA level in human cells by transfection of different PROS1 siRNAs.

Example 4—Reduction of Human PROS1 mRNA Level in Human Hep3B Cells by Transfection of PROS1 siRNAs In vitro testing shows over 70% reduction of PROS1 mRNA levels in human Hep3B cells by transfection of any of PROS1 siRNA molecules EU060 to EU083. Hep3B cells were seeded at a density of 12 000 cells per well in 96-well plates. The following day the cells were transfected with 10 nM, 1 nM or 0.1 nM PROS1 siRNA or non-targeting control siRNA (EU012) and 1 µg/ml AtuFECT. 24 hours thereafter cells were lysed for RNA extraction and PROS1 and Actin mRNA levels were determined by Taqman qRT-PCR. Values obtained for PROS1 mRNA were normalized to values generated for the house keeping gene Actin and related to the mean of untreated sample (ut) set at 1-fold target gene expression. Each bar represents mean+/−SD from three biological replicates. siRNA duplexes used in this study are listed in Table 2. Results are shown in FIG. 2.

Figure 3:
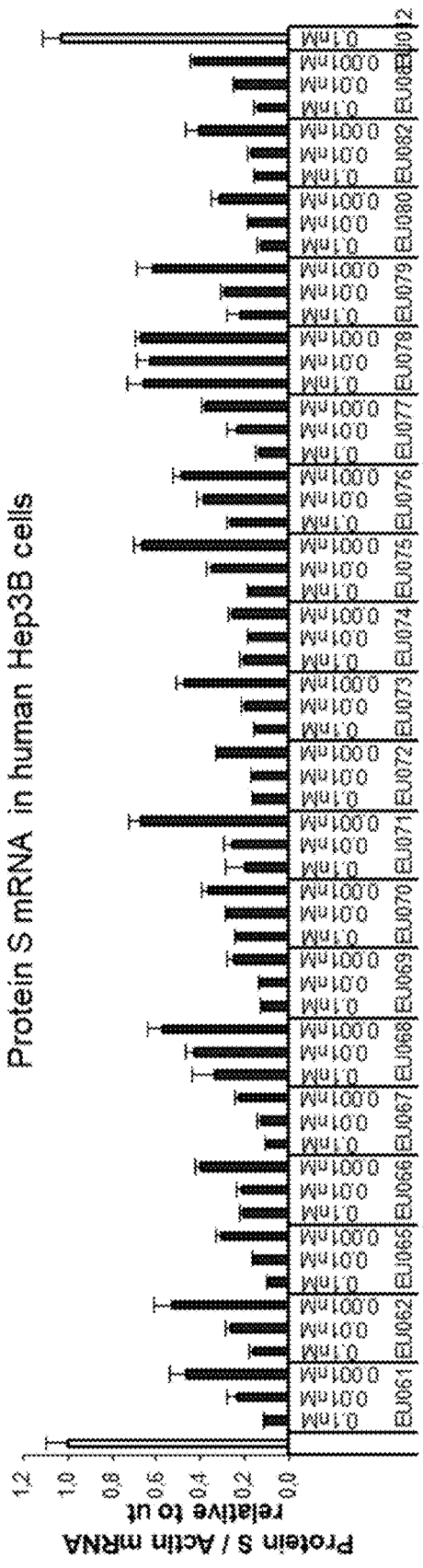
FIG. 3 shows dose response tests for reduction of the PROS1 mRNA level in human cells by transfection of PROS1 siRNAs.

Example 5—Dose Dependent Reduction of PROS1 mRNA Level in Human Cells by Transfection of PROS1 siRNAs In vitro testing shows dose dependent reduction of PROS1 mRNA levels in human Hep3B cells by a number of PROS1 siRNA molecules. Hep3B cells were seeded at a density of 12 000 cells per well in 96-well plates. The following day the cells were transfected with 0.1 nM, 0.01 nM or 0.001 nM PROS1 siRNA or 0.1 nM non-targeting control siRNA (EU012) and 1 µg/ml AtuFECT. 24 hours thereafter cells were lysed for RNA extraction and PROS1 and Actin mRNA levels were determined by Taqman qRT-PCR. Values obtained for PROS1 mRNA were normalized to values generated for the house keeping gene Actin and related to mean of untreated sample (ut) set at 1-fold target gene expression. Each bar represents mean+/−SD from three biological replicates. siRNA duplexes used in this study are listed in Table 2. Results are shown in FIG. 3.

Figure 4:
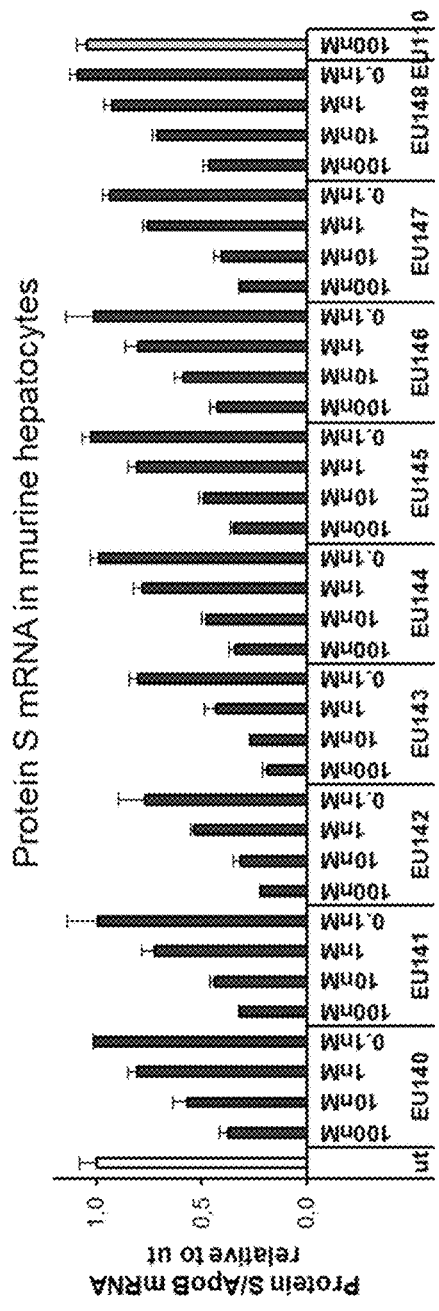
FIG. 4 shows inhibition of PROS1 target gene expression in primary murine hepatocytes by receptor mediated uptake of PROS1 siRNA conjugates.

Example 6—Inhibition of PROS1 Target Gene Expression in Primary Mouse Hepatocytes by Receptor Mediated Uptake of PROS1 siRNA Conjugates The example shows dose dependent reduction of PROS1 mRNA levels in primary hepatocytes by receptor mediated uptake of EU140 to EU148. Primary mouse hepatocytes were seeded in a 96-well plate at a density of 25 000 cells per well. After attachment, they were incubated with PROS1 siRNA conjugates in the cell culture medium at 100 nM, 10 nM, 1 nM and 0.1 nM as indicated below, or they were incubated with 100 nM non-targeting control conjugates (EU110). The following day, cells were lysed for RNA extraction and PROS1 and ApoB mRNA levels were determined by Taqman qRT-PCR. Values obtained for PROS1 mRNA were normalized to values generated for the house keeping gene ApoB and related to mean of untreated sample (ut) set at 1-fold target gene expression. Each bar represents mean+/−SD from three biological replicates. siRNA conjugates used in this study are listed in Table 2. Results are shown in FIG. 4.

Figure 5:
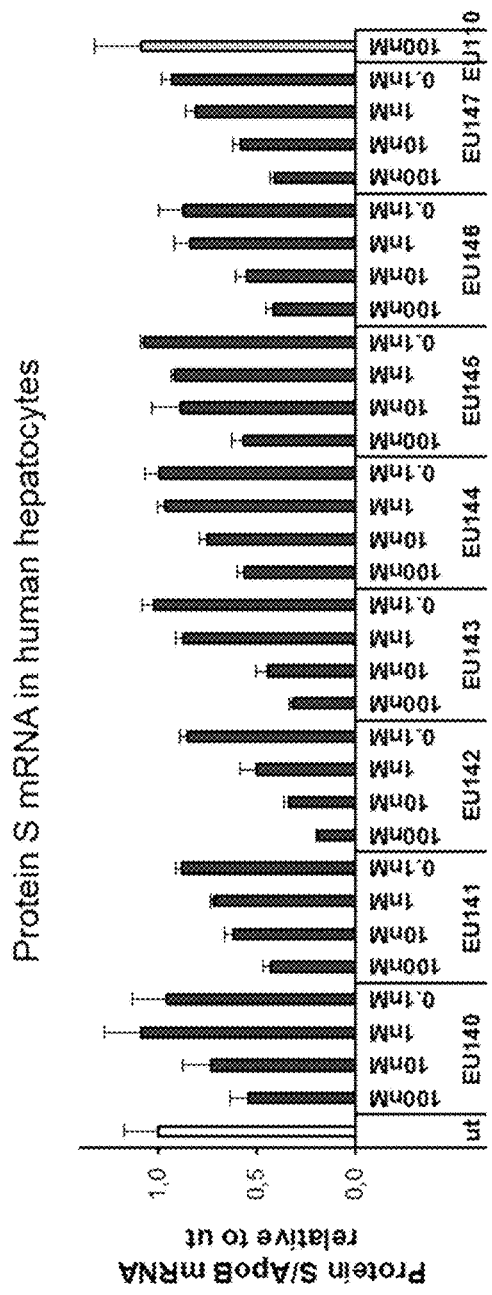
FIG. 5 shows inhibition of PROS1 target gene expression in primary human hepatocytes by receptor mediated uptake of PROS1 siRNA conjugates.

Example 7—Inhibition of Human PROS1 Gene Expression in Primary Human Hepatocytes by Receptor Mediated Uptake of PROS1 siRNA Conjugates The example shows dose dependent reduction of human PROS1 mRNA levels by EU140 to 147 in primary human hepatocytes. Primary human hepatocytes (Life Technologies) were seeded in a 96-well plate at a density of 35 000 cells per well in plating medium and were subsequently incubated with PROS1 siRNA conjugates EU140 to EU147, in concentrations of 100 nM, 10 nM, 1 nM and 0.1 nM as shown in FIG. 5, or they were incubated with non-targeting control conjugates at 100 nM (EU110). Values obtained for PROS1 mRNA were normalized to values generated for the house keeping gene ApoB and related to mean of untreated sample (ut) set at 1-fold target gene expression. Each bar represents mean+/−SD from three biological replicates. siRNA conjugates used in this study are listed in Table 2. Results are shown in FIG. 5.

Example 8—Loss of X-Ase Activity Rescues Pros1$^{-/-}$ Mice

Figure 6:
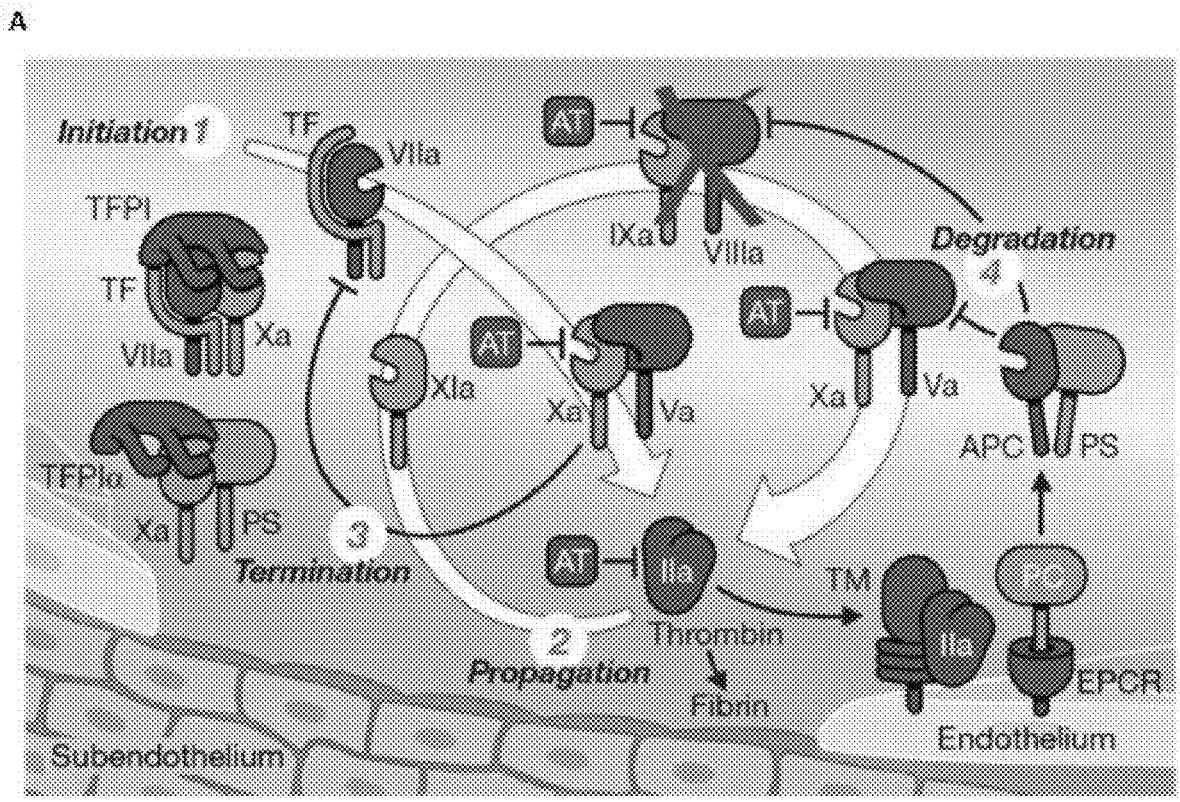
FIG. 6 shows that loss of X-ase activity rescues $Pros1^{-/-}$ mice. Panel A, Schematic model of thrombin generation in haemophilic condition. One of the major coagulation complexes is the intrinsic tenase (X-ase) complex. X-ase comprises activated FIX (FIXa) as the protease, activated FVIII (FVIIIa) as the cofactor, and factor X (FX) as the substrate. Although the generation or exposure of tissue factor (TF) at the site of injury is the primary event in initiating coagulation via the extrinsic pathway, the intrinsic pathway X-ase is important because of the limited amount of available active TF in vivo and the presence of TFPI which, when complexed with activated FX (FXa), inhibits the TF/activated factor VII (FVIIa) complex (FIG. 6, Panel A). Thus, sustained thrombin generation depends upon the activation of both FIX and FVIII (FIG. 6, Panel A). This process is amplified because FVIII is activated by both FXa and thrombin, and FIX, by both FVIIa and activated factor XI (FXIa), the latter factor being previously activated by thrombin. Consequently, a progressive increase in FVIII and FIX activation occurs as FXa and thrombin are formed Panel B, the experimental approach to enhance thrombin generation in severe haemophilia A and B by targeting Pros1. Panels C-D, Murine model validation and evaluation of DIC hematologic parameters in haemophilic adult mice with and without Pros1 deficiency: PS (Protein S; antigenic), FVIII (coagulant activity) or FIX (coagulant activity) plasma levels in $F8^{-/-}Pros1^{+/+}$, $F8^{-/-}Pros1^{+/-}$ and $F8^{-/-}Pros1^{-/-}$ (Panel C), and $F9^{-/-}Pros1^{+/+}$, $F9^{-/-}Pros1^{+/-}$ and $F9^{-/-}Pros1^{-/-}$ adult mice (Panel D) (n=5/group); platelets (n=7/group), fibrinogen (n=8/group), PT (n=6/group) and TAT (n=6/group) in haemophilia A group (Panel C); and platelets (n=5/group), fibrinogen (n=4/group), PT (n=4/group) and TAT (n=4/group) in haemophilia B group (Panel D). Panels E-F, Macroscopic image of lungs from $F8^{-/-}Pros1^{-/-}$ mice 24 h after a single intravenous injection of 2 U/g recombinant FVIII (Advate®) infusion (Panel E) and corresponding microscopic evaluation of fibrin clots in lung section (Panel F). Panel G, Recombinant FVIII (Advate®) administration in $F8^{-/-}Pros1^{+/+}$ and $F8^{-/-}Pros1^{-/-}$: plasma levels of fibrinogen and TAT at 24 h following 5 injection of 0.3 U/g Advate® i.v. (injection time-points: 1 h before catheter insertion and 1 h, 4 h, 8 h and 16 h after catheter insertion) (n=3) (Panel G, white and black columns) and 24 h after a single i.v. injection in $F8^{-/-}Pros1^{-/-}$ (n=3) (Panel G, dashed column), and representative immunohistochemistry allowing the detection of fibrin clots in lungs and liver sections in $F8^{-/-}Pros1^{-/-}$ 24 h after 0.3 U/g repeated i.v. injections of Advate® (Panel H) and after a single i.v. injection of 0.3 U/g Advate® i.v. (i). All data are expressed as mean±s.e.m.; ns, not significant; *, P<0.05**; P<0.005.
Figure 6:
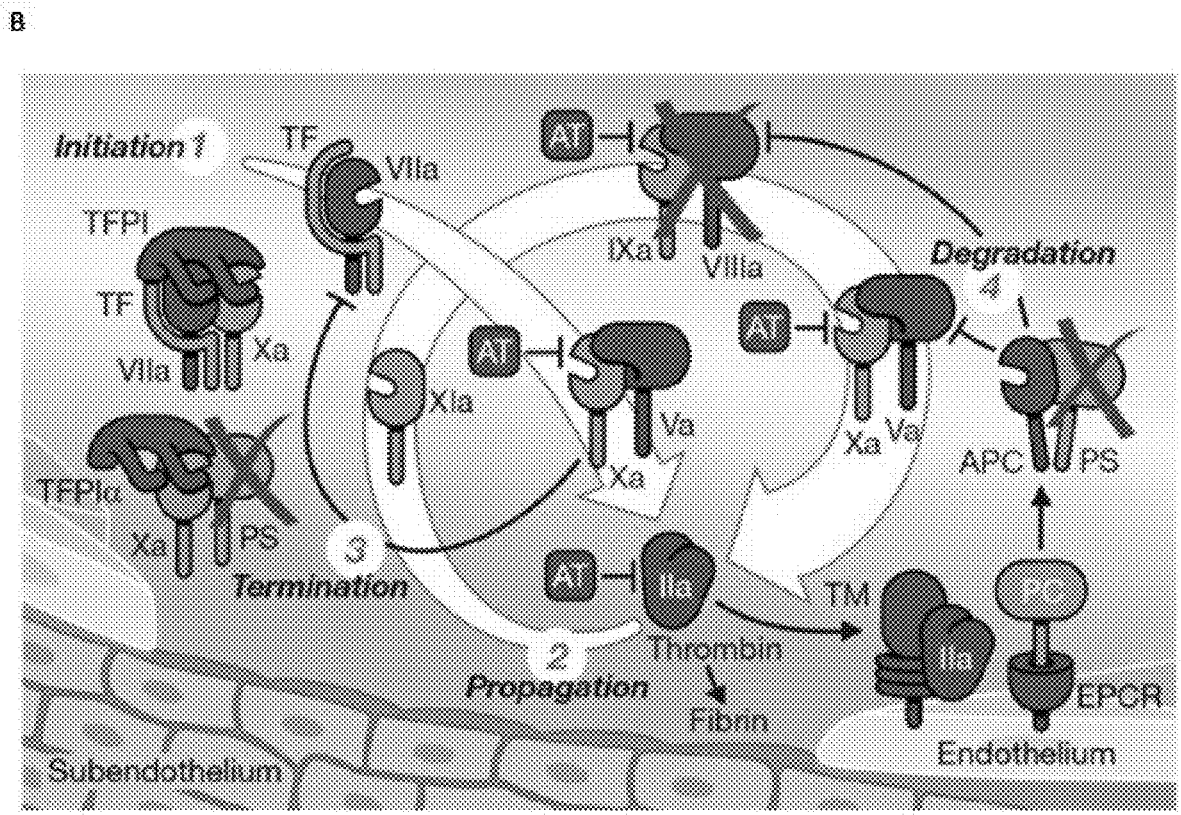
Figure 6:
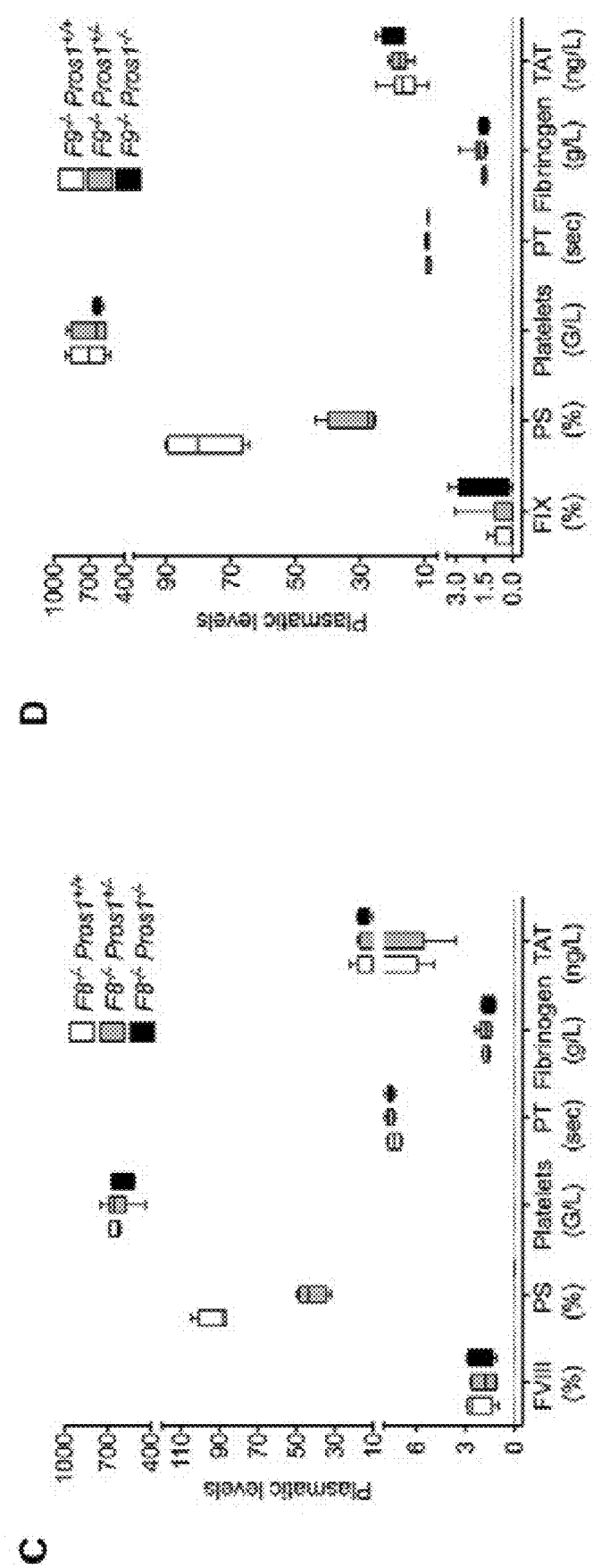
Figure 6:
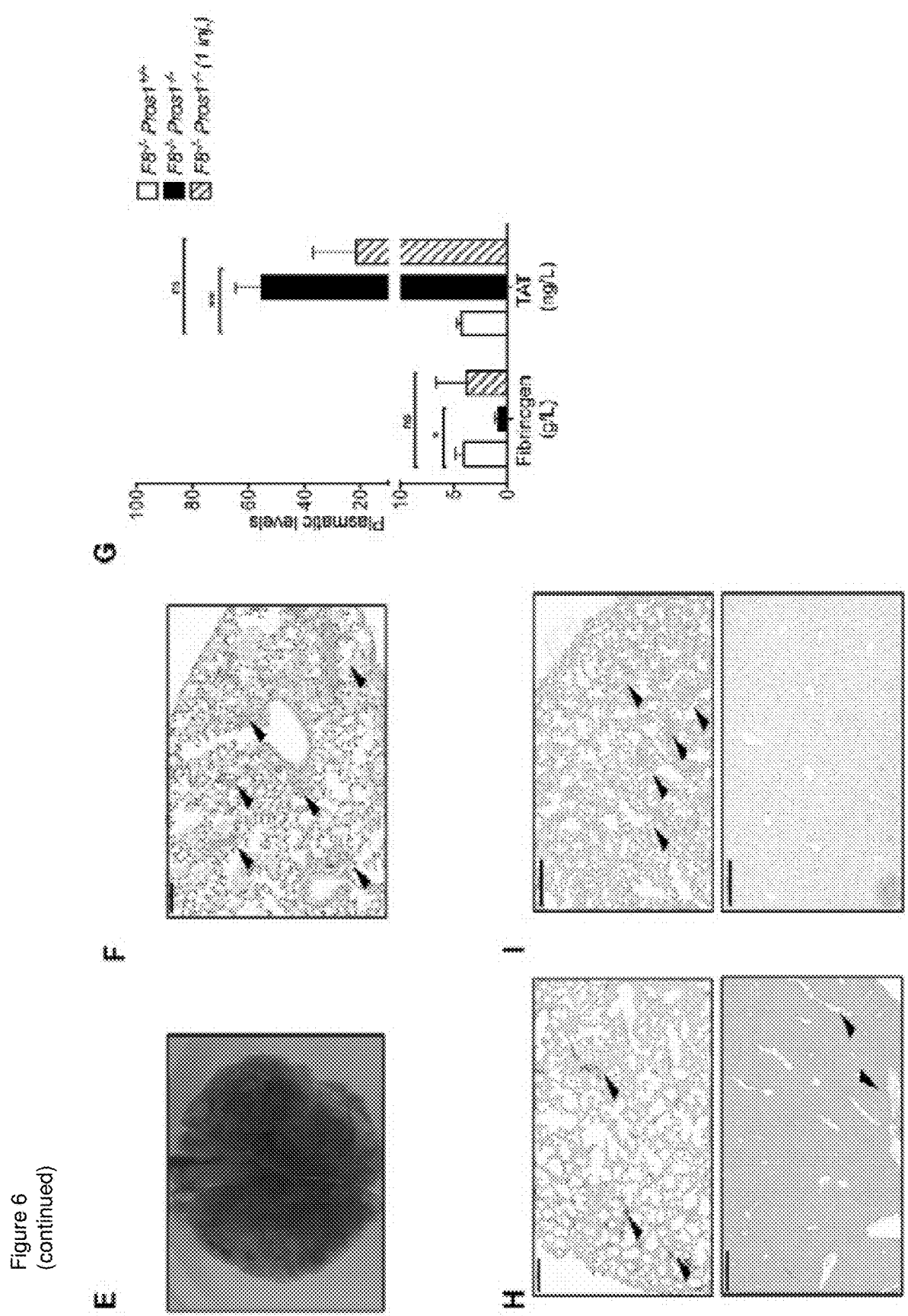
Figure 13:
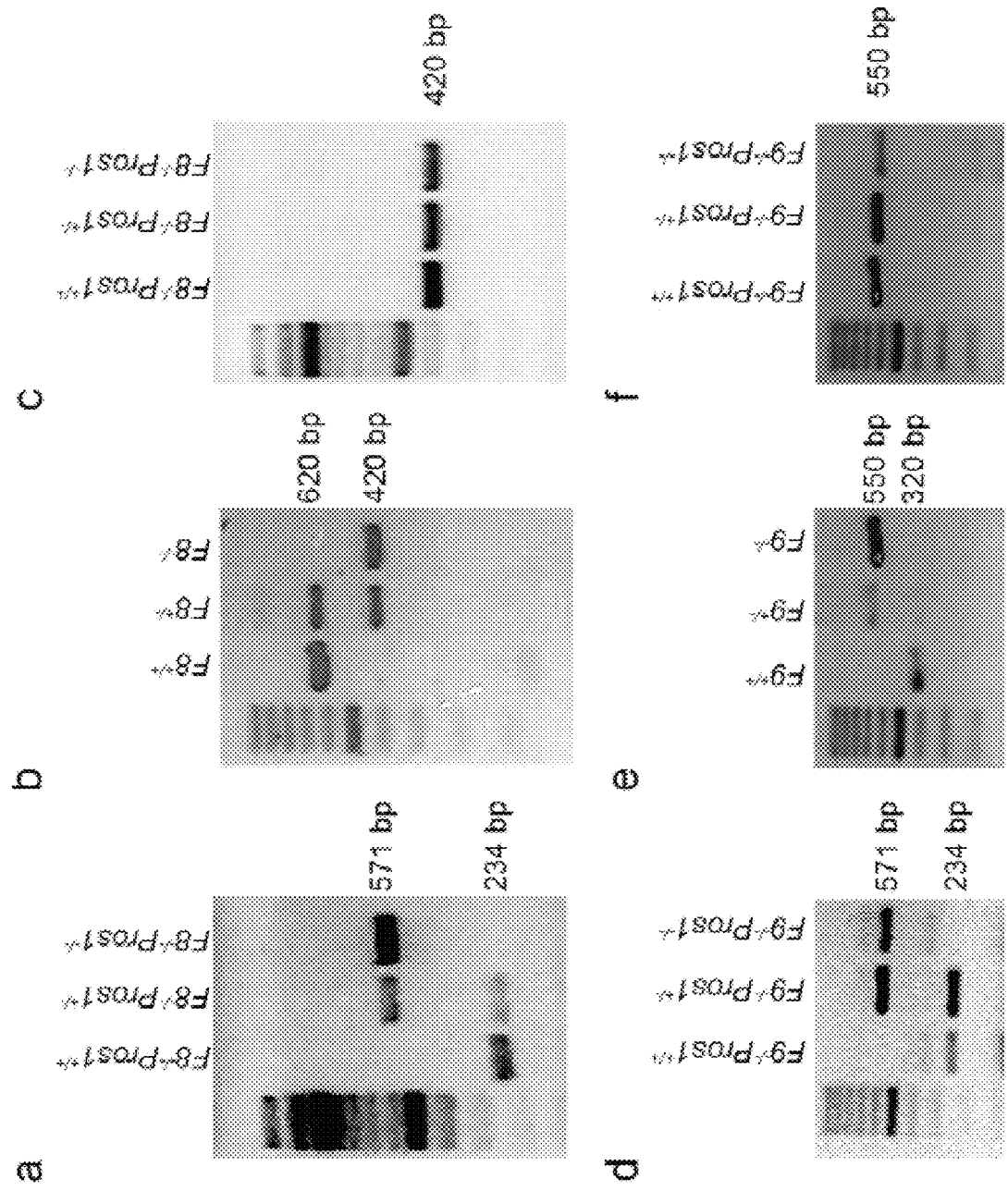
FIG. 13 shows genotyping approaches. Genotypes obtained by crossing $F8^{-/-}Pros1^{+/-}$ (Panels a-c) and $F9^{-/-}Pros1^{+/-}$ (Panels d-f) mice. Panel a, Pros1 alleles were amplified by a multiplex PCR. PCR products were then subjected to electrophoresis; the wt band has a lower molecular weight (234 bp) compared to the null band (571 bp), in accordance to Saller, 2009. Panel b, Set-up of multiplex PCR to amplify the wt band (620 bp) and the null band (420 bp) of F8 alleles from genomic DNA. Panel c, PCR products of F8 alleles amplification (null band: 420 bp) on the same samples than in (Panel a). Panel d, Pros1 alleles were amplified by a multiplex PCR. PCR products were then subjected to electrophoresis; the wt band has a lower molecular weight (234 bp) compared to the null band (571 bp), in accordance to Saller, 2009. Panel e, Set-up of multiplex PCR to amplify the wt band (320 bp) and the null band (550 bp) of F9 alleles from genomic DNA. f, PCR products of F9 alleles amplification (null band: 550 bp) on the same samples than in (Panel d).

Pros1$^{+/-}$ females crossed with F8$^{-/-}$ males produced 25% F8$^{+/-}$Pros1$^{+/-}$ progeny. F8$^{+/-}$Pros1$^{+/-}$ females bred with F8$^{-/-}$ males resulted in 25% F8$^{-/-}$Pros1$^{+/-}$ progeny (FIGS. 13a-c). Similar observations were made with F9$^{-/-}$Pros1$^{+/-}$ mice (FIGS. 13d-f). As expected, F8$^{-/-}$Pros1$^{-/-}$ and F9$^{-/-}$Pros1$^{-/-}$ mice did not display FVIII and FIX plasma activity, respectively, and PS (protein S) was not detected in F8$^{-/-}$Pros1$^{-/-}$ and F9$^{-/-}$Pros1$^{-/-}$ mice plasma (FIGS. 6C-D). PS levels in F8$^{-/-}$Pros1$^{+/-}$ and F9$^{-/-}$Pros1$^{+/-}$ were ~50-60% less than in F8$^{-/-}$Pros1$^{+/+}$ and F9$^{-/-}$Pros1$^{+/+}$ mice (FIGS. 6C-D), as reported.

Of 295 pups from F8$^{-/-}$Pros1$^{+/-}$ breeding pairs, 72 (24%) were F8$^{-/-}$Pros1$^{+/+}$, 164 (56%) were F8$^{-/-}$Pros1$^{+/-}$ and 59 (20%) were F8$^{-/-}$Pros1$^{-/-}$ ($\chi^2$=4.8, P=0.09). Thus, F8$^{-/-}$Pros1$^{-/-}$ mice were present at the expected Mendelian ratio. In contrast, of 219 pups from F9$^{-/-}$Pros1$^{-/-}$ breeding pairs, 56 (26%) were F9$^{-/-}$Pros1$^{+/+}$, 132 (60%) were F9$^{-/-}$Pros1$^{+/+}$ and 31 (14%) were F9$^{-/-}$Pros1$^{-/-}$ ($\chi^2$=14.95, P=0.001). This is compatible with a transmission ratio distortion for F9$^{-/-}$Pros1$^{-/-}$ mice consistent with the decreased litter sizes compared to those of matings from F9$^{+/+}$Pros1$^{+/+}$ mice (5.2±0.7 versus 9.8±1.8, n=4 matings/over $3^t$ generations, P=0.046).

F8$^{-/-}$Pros1$^{-/-}$ and F9$^{-/-}$Pros1$^{-/-}$ mice appeared completely normal. Their viability was monitored up to 20 (n=4) and 16 months (n=2), respectively, without showing any difference compared to F8$^{-/-}$Pros1$^{+/+}$ and F9$^{-/-}$Pros1$^{+/+}$ mice, respectively.

Figure 14:
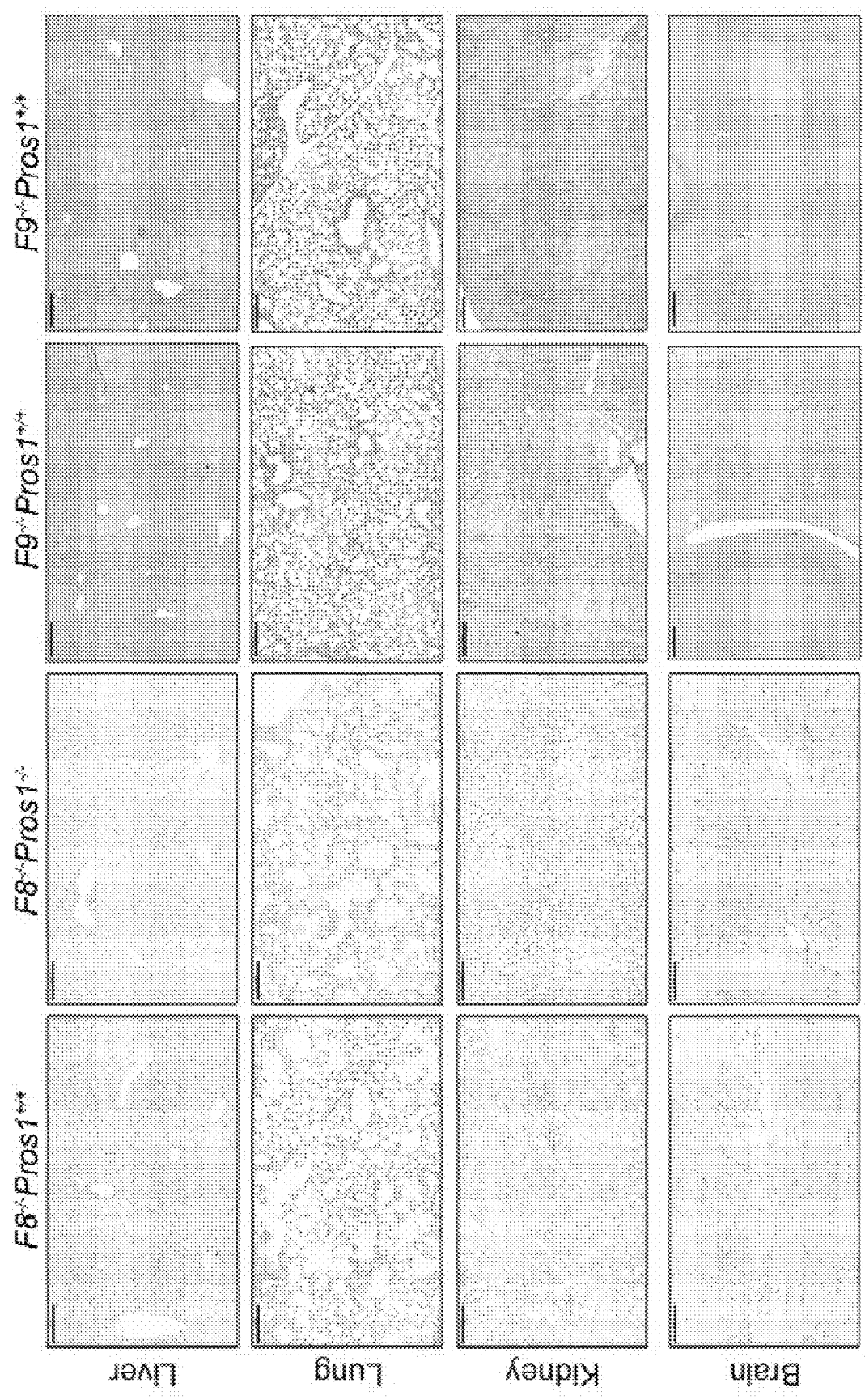
FIG. 14 shows histology in physiologic condition. Immunostaining for insoluble fibrin on liver, lung, kidney, brain sections in $F8^{-/-}Pros1^{-/-}$ and in $F8^{-/-}Pros1^{+/+}$ mice as well as in $F9^{-/-}Pros1^{+/+}$ and $F9^{-/-}Pros1^{-/-}$. Scale bar: 100 μm.

As a complete Pros1 deficiency in mice leads to consumptive coagulopathy, we assessed whether F8$^{-/-}$Pros1$^{-/-}$ and F9$^{-/-}$Pros1$^{-/-}$ mice developed DIC. DIC parameters were comparable in F8$^{-/-}$Pros1$^{+/+}$, F8$^{-/-}$Pros1$^{+/-}$ and F8$^{-/-}$Pros1$^{-/-}$ mice (FIG. 6C), and in F9$^{-/-}$, Pros1$^{+/+}$, F9$^{-/-}$Pros1$^{+/-}$ and F9$^{-/-}$Pros1$^{-/-}$ mice (FIG. 6D). Activated partial thromboplastin time (aPTT) was equally prolonged in F8$^{-/-}$Pros1$^{+/+}$ (69±2 sec), F8$^{-/-}$Pros1+(68±3 sec) and F8$^{-/-}$Pros1$^{-/-}$ (63±3 sec) mice (mean+s.e.m., n=6 per group, P=0.3) because of the absence of FVIII. Comparable data were obtained with F9$^{-/-}$Pros1$^{+/+}$, F9$^{-/-}$Pros1$^{+/-}$ and F9$^{-/-}$ Pros1$^{-/-}$ mice. Moreover, no thrombosis or fibrin deposition was found in brain, lungs, liver and kidney of F8$^{-/-}$Pros1$^{-/-}$ and F9$^{-/-}$Pros1$^{-/-}$ mice (FIG. 14).

Therefore, loss of X-ase activity rescues the embryonic lethality of complete Pros1 deficiency. However, the rescue was only partial with the loss of FIX activity. A possible explanation is that severe HB appears to be a less serious condition compared to severe HA. Consequently, F9 disruption in Pros1$^{-/-}$ mice was less efficient in rebalancing coagulation than F8 disruption.

To explore whether restoring intrinsic X-ase activity by FVIII infusion induces DIC, thrombosis and purpura fulminans in F8$^{-/-}$Pros1$^{-/-}$ mice, we administered recombinant FVIII (rFVIII) intravenously. No mouse died following rFVIII injection. Thrombi in numerous blood vessels and bleeding in the lungs were found in F8$^{-/-}$Pros1$^{-/-}$ mice 24 h after a single injection of an overdose of rFVIII (FIGS. 6E-F). 24 hours after repeated administration of a normal dose of rFVIII, coagulation analyses showed incoagulable prothrombin time (PT) (not shown), low fibrinogen and high thrombin-antithrombin (TAT) levels, compatible with an overt DIC (FIG. 6G). In contrast, after a single injection of a normal dose of rFVIII in F8$^{-/-}$Pros1$^{-/-}$ mice, fibrinogen and TAT levels were comparable to those of untreated F8$^{-/-}$Pros1$^{-/-}$ mice (FIG. 6G). Although numerous thrombi were visible in lungs and liver (FIGS. 6H-I), none of these mice developed purpura fulminans.

Figure 7:
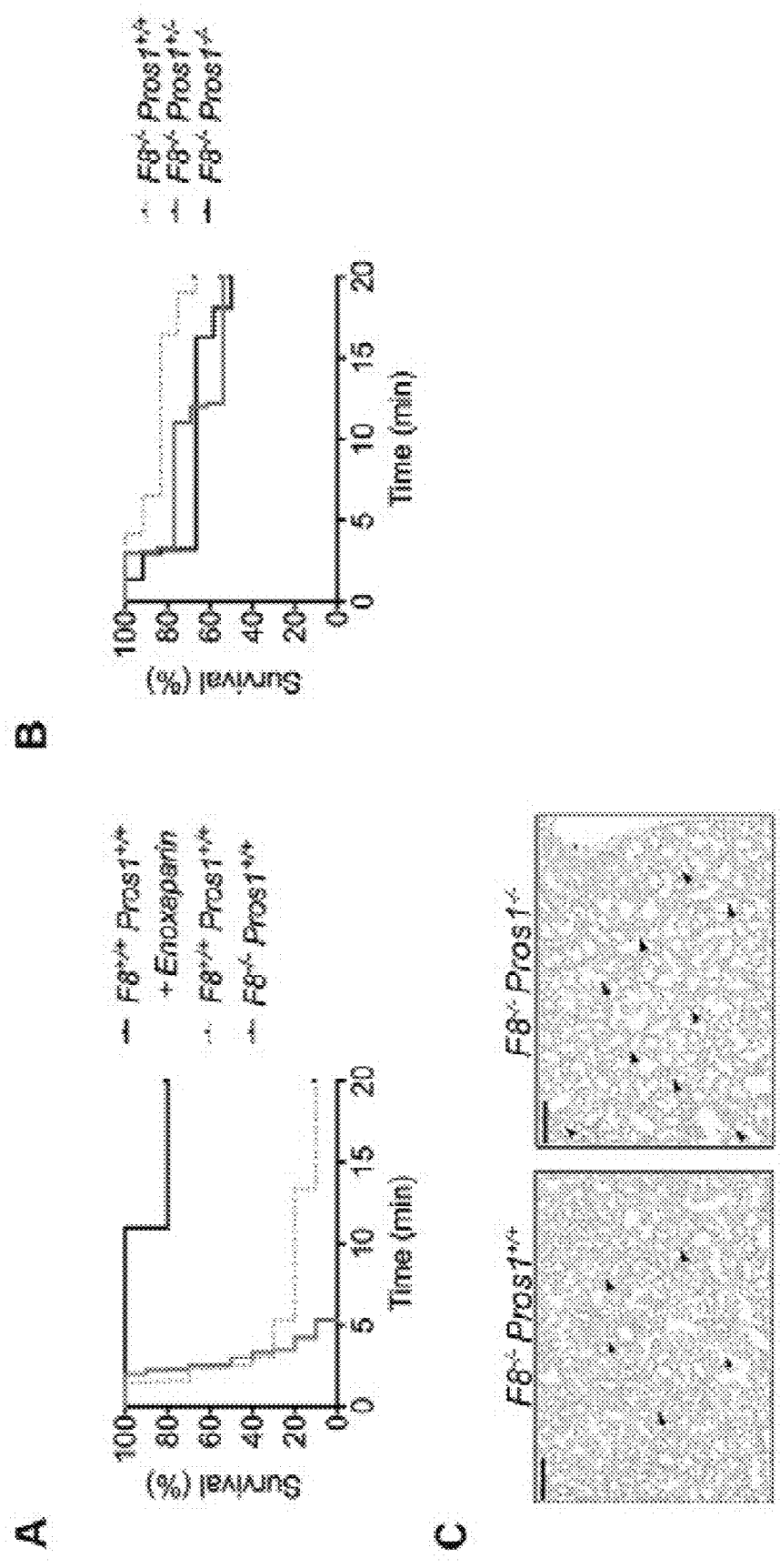
FIG. 7 shows murine models of thrombosis. Panels A-C, TF-induced venous thromboembolism in $F8^{+/+}Pros1^{+/+}$, $F8^{-/-}Pros1^{+/+}$, $F8^{-/-}Pros1^{+/-}$ and $F8^{-/-}Pros1^{-/-}$ mice (n=10/genotype). Anesthetized mice were injected intravenously via the inferior vena cava with different doses of recombinant TF (Innovin): ½ dilution (~4.3 nM TF) in Panel A and ¼ dilution (~2.1 nM TF) in Panels B-C. In (Panel A), one group of $F8^{+/+}Pros1^{+/+}$ mice received an injection of the low molecular weight heparin (enoxaparin 60 µg/g s.c.). The time to the onset of respiratory arrest that lasted at least 2 min was recorded. Experiments were terminated at 20 min. Kaplan-Meier survival curves (Panels A-B). Panel C, 2 min after onset of respiratory arrest or at the completion of the 20-min observation period, lungs were excised and investigated for fibrin clots (immunostaining for insoluble fibrin, mAb clone 102-10). Panel D, Thrombus formation in $FeCl_3$-injured mesenteric arteries recorded by intravital microscopy in $F8^{+/+}$ $Pros1^{+/+}$, $F8^{-/-}Pros1^{+/+}$ and $F8^{-/-}Pros1^{-/-}$ mice, representative experiment (n=3/genotype). Panel D, Thrombus formation in $FeCl_3$-injured mesenteric arteries recorded by intravital microscopy in $F8^{+/+}Pros1^{+/+}$, $F8^{-/-}$ $Pros1^{+/+}$ and $F8^{-/-}Pros1^{-/-}$ mice, representative experiment (n=3/genotype).
Figure 7:
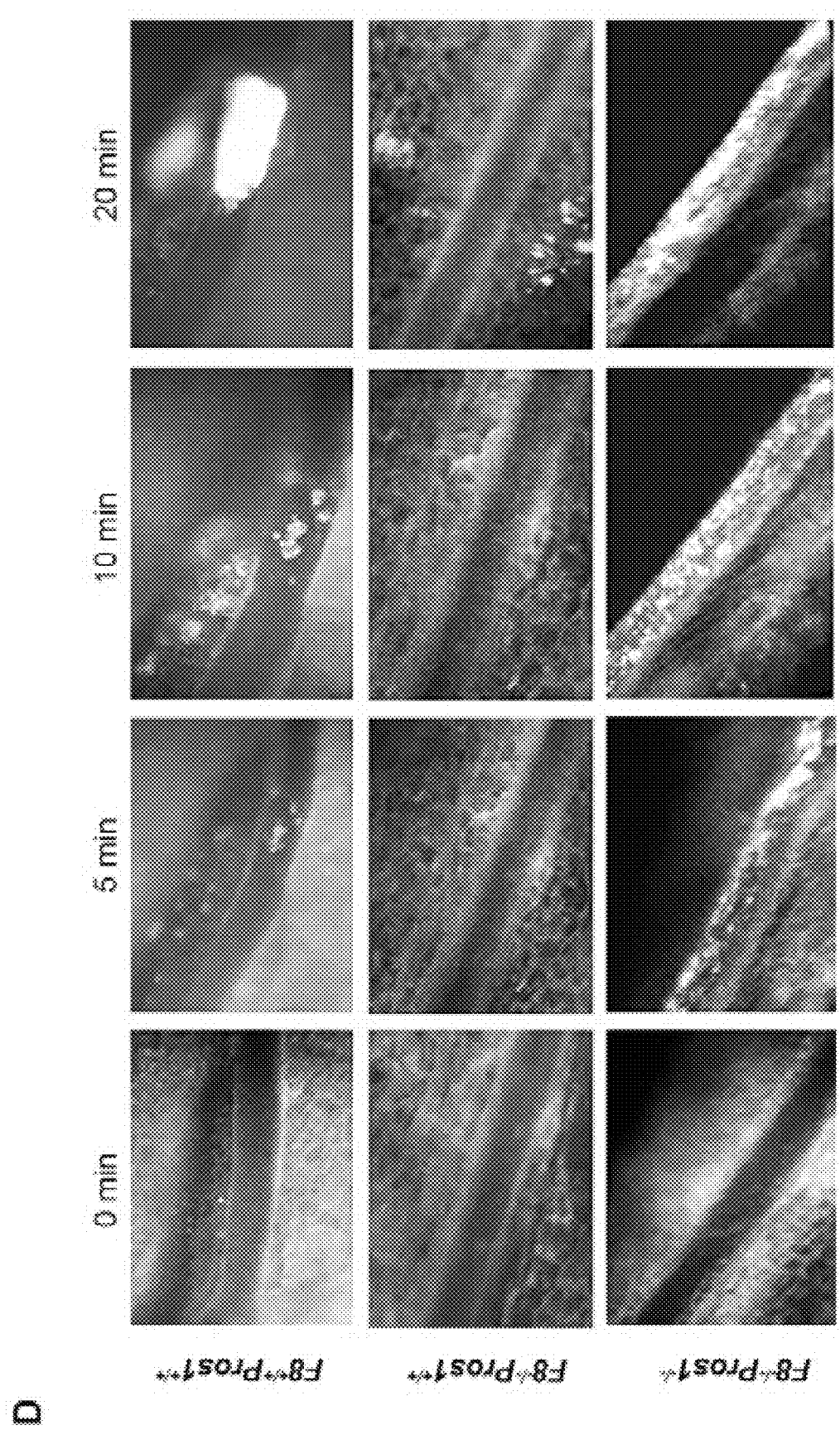

Example 9—Loss of X-Ase Activity does not Prevent Lethality Caused by TF-Induced Thromboembolism in Pros1$^{-/-}$ Mice We demonstrated previously that, although 88% of Pros1$^{+/+}$ mice survived to a TF-induced thromboembolism model, only 25% of Pros1$^{+/-}$ mice were still alive 20 min after a low TF dose injection (~1.1 nM). When using a higher TF dosage (~4.3 nM), both Pros1$^{+/+}$ and Pros1$^{+/-}$ mice died within 20 min. However, Pros1$^{+/-}$ died earlier than Pros1$^{+/+}$. HA and WT mice were equally sensitive to this high TF-dose with more than 85% of them succumbing within 15 min (FIG. 7A). In contrast, >75% WT mice under thromboprophylaxis with a low molecular weight heparin (LMWH) survived (FIG. 7A). Thus, in contrast with LMWH, HA does not protect mice against TF-induced thromboembolism. We then investigated F8$^{-/-}$Pros1$^{+/+}$, F8$^{-/-}$Pros1$^{+/-}$ and F8$^{-/-}$Pros1$^{-/-}$ mice in the same model. After the infusion of TF (~2.1 nM), 40-60% of the mice died (P>0.05), independently of their Pros1 genotype (FIG. 7B). However, there was a trend for F8$^{-/-}$Pros1$^{-/-}$ and F8$^{-/-}$Pros1$^{+/-}$ succumbing earlier than F8$^{-/-}$Pros1$^{+/+}$ mice, and for F8$^{-/-}$Pros1$^{+/-}$ dying earlier than F8$^{-/-}$Pros1$^{+/+}$ mice (mean time to death: 12±4 min for F8$^{-/-}$Pros1$^{+/+}$, 7±2 min for F8$^{-/-}$Pros1$^{+/-}$, 8±3 min for F8$^{-/-}$Pros1$^{-/-}$ mice, n=4-6/group, P=0.43). Similar data were obtained with F9$^{-/-}$Pros1$^{+/+}$, F9$^{-/-}$Pros1$^{+/-}$ and F9$^{-/-}$Pros1$^{-/-}$ mice (data not shown).

Fibrin clots were detected in lung arteries of F8$^{-/-}$Pros1$^{+/+}$ and F8$^{-/-}$Pros1$^{-/-}$ mice that died during the TF-induced thromboembolic challenge (FIG. 7C). Importantly, there were more thrombi in lungs from F8$^{-/-}$Pros1$^{-/-}$ than from F8$^{-/-}$Pros1$^{+/+}$ mice (n=48 versus 26, respectively). Moreover, most arteries in F8$^{-/-}$Pros1$^{-/-}$ lungs were completely occluded while they were only partially occluded in F8$^{-/-}$Pros1$^{+/+}$ lungs.

None of the F8$^{-/-}$Pros1$^{-/-}$ mice that succumbed during the TF-induced thromboembolic-challenge developed purpura fulminans. Similar data were obtained with F9$^{-/-}$Pros1$^{+/+}$, F9$^{-/-}$Pros1$^{+/-}$ and F9$^{-/-}$Pros1$^{-/-}$ mice (not shown).

Example 10—Loss of FVIII Partially Protects Pros1$^{-/-}$ Mice Against Thrombosis in Mesenteric Arterioles We then recorded thrombus formation in mesenteric arterioles, a model sensitive to defects in the intrinsic pathway of coagulation. In F8$^{+/+}$Pros1$^{+/+}$ mice, thrombi grew to occlusive size in 20 min, and all injured arterioles were occluded (FIG. 7D). As expected, none of the arterioles of F8$^{-/-}$Pros1$^{+/+}$ displayed thrombosis, whereas F8$^{-/-}$Pros1$^{-/-}$ mice showed partial thrombi (FIG. 7D).

Emboli were generated during thrombus formation in F8$^{+/+}$Pros1$^{+/+}$ mice, but not in F8$^{-/-}$Pros1$^{+/+}$ mice. In F8$^{-/-}$Pros1$^{-/-}$ mice, multiple micro-emboli detached during partial thrombus growth, preventing the formation of occlusive thrombi.

Example 11—Pros1 Targeting Limits but does not Abrogate Tail Bleeding in Mice with HA The bleeding phenotype was assessed by tail transection using a mild or a severe bleeding model.

Figure 8:
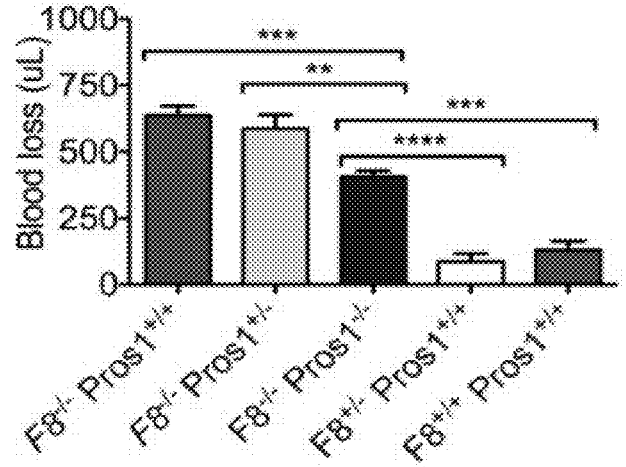
FIG. 8 shows tail bleeding models. Blood was collected after 2 mm (Panel A) and 4 mm (Panel B) tail transection for 30 min (Panel A) and 10 min (Panel B) in a fresh tube of saline; total blood loss (µl) was then measured. $F8^{+/-}Pros1^{+/+}$ and $F8^{+/+}Pros1^{+/+}$ mice (white columns) served as controls (n=5 for all groups in Panel A, n=6 for all groups in Panel A). Panel C, An anti-human PS antibody altered tail bleeding after 4 mm transection.
Figure 8:
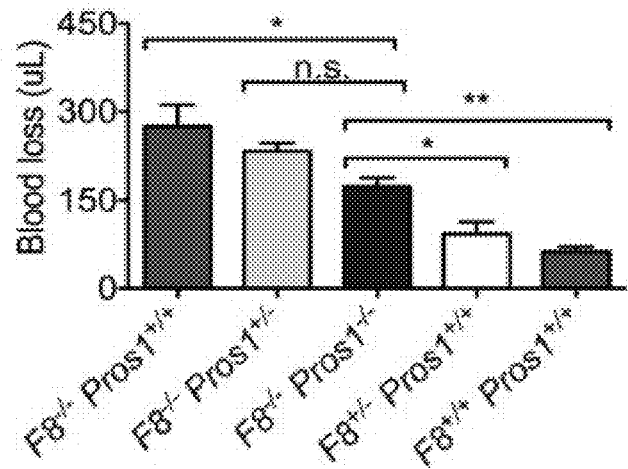
Figure 8:
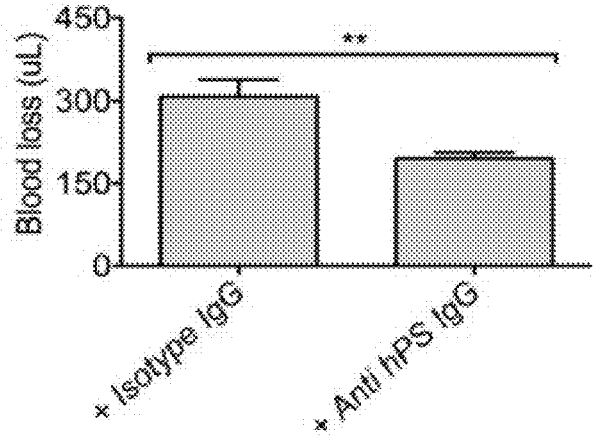

In both models, blood loss was reduced in F8$^{-/-}$Pros1$^{-/-}$ compared to F8$^{-/-}$Pros1$^{+/+}$ mice (FIG. 8A-B). When challenged by the mild model, F8$^{-/-}$Pros1$^{+/-}$ mice bled less than F8$^{-/-}$Pros1$^{+/+}$ mice (FIG. 8A). In contrast, when exposed to the severe model, F8$^{-/-}$Pros1$^{-/-}$ and F8$^{-/-}$Pros1$^{+/-}$ mice displayed comparable blood loss (FIG. 8B). However, F8$^{-/-}$Pros1$^{-/-}$ mice bled more than F8$^{+/-}$ Pros1$^{+/+}$ and F8$^{+/+}$Pros1$^{+/+}$ mice in both models (FIGS. 8A-B), indicating that the loss of Pros1 in F8$^{-/-}$ mice partially correct the bleeding phenotype of F8$^{-/-}$ mice.

Then, an PS-neutralizing antibody was used to investigate how inhibition of PS activity alters tail bleeding in F8$^{-/-}$Pros1$^{+/-}$ mice. This antibody limited blood loss in F8$^{-/-}$Pros1$^{+/-}$ mice (FIG. 8C) to the same degree as complete genetic loss of Pros1 (FIG. 8B).

Example 12—Pros1 Targeting or PS Inhibition Fully Protects HA or HB Mice from Acute Hemarthrosis (AH)

Figure 9:
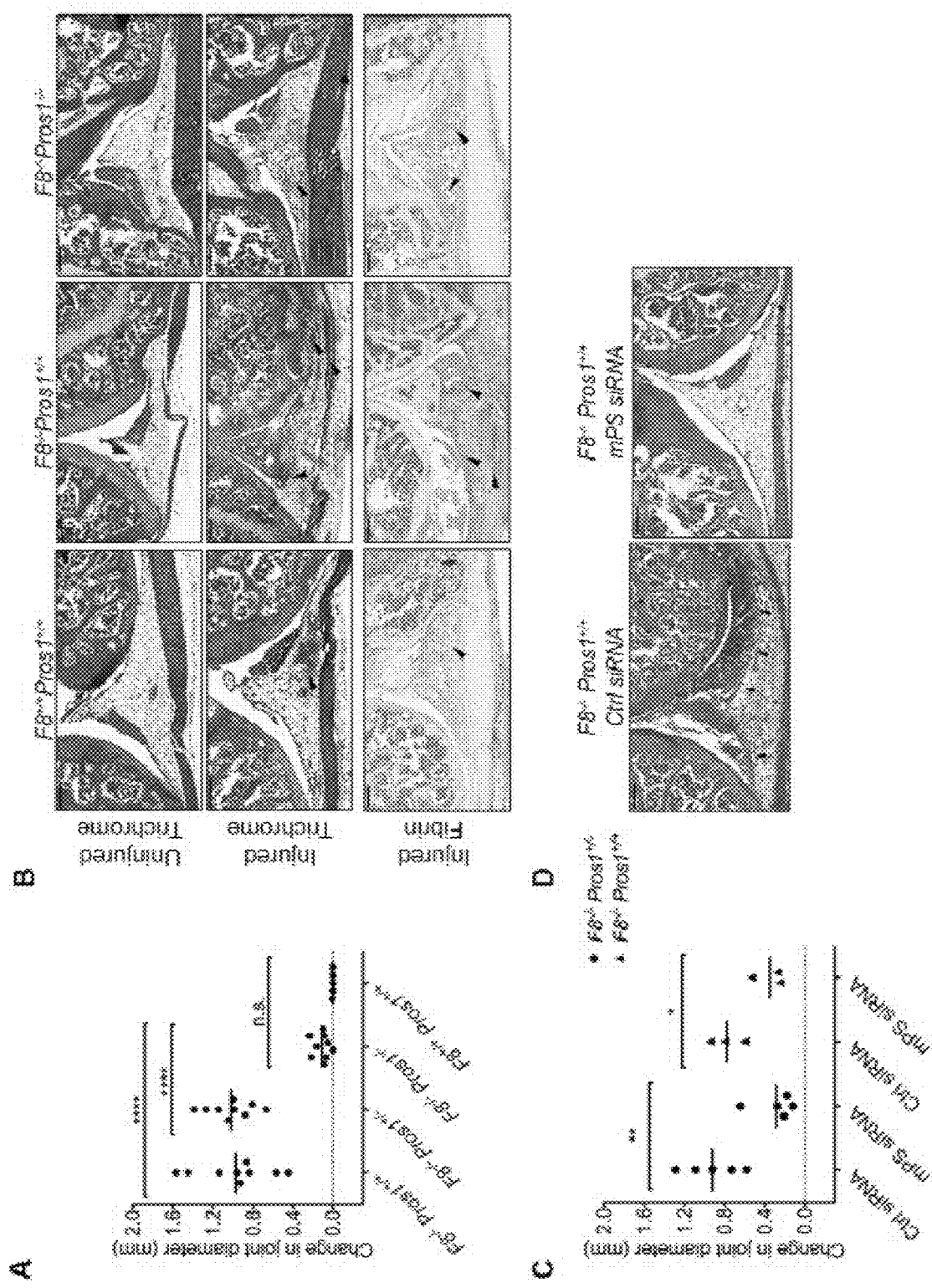
FIG. 9 shows an acute hemarthrosis model. Panel A, Difference between the knee diameter 72 h after the injury and before the injury in $F8^{-/-}Pros1^{+/+}$, $F8^{-/-}Pros1^{+/-}$, $F8^{-/-}Pros1^{-/-}$ and $F8^{+/+}Pros1^{+/+}$ mice. Panel B, Microscopic evaluation (Masson's trichrome stain and immunostaining for insoluble fibrin) of the knee intra-articular space of a representative not injured and injured legs after 72 h in $F8^{+/+}Pros1^{+/+}$, $F8^{-/-}Pros1^{+/+}$ and $F8^{-/-}Pros1^{-/-}$ mice. Panel C, In vivo mPS silencing using specific siRNA: evaluation of the joint diameter 72 h after injury in $F8^{-/-}Pros1^{+/-}$ and $F8^{-/-}Pros1^{+/+}$ mice treated with a single i.p. infusion of mPS siRNA or control siRNA. Panel D, Microscopic evaluation (Masson's trichrome stain) of the knee intra-articular space of a representative injured leg after 72 h in $F8^{-/-}Pros1^{+/+}$ mice previously treated with mPS siRNA or Ctrl siRNA. Measurements are presented as mean±s.e.m. *, P<0.05; , P<0.005; *, P<0.0005; ****, P<0.0001.
Figure 15:
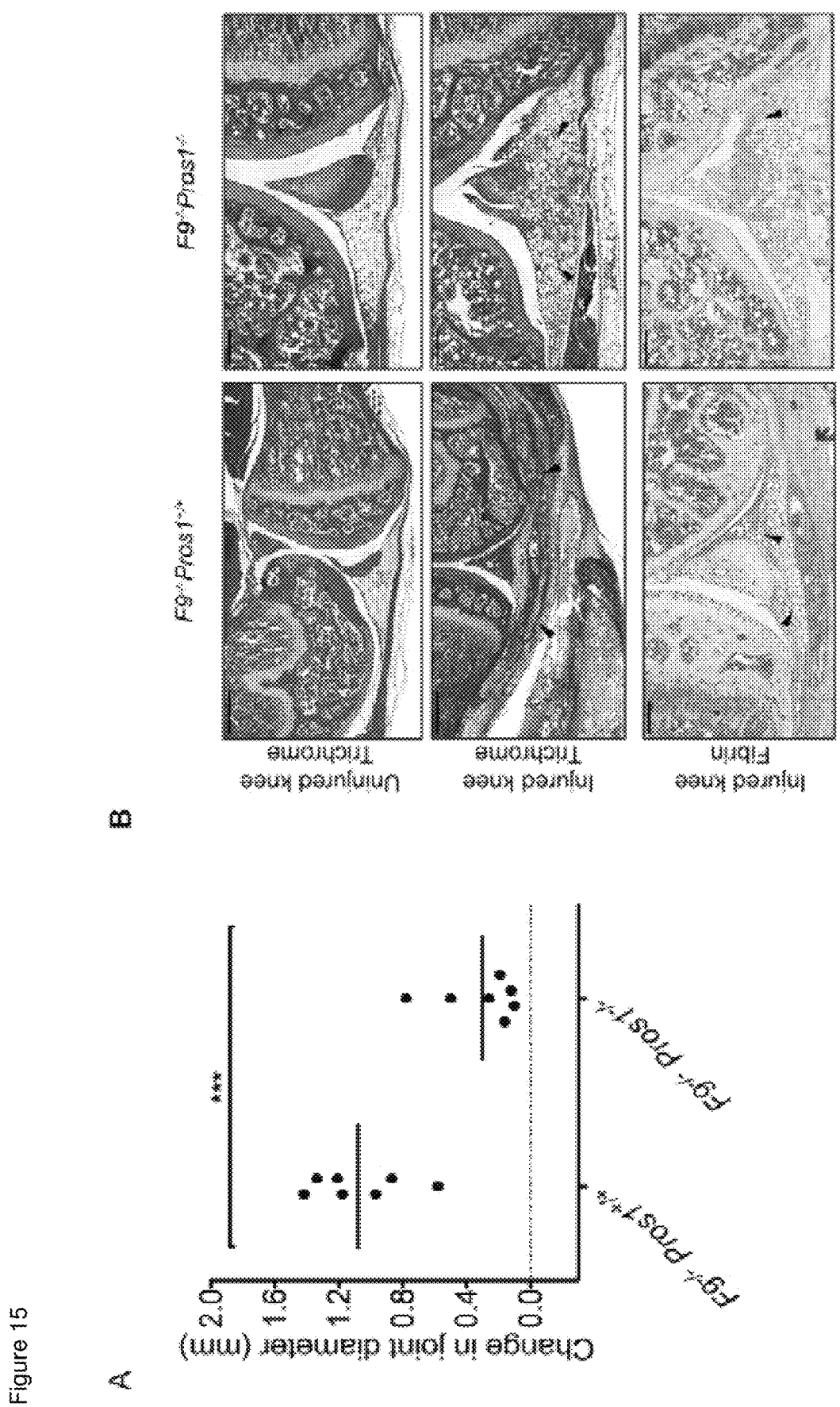
FIG. 15 shows that genetic loss of Pros1 prevents hemarthrosis in mice with haemophilia B. Panel A, Difference between the knee diameter 72 h after the injury and before the injury in $F9^{-/-}Pros1^{+/+}$, $F9^{-/-}Pros1^{+/-}$, $F9^{-/-}Pros^{-/-}$ and $F9^{+/+}Pros1^{+/+}$ mice. Panel B, Microscopic evaluation (Masson's trichrome stain and staining for insoluble fibrin, mAb clone 102-10) of the knee intra-articular space of a representative not injured and injured legs after 72 h in $F9^{+/+}$ $Pros1^{+/+}$, $F9^{-/-}Pros1^{+/+}$ and $F9^{-/-}Pros1^{-/-}$ mice. Scale bar: 500 μm. Measurements are presented as mean±s.e.m. ***, P<0.0005.

Although bleeding may appear anywhere in haemophilia patients, most of haemorrhages occur in the joints. To determine whether Pros1 loss prevents hemarthrosis in haemophilic mice, we applied an AH model to F8$^{-/-}$Pros1$^{+/+}$, F8$^{-/-}$Pros1$^{+/-}$, F8$^{-/-}$Pros1$^{-/-}$ and F8$^{+/+}$Pros1$^{+/+}$ mice. Knee swelling after injury was reduced in F8$^{-/-}$Pros1$^{-/-}$ and F8$^{+/+}$Pros1$^{+/+}$ mice compared to F8$^{-/-}$Pros1$^{+/+}$ and F8$^{-/-}$Pros1$^{+/-}$ mice (FIG. 9A). There was also no difference in knee swelling between F8$^{-/-}$Pros1$^{-/-}$ and F8$^{+/+}$Pros1$^{+/+}$ mice (FIG. 9A). Bleeding was observed in the joint space and synovium of F8$^{-/-}$Pros1$^{+/+}$ (IBS=2, n=5) but not of F8$^{-/-}$Pros1$^{-/-}$ (IBS=0, n=5) and F8$^{+/+}$Pros1$^{+/+}$ mice (IBS=0, n=5) (FIG. 9B). There was more fibrin in joint space and synovium from F8$^{-/-}$Pros1$^{+/+}$ than from F8$^{-/-}$Pros1$^{-/-}$ and F8$^{+/+}$Pros1$^{+/+}$ mice (FIG. 9B). Similar data were obtained with F9$^{-/-}$Pros1$^{+/+}$ and F9$^{-/-}$Pros1$^{-/-}$ mice (IBS=0, n=3 and IBS=2, n=3, respectively) (FIGS. 15A-B).

These results were confirmed by the continuous subcutaneous infusion during 4 days of a PS-neutralizing antibody or a control antibody in F8$^{-/-}$Pros1$^{+/-}$ mice (starting 1 day before AH induction) (knee swelling in PS-neutralizing antibody group was 0.43±0.07 versus 0.69±0.09 mm in control group, n=9, P=0.04). PS plasma level in PS-neutralizing antibody group was 26±6% versus 45±3% in the controls (n=5, P=0.017). In addition, PS inhibition was alternatively achieved by intravenous injection of a murine PS (mPS) siRNA prior to the AH challenge in $F8^{-/-}Pros1^{+/-}$ and $F8^{-/-}Pros1^{+/+}$ mice (FIGS. 9C-D). The IBS assessment confirmed the lack of intra-articular bleeding in $F8^{-/-}Pros1^{+/+}$ mice treated with mPS siRNA (IBS=0.5, n=3) when compared to those treated with control siRNA (IBS=2, n=3), (FIG. 9C). Importantly, PS expression was reduced by mPS siRNA both in plasma (26±3% versus 84±11% in controls, n=3, P=0.006) and in the synovium (FIG. 10A).

Example 13—Both PS and TFPI are Expressed in the Synovium of Mice

To understand the prominent intra-articular haemostatic effect of the genetic loss of Pros1 and PS inhibition in haemophilic mice, knee sections were immunostained for PS and TFPI. PS was mainly present at the lining layer of the synovial tissue of $F8^{-/-}Pros1^{+/+}$ mice with AH treated with control siRNA, whereas synovial staining for PS was remarkably reduced in $F8^{-/-}Pros1^{+/+}$ mice with AH that received mPS siRNA (FIG. 10A). In contrast, TFPI staining was more prominent in synovial tissue from haemophilic mice that received the mPS siRNA than in those that were treated by the control siRNA (FIG. 10A). However, TFPI expression was comparable in synovial lining layer of both $F8^{-/-}Pros1^{+/+}$ and $F8^{-/-}Pros1^{-/-}$ mice (FIG. 10B).

To demonstrate further that PS is expressed by fibroblast-like synoviocytes (FLS), we performed western blots on conditioned media collected from $F8^{-/-}Pros1^{+/+}$, $F8^{-/-}Pros1^{+/+}$ and $F8^{-/-}Pros1^{-/-}$FLS. As shown in FIG. 10C, media of $F8^{-/-}Pros1^{+/+}$ and $F8^{-/-}Pros1^{+/+}$ FLS displayed a band at a molecular weight ~75 kDa comparable to PS and similar to the one observed in plasma and platelets. As expected, no staining was detected in media obtained from $F8^{+/+}Pros1^{-/-}$ FLS (FIG. 10C).

We also studied TFPI expression in $F8^{-/-}Pros1^{+/+}$ and $F8^{-/-}Pros1^{-/-}$ FLS conditioned media (FIG. 10D). All media displayed a band at ~50 kDa similar to the one observed with placenta lysates. TFPI isoform expression was investigated following protein deglycosylation because fully glycosylated TFPIα and TFPIβ migrate at the same molecular weight. Deglycosylated TFPI from FLS media migrated as a single band at the molecular weight of TFPIα similar to placenta TFPI (positive control for TFPIα) (FIG. 10D). This indicates that FLS express TFPIα but not TFPIβ. Moreover, PS and TFPI expression increased in $F8^{-/-}Pros1^{+/+}$ FLS after stimulation with thrombin (FIGS. 10E-F).

Example 14—Both PS and TFPI are Expressed in the Synovium of Patients with HA or HB Human HA, HB and osteoarthritis knee synovial tissues were then analysed for both PS and TFPI (FIG. 11A). A strong signal was found for TFPI and PS in the synovial lining and sublining layers of HA patients on demand (n=7). By contrast, immunostaining for both PS and TFPI was decreased in HA patients under prophylaxis (n=5). HB patients on demand displayed less signal for both PS and TFPI in the synovial lining and sublining layers (n=4) than HA patients on demand. Sections from osteoarthritis patients (n=7) did not show an intense staining for TFPI and PS similarly to haemophilic patients under prophylaxis. To evaluate which isoform of TFPI is expressed by human FLS, western blotting on conditioned media of human FLS isolated from healthy subjects and patients with osteoarthritis was performed. Similarly to murine FLS, human FLS express TFPIα but not TFPIβ (FIG. 11B).

Example 15—Loss of Pros1 is Responsible for the Lack of TFPI-Dependent PS Activity and Resistance to APC in HA Mice The full protection against AH in HA or HB mice lacking Pros1 or in which PS was inhibited could be explained at least partly by the lack of PS cofactor activity for APC and TFPI in the joint. However, the reason for a partial haemostatic effect of the lack of Pros1 or PS inhibition in HA mice challenged in the tail bleeding models needs to be further investigated.

Ex vivo TF-initiated thrombin generation testing has shown a correlation between the capacity of plasma to generate thrombin and the clinical severity of haemophilia. Therefore, we investigated the impact of Pros1 loss on thrombin generation in plasma of HA mice. TFPI-dependent PS activity was not assessed in platelet-free plasma (PFP) but in platelet-rich plasma (PRP) because TFPI-cofactor activity of PS cannot be demonstrated in mouse plasma using thrombin generation tests. This is explained by the lack of TFPIα in mouse plasma and its presence in mouse platelets.

Figure 12:
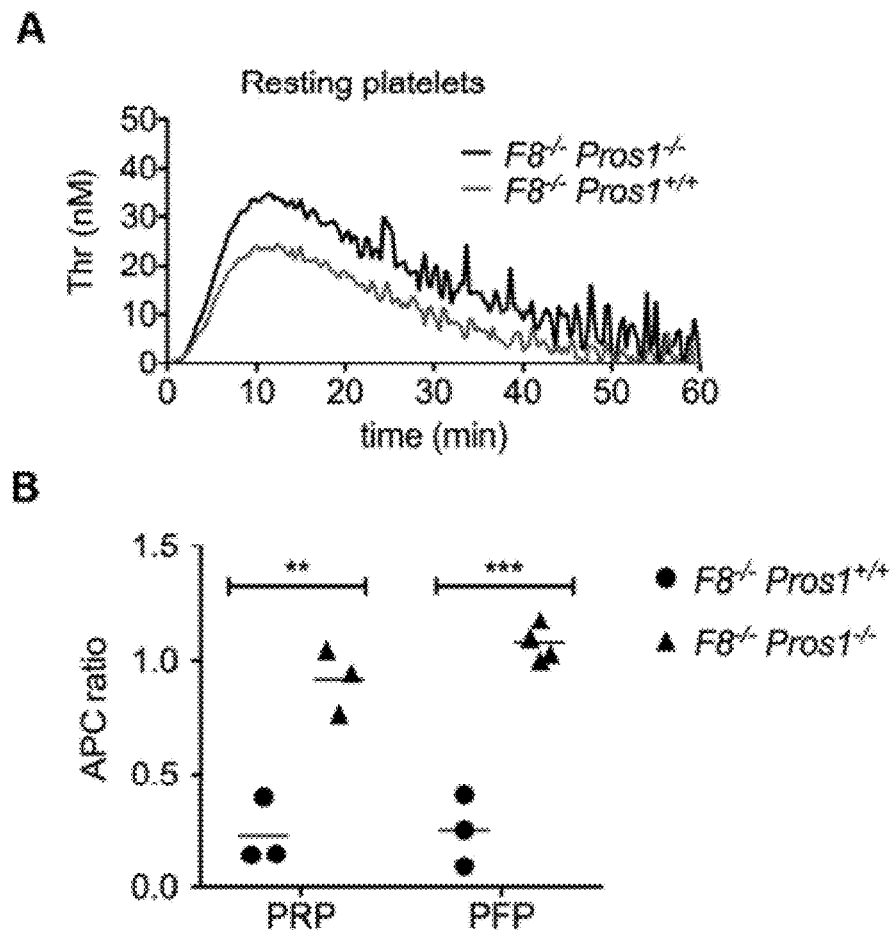
FIG. 12 shows thrombin generation and fibrin network in haemophilia. Panel A, TF- (1 pM) induced thrombin generation in PRP from $F8^{-/-}Pros1^{+/+}$ and $F8^{-/-}Pros1^{-/-}$ mice depicting TFPI-dependent PS activity. Panel B, APC-dependent PS activity in PRP and PFP from $F8^{-/-}Pros1^{+/+}$ and $F8^{-/-}Pros1^{-/-}$ mice. Panel C, Representative scanning electron microscopy images from $F8^{+/+}Pros1^{+/+}$, $F8^{-/-}Pros1^{+/+}$ and $F8^{-/-}Pros1^{-/-}$, and from $F9^{+/+}Pros1^{+/+}$, $F9^{-/-}Pros1^{+/+}$ and $F9^{-/-}Pros1^{-/-}$ fibrin structure. Panels D-G, Thrombin generation triggered by low TF concentration (1 pM) in PFP (Panels D-E) and PRP (Panels F-G) from severe HA patients (FVIII<1%) without (Panels D, F) and with a high titer of inhibitor (Panels E, G). Measurements are presented as mean±s.e.m. , P<0.005; *, P<0.0005.
Figure 12:
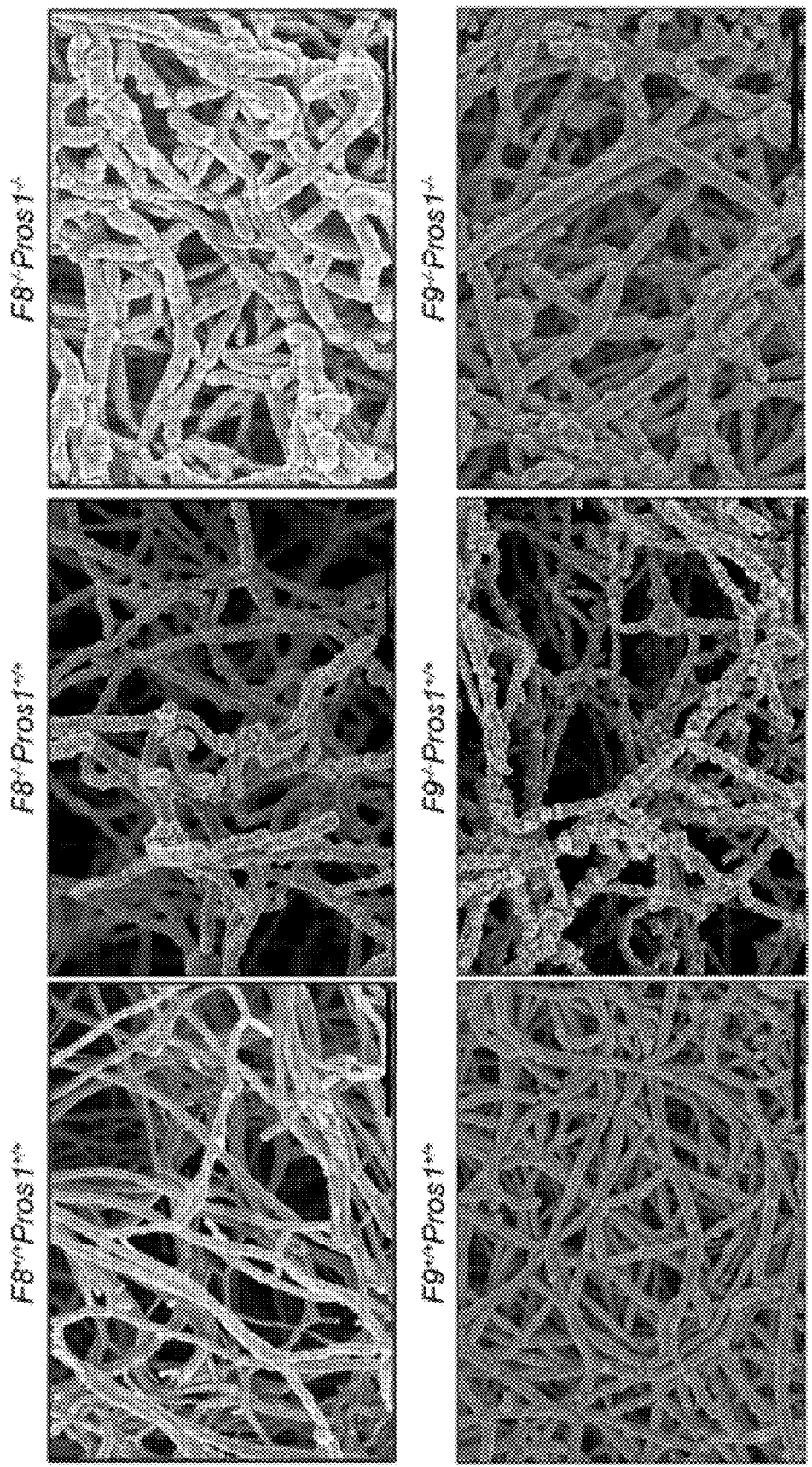
Figure 12:
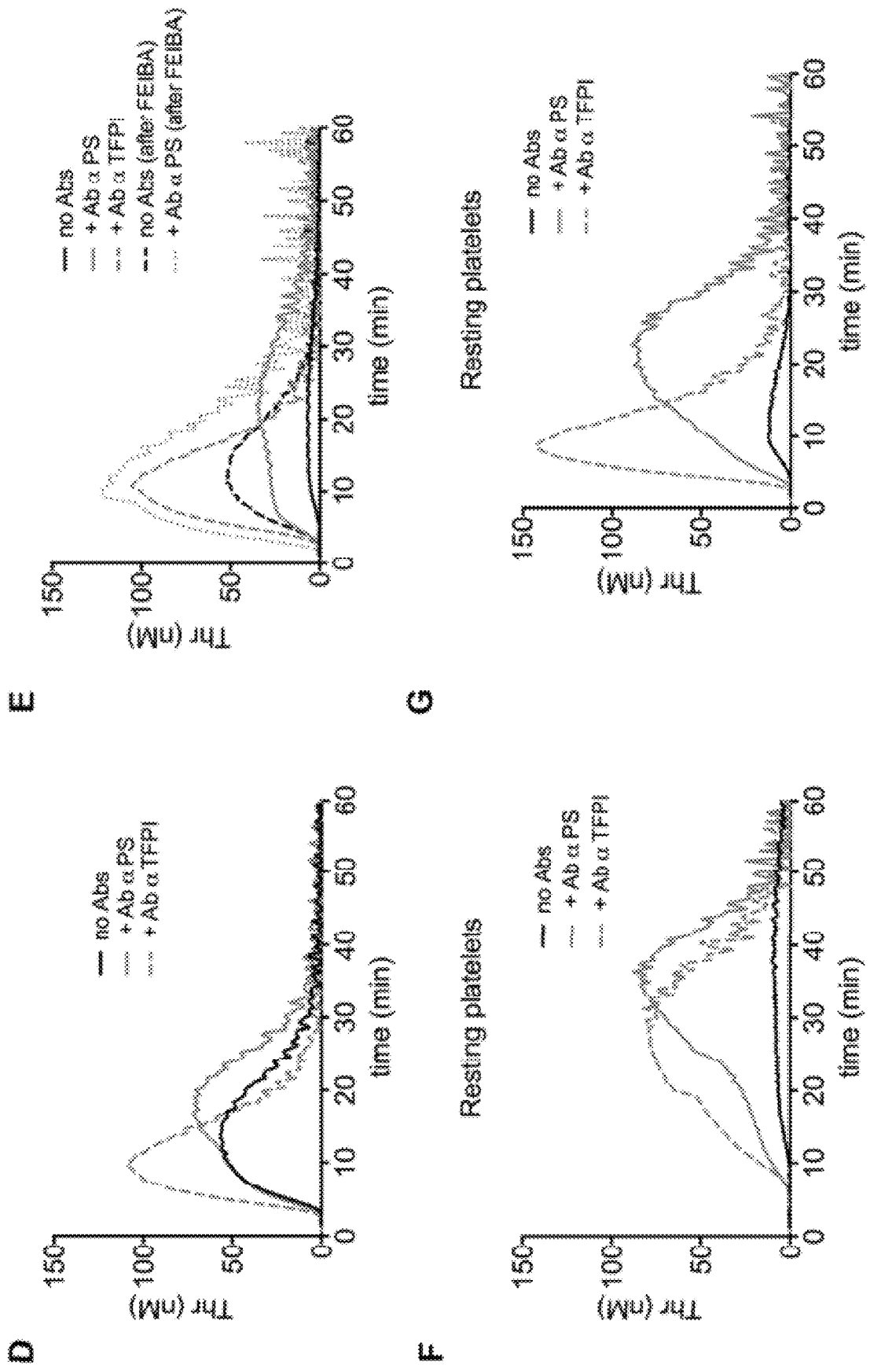

Both thrombin peak and endogenous thrombin potential (ETP) were significantly higher in $F8^{-/-}Pros1^{-/-}$ than in $F8^{-/-}Pros1^{+/+}$ PRP in response to 1 pM TF (1072±160 vs 590±10 nmol/L·min, n=3/group, P=0.04), suggesting the lack of PS TFPI-cofactor activity in $F8^{-/-}Pros1^{-/-}$ PRP (FIG. 12A). Consistent with previous work, both thrombin peak and ETP were comparable in PFP of $F8^{-/-}Pros1^{+/+}$ and $F8^{-/-}Pros1^{-/-}$ mice in presence of 1, 2.5 or 5 pM TF (data not shown).

To assess whether $F8^{-/-}Pros1^{-/-}$ mice exhibited defective functional APC-dependent PS activity, we used thrombin generation testing in $Ca^{2+}$ ionophore-activated PRP in the absence of APC, in the presence of wild-type (WT) recombinant APC, or in the presence of a mutated (L38D) recombinant mouse APC (L38D APC, a variant with ablated PS cofactor activity). In this assay, APC titration showed that the addition of 8 nM WT APC was able to reduce ETP by 90% in activated PRP of WT mice whereas the same concentration of L38D APC diminished ETP by only 30% (data not shown). Based on these data, thrombin generation curves were recorded for activated PRP (3 mice/assay). The calculated APC ratio ($ETP_{+APC\ WT}/ETP_{+APC\ L38D}$) indicated an APC resistance in $F8^{-/-}Pros1^{-/-}$ plasma but not in $F8^{-/-}Pros1^{+/+}$ plasma (0.87±0.13 versus 0.23±0.08, respectively, P=0.01) (FIG. 12B).

APC-dependent PS activity was also tested in PFP from $F8^{-/-}Pros1^{+/+}$ and $F8^{-/-}Pros1^{-/-}$ mice (2 mice/assay) in the presence of 2 nM WT APC and L38D APC. Calculated APC ratio showed an APC resistance in $F8^{-/-}Pros1^{-/-}$ but not in $F8^{-/-}Pros1^{+/+}$ mice (1.08±0.04 versus 0.25±0.09, respectively, P=0.0003) (FIG. 12B).

Example 16—Improved Fibrin Network in HA Mice Lacking Pros1 Mice

Figure 16:
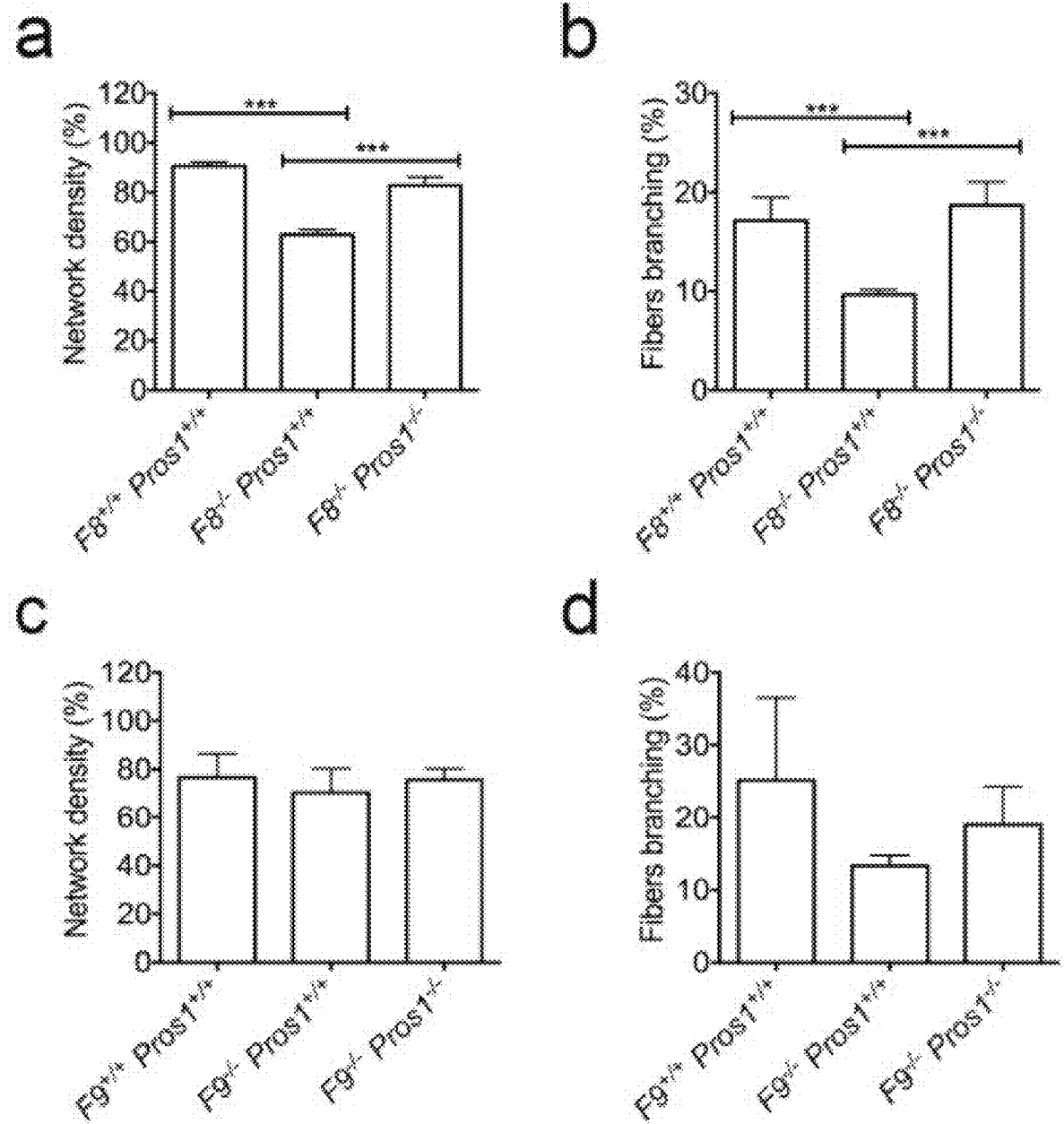
FIG. 16 shows that quantification of fibrin network density and fibres branching. Panels a-b, Fibrin network from $F8^{+/+}Pros1^{+/+}$, $F8^{-/-}Pros1^{+/+}$ and $F8^{-/-}Pros1^{-/-}$ mice. Panels c-d, Fibrin network from $F9^{+/+}Pros1^{+/+}$, $F9^{-/-}Pros1^{+/+}$ and $F9^{-/-}Pros1^{-/-}$. Quantification of fibrin network density (Panels a and c). Quantification of fibres branching (Panels b and d). Measurements are presented as mean±s.e.m. ***, P<0.0005.

Tail bleeding mouse models are not only sensitive to platelet dysfunction but also to coagulation and fibrinolysis alterations. To understand the differences between studied genotypes regarding tail bleeding, we used scanning electron microscopic imaging to investigate fibrin structure (FIG. 12C). Clots from $F8^{+/+}Pros1^{+/+}$ and $F8^{-/-}Pros1^{-/-}$ plasma showed a denser network of highly branched fibrin fibres compared to F8$^{-/-}$Pros1$^{+/+}$ plasma clots (FIGS. 16a-b). In contrast, clots from F9$^{-/-}$Pros1$^{+/+}$ and F9$^{-/-}$Pros1$^{-/-}$ plasma did not display a denser network than F9$^{-/-}$Pros1$^{+/+}$ plasma clots, but a trend for augmented fibres branching (FIGS. 16c-d).

Fibrin fibres from F8$^{-/-}$Pros1$^{-/-}$ and F8$^{-/-}$Pros1$^{+/+}$ mice, and from F9$^{-/-}$Pros1$^{-/-}$ and F9$^{-/-}$Pros1$^{+/+}$ mice, displayed a larger diameter compared to fibres from F8$^{+/+}$Pros1$^{+/+}$ mice or F9$^{+/+}$Pros1$^{+/+}$ mice, respectively. Nevertheless, the fibre surface of F8$^{-/-}$Pros1$^{-/-}$ and F9$^{-/-}$Pros1$^{-/-}$ mice showed less porosity as compared to F8$^{-/-}$Pros1$^{+/+}$ or F9$^{-/-}$Pros1$^{+/+}$ mice, respectively, suggesting that F8$^{-/-}$Pros1$^{-/-}$ and F9$^{-/-}$Pros1$^{-/-}$-derived fibres might be less permeable and thereby more resistant to fibrinolysis than F8$^{-/-}$Pros1$^{+/+}$ or F9$^{-/-}$Pros1$^{+/+}$-derived fibers. These data, in complement to both TFPI and APC cofactor activity results (FIGS. 12A-B), help to explain why tail bleeding in F8$^{-/-}$Pros1$^{-/-}$ was improved when compared to F8$^{-/-}$Pros1$^{+/+}$ mice but not completely corrected as in F8$^{+/+}$Pros1$^{+/+}$ mice.

Example 17—PS Inhibition in Plasma Restores Thrombin Generation in Patients with HA We then examined the effect of PS inhibition on thrombin generation in human HA plasma. ETP in PFP increased 2-4-fold in presence of a PS-neutralizing antibody. Similar results were obtained using an anti-human TFPI antibody against the C-terminal domain for efficient FXa inhibition, even in the presence of FVIII inhibitor (FIGS. 12D-E). PS inhibition had a remarkable effect in PRP samples where it increased ETP more than 10 times (1912±37 and 1872±64 nM*min) (FIGS. 12F and G, respectively). Thus, PS inhibition completely restored ETP in haemophilic plasma (for comparison, ETP in normal plasma: 1495±2 nM*min). Similar results were obtained using the anti-TFPI antibody (FIGS. 12D-G). These data confirm in humans the improvement of thrombin generation in HA PFP and PRP driven by PS inhibition that we observed in mice.

Example 18—Materials and Methods for Examples 6-17

Mice

F8$^{-/-}$ mice (B6; 129S4-F8$^{tm1Kaz}$/J) and F9$^{-/-}$ mice (B6.129P2-F9$^{tm1Dws}$/J) with C57BL/6J background were obtained from The Jackson Laboratory. Pros1$^{+/-}$ mice were progeny of the original colony. The Swiss Federal Veterinary Office approved the experiments.

TF-Induced Pulmonary Embolism

Anesthetized mice, aged 6-9 weeks, received human recombinant TF (hrTF, Dade Innovin, Siemens) intravenously (2 μL/g) at 4.25 nM (1:2 dilution) or 2.1 nM (1:4 dilution). Two minutes after the onset of respiratory arrest or at the completion of the 20-min observation period, lungs were harvested and fixed in 4% PFA. Lung sections were stained with hematoxylin and eosin, and for fibrin. The extent of fibrin clots in the lungs was assessed as number of intravascular thrombi in 10 randomly chosen non overlapping fields (×10 magnification).

Tail Clipping Model in HA Mice

Two different tail clipping models to evaluate bleeding phenotype were assessed as described[14]. Briefly, the distal tail of 8-10 week old mice was transected at 2 mm (mild injury) and the bleeding was venous or at 4 mm (severe injury) and the bleeding was arterial and venous. Bleeding was quantified as blood lost after 30 or 10 min, respectively.

In the severe injury model some F8$^{-/-}$Pros1$^{+/-}$ mice received a rabbit anti-human PS-IgG (Dako) or rabbit isotype IgG (R&D Systems) intravenously at a dose of 2.1 mg/kg 2 min before tail transection.

Acute Hemarthrosis Model

Joint diameters were measured at 0 and 72 h with a digital calliper (Mitutoyo 547-301, Kanagawa). At 72 h, mice were sacrificed, knees were isolated, fixed in 4% PFA, decalcified and embedded in paraffin. The intra-articular bleeding score (IBS) was assessed as described.

In Vivo PS Inhibition 10-week-old mice received a continuous infusion of rabbit anti-human PS-IgG (Dako Basel, Switzerland) or rabbit isotype IgG (R&D Systems) at 1 mg/kg/day through subcutaneous osmotic minipumps (model2001, Alzet).

Alternatively, 10-week-old mice were treated with a single dose of mouse specific siRNA (s72206, Life Technologies) or control siRNA (4459405, In vivo Negative Control #1 Ambion, Life Technologies) at 1 mg/kg using a transfection agent (Invivofectamine 3.0, Invitrogen, Life Technologies) following the manufacturer's instructions. Acute hemarthrosis model was applied 2.5 days after PS inhibition.

Statistical Methods

Values were expressed as mean±sem. Chi-square for non-linked genetic loci was used to assess the Mendelian allele segregation. Survival data in the TF-induced venous thromboembolism model were plotted using the of Kaplan-Meier method. A log-rank test was used to statistically compare the curves (Prism 6.0d; GraphPad). The other data were analysed by t-test, one-way and two-way ANOVA test with GraphPad Prism 6.0d. A P-value of less than 0.05 was considered statistically significant.

Preparation of Murine Plasma

Mice aged 6-9 weeks were anesthetized with pentobarbital (40 mg/kg), and whole blood was drawn from the inferior vena cava into 3.13% citrate (1 vol anticoagulant/9 vol blood). Blood was centrifuged at 1031 g for 10 min with the centrifuge pre-warmed to 26° C. to obtain platelet rich plasma (PRP). Alternatively, blood was centrifuged at 2400 g for 10 min at room temperature (RT), to obtain platelet-poor plasma (PPP). To obtain platelet-free plasma (PFP), an additional centrifugation at 10000 g for 10 min was performed.

Platelet Count and Measurement of Coagulation Parameters

Platelet counts were carried out with an automated cell counter (Procyte Dx Hematology Analyzer, IDEXX). Fibrinogen, FVIII and FIX activity were measured on an automated Sysmex CA-7000 coagulation analyser (Sysmex Digitana). Prothrombin time (PT) and activated partial thromboplastin time (APTT) were measured on a coagulometer (MC4plus, Merlin Medical).

Measurement of Murine PS Antigen and TAT Complexes by ELISA

Wells from 96-well plates (Maxisorb, Thermo) were coated with 50 μL per well of 10 μg/mL of rabbit polyclonal anti-human PS (DAKO Cytomation) and incubated overnight at 4° C. After 3 washes with TBS buffer (0.05 M tris(hydroxymethyl)aminomethane, 0.15 M NaCl, pH 7.5, 0.05% Tween 20), the plate was blocked with TBS-BSA 2%. Diluted plasma samples (dilution range: 1:300-1:600) were added to the wells and incubated at RT for 2 h. After 3 washed, 50 μL of 1 μg/mL biotinylated chicken polyclonal anti-murine protein S were added and incubated for 2 h at RT. Signal was amplified by streptavidin-HRP conjugated horseradish peroxidase (Thermo) was added and plates incubated for 1 h. The plates were washed 3 times and 100 µLTMB substrate (KPL) was added. Reactions were stopped by adding 100 µL HCl (1M). Absorbance was measure at 450 nm. Standard curves were set up by using serial dilution of pooled normal plasma obtained from 14 healthy mice (8 males and 6 females, 7-12 weeks old). Results were expressed in percentage relative to the pooled normal plasma.

TAT level was measured in duplicate for each plasma sample using a commercially available ELISA (Enzygnost TAT micro, Siemens), according to the manufacturer's instructions.

Mouse Tissue Processing and Sectioning, Immunohistochemistry and Microscopy Tissue sections (4 µm) with no pre-treatment were stained with haematoxylin/eosin or Masson Trichrome or immunostained for insoluble fibrin, PS or TFPI. The following antibodies were used: fibrin (mAb clone 102-10)[1] final concentration 15.6 µg/mL, incubation for 30 min at RT, secondary antibody rabbit anti-human, (ab7155 Abcam, Cambridge, UK) 1:200 dilution, incubation for 30 min at RT; PS (MAB 4976, R&D, dilution 1:50) incubation for 30 min at RT, secondary antibody rabbit anti-rat, (ab7155 Abcam)-1:200 dilution, incubation for 30 min at RT; TFPI (PAHTFPI-S, Hematological Technologies) final concentration 18.6 µg/mL, incubation for 30 min at RT, secondary antibody rabbit anti-sheep IgG (ab7106, Abcam) 1:200 dilution, incubation for 30 min at RT. All the stainings were performed with the immunostainer BOND RX (Leica Biosystems, Muttenz, Switzerland) following manufacturer's instructions. Whole slides were scanned using 3D HISTECH Panoramic 250 Flash II, with 20× (NA 0.8), 40× (NA 0.95) air objectives. Images processing was done using Panoramic Viewer software.

In Vivo Administration of FVIII to Mice with Complete Genetic Loss of F8

Mice, aged 6-9 week, were anesthetized with ketamine (80 mg/kg) and xylazine (16 mg/kg). We administered intravenously either 0.3 U/kg of recombinant FVIII (Advate®, Baxalta) to reach a FVIII level of 100% at 1 h (normal dose) or an overdose of recombinant FVIII (2 U/kg) to reach >200% at 1 h. Either the normal dose or the overdose was injected 1 h before and 1 h after the introduction of a jugular vein catheter (Mouse JVC 2Fr PU 10 cm, Instech) and then 4 h, 8 h and 16 h after the placement of the central line. Mice were sacrificed 24 h after the first injection. Blood was drawn and organs were harvested. FVIII, fibrinogen and thrombin-antithrombin complexes (TAT) were measured as described in the examples. Lungs were isolated, fixed in 4% paraformaldehyde (PFA) and embedded in paraffin.

FeCl$_3$ Injury Thrombosis Model in Mesenteric Arteries

A model of thrombosis in mesenteric arteries using intravital microscopy was performed according to reference[2] with minor modifications. Mice were anesthetized by intraperitoneal injection of a mixture of ketamine (80 mg/kg) and xylazine (16 mg/kg). Platelets were directly labelled in vivo by the injection of 100 µL rhodamine 6G (1.0 mM). After selection of the studied field, vessel wall injury was generated by a filter paper (1 mm diameter patch of 1 M Whatman paper) saturated with 10% FeCl$_3$ applied topically for 1 min. Thrombus formation was monitored in real time under a fluorescent microscope (IV-500, Micron instruments, San Diego, Calif.) with an FITC filter set, equipped with an affinity corrected water-immersion optics (Zeiss, Germany). The bright fluorescent labelled platelets and leucocytes allowed the observation of 1355 µm×965 µm field of view through video triggered stroboscopic epi-illumination (Chadwick Helmuth, El Monte, Calif.). A 10× objective Zeiss Plan-Neofluar with NA0.3. was used. All scenes were recorded on video-tape using a customized low-lag silicon-intensified target camera (Dage MTI, Michigan city, IN), a time base generator and a Hi-8 VCR (EV, C-100, Sony, Japan). Time to vessel wall occlusion was measured, as determined by cessation of the blood cell flow.

Fibroblast-Like Synoviocytes (FLS) Isolation, Culture and Flow Cytometry

Murine FLS from 8-10 weeks old mice were isolated and cultured according to[3]. After three passages, phase contrast images of cells were taken, and cells were incubated with FITC-conjugated rat anti-mouse CD11b antibody (M1/70, Pharmingen, BD Biosciences), PE-conjugated rat anti-mouse CD90.2 antibody (30-H12, Pharmingen, BD Biosciences), FITC-conjugated rat anti-mouse CD106 antibody (429 MVCAM.A, Pharmingen, BD Biosciences), PE-conjugated hamster anti-mouse CD54 antibody (3E2, Pharmingen, BD Biosciences), and fluorochrome-conjugated isotype control antibodies for 30 min at 4° C. in the dark. After a final washing and centrifugation step, all incubated cells were analysed on an LSR II flow cytometer (BD Biosciences) and FACS Diva 7.0 software (BD Biosciences). Human FLS from healthy individual and OA patient were purchased from Asterand, Bioscience and cultured according to manufacture instructions.

Western Blotting

PS and TFPI were detected in human and mouse samples by sodium dodecyl sulfate-polyacrylamide gel electrophoresis (12% gradient SDS-PAGE, Bio-Rad) under reducing conditions. The proteins were transferred to nitrocellulose membranes (Bio-Rad), and then visualized using: 2 ug/mL monoclonal MAB-4976 (R&D system) for murine PS, 1 µg/mL polyclonal AF2975 for murine TFPI (R&D system). Recombinant murine PS[4] (30 ng), recombinant human TFPI full length (provided by T. Hamuro, Kaketsuken, Japan), lysate of washed platelets, PFP from F8$^{-/-}$Pros1$^{+/+}$ mice and placenta lysates from F8$^{-/-}$Pros1$^{+/+}$ mice were used as PS, TFPIα controls. Samples from confluent murine and human FLS conditioned media were collected after 24 h-incubation in a serum-free media (OptiMem) and concentrated 40 times using Amicon filter devices (Millipore, 10 kDa cut-off). For TFPI western blotting, samples were treated with a mixture of five protein deglycosidases (PNGase F, O-Glycosidase, Neuraminidase, β1-4 Galactosidase, β-N-Acetylglucosaminidase, Deglycosylation kit, V4931, Promega) for 12 h at 37° C. before being loaded on the gel. Final detection was completed by using a horseradish peroxidase-conjugated secondary antibody (Dako) and the Supersignal West Dura Extended Duration Chemiluminescence Substrate (Pierce), monitored with a Fuji LAS 30001R CCD camera.

Immunohistochemistry on Human Knee Synovium

Paraffin-embedded specimens of synovial tissue from twelve HA patients and four HB patients who underwent arthroplasty for severe knee arthropathy were collected at the archives of the Section of Anatomy and Histology, Department of Experimental and Clinical Medicine, University of Florence. Seven HA patients were treated on demand and five with secondary prophylaxis. All four HB patients were treated on demand. Synovial samples from seven osteoarthritis (OA) patients were used as controls. For immunohistochemistry analysis, synovial tissue sections (5 µm thick) were deparaffinized, rehydrated, boiled for 10 minutes in sodium citrate buffer (10 mM, pH 6.0) for antigen retrieval and subsequently treated with 3% H$_2$O$_2$ in methanol for 15 min at room temperature to block endogenous peroxidase activity. Sections were then washed in PBS and incubated with Ultra V block (UltraVision Large Volume Detection System Anti-Polyvalent, HRP, catalogue number TP-125-HL, LabVision) for 10 min at RT according to the manufacturer's protocol. After blocking non-specific site binding, slides were incubated overnight at 4° C. with rabbit polyclonal anti-human Protein S/PROS1 antibody (1:50 dilution, catalogue number NBP1-87218, Novus Biologicals) or sheep polyclonal anti-human Tissue Factor Pathway Inhibitor (TFPI) antibody (1:500 dilution, catalogue number PAHTFPI-S, Haematologic Technologies) diluted in PBS. For PS immunostaining, tissue sections were then incubated with biotinylated secondary antibodies followed by streptavidin peroxidase (UltraVision Large Volume Detection System Anti-Polyvalent, HRP; LabVision) according to the manufacturer's protocol. For TFPI immunostaining, tissue sections were instead incubated with HRP-conjugated donkey anti-sheep IgG (1:1000 dilution; catalogue number ab97125; Abcam) for 30 min. Immunoreactivity was developed using 3-amino-9-ethylcarbazole (AEC kit, catalogue number TA-125-SA; LabVision) as chromogen. Synovial sections were finally counterstained with Mayer's haematoxylin (Bio-Optica), washed, mounted in an aqueous mounting medium and observed under a Leica DM4000 B microscope (Leica Microsystems). Sections not exposed to primary antibodies or incubated with isotype-matched and concentration-matched non-immune IgG (Sigma-Aldrich) were included as negative controls for antibody specificity. Light microscopy images were captured with a Leica DFC310 FX 1.4-megapixel digital colour camera equipped with the Leica software application suite LAS V3.8 (Leica Microsystems).

Fibrin Clot Ultrastructure Investigation

Fibrin clots were prepared at 37° C. from PFP by the addition of ~5 nM TF (Dade Innovin, Siemens). They were then fixed in 2% glutaraldehyde, dehydrated, dried and sputter-coated with gold palladium for visualization using scanning electron microscopy. Semi quantitative evaluation of network density and fibers branching were performed using STEPanizer software (www.stepanizer.com).

Calibrated Automated Thrombography Assays in Murine Samples

Thrombin generation in PFP and PRP was determined using the calibrated automated thrombogram (CAT) method.

TFPI dependent PS activity was assessed in PRP (150 G/L), as follows. Briefly, 10 µL mouse PRP (150 G/L) was mixed with 10 µL PRP reagent (Diagnostica Stago), and 30 µL of buffer A (25 mm Hepes, 175 mm NaCl, pH 7.4, 5 mg/mL BSA). Thrombin generation was initiated at 37° C. with 10 µL of a fluorogenic substrate/$CaCl_2$ mixture. Final concentrations were as follows: 16.6% mouse plasma, 1 pM hrTF, 4 µM phospholipids, 16 mM $CaCl_2$, and 0.42 mM fluorogenic substrate.

APC dependent PS activity was assessed in a CAT-based APC resistance test in mouse PFP and PRP. PRP (150 G/L) was previously activated using 40 µM $Ca^{2+}$ ionophore (A23187) for 5 min at 37 C. Final concentrations were as follows: 16.6% mouse plasma, 22 µM A23187, 1 pM hrTF, 4 µM phospholipids, 2 nM (for PFP) or 8 nM (for PRP) wild type recombinant mouse APC (wt-rmAPC) or mutated recombinant mouse APC (rmAPC L38D), 16 mM $CaCl_2$, and 0.42 mM fluorogenic substrate.

For TF titration on PFP, the following reagents were used: PPP reagent and MP reagent (Diagnostica Stago).

Fluorescence was measured using a Fluoroscan Ascent® fluorometer, equipped with a dispenser. Fluorescence intensity was detected at wavelengths of 390 nm (excitation filter) and 460 nm (emission filter). A dedicated software program, Thrombinoscope® version 3.0.0.29 (Thrombinoscope bv) enabled the calculation of thrombin activity against the calibrator (Thrombinoscope bv) and displayed thrombin activity with the time. All experiences were carried out in duplicate at 37° C. and the measurements usually lasted 60 min.

CAT Assay in Human Samples

Written informed consent was obtained from patients. Venous blood was drawn by venipuncture in 3.2% sodium citrate (vol/vol) and centrifuged at 2000 g for 5 min. Platelet-poor plasma (PPP) was then centrifuged at 10000 g for 10 min to obtain PFP. PFP was aliquoted, snap-frozen, and stored at −80° C. until use. For PRP, blood was centrifuged at 180 g×10 min. All subjects gave informed consent to participation. Thrombin generation was assessed in human PFP and PRP, according to ref[13] with minor changes. Briefly, 68 µL PFP or PRP (150 G/L) was incubated for 15 min at 37° C. with 12 µL of either a polyclonal rabbit anti-human PS-IgG antibody (0.42 mg/mL, Dako) or monoclonal antibodies against TFPI (0.66 µm, MW1848, Sanquin) or buffer A. Coagulation was initiated with 20 µL of a 7:1 mixture of the PPP low and PPP 5 pm reagents (Diagnostica Stago) for PFP samples or with PRP reagent (Diagnostica stago) for PRP samples. After addition of 20 µL of $CaCl_2$ and fluorogenic substrate (1-1140; Bachem), the thrombin generation was followed in a Fluoroskan Ascent reader (Thermo Labsystems).

Discussion of Examples 6-17

As PS is a key regulator of thrombin generation, we considered that targeting PS could constitute a potential therapy for haemophilia.

Figure 10:
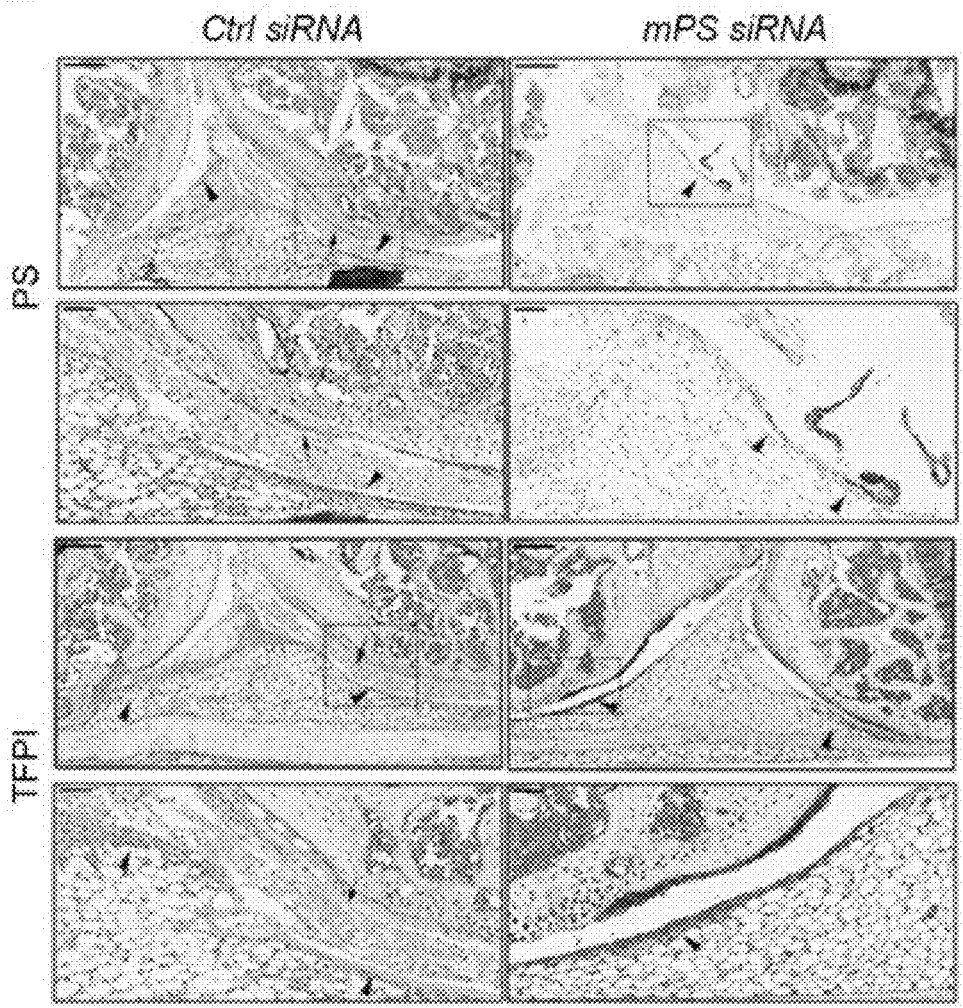
FIG. 10 shows that both PS and TFPI are expressed in murine synovium. Panel A, Immunostaining for PS and TFPI in the knee intra-articular space of injured knees from $FB^{-/-}$ $Pros1^{+/+}$ mice previously treated with Ctrl-siRNA or mPS-siRNA. Arrow heads point to synovial tissue and arrows, to vascular structures, all positive for both PS and TFPI. Boxes in the upper figures (Scale bars: 200 µm) show the area enlarged in the panel below (Scale bars: 50 µm). Panel B, Immunostaining for TFPI in the knee intra-articular space of not injured knees from $F8^{-/-}Pros1^{+/+}$ and $F8^{-/-}Pros1^{-/-}$ mice. Panels C-E, Western blot analysis of conditioned media from primary murine fibroblast-like synoviocytes (FLS) cultures using anti-PS (Panel C) and anti-TFPI (Panel d) antibodies. Platelet-free plasma (PFP), protein lysates from platelets (PLT), murine PS (mPS) were used as positive controls (Panel C). TFPI isoform expression determined by comparing molecular weights of deglycosylated TFPI and of fully glycosylated TFPI. Murine placenta was used as positive control for TFPIα. Panels E-F, Western blot analysis of total protein lysates isolated from FLS after 24 h of culture in presence of thrombin (Thr, +) or of a vehicle (−) using anti-PS (Panel F) and anti-TFPI (Panel E) antibodies. Human recombinant TFPI full length was used as positive control for TFPIα (hrTFPI). Blots are representative of three independent experiments.
Figure 10:
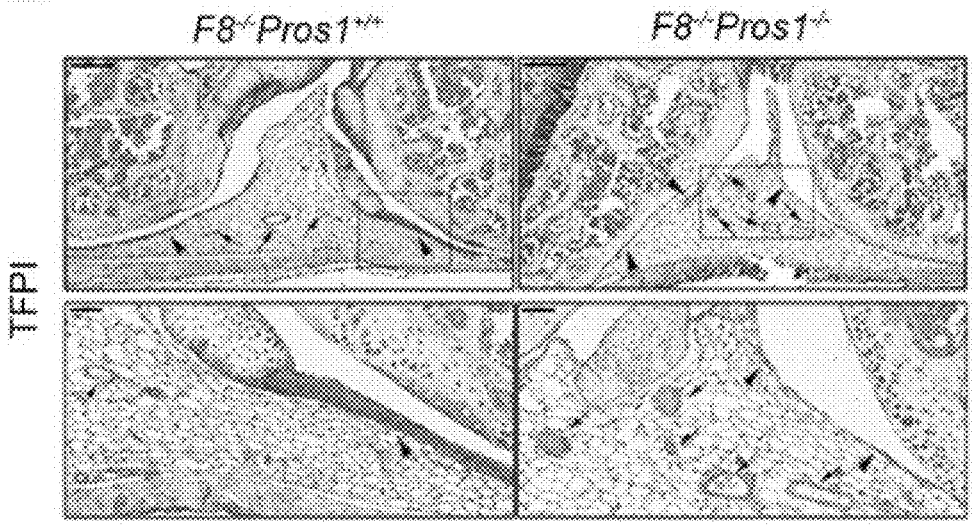
Figure 10:
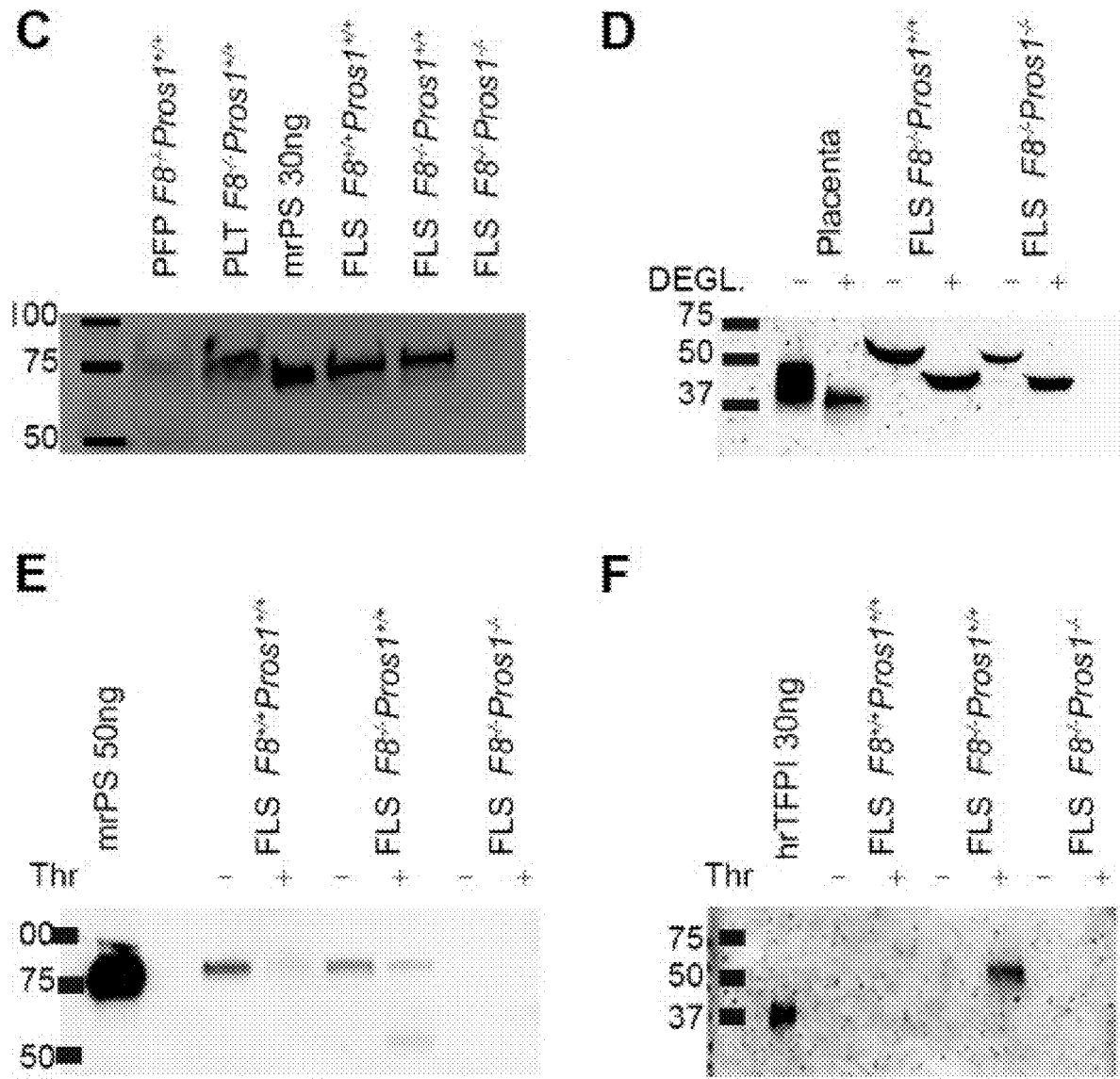

Extensive studies in mice provide proof of concept data supporting a central role for PS and TFPI as contributing to bleeding and serious joint damage in haemophilic mice. Targeting Pros1 or inhibiting PS has the ability to ameliorate haemophilia in mice as judged by the in vivo improvement of the bleeding phenotype in the tail bleeding assays and the full protection against hemarthrosis (FIGS. 8A-C and 9). Because joints display a very weak expression of TF and synovial cells produce a high amount of TFPIα and PS (FIG. 10), the activity of the extrinsic pathway is greatly reduced intra-articularly, predisposing haemophilic joints to bleed. Moreover, both thrombomodulin (TM) and endothelial protein C receptor (EPCR) are expressed by FLS, suggesting that the TM-thrombin complex activates EPCR bound-PC to generate the very potent anticoagulant, APC, in the context of AH. Importantly, the expression of TFPIα is upregulated by thrombin (FIG. 10F). Thus, AH that usually results in marked local inflammation and joint symptoms that can last for days to weeks also promotes the local generation and secretion of multiple anticoagulants, namely APC, TFPIα, and their mutual cofactor PS, that could help explain the pathophysiology of joint damage in haemophilia.

Figure 11:
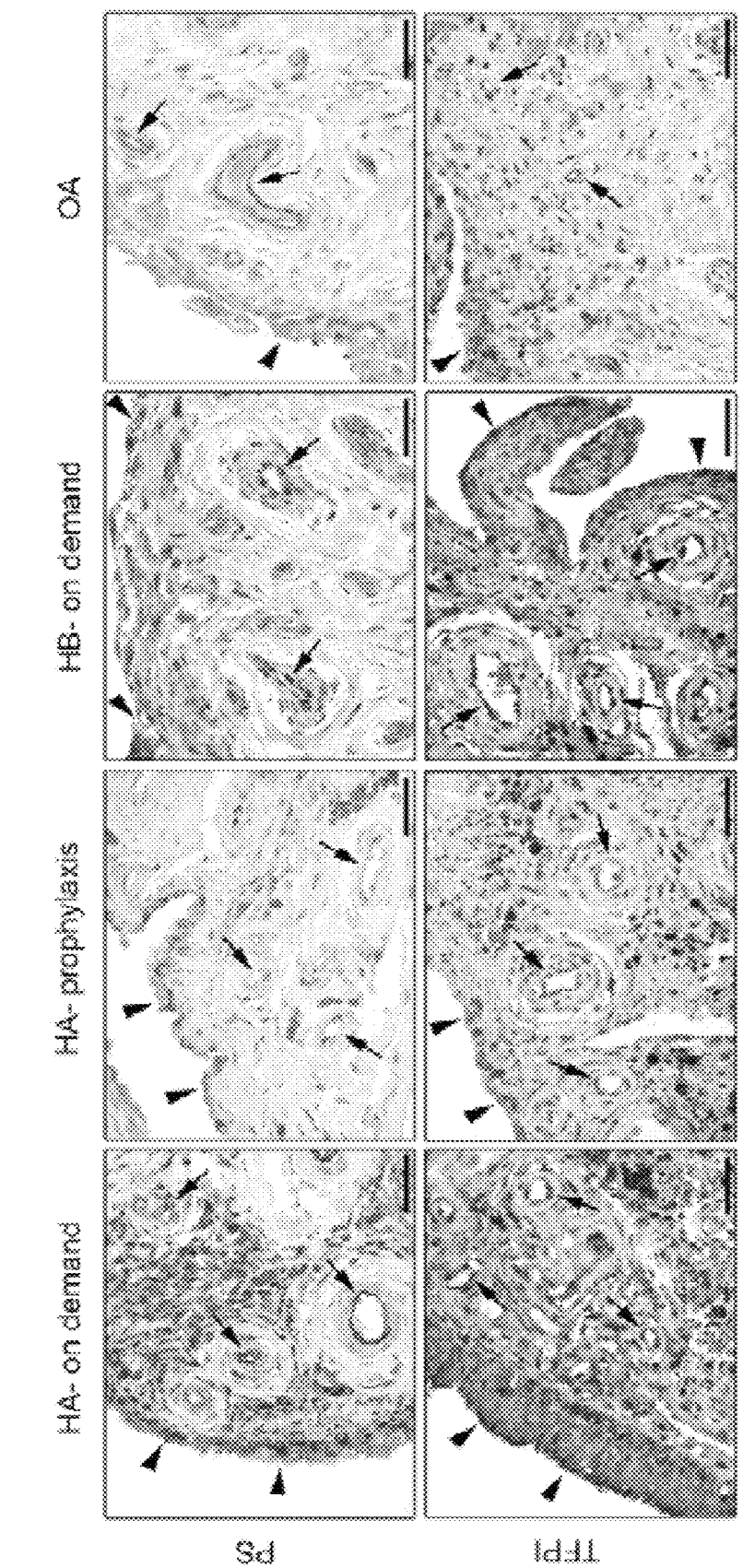
FIG. 11 shows PS and TFPI in human synovium. Panel A, PS and TFPI are expressed in synovial tissue of patients with HA (on demand and on prophylaxis), HB on demand or osteoarthritis (OA). Arrowheads point to synovial lining layer and arrows, to vascular structures in the sublining layer, all positive for both PS and TFPI. Scale bars: 50 μm. Panel B, Western blot analysis of conditioned media of primary human FLS (hFLS) cultures from a healthy individual and an OA patient before and after deglycosylation using anti-TFPI antibody. Human platelet lysate (hPLT) was used as positive control for TFPIα. Blots are representative of three independent experiments.
Figure 11:
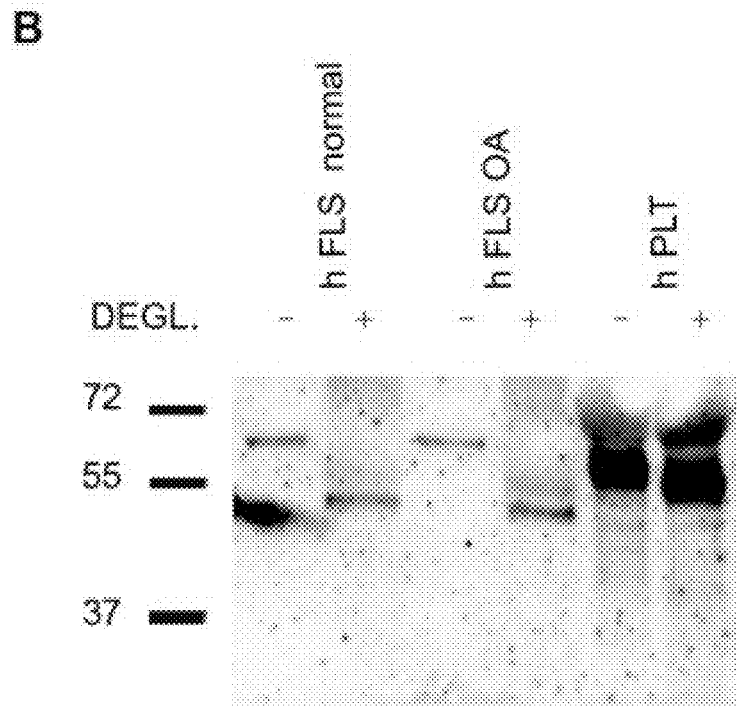

Observations using clinical samples from haemophilic patients are consistent with the lessons learned from murine studies. In humans, blocking PS in plasma from patients with HA with or without inhibitors normalizes the ETP (FIGS. 12D-G). Patients with HB display less intra-articular expression of TFPI and PS than patients with HA, consistent with current knowledge that patients with HB bleed less than those with HA (FIG. 11). Moreover, patients with HA receiving prophylaxis display less TFPI and PS synovial expression than patients receiving FVIII concentrates only in the context of bleeding, i.e., so called "on demand therapy" (FIG. 11A). Finally, human FLS secrete both TFPIα and PS as observed in mice, thus strengthening the extrapolation of murine haemophilia data to humans.

The extensive findings in this report lead us to propose that targeting PS may potentially be translated to therapies useful for haemophilia. PS in human and murine joints is a novel pathophysiological contributor to hemarthrosis and constitutes an attractive potential therapeutic target especially because of its dual cofactor activity for both APC and TFPIα within the joints. In the presence of PS, hemarthrosis increases TFPIα expression in the synovia. Targeting PS in mice protects them from hemarthrosis. Thus, we propose that TFPIα and its cofactor PS, both produced by FLS, together with the TM-EPCR-PC pathway, comprise a potent intra-articular anticoagulant system that has an important pathologic impact on hemarthrosis. The murine PS silencing RNA that we successfully used in haemophilic mice (FIGS. 9H-I and FIG. 10A) is a therapeutic approach that we would develop for haemophilic patients. The advantage of silencing RNA over current factor replacement therapy is its longer half-life reducing the frequency of the injections and its possible subcutaneous administration route.

Example 19—Inhibition of PROS1 Target Gene Expression in Primary Hepatocytes by PROS1 siRNA Conjugates The example shows dose dependent reduction of PROS1 mRNA levels in primary hepatocytes by EU149 to EU160 by receptor mediated uptake.

Figure 17:
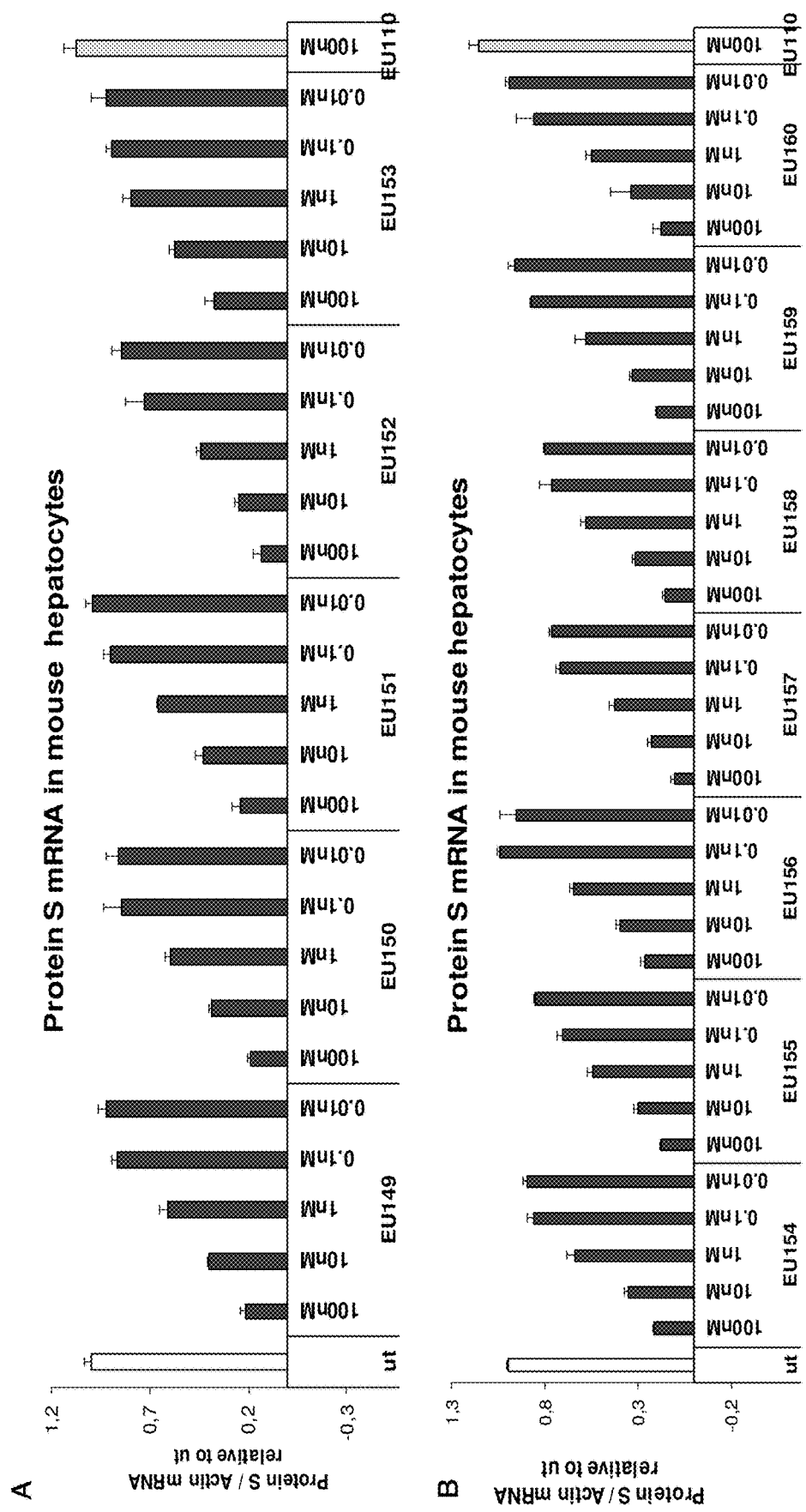
FIG. 17, Panels A and B show inhibition of PROS1 target gene expression in primary hepatocytes by different PROS1 siRNA conjugates.

Primary mouse hepatocytes were seeded in a 96 well plate at a density of 25 000 cells per well. After attachment they were incubated with PROS1 siRNA conjugates in the cell culture medium at 100 nM, 10 nM, 1 nM, 0.1 nM and 0.01 nM as indicated in FIG. 17, or they were incubated with 100 nM non-targeting control conjugates (EU110). The following day cells were lysed for RNA extraction and PROS1 and Actin mRNA levels were determined by Taqman qRT-PCR. Values obtained for PROS1 mRNA were normalized to values generated for the house keeping gene Actin, and related to mean of untreated sample (ut) set at 1-fold target gene expression. Each bar represents mean+/−SD from three biological replicates. siRNA conjugates used in this study are listed in Table 2. Results with EU149 to 153 are shown in FIG. 17A, results with EU154 to EU160 are shown in FIG. 17B.

Example 20—Inhibition of Human PROS1 Gene Expression in Primary Human Hepatocytes by Receptor Mediated Uptake The example shows dose dependent reduction of human PROS1 mRNA levels by EU149 to EU152, EU156, EU159 and EU160 in primary human hepatocytes by receptor mediated uptake.

Figure 18:
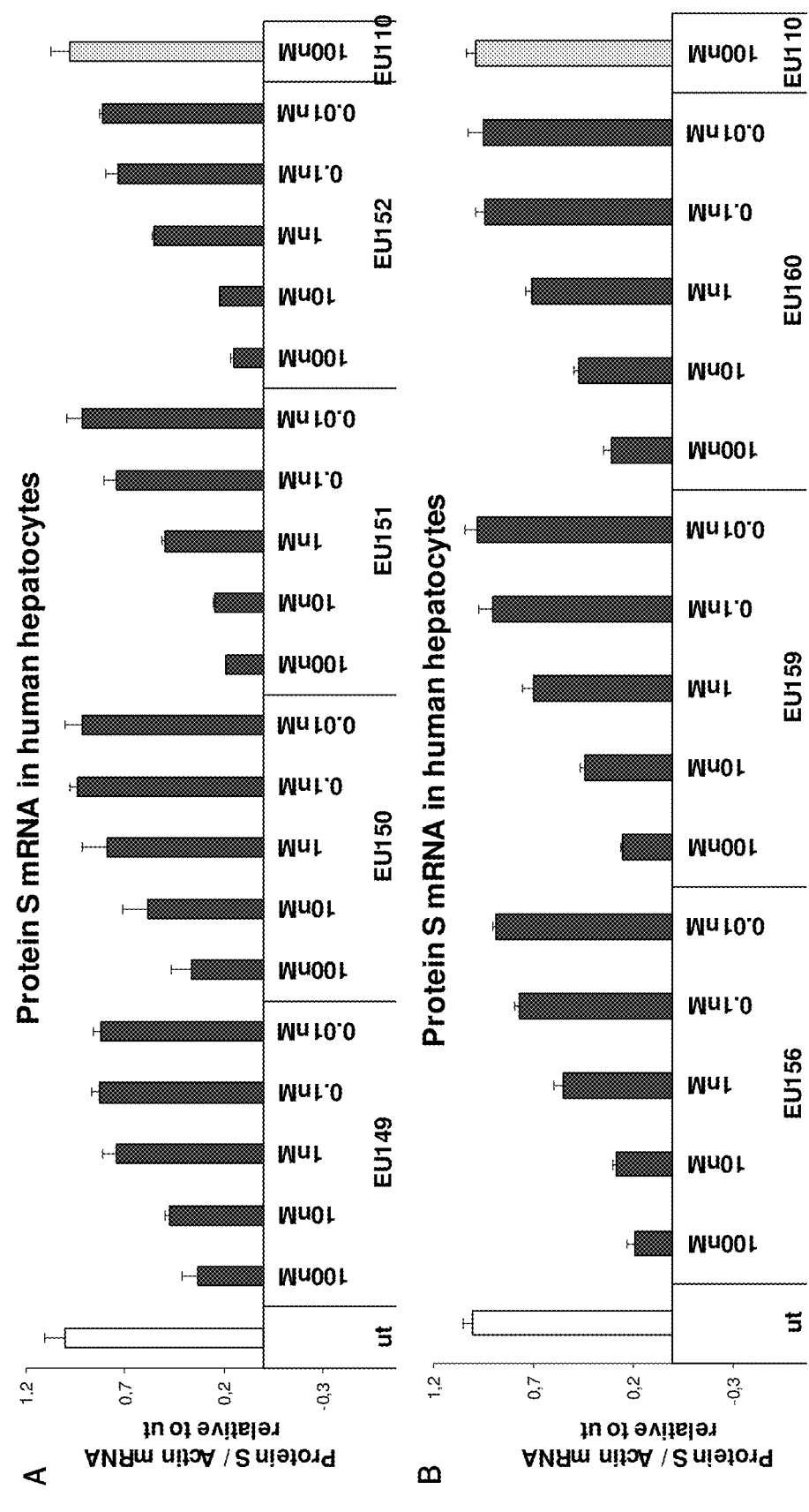
FIG. 18, Panels A and B show inhibition of human PROS1 gene expression in primary human hepatocytes by receptor mediated uptake of different PROS1 siRNA conjugates.

Primary human hepatocytes (Life Technologies) were seeded in a 96 well plate at a density of 35 000 cells per well in plating medium and were subsequently incubated with PROS1 siRNA conjugates EU149 to EU152, EU156, EU159 and EU160, in concentrations of 100 nM, 10 nM, 1 nM, 0.1 nM or 0.01 nM as shown in FIG. 18, or they were incubated with non-targeting control conjugates at 100 nM (EU110). Values obtained for PROS1 mRNA were normalized to values generated for the house keeping gene Actin and related to mean of untreated sample (ut) set at 1-fold target gene expression. Each bar represents mean+/−SD from three biological replicates. siRNA conjugates used in this study are listed in Table 2. Results with EU149 to 153 are shown in FIG. 18A, results with EU156, EU159 and EU160 are shown in FIG. 18B.

Example 21—Inhibition of PROS1 Gene Expression In Vivo by Single Administration of PROS1 siRNA Conjugates The example shows dose dependent in vivo reduction of PROS1 mRNA levels in the liver of mice treated with EU140 to EU145, EU150 to EU152 or by EU159.

Figure 19:
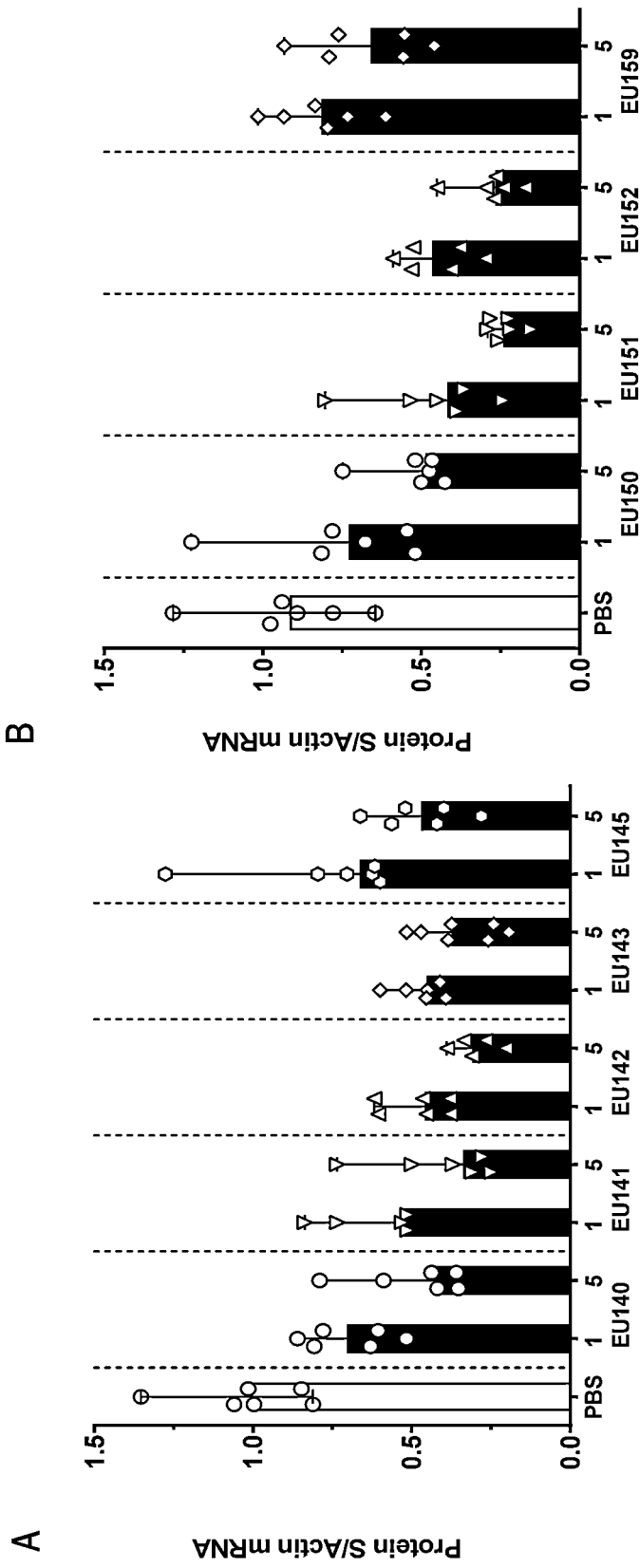
FIG. 19, Panels A and B show inhibition of PROS1 gene expression in vivo by single administration of different PROS1 siRNA conjugates.

9 to 12-week old C57BL/6 mice were treated by subcutaneous injection with a dose of 1 or 5 mg conjugate (EU140 to EU145, EU150 to EU152 or EU159) per kg body weight or with the vehicle PBS as indicated in FIGS. 19A and 19B. 2 weeks after the treatment, liver samples were collected from all mice and snap frozen. RNA was extracted from liver samples and PROS1 and Actin mRNA levels were determined by Taqman qRT-PCR. Values obtained for PROS1 mRNA were normalized to values generated for the house keeping gene Actin and related to the mean of liver samples derived from vehicle treated group (PBS) and set at 1-fold target gene expression. Each bar in the scatter dot plot represents median value from 5-7 animals with 95% confidence interval.

siRNA conjugates used in this study are listed in Table 2. The dose-dependent reduction of PROS1 mRNA in mouse liver after treatment with PROS1 siRNA conjugates is shown in FIGS. 19A and 19B.

Example 22—Inhibition of PROS1 Gene Expression in Haemophilic Mice by Single Administration of PROS1 siRNA Conjugate The example shows the reduction of PROS1 mRNA levels in the liver and of PROS1 levels in serum of haemophilia A mouse model treated with EU152.

Figure 20:
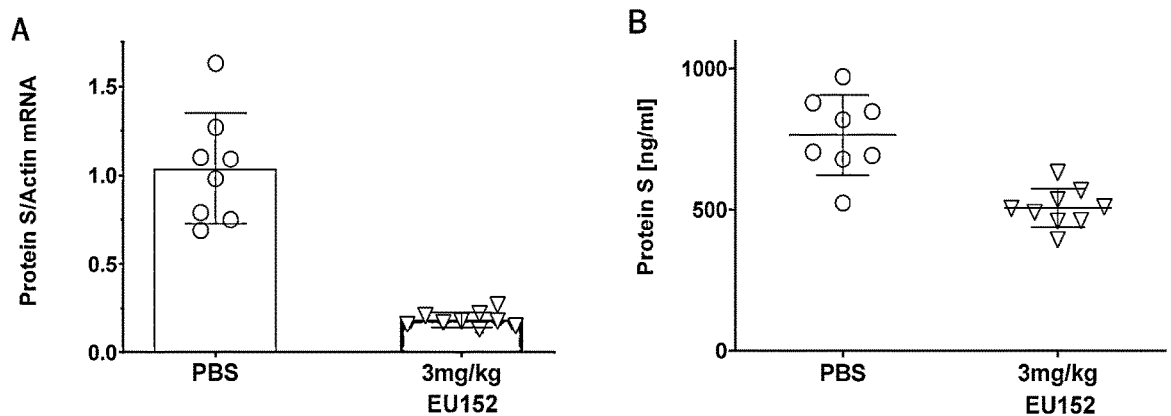
FIG. 20, Panels A and B show inhibition of PROS1 gene expression in haemophilic mice by single administration of a PROS1 siRNA conjugate.

9 to 12-week old Factor 8 knock-out mice ($F8^{-/-}$ mice; Prince et al. Blood (2018) 131 (12): 1360-1371) were treated by subcutaneous injection with 3 mg EU152 per kg body weight or with the vehicle PBS as indicated in FIGS. 20A and 20B. 8 days after the injection, liver samples were collected from all mice and snap frozen. Plasma was prepared from blood collected at the same time point. RNA was extracted from liver samples and PROS1 and Actin mRNA levels were determined by Taqman qRT-PCR. Values obtained for PROS1 mRNA were normalized to values generated for the house keeping gene Actin and related to the mean of liver samples derived from vehicle treated group (PBS) and set at 1-fold target gene expression. PROS1 level in in plasma samples were measured by specific ELISA method (Prince et al., 2018).

Each bar (A) or line (B) in the scatter dot plot represents the mean value with standard deviation from 8-9 animals.

siRNA conjugates used in this study are listed in Table 2. The reduction of PROS1 mRNA in mouse liver after treatment with PROS1 siRNA conjugates is shown in FIG. 20A, the reduction of PROS1 level in plasma is depicted in FIG. 20B.

Example 23—Treatment with PROS1 siRNA Conjugate Reduces Knee Swelling in an Acute Hemarthrosis Model The example shows the difference between knee diameter before and 72 hours after knee injury of $F8^{-/-}$ mice. Joint swelling is reduced in the cohort of mice treated prophylactically with EU152.

Figure 21:
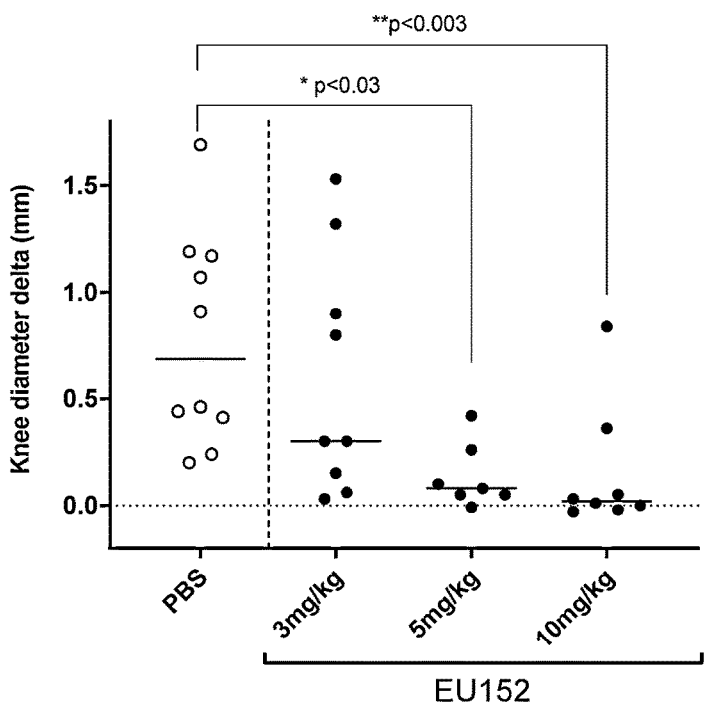
FIG. 21 shows that treatment with a PROS1 siRNA conjugate reduces knee swelling in an acute hemarthrosis model.

9 to 12 week old Factor 8 knock-out mice (F8$^{-/-}$ mice; Prince et al. 2018) were treated by subcutaneous injection with 3 mg, 5 mg or 10 mg EU152 per kg body weight or with the vehicle PBS as indicated in FIG. 21. 5 days after injection, knee diameters were measured and knee injury was performed under analgesic coverage (Prince et al., 2018). 72 hours later, knee diameters were measured again to assess swelling.

The scatter dot plot represents the median value from 7-10 animals. Statistics: Kruskal-Wallis test with Dunn's multiple comparisons test against control group (PBS).

The siRNA conjugate used in this study is listed in Table 2. The difference in knee diameter before and 72 hours after knee injury of F8$^{-/-}$ mice is shown in FIG. 21. Haemophilic mice treated with EU152 prior to the injury display dose-dependent reduction in knee swelling compared to haemophilic animals treated with the vehicle (PBS).

Example 24—Treatment with PROS1 siRNA Conjugate Improves the Haemostatic Profile of Haemophilia a Animal Model The example shows clotting time, clot formation time and the alpha angle of whole blood samples collected from wild type mice, haemophilia A mouse model (F8$^{-/-}$) or from haemophilia A mouse model treated with PROS1 siRNA (F8$^{-/-}$ EU152). Clot formation was assessed by Rotational Thromboelastometry (ROTEM), a viscoelastic assay of haemostasis which allows the measurement of global clot formation in real time (Gorlinger et al, Ann Card Anaesth (2016), 19:516-20). In haemophilic mice clotting time and clot formation time is reduced while alpha angle is increased compared to the assessment of these haemostatic parameters in wild type mice. Treatment of haemophilic mice with PROS1 siRNA reduces clotting time, clot formation time and increases the alpha angle.

Figure 22:
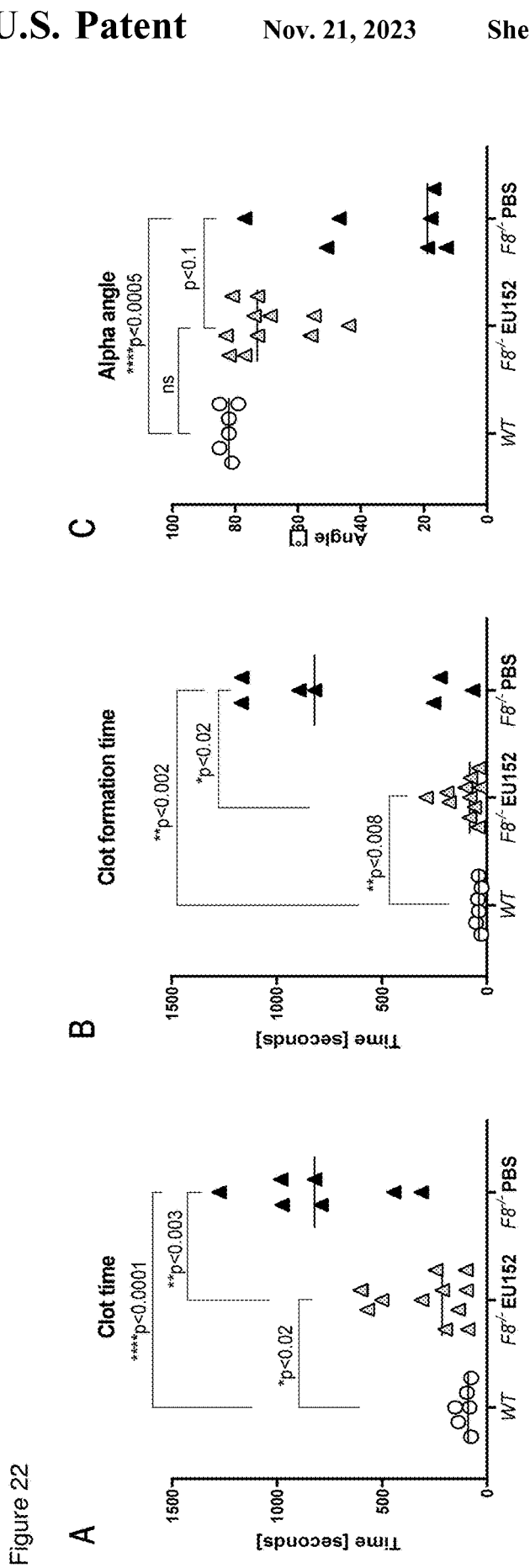
FIG. 22, Panels A-C show that treatment with a PROS1 siRNA conjugate improves the haemostatic profile of haemophilia A animal model.

9 to 12 week old Factor 8 knock-out mice (F8$^{-/-}$ mice; Prince et al. 2018) were treated by subcutaneous injection with 5 mg EU152 per kg body weight or with the vehicle PBS as indicated in FIG. 22A-C. 7 days after the treatment terminal blood samples were collected and clotting time, clot formation time and alpha angle were determined by ROTEM. For comparison, whole blood samples from wild type mice were collected and analysed by the same method.

The scatter dot plot represents the median value from 6-11 animals. Statistic: Welch's Anova with Dunnett's T3 post-hoc test on log-transformed values.

The siRNA conjugate used in this study is listed in Table 2. The blood clotting time of blood samples collected from wild type mice (WT), haemophilia A mice treated with PBS (F8$^{-/-}$ PBS) or haemophilia A mice treated with PROS1 siRNA EU152 (F8$^{-/-}$ EU152) is shown in FIG. 22A. Clot formation time and alpha angle of blood samples collected from the same treatment groups are depicted in FIG. 22B and FIG. 22C, respectively.

Example 25—Reduction of Human Protein S mRNA Level in Human Hep3B Cells by Transfection of Protein S siRNAs In vitro test shows dose-dependent reduction of Protein S mRNA levels in human Hep3B cells by transfection of Protein S siRNA molecules (EU199 to EU222).

Hep3B cells were seeded at a density of 12 000 cells per well in the 96-well plate. The following day, the cells were transfected with 0.1 nM, 0.01 nM or 0.001 nM Protein S siRNA or with non-targeting control siRNA (EU198) and 1 µg/ml AtuFECT. 24 hours later, cells were lysed for RNA extraction and Protein S and Actin mRNA levels were determined by Taqman qRT-PCR. Values obtained for Protein S mRNA normalised to values generated for the house keeping gene Actin and related to mean of untreated sample (ut) set at 1-fold target gene expression are listed in Table A. +/−SD represents standard deviation from three biological replicates. siRNA duplexes used in this study are listed in Table 2.

TABLE A

| siRNA duplex | siRNA conc. | ProS mRNA level normalized to actin mRNA level and relative to ut set to 1 | +/− SD |
|---|---|---|---|
| Ut |  | 1.00 | 0.07 |
| EU199 | 0.1 nM | 0.34 | 0.05 |
|  | 0.01 nM | 0.29 | 0.06 |
|  | 0.001 nM | 0.40 | 0.11 |
| EU200 | 0.1 nM | 0.28 | 0.09 |
|  | 0.01 nM | 0.38 | 0.04 |
|  | 0.001 nM | 0.53 | 0.15 |
| EU201 | 0.1 nM | 0.46 | 0.13 |
|  | 0.01 nM | 0.66 | 0.21 |
|  | 0.001 nM | 0.89 | 0.11 |
| EU202 | 0.1 nM | 0.46 | 0.10 |
|  | 0.01 nM | 0.46 | 0.14 |
|  | 0.001 nM | 0.62 | 0.09 |
| EU203 | 0.1 nM | 0.20 | 0.01 |
|  | 0.01 nM | 0.29 | 0.03 |
|  | 0.001 nM | 0.54 | 0.06 |
| EU204 | 0.1 nM | 0.40 | 0.07 |
|  | 0.01 nM | 0.67 | 0.10 |
|  | 0.001 nM | 0.71 | 0.12 |
| EU205 | 0.1 nM | 0.44 | 0.03 |
|  | 0.01 nM | 0.58 | 0.11 |
|  | 0.001 nM | 0.57 | 0.03 |
| EU206 | 0.1 nM | 0.26 | 0.04 |
|  | 0.01 nM | 0.35 | 0.13 |
|  | 0.001 nM | 0.44 | 0.11 |
| EU207 | 0.1 nM | 0.27 | 0.12 |
|  | 0.01 nM | 0.45 | 0.05 |
|  | 0.001 nM | 0.79 | 0.17 |
| EU208 | 0.1 nM | 0.41 | 0.02 |
|  | 0.01 nM | 0.35 | 0.05 |
|  | 0.001 nM | 0.41 | 0.01 |
| EU209 | 0.1 nM | 0.40 | 0.08 |
|  | 0.01 nM | 0.44 | 0.02 |
|  | 0.001 nM | 0.74 | 0.11 |
| EU210 | 0.1 nM | 0.76 | 0.27 |
|  | 0.01 nM | 1.28 | 0.20 |
|  | 0.001 nM | 1.32 | 0.00 |
| EU211 | 0.1 nM | 0.34 | 0.05 |
|  | 0.01 nM | 0.33 | 0.04 |
|  | 0.001 nM | 0.39 | 0.02 |
| EU212 | 0.1 nM | 0.33 | 0.09 |
|  | 0.01 nM | 0.43 | 0.09 |
|  | 0.001 nM | 0.63 | 0.19 |
| EU213 | 0.1 nM | 0.31 | 0.11 |
|  | 0.01 nM | 0.65 | 0.13 |
|  | 0.001 nM | 1.27 | 0.29 |
| EU214 | 0.1 nM | 0.51 | 0.13 |
|  | 0.01 nM | 0.70 | 0.15 |
|  | 0.001 nM | 0.98 | 0.08 |
| EU215 | 0.1 nM | 0.23 | 0.05 |
|  | 0.01 nM | 0.34 | 0.03 |
|  | 0.001 nM | 0.58 | 0.15 |
| EU216 | 0.1 nM | 0.29 | 0.05 |
|  | 0.01 nM | 0.68 | 0.08 |
|  | 0.001 nM | 1.14 | 0.19 |
| EU217 | 0.1 nM | 0.52 | 0.11 |
|  | 0.01 nM | 0.74 | 0.13 |
|  | 0.001 nM | 0.85 | 0.20 |

TABLE A-continued

| siRNA duplex | siRNA conc. | ProS mRNA level normalized to actin mRNA level and relative to ut set to 1 | +/− SD |
|---|---|---|---|
| EU218 | 0.1 nM | 0.29 | 0.08 |
|  | 0.01 nM | 0.35 | 0.01 |
|  | 0.001 nM | 0.45 | 0.07 |
| EU219 | 0.1 nM | 0.20 | 0.08 |
|  | 0.01 nM | 0.51 | 0.11 |
|  | 0.001 nM | 1.09 | 0.27 |
| EU220 | 0.1 nM | 0.34 | 0.13 |
|  | 0.01 nM | 0.36 | 0.09 |
|  | 0.001 nM | 0.48 | 0.07 |
| EU221 | 0.1 nM | 0.19 | 0.01 |
|  | 0.01 nM | 0.15 | 0.02 |
|  | 0.001 nM | 0.28 | 0.05 |
| EU222 | 0.1 nM | 0.57 | 0.05 |
|  | 0.01 nM | 1.19 | 0.03 |
|  | 0.001 nM | 1.57 | 0.02 |
| EU198 | 0.1 nM | 0.81 | 0.03 |
|  | 0.1 nM | 0.81 | 0.15 |
|  | 0.1 nM | 0.85 | 0.02 |

Example 26—Dose Dependent Reduction of Protein S mRNA Level in Human Cells by Transfection of Protein S siRNAs at Concentration Between 1 nM and 0.00001 nM In vitro test shows dose-dependent reduction of Protein S mRNA levels in human Hep3B cells by transfection of Protein S siRNA molecules.

Figure 23:
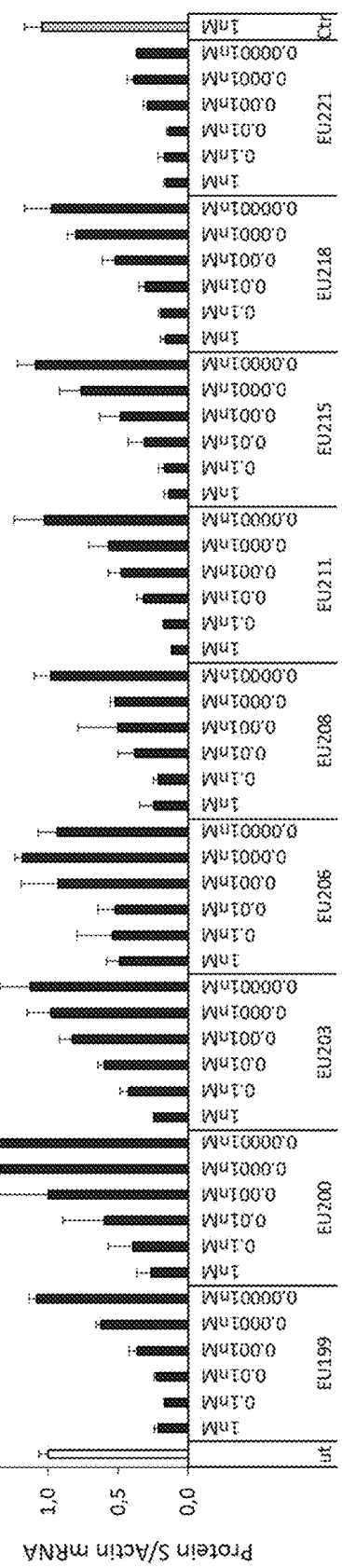
FIG. 23 shows dose-dependent reduction of Protein S mRNA levels in human cells by transfection of Protein S siRNAs at concentration between 1 nM and 0.00001 nM.

Hep3B cells were seeded at a density of 12 000 cells per well in the 96-well plate. The following day, the cells were transfected with 1 nM, 0.01 nM, 0.001 nM, 0.0001 nM or 0.00001 nM Protein S siRNA or 1 nM non-targeting control siRNA (EU0198) and 1 µg/ml AtuFECT. 24 hours later, cells were lysed for RNA extraction and Protein S and Actin mRNA levels were determined by Taqman qRT-PCR. Values obtained for Protein S mRNA were normalized to values generated for the house keeping gene Actin and related to mean of untreated sample (ut) set at 1-fold target gene expression. Each bar represents mean+/−SD from three biological replicates. siRNA duplexes used in this study are listed in Table 2. Results are shown in FIG. 23.

Example 27—Inhibition of Human Protein S Gene Expression in Primary Human Hepatocytes by Receptor Mediated Uptake In vitro test shows dose-dependent reduction of human Protein S mRNA levels by conjugated siRNAs EU161 to EU171 in primary human hepatocytes.

Figure 24:
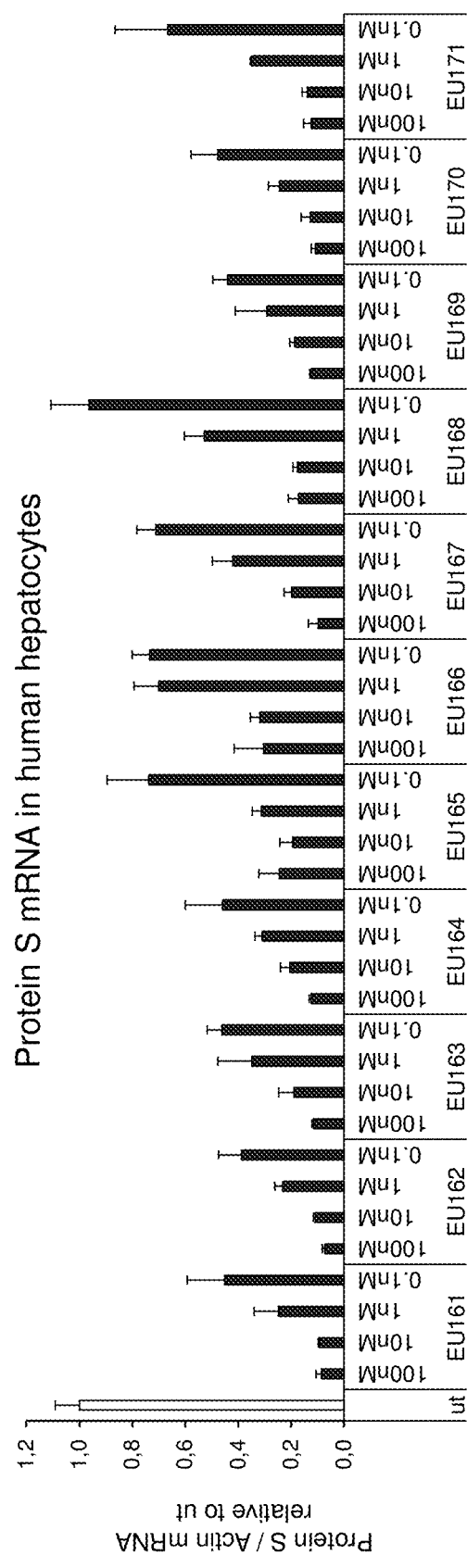
FIG. 24 shows inhibition of PROS1 target gene expression in primary human hepatocytes by receptor mediated uptake of PROS1 siRNA conjugates.

Primary human hepatocytes (Life Technologies) were seeded in a 96-well plate at a density of 35 000 cells per well in plating medium and were subsequently incubated with Protein S siRNA conjugates EU161 to EU171 in concentrations of 100 nM, 10 nM, 1 nM or 0.1 nM as shown in FIG. 24. Values obtained for Protein S mRNA were normalized to values generated for the house keeping gene Actin and related to mean of untreated sample (ut) set at 1-fold target gene expression. Each bar represents mean+/−SD from three biological replicates. siRNA conjugates used in this study are listed in Table 2. Results with EU161 to 171 are shown in FIG. 24.

Example 28—Inhibition of Protein S Gene Expression in Primary Cynomolgus Hepatocytes by Receptor Mediated Uptake In vitro test shows dose dependent reduction of cynomolgus Protein S mRNA levels by conjugated siRNAs EU161 to EU171 in primary cynomolgus hepatocytes.

Figure 25:
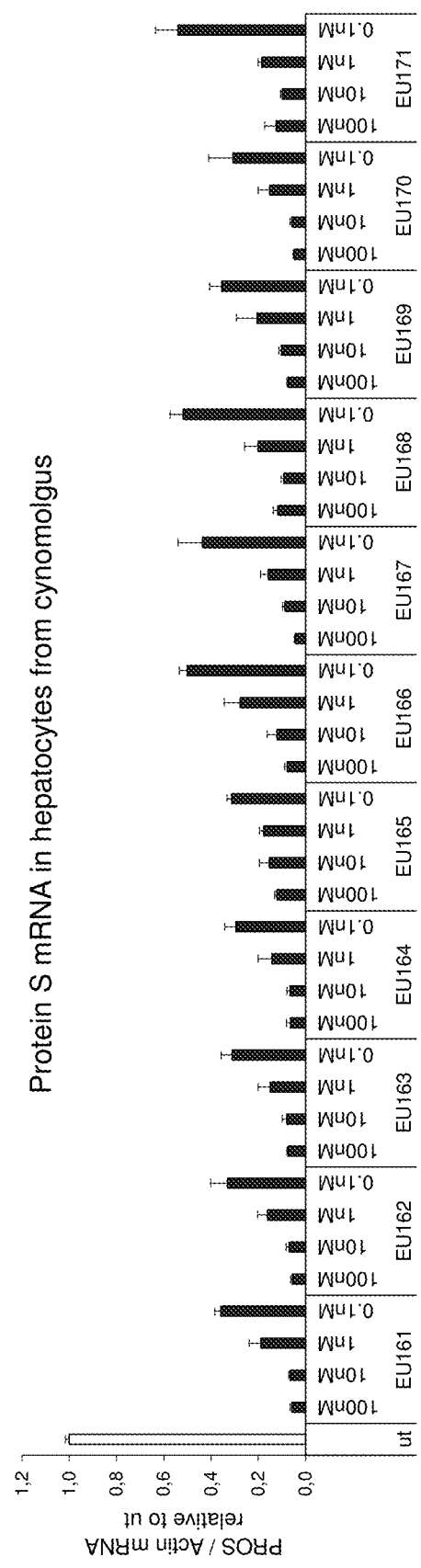
FIG. 25 shows inhibition of PROS1 target gene expression in primary cynomolgus hepatocytes by receptor mediated uptake of PROS1 siRNA conjugates.

Primary cynomolgus hepatocytes (Life Technologies) were seeded in a 96-well plate at a density of 45 000 cells per well in plating medium and were subsequently incubated with Protein S siRNA conjugates EU161 to EU171 in concentrations of 100 nM, 10 nM, 1 nM or 0.1 nM as shown in FIG. 25. Values obtained for Protein S mRNA were normalized to values generated for the house keeping gene Actin and related to mean of untreated sample (ut) set at 1-fold target gene expression. Each bar represents mean+/−SD from three biological replicates. siRNA conjugates used in this study are listed in Table 2. Results with EU161 to 171 are shown in FIG. 25.

Summary Tables

TABLE 2

Summary duplex table

| Duplex | Single Strands |
|---|---|
| EU012 | EU012A |
|  | EU012B |
| EU060 | EU060A |
|  | EU060B |
| EU061 | EU061A |
|  | EU061B |
| EU062 | EU062A |
|  | EU062B |
| EU063 | EU063A |
|  | EU063B |
| EU064 | EU064A |
|  | EU064B |
| EU065 | EU065A |
|  | EU065B |
| EU066 | EU066A |
|  | EU066B |
| EU067 | EU067A |
|  | EU067B |
| EU068 | EU068A |
|  | EU068B |
| EU069 | EU069A |
|  | EU069B |
| EU070 | EU070A |
|  | EU070B |
| EU071 | EU071A |
|  | EU071B |
| EU072 | EU072A |
|  | EU072B |
| EU073 | EU073A |
|  | EU073B |
| EU074 | EU074A |
|  | EU074B |
| EU075 | EU075A |
|  | EU075B |
| EU076 | EU076A |
|  | EU076B |
| EU077 | EU077A |
|  | EU077B |
| EU078 | EU078A |
|  | EU078B |
| EU079 | EU079A |
|  | EU079B |
| EU080 | EU080A |
|  | EU080B |
| EU081 | EU081A |
|  | EU081B |
| EU082 | EU082A |
|  | EU082B |

TABLE 2-continued

Summary duplex table

| Duplex | Single Strands |
|---|---|
| EU083 | EU083A |
|  | EU083B |
| EU110 | EU109A |
|  | EU110B |
| EU140 | EU140A |
|  | EU140B |
| EU141 | EU141A |
|  | EU141B |
| EU142 | EU142A |
|  | EU142B |
| EU143 | EU143A |
|  | EU143B |
| EU144 | EU144A |
|  | EU144B |
| EU145 | EU145A |
|  | EU145B |
| EU146 | EU146A |
|  | EU146B |
| EU147 | EU147A |
|  | EU147B |
| EU148 | EU148A |
|  | EU148B |
| EU149 | EU149A |
|  | EU140B |
| EU150 | EU150A |
|  | EU141B |
| EU151 | EU151A |
|  | EU142B |
| EU152 | EU152A |
|  | EU143B |
| EU153 | EU153A |
|  | EU145B |
| EU154 | EU151A |
|  | EU154B |
| EU155 | EU155A |
|  | EU155B |
| EU156 | EU155A |
|  | EU156B |
| EU157 | EU152A |
|  | EU157B |
| EU158 | EU158A |
|  | EU158B |
| EU159 | EU158A |
|  | EU159B |
| EU160 | EU158A |
|  | EU160B |
| EU161 | EU161A |
|  | EU161B |
| EU162 | EU162A |
|  | EU162B |
| EU163 | EU163A |
|  | EU163B |
| EU164 | EU164A |
|  | EU164B |
| EU165 | EU165A |
|  | EU165B |
| EU166 | EU166A |
|  | EU166B |
| EU167 | EU167A |
|  | EU167B |
| EU168 | EU168A |
|  | EU168B |
| EU169 | EU169A |
|  | EU169B |
| EU170 | EU170A |
|  | EU170B |
| EU171 | EU171A |
|  | EU171B |
| EU198 | EU198A |
|  | EU198B |
| EU199 | EU199A |
|  | EU199B |
| EU200 | EU200A |
|  | EU200B |
| EU201 | EU201A |
|  | EU201B |
| EU202 | EU202A |
|  | EU202B |
| EU203 | EU203A |
|  | EU203B |
| EU204 | EU204A |
|  | EU204B |
| EU205 | EU205A |
|  | EU205B |
| EU206 | EU206A |
|  | EU206B |
| EU207 | EU207A |
|  | EU207B |
| EU208 | EU208A |
|  | EU208B |
| EU209 | EU209A |
|  | EU209B |
| EU210 | EU210A |
|  | EU210B |
| EU211 | EU211A |
|  | EU211B |
| EU212 | EU212A |
|  | EU212B |
| EU213 | EU213A |
|  | EU213B |
| EU214 | EU214A |
|  | EU214B |
| EU215 | EU215A |
|  | EU215B |
| EU216 | EU216A |
|  | EU216B |
| EU217 | EU217A |
|  | EU217B |
| EU218 | EU218A |
|  | EU218B |
| EU219 | EU219A |
|  | EU219B |
| EU220 | EU220A |
|  | EU220B |
| EU221 | EU221A |
|  | EU221B |
| EU222 | EU222A |
|  | EU222B |

TABLE 3

Summary abbreviations table

| Abbreviation | Meaning |
| --- | --- |
| mA, mU, mC, mG | 2'-O-Methyl RNA nucleotides |
| 2'-OMe | 2'-O-Methyl modification |
| fA, fU, fC, fG | 2' deoxy-2'-F RNA nucleotides |
| 2'-F | 2'-fluoro modification |
| (ps) | phosphorothioate |
| (ps2) | phosphorodithioate |
| (vp) | Vinyl-(E)-phosphonate |
| (vp)-mU | |
| (vp)-mU-phos | |
| ivA, ivC, ivU, ivG | inverted RNA (3'-3') nucleotides |
| ST23 | |
| ST23-phos | |
| ST43 (or C6XLT) | 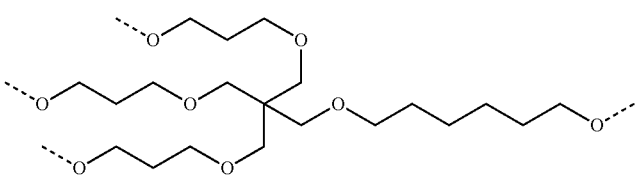 |
| ST43-phos (or C6XLT-phos) | 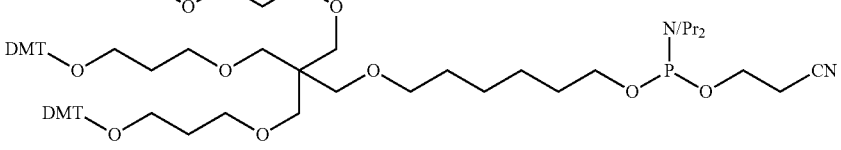 |
| Ser (GN) (when at the end of a chain, one of the O - - - is OH) | 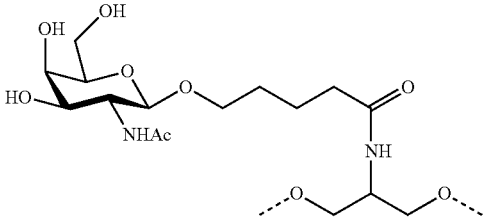 |
| [ST23 (ps)]3 ST43 (ps) | 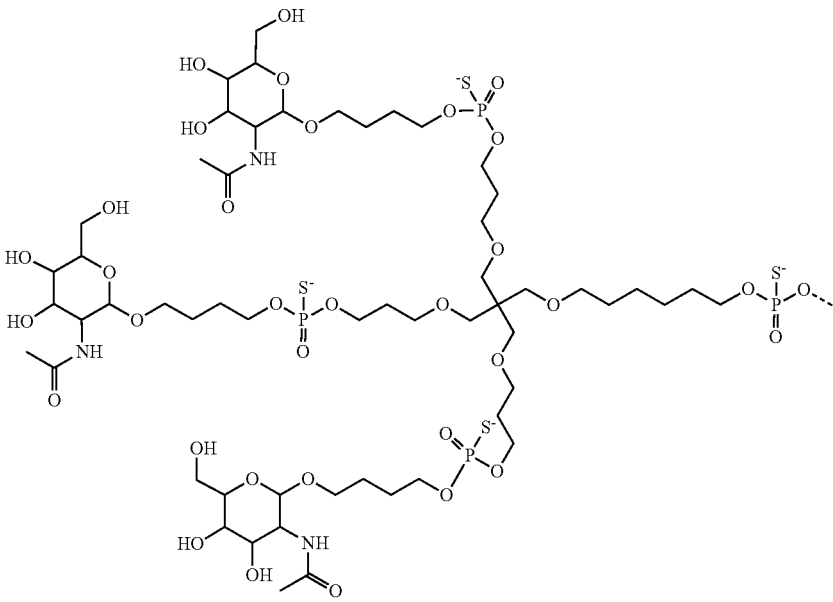 |

TABLE 3-continued

Summary abbreviations table

| Abbreviation | Meaning |
|---|---|
| [ST23]3 ST43 | (chemical structure) |
| [ST23(ps)]3 ST41(ps) | (chemical structure) |
| [ST23]3 ST41 | (chemical structure) |

The abbreviations as shown in the above abbreviation table may be used herein. The list of abbreviations may not be exhaustive and further abbreviations and their meaning may be found throughout this document.

TABLE 4

Summary sequence table

| SEQ ID NO: | Name (A = 1st strand; B = 2nd strand) | Sequence 5'-3' | Unmodified sequence 5'-3' counterpart |
|---|---|---|---|
| 1 | EU060Aun | UGCUUUCAUUGCUUUGUCC | UGCUUUCAUUGCUUUGUCC |
| 2 | EU060Bun | GGACAAAGCAAUGAAAGCA | GGACAAAGCAAUGAAAGCA |
| 3 | EU061Aun | UUCCACAGACACCAUAUUC | UUCCACAGACACCAUAUUC |
| 4 | EU061Bun | GAAUAUGGUGUCUGUGGAA | GAAUAUGGUGUCUGUGGAA |
| 5 | EU062Aun | UAUUCCAGAAGCUCCUUGC | UAUUCCAGAAGCUCCUUGC |
| 6 | EU062Bun | GCAAGGAGCUUCUGGAAUA | GCAAGGAGCUUCUGGAAUA |
| 7 | EU063Aun | UUUGUGUCAAGGUUCAAGG | UUUGUGUCAAGGUUCAAGG |
| 8 | EU063Bun | CCUUGAACCUUGACACAAA | CCUUGAACCUUGACACAAA |
| 9 | EU064Aun | AUUGACACAGCUUCUUAGG | AUUGACACAGCUUCUUAGG |
| 10 | EU064Bun | CCUAAGAAGCUGUGUCAAU | CCUAAGAAGCUGUGUCAAU |
| 11 | EU065Aun | UUCUAAUUCUUCCACAGAC | UUCUAAUUCUUCCACAGAC |
| 12 | EU065Aun | GUCUGUGGAAGAAUUAGAA | GUCUGUGGAAGAAUUAGAA |
| 13 | EU066Aun | AUAUCCAUCUUCAUUGCAU | AUAUCCAUCUUCAUUGCAU |
| 14 | EU066Bun | AUGCAAUGAAGAUGGAUAU | AUGCAAUGAAGAUGGAUAU |
| 15 | EU067Aun | UUUUCAAAGACCUCCCUGG | UUUUCAAAGACCUCCCUGG |
| 16 | EU067Bun | CCAGGGAGGUCUUUGAAAA | CCAGGGAGGUCUUUGAAAA |
| 17 | EU068Aun | AGUUUGAAUCCUUUCUUCC | AGUUUGAAUCCUUUCUUCC |
| 18 | EU068Bun | GGAAGAAAGGAUUCAAACU | GGAAGAAAGGAUUCAAACU |
| 19 | EU069Aun | UUUCAUUGCUUUGUCCAAG | UUUCAUUGCUUUGUCCAAG |
| 20 | EU069Bun | CUUGGACAAAGCAAUGAAA | CUUGGACAAAGCAAUGAAA |
| 21 | EU070Aun | CAUUGCUUUGUCCAAGACG | CAUUGCUUUGUCCAAGACG |
| 22 | EU070Bun | CGUCUUGGACAAAGCAAUG | CGUCUUGGACAAAGCAAUG |
| 23 | EU071Aun | UAUGUUUAGAAAUGGCUUC | UAUGUUUAGAAAUGGCUUC |
| 24 | EU071Bun | GAAGCCAUUUCUAAACAUA | GAAGCCAUUUCUAAACAUA |
| 25 | EU072Aun | UGUUCUUGCACACAGCUGU | UGUUCUUGCACACAGCUGU |
| 26 | EU072Bun | ACAGCUGUGUGCAAGAACA | ACAGCUGUGUGCAAGAACA |
| 27 | EU073Aun | AUCUUGGGCAAGUUUGAAU | AUCUUGGGCAAGUUUGAAU |
| 28 | EU073Bun | AUUCAAACUUGCCCAAGAU | AUUCAAACUUGCCCAAGAU |
| 29 | EU074Aun | AACUCUUCUGAUCUUGGGC | AACUCUUCUGAUCUUGGGC |
| 30 | EU074Bun | GCCCAAGAUCAGAAGAGUU | GCCCAAGAUCAGAAGAGUU |
| 31 | EU075Aun | UUCUUCCACAGACACCAUA | UUCUUCCACAGACACCAUA |
| 32 | EU075Bun | UAUGGUGUCUGUGGAAGAA | UAUGGUGUCUGUGGAAGAA |
| 33 | EU076Aun | GUCAGGAUAAGCAUUAGUU | GUCAGGAUAAGCAUUAGUU |
| 34 | EU076Bun | AACUAAUGCUUAUCCUGAC | AACUAAUGCUUAUCCUGAC |
| 35 | EU077Aun | ACAGACACCAUAUUCCAUA | ACAGACACCAUAUUCCAUA |
| 36 | EU077Bun | UAUGGAAUAUGGUGUCUGU | UAUGGAAUAUGGUGUCUGU |
| 37 | EU078Aun | UUUGGAUAAAAAUAAUCCG | UUUGGAUAAAAAUAAUCCG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 38 | EU078Bun | CGGAUUAUUUUAUCCAAA | CGGAUUAUUUUAUCCAAA |
| 39 | EU079Aun | CUCACAACUCUUCUGAUCU | CUCACAACUCUUCUGAUCU |
| 40 | EU079Bun | AGAUCAGAAGAGUUGUGAG | AGAUCAGAAGAGUUGUGAG |
| 41 | EU080Aun | GCAUUCACUGGUGUGGCAC | GCAUUCACUGGUGUGGCAC |
| 42 | EU080Bun | GUGCCACACCAGUGAAUGC | GUGCCACACCAGUGAAUGC |
| 43 | EU081Aun | UAGGUCAGGAUAAGCAUUA | UAGGUCAGGAUAAGCAUUA |
| 44 | EU081Bun | UAAUGCUUAUCCUGACCUA | UAAUGCUUAUCCUGACCUA |
| 45 | EU082Aun | AGCACACAUGUUCUCAGAG | AGCACACAUGUUCUCAGAG |
| 46 | EU082Bun | CUCUGAGAACAUGUGUGCU | CUCUGAGAACAUGUGUGCU |
| 47 | EU083Aun | UCCACAGACACCAUAUUCC | UCCACAGACACCAUAUUCC |
| 48 | EU083Bun | GGAAUAUGGUGUCUGUGGA | GGAAUAUGGUGUCUGUGGA |
| 49 | EU146Aun | UCAUUCACUGGUGUGGCAC | UCAUUCACUGGUGUGGCAC |
| 50 | EU012A | mU fC mG fA mA fG mU fA mU fU mC fC mG fC mG fU mA fC mG | UCGAAGUAUUCCGCGUACG |
| 51 | EU012B | fC mG fU mA fC mG fC mG fG mA fA mU fA mC fU mU fC mG fA | CGUACGCGGAAUACUUCGA |
| 52 | EU060A | mU fG mC fU mU fU mC fA mU fU mG fC mU fU mU fG mU fC mC | UGCUUUCAUUGCUUUGUCC |
| 53 | EU060B | mG mG mA mC mA mA fA fG fC mA mA mU mG mA mA mA mG mC mA | GGACAAAGCAAUGAAAGCA |
| 54 | EU061A | mU fU mC fC mA fC mA fG mA fC mA fC mC fA mU fA mU fU mC | UUCCACAGACACCAUAUUC |
| 55 | EU061B | mG mA mA mU mA mU fG fG fU mG mU mC mU mG mU mG mG mA mA | GAAUAUGGUGUCUGUGGAA |
| 56 | EU062A | mU fA mU fU mC fC mA fG mA fA mG fC mU fC mC fU mU fG mC | UAUUCCAGAAGCUCCUUGC |
| 57 | EU062B | mG mC mA mA mG mG fA fG fC mU mU mC mU mG mG mA mA mU mA | GCAAGGAGCUUCUGGAAUA |
| 58 | EU063A | mU fU mU fG mU fG mU fC mA fA mG fG mU fU mC fA mA fG mG | UUUGUGUCAAGGUUCAAGG |
| 59 | EU063B | mC mC mU mU mG mA fA fC fC mU mU mG mA mC mA mC mA mA mA | CCUUGAACCUUGACACAAA |
| 60 | EU064A | mA fU mU fG mA fC mA fC mA fG mC fU mU fC mU fU mA fG mG | AUUGACACAGCUUCUUAGG |
| 61 | EU064B | mC mC mU mA mA mG fA fA fG mC mU mG mU mG mU mC mA mA mU | CCUAAGAAGCUGUGUCAAU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 62 | EU065A | mU fU mC fU mA fA mU fU mC fU mU fC mC fA mC mG fA mC | UUCUAAUUCUUCCACAGAC |
| 63 | EU065A | mG mU mC mU mG mU fG fG fA mA mG mA mA mU mU mA mG mA mA | GUCUGUGGAAGAAUUAGAA |
| 64 | EU066A | mA fU mA fU mC fC mA fU mC fU mU fC mA fU mU fG mC fA mU | AUAUCCAUCUUCAUUGCAU |
| 65 | EU066B | mA mU mG mC mA mA fU fG fA mA mG mA mU mG mG mA mU mA mU | AUGCAAUGAAGAUGGAUAU |
| 66 | EU067A | mU fU mU fU mC fA mA fA mG fA mC fC mU fC mC fC mU fG mG | UUUUCAAAGACCUCCCUGG |
| 67 | EU067B | mC mC mA mG mG mG fA fG fG mU mC mU mU mU mG mA mA mA mA | CCAGGGAGGUCUUUGAAAA |
| 68 | EU068A | mA fG mU fU mU fG mA fA mU fC mC fU mU fU mC fU mU fC mC | AGUUUGAAUCCUUUCUUCC |
| 69 | EU068B | mG mG mA mA mG mA fA fA mG mG mA mU mU mC mA mA mA mC mU | GGAAGAAAGGAUUCAAACU |
| 70 | EU069A | mU fU mU fC mA fU mU fG mC fU mU fU mG fU mC fC mA fA mG | UUUCAUUGCUUUGUCCAAG |
| 71 | EU069B | mC mU mU mG mG mA fC fA mA mA mG mC mA mA mU mG mA mA mA | CUUGGACAAAGCAAUGAAA |
| 72 | EU070A | mC fA mU fU mG fC mU fU mU fG mU fC mC fA mA fG mA fC mG | CAUUGCUUUGUCCAAGACG |
| 73 | EU070B | mC mG mU mC mU mU fG fG mA mC mA mA mA mG mC mA mA mU mG | CGUCUUGGACAAAGCAAUG |
| 74 | EU071A | mU fA mU fG mU fU mU fA mG fA mA fA mU fG mG fC mU fU mC | UAUGUUUAGAAAUGGCUUC |
| 75 | EU071B | mG mA mA mG mC mC fA fU fU mU mC mU mA mA mA mC mA mU mA | GAAGCCAUUUCUAAACAUA |
| 76 | EU072A | mU fG mU fU mC fU mU fG mC fA mC fA mC fA mG fC mU fG mU | UGUUCUUGCACACAGCUGU |
| 77 | EU072B | mA mC mA mG mC mU fG fU fG mU mG mC mA mA mG mA mA mC mA | ACAGCUGUGUGCAAGAACA |
| 78 | EU073A | mA fU mC fU mU fG mG fG mC fA mA fG mU fU mU fG mA fA mU | AUCUUGGGCAAGUUUGAAU |
| 79 | EU073B | mA mU mU mC mA mA fA fC fU mU mG mC mC mC mA mA mG mA mU | AUUCAAACUUGCCCAAGAU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 80 | EU074A | mA fA mC fU mC fU mU fC mU fG mA fU mC fU mU fG mG fG mC | AACUCUUCUGAUCUUGGGC |
| 81 | EU074B | mG mC mC mC mA mA fG fA fU mC mA mG mA mA mG mA mG mU mU | GCCCAAGAUCAGAAGAGUU |
| 82 | EU075A | mU fU mC fU mU fC mC fA mC fA mG fA mC fA mC fC mA fU mA | UUCUUCCACAGACACCAUA |
| 83 | EU075B | mU mA mU mG mG mU fG fU fC mU mG mU mG mG mA mA mG mA mA | UAUGGUGUCUGUGGAAGAA |
| 84 | EU076A | mG fU mC fA mG fG mA fU mA fA mG fC mA fU mU fA mG fU mU | GUCAGGAUAAGCAUUAGUU |
| 85 | EU076B | mA mA mC mU mA mA fU fG fC mU mU mA mU mC mC mU mG mA mC | AACUAAUGCUUAUCCUGAC |
| 86 | EU077A | mA fC mA fG mA fC mA fC mC fA mU fA mU fU mC fC mA fU mA | ACAGACACCAUAUUCCAUA |
| 87 | EU077B | mU mA mU mG mG mA fA fU fA mU mG mG mU mG mU mC mU mG mU | UAUGGAAUAUGGUGUCUGU |
| 88 | EU078A | mU fU mU fG mG fA mU fA mA fA mA fA mU fA mA fU mC fC mG | UUUGGAUAAAAAUAAUCCG |
| 89 | EU078B | mC mG mG mA mU mU fA fU fU mU mU mU mA mU mC mC mA mA mA | CGGAUUAUUUUUAUCCAAA |
| 90 | EU079A | mC fU mC fA mC fA mA fC mU fC mU fU mC fU mG fA mU fC mU | CUCACAACUCUUCUGAUCU |
| 91 | EU079B | mA mG mA mU mC mA fG fA fA mG mA mG mU mU mG mU mG mA mG | AGAUCAGAAGAGUUGUGAG |
| 92 | EU080A | mG fC mA fU mU fC mA fC mU fG mG fU mG fU mG fG mC fA mC | GCAUUCACUGGUGUGGCAC |
| 93 | EU080B | mG mU mG mC mC mA fC fA fC mC mA mG mU mG mA mA mU mG mC | GUGCCACACCAGUGAAUGC |
| 94 | EU081A | mU fA mG fG mU fC mA fG mG fA mU fA mA fG mC fA mU fU mA | UAGGUCAGGAUAAGCAUUA |
| 95 | EU081B | mU mA mA mU mG mC fU fU fA mU mC mC mU mG mA mC mC mU mA | UAAUGCUUAUCCUGACCUA |
| 96 | EU082A | mA fG mC fA mC fA mC fA mU fG mU fU mC fU mC fA mG fA mG | AGCACACAUGUUCUCAGAG |
| 97 | EU082B | mC mU mC mU mG mA fG fA fA mC mA mU mG mU mG mU mG mC mU | CUCUGAGAACAUGUGUGCU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 98 | EU083A | mU fC mC fA mC fA mG fA mC fA mC fC mA fU mA fU mU fC mC | UCCACAGACACCAUAUUCC |
| 99 | EU083B | mG mG mA mA mU mA fU fG fG mU mG mU mC mU mG mU mG mG mA | GGAAUAUGGUGUCUGUGGA |
| 100 | EU109A | mU (ps) fC (ps) mG fA mA fG mU fA mU fU mC fC mG fC mG fU mA (ps) fC (ps) mG | UCGAAGUAUUCCGCGUACG |
| 101 | EU110B | [ST23 (ps)]3 ST43 (ps) fC mG fU mA fC mG fC mG fG mA fA mU fA mC fU mU fC (ps) mG (ps) fA | CGUACGCGGAAUACUUCGA |
| 102 | EU140A | mU (ps) fU (ps) mC fC mA fC mA fG mA fC mA fC mC fA mU fA mU (ps) fU (ps) mC | UUCCACAGACACCAUAUUC |
| 103 | EU140B | [ST23 (ps)]3 ST43 (ps) mG mA mA mU mA mU fG fG fU mG mU mC mU mG mU mG mG (ps) mA (ps) mA | GAAUAUGGUGUCUGUGGAA |
| 104 | EU141A | mU (ps) fU (ps) mC fU mA fA mU fU mC fU mU fC mC fA mC fA mG (ps) fA (ps) mC | UUCUAAUUCUUCCACAGAC |
| 105 | EU141B | [ST23 (ps)]3 ST43 (ps) mG mU mC mU mG mU fG fG fA mA mG mA mA mU mU mA mG (ps) mA (ps) mA | GUCUGUGGAAGAAUUAGAA |
| 106 | EU142A | mU (ps) fU (ps) mU fU mC fA mA fA mG fA mC fC mU fC mC fC mU (ps) fG (ps) mG | UUUUCAAAGACCUCCCUGG |
| 107 | EU142B | [ST23 (ps)]3 ST43 (ps) mC mC mA mG mG mG fA fG fG mU mC mU mU mU mG mA mA (ps) mA (ps) mA | CCAGGGAGGUCUUUGAAAA |
| 108 | EU143A | mU (ps) fU (ps) mU fC mA fU mU fG mC fU mU fU fG mU fC mC fA (ps) fA (ps) mG | UUUCAUUGCUUUGUCCAAG |
| 109 | EU143B | [ST23 (ps)]3 ST43 (ps) mC mU mU mG mG mA fC fA fA mG mC mA mA mU mG mA mA (ps) mA (ps) mA | CUUGGACAAAGCAAUGAAA |
| 110 | EU144A | mU (ps) fG (ps) mU fU mC fU mU fG mC fA mC fA mC fA mG fC mU (ps) fG (ps) mU | UGUUCUUGCACACAGCUGU |
| 111 | EU144B | [ST23 (ps)]3 ST43 (ps) mA mC mA mG mC mU fG fU mG fU mG mC mA mA mG mA mA (ps) mC (ps) mA | ACAGCUGUGUGCAAGAACA |
| 112 | EU145A | mA (ps) fC (ps) mA fG mA fC mA fC mC fA mU fA mU fU mC fC mA (ps) fU (ps) mA | ACAGACACCAUAUUCCAUA |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 113 | EU145B | [ST23 (ps)]3 ST43 (ps) mU mA mU mG mG mA fU fA mU mG mG mU mG mU mC mU (ps) mG (ps) mU | UAUGGAAUAUGGUGUCUGU |
| 114 | EU146A | mU (ps) fC (ps) mA fU mU fC mA fC mU fG mG fU mG fU mG fG mC (ps) fA (ps) mC | UCAUUCACUGGUGUGGCAC |
| 115 | EU146B | [ST23 (ps)]3 ST43 (ps) mG mU mG mC mC mA fC fA fC mC mA mG mU mG mA mA mU (ps) mG (ps) mC | GUGCCACACCAGUGAAUGC |
| 116 | EU147A | mA (ps) fG (ps) mC fA mC fA mC fA mU fG mU fU mC fU mC fA mG (ps) fA (ps) mG | AGCACACAUGUUCUCAGAG |
| 117 | EU147B | [ST23 (ps)]3 ST43 (ps) mC mU mC mU mG mA fG fA fA mC mA mU mG mU mG mG (ps) mC (ps) mU | CUCUGAGAACAUGUGUGCU |
| 118 | EU148A | mU (ps) fC (ps) mC fA mC fA mG fA mC fA mC fC mA fU mA fU mU (ps) fC (ps) mC | UCCACAGACACCAUAUUCC |
| 119 | EU148B | [ST23 (ps)]3 ST43 (ps) mG mG mA mA mU mA fU fG fG mU mG mU mC mU mG mU mG (ps) mG (ps) mA | GGAAUAUGGUGUCUGUGGA |
| 120 | EU149A | (vp) mU fU mC fC mA fC mA fG mA fC mA fC mC fA mU fA mU (ps) fU (ps) mC | UUCCACAGACACCAUAUUC |
| 121 | EU150A | (vp) mU fU mC fU mA fA mU fU mC fU mU fC mC fA mC fA mG (ps) fA (ps) mC | UUCUAAUUCUUCCACAGAC |
| 122 | EU151A | (vp) mU fU mU fU mC fA mA fA mG fA mC fC mU fC mC fC mU (ps) fG (ps) mG | UUUUCAAAGACCUCCCUGG |
| 123 | EU152A | (vp) mU fU mU fC mA fU mU fG mC fU mU fU mG fU mC fC mA (ps) fA (ps) mG | UUUCAUUGCUUUGUCCAAG |
| 124 | EU153A | (vp) mU fC mA fG mA fC mA fC mC fA mU fA mU fU mC fC mA (ps) fU (ps) mA | UCAGACACCAUAUUCCAUA |
| 125 | EU154B | Ser (GN) (ps) mC (ps) mC (ps) mA mG mG fA fG fG mU mC mU mU mG mA mA (ps) mA (ps) mA (ps) Ser (GN) | CCAGGGAGGUCUUUGAAAA |
| 126 | EU155A | (vp) mU fUmU fU mC fA mA fA mG fA mC fC mU fC mC fC mU fG (ps2) mG | UUUUCAAAGACCUCCCUGG |
| 127 | EU155B | Ser (GN) mC (ps2) mC mA mG mG mG fA fG fG mU mC mU mU mU mG mA mA mA (ps2) mA Ser (GN) | CCAGGGAGGUCUUUGAAAA |
| 128 | EU155A | (vp) mU fU mU fU mC fA mA fA mG fA mC fC mU fC mC fC mU fG (ps2) mG | UUUUCAAAGACCUCCCUGG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 129 | EU156B | [ST23]3 ST43 mC (ps2) mC mA mG mG mG fA fG fG mU mC mU mU mU mG mA mA mA (ps2) mA | CCAGGGAGGUCUUUGAAAA |
| 130 | EU157B | Ser (GN) (ps) mC (ps) mU (ps) mU mG mG mA fC fA fA mA mG mC mA mA mU mG mA (ps) mA (ps) mA (ps) Ser (GN) | CUUGGACAAAGCAAUGAAA |
| 131 | EU158A | (vp) mU fU mU fC mA fU mU fG mC fU mU fU mG fU mC fC mA fA (ps2) mG | UUUCAUUGCUUUGUCCAAG |
| 132 | EU158B | Ser (GN) mC (ps2) mU mU mG mG mA fC fA fA mA mG mC mA mA mU mG mA mA (ps2) mA Ser (GN) | CUUGGACAAAGCAAUGAAA |
| 133 | EU159B | [ST23]3 ST43 mC (ps2) mU mU mG mG mA fC fA fA mA mG mC mA mA mU mG mA mA (ps2) mA | CUUGGACAAAGCAAUGAAA |
| 134 | EU160B | [ST23]3 ST43 mC (ps2) mU mU mG mG mA fC fA fA mA mG mC mA mA mU mG mA mA irA | CUUGGACAAAGCAAUGAAA |
| 135 | EU142B without ligand | mC mC mA mG mG mG fA fG fG mU mC mU mU mU mG mA mA (ps) mA (ps) mA | CCAGGGAGGUCUUUGAAAA |
| 136 | EU143B without ligand | mC mU mU mG mG mA fC fA fA mA mG mC mA mA mU mG mA (ps) mA (ps) mA | CUUGGACAAAGCAAUGAAA |
| 137 | EU198A | mU fC mG fA mA fG mU fA mU fU mC fC mG fC mG fU mA fC mG | UCGAAGUAUUCCGCGUACG |
| 138 | EU198B | fC mG fU mA fC mG fC mG fG mA fA mU fA mC fU mU fC mG fA | CGUACGCGGAAUACUUCGA |
| 139 | EU199A | mU (ps) fU (ps) mU fU mC fA mA fA mG fA mC fC mU fC mC fC mU (ps) fG (ps) mG | UUUUCAAGACCUCCCUGG |
| 140 | EU199B | mC (ps) mC (ps) mA mG mG mG fA fG fG mU mC mU mU mU mG mA mA (ps) mA (ps) mA | CCAGGGAGGUCUUUGAAAA |
| 141 | EU200A | mU (ps) fU (ps) mA fU mA fA mA fA mG fG mC fA mU fU mC fA mC (ps) fU (ps) mG | UUAUAAAGGCAUUCACUG |
| 142 | EU200B | mC (ps) mA (ps) mG mU mG mA fA fU fG mC mC mU mU mU mU mA mU (ps) mA (ps) mA | CAGUGAAUGCCUUUUAUAA |
| 143 | EU201A | mU (ps) fU (ps) mU fU mG fU mA fA mU fG mU fA mG fA mC fC mU (ps) fU (ps) mG | UUUUGUAAUGUAGACCUUG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 144 | EU201B | mC (ps) mA (ps) mA mG mG mU fC fU fA mC mA mU mA mC mA mA (ps) mA (ps) mA | CAAGGUCUACAUUACAAAA |
| 145 | EU202A | mA (ps) fU (ps) mU fA mA fU mA fU mU fC mA fC mU fU mC fC mA (ps) fU (ps) mG | AUUAAUAUUCACUUCCAUG |
| 146 | EU202B | mC (ps) mA (ps) mU mG mG mA fA fG fU mG mA mA mU mA mU mU mA (ps) mA (ps) mU | CAUGGAAGUGAAUAUUAAU |
| 147 | EU203A | mU (ps) fU (ps) mG fU mA fC mU fU mC fA mA fC mA fA mU fC mA (ps) fC (ps) mA | UUGUACUUCAACAAUCACA |
| 148 | EU203B | mU (ps) mG (ps) mU mG mA mU fU fG fU mU mG mA mA mG mU mA mC (ps) mA (ps) mA | UGUGAUUGUUGAAGUACAA |
| 149 | EU204A | mC (ps) fU (ps) mU fU mA fU mU fG mC fA mC fA mG fU mU fC mU (ps) fU (ps) mC | CUUUAUUGCACAGUUCUUC |
| 150 | EU204B | mG (ps) mA (ps) mA mG mA mA fC fU fG mU mG mC mA mA mU mA mA (ps) mA (ps) mG | GAAGAACUGUGCAAUAAAG |
| 151 | EU205A | mU (ps) fA (ps) mU fU fU mU fG mA fG mG fG mA fU mC fU mU fU mG (ps) fC (ps) mA | UAUUUGAGGGAUCUUUGCA |
| 152 | EU205B | mU (ps) mG (ps) mC mA mA mA fG fA fU mC mC mC mU mC mA mA mA (ps) mU (ps) mA | UGCAAAGAUCCCUCAAAUA |
| 153 | EU206A | mA (ps) fU (ps) mA fU mU fC mA fC mU fU mC fC mA fU mG fC mA (ps) fG (ps) mC | AUAUUCACUUCCAUGCAGC |
| 154 | EU206B | mG (ps) mC (ps) mU mG mC mA fU fG fG mA mA mG mU mG mA mA mU (ps) mA (ps) mU | GCUGCAUGGAAGUGAAUAU |
| 155 | EU207A | mA (ps) fG (ps) mU fA mU fA mA fU mU fA mC fA mC fA mC fA mA (ps) fG (ps) mG | AGUAUAAUUACACACAAGG |
| 156 | EU207B | mC (ps) mC (ps) mU mU mG mU fG fU fG mU mA mA mU mU mA mU mA (ps) mC (ps) mU | CCUUGUGUGUAAUUAUACU |
| 157 | EU208A | mU (ps) fA (ps) mA fU mA fG mA fC mC fA mC fC mA fU mC fU mC (ps) fU (ps) mU | UAAUAGACCACCAUCUCUU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 158 | EU208B | mA (ps) mA (ps) mG mA mG mA fU fG fG mU mG mG mU mC mU mA mU (ps) mU (ps) mA | AAGAGAUGGUGGUCUAUUA |
| 159 | EU209A | mA (ps) fA (ps) mA fU mG fC mA fU mC fA mC fA mG fU mA fC mC (ps) fA (ps) mG | AAAUGCAUCACAGUACCAG |
| 160 | EU209B | mC (ps) mU (ps) mG mG mU mA fC fU fG mU mG mA mU mG mC mA mU (ps) mU (ps) mU | CUGGUACUGUGAUGCAUUU |
| 161 | EU210A | mG (ps) fU (ps) mC fA mU fU mU fU mC fA mA fA mG fA mC fC mU (ps) fC (ps) mC | GUCAUUUCAAAGACCUCC |
| 162 | EU210B | mG (ps) mG (ps) mA mG mG mU fC fU fU mU mG mA mA mA mA mU mG (ps) mA (ps) mC | GGAGGUCUUUGAAAAUGAC |
| 163 | EU211A | mU (ps) fU (ps) mG fA mA fA mA fG mA fG mC fG mA fA mG fA mC (ps) fA (ps) mA | UUGAAAGAGCGAAGACAA |
| 164 | EU211B | mU (ps) mU (ps) mG mU mC mU fU fC fG mC mU mC mU mU mU mC (ps) mA (ps) mA | UUGUCUUCGCUCUUUUCAA |
| 165 | EU212A | mU (ps) fG (ps) mU fA mU fG mU fU mC fA mU fU mC fU mU fA mA (ps) fG (ps) mC | UGUAUGUUCAUUCUUAAGC |
| 166 | EU212B | mG (ps) mC (ps) mU mU mA mA fG fA fA mU mG mA mA mC mA mU mA (ps) mC (ps) mA | GCUUAAGAAUGAACAUACA |
| 167 | EU213A | mU (ps) fU (ps) mA fA mU fG mA fG mU fU mC fA mC fU mU fC (ps) fC (ps) mA | UUAAUGAGUUCACUUCCA |
| 168 | EU213B | mU (ps) mG (ps) mG mA mA mA fG fU fG mA mA mC mU mC mA mU mU (ps) mA (ps) mA | UGGAAAGUGAACUCAUUAA |
| 169 | EU214A | mU (ps) fU (ps) mU fU mA fC mA fG mG fA mA fC mA fG mU mG (ps) fU (ps) mA | UUUUACAGGAACAGUGGUA |
| 170 | EU214B | mU (ps) mA (ps) mC mC mA mC fU fG fU mU mC mC mU mG mU mA mA (ps) mA (ps) mA | UACCACUGUUCCUGUAAAA |
| 171 | EU215A | mC (ps) fA (ps) mU fU mC fU mU fA mA fG mC fU mG fA mA fC mU (ps) fU (ps) mC | CAUUCUUAAGCUGAACUUC |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 172 | EU215B | mG (ps) mA (ps) mA mG mU mU fC fA fG mC mU mU mA mA mG mA mA (ps) mU (ps) mG | GAAGUUCAGCUUAAGAAUG |
| 173 | EU216A | mC (ps) fA (ps) mU fU mA fU mU fA mU fA mA fU mC fU mA fU mG (ps) fU (ps) mG | CAUUAUUAUAAUCUAUGUG |
| 174 | EU216B | mC (ps) mA (ps) mC mA mU mA fG fA fU mU mA mU mA mU mA mA (ps) mU (ps) mG | CACAUAGAUUAUAAUAAUG |
| 175 | EU217A | mC (ps) fG (ps) mA fA mU fA mU fU mC fA mA fG mG fU mC fA mC (ps) fA (ps) mU | CGAAUAUUCAAGGUCACAU |
| 176 | EU217B | mA (ps) mU (ps) mG mU mG mA fC fC fU mU mG mA mA mU mA mU (ps) mC (ps) mG | AUGUGACCUUGAAUAUUCG |
| 177 | EU218A | mC (ps) fA (ps) mC fU mG fA mA fU mG fG mA fA mC fA mU fC mU (ps) fG (ps) mG | CACUGAAUGGAACAUCUGG |
| 178 | EU218B | mC (ps) mC (ps) mA mG mA mU fG fU fU mC mC mA mU mU mC mA mG (ps) mU (ps) mG | CCAGAUGUUCCAUUCAGUG |
| 179 | EU219A | mU (ps) fC (ps) mU fG mG fA mA fU mG fG mC fA mU fU mG fA mC (ps) fA (ps) mC | UCUGGAAUGGCAUUGACAC |
| 180 | EU219B | mG (ps) mU (ps) mG mU mC mA fA fU fG mC mC mA mU mU mC mC mA (ps) mG (ps) mA | GUGUCAAUGCCAUUCCAGA |
| 181 | EU220A | mA (ps) fA (ps) mG fU mU fU mG fC mC fU mC fU mG fA mG fA mC (ps) fG (ps) mG | AAGUUUGCCUCUGAGACGG |
| 182 | EU220B | mC (ps) mC (ps) mG mU mC mU fC fA fG mA mG mG mC mA mA mA mC (ps) mU (ps) mU | CCGUCUCAGAGGCAAACUU |
| 183 | EU221A | mU (ps) fU (ps) mC fG mU fA mU fA mC fA mU fC mC fA mU fC mU (ps) fA (ps) mG | UUCGUAUACAUCCAUCUAG |
| 184 | EU221B | mC (ps) mU (ps) mA mG mA mU fG fG fA mU mG mU mA mU mA mC mG (ps) mA (ps) mA | CUAGAUGGAUGUAUACGAA |
| 185 | EU222A | mC (ps) fU (ps) mU fA mG fG mG fC mC fU mG fU mA fU mC fC mG (ps) fA (ps) mU | CUUAGGGCCUGUAUCCGAU |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 186 | EU222B | mA (ps) mU (ps) mC mG mG mA fU fA fC mA mG mG mC mC mC mU mA (ps) mA (ps) mG | AUCGGAUACAGGCCCUAAG |
| 187 | EU200Aun | UUAUAAAGGCAUUCACUG | UUAUAAAGGCAUUCACUG |
| 188 | EU200Bun | CAGUGAAUGCCUUUUAUAA | CAGUGAAUGCCUUUUAUAA |
| 189 | EU201Aun | UUUUGUAAUGUAGACCUUG | UUUUGUAAUGUAGACCUUG |
| 190 | EU201Bun | CAAGGUCUACAUUACAAAA | CAAGGUCUACAUUACAAAA |
| 191 | EU202Aun | AUUAAUAUUCACUUCCAUG | AUUAAUAUUCACUUCCAUG |
| 192 | EU202Bun | CAUGGAAGUGAAUAUUAAU | CAUGGAAGUGAAUAUUAAU |
| 193 | EU203Aun | UUGUACUUCAACAAUCACA | UUGUACUUCAACAAUCACA |
| 194 | EU203Bun | UGUGAUUGUUGAAGUACAA | UGUGAUUGUUGAAGUACAA |
| 195 | EU204Aun | CUUUAUUGCACAGUUCUUC | CUUUAUUGCACAGUUCUUC |
| 196 | EU204Bun | GAAGAACUGUGCAAUAAAG | GAAGAACUGUGCAAUAAAG |
| 197 | EU205Aun | UAUUUGAGGGAUCUUUGCA | UAUUUGAGGGAUCUUUGCA |
| 198 | EU205Bun | UGCAAAGAUCCCUCAAAUA | UGCAAAGAUCCCUCAAAUA |
| 199 | EU206Aun | AUAUUCACUUCCAUGCAGC | AUAUUCACUUCCAUGCAGC |
| 200 | EU206Bun | GCUGCAUGGAAGUGAAUAU | GCUGCAUGGAAGUGAAUAU |
| 201 | EU207Aun | AGUAUAAUUACACACAAGG | AGUAUAAUUACACACAAGG |
| 202 | EU207Bun | CCUUGUGUGUAAUUAUACU | CCUUGUGUGUAAUUAUACU |
| 203 | EU208Aun | UAAUAGACCACCAUCUCUU | UAAUAGACCACCAUCUCUU |
| 204 | EU208Bun | AAGAGAUGGUGGUCUAUUA | AAGAGAUGGUGGUCUAUUA |
| 205 | EU209Aun | AAAUGCAUCACAGUACCAG | AAAUGCAUCACAGUACCAG |
| 206 | EU209Bun | CUGGUACUGUGAUGCAUUU | CUGGUACUGUGAUGCAUUU |
| 207 | EU210Aun | GUCAUUUCAAAGACCUCC | GUCAUUUCAAAGACCUCC |
| 208 | EU210Bun | GGAGGUCUUUGAAAAUGAC | GGAGGUCUUUGAAAAUGAC |
| 209 | EU211Aun | UUGAAAAGAGCGAAGACAA | UUGAAAAGAGCGAAGACAA |
| 210 | EU211Bun | UUGUCUUCGCUCUUUUCAA | UUGUCUUCGCUCUUUUCAA |
| 211 | EU212Aun | UGUAUGUUCAUUCUUAAGC | UGUAUGUUCAUUCUUAAGC |
| 212 | EU212Bun | GCUUAAGAAUGAACAUACA | GCUUAAGAAUGAACAUACA |
| 213 | EU213Aun | UUAAUGAGUUCACUUUCCA | UUAAUGAGUUCACUUUCCA |
| 214 | EU213Bun | UGGAAAGUGAACUCAUUAA | UGGAAAGUGAACUCAUUAA |
| 215 | EU214Aun | UUUUACAGGAACAGUGGUA | UUUUACAGGAACAGUGGUA |
| 216 | EU214Bun | UACCACUGUUCCUGUAAAA | UACCACUGUUCCUGUAAAA |
| 217 | EU215Aun | CAUUCUUAAGCUGAACUUC | CAUUCUUAAGCUGAACUUC |
| 218 | EU215Bun | GAAGUUCAGCUUAAGAAUG | GAAGUUCAGCUUAAGAAUG |
| 219 | EU216Aun | CAUUAUUAUAAUCUAUGUG | CAUUAUUAUAAUCUAUGUG |
| 220 | EU216Bun | CACAUAGAUUAUAAUAAUG | CACAUAGAUUAUAAUAAUG |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 221 | EU217Aun | CGAAUAUUCAAGGUCACAU | CGAAUAUUCAAGGUCACAU |
| 222 | EU217Bun | AUGUGACCUUGAAUAUUCG | AUGUGACCUUGAAUAUUCG |
| 223 | EU218Aun | CACUGAAUGGAACAUCUGG | CACUGAAUGGAACAUCUGG |
| 224 | EU218Bun | CCAGAUGUUCCAUUCAGUG | CCAGAUGUUCCAUUCAGUG |
| 225 | EU219Aun | UCUGGAAUGGCAUUGACAC | UCUGGAAUGGCAUUGACAC |
| 226 | EU219Bun | GUGUCAAUGCCAUUCCAGA | GUGUCAAUGCCAUUCCAGA |
| 227 | EU220Aun | AAGUUUGCCUCUGAGACGG | AAGUUUGCCUCUGAGACGG |
| 228 | EU220Bun | CCGUCUCAGAGGCAAACUU | CCGUCUCAGAGGCAAACUU |
| 229 | EU221Aun | UUCGUAUACAUCCAUCUAG | UUCGUAUACAUCCAUCUAG |
| 230 | EU221Bun | CUAGAUGGAUGUAUACGAA | CUAGAUGGAUGUAUACGAA |
| 231 | EU222Aun | CUUAGGGCCUGUAUCCGAU | CUUAGGGCCUGUAUCCGAU |
| 232 | EU222Bun | AUCGGAUACAGGCCCUAAG | AUCGGAUACAGGCCCUAAG |
| 233 | EU161A | mA (ps) fU (ps) mA fU mU fC mA fC mU fU mC fC mA fU mG fC mA (ps) fG (ps) mC | AUAUUCACUUCCAUGCAGC |
| 234 | EU161B | [ST23 (ps)]3 ST41 (ps) mG mC mU mG mC mA fU fG fG mA mA mG mU mG mA mA mU (ps) mA (ps) mU | GCUGCAUGGAAGUGAAUAU |
| 235 | EU162A | (vp)-mU fU mA fU mU fC mA fC mU fU mC fC mA fU mG fC mA (ps) fG (ps) mC | UUAUUCACUUCCAUGCAGC |
| 236 | EU162B | [ST23 (ps)]3 ST41 (ps) mG mC mU mG mC mA fU fG fG mA mA mG mU mG mA mA mU (ps) mA (ps) mU | GCUGCAUGGAAGUGAAUAU |
| 237 | EU163A | mU (ps) fA (ps) mA fU mA fG mA fC mC fA mC fC mU fC mU fC (ps) fU (ps) mU | UAAUAGACCACCAUCUCUU |
| 238 | EU163B | [ST23 (ps)]3 ST41 (ps) mA mA mG mA mG mA fU fG fG mU mG mG mU mC mU mA mU (ps) mU (ps) mA | AAGAGAUGGUGGUCUAUUA |
| 239 | EU164A | (vp)-mU fA mA fU mA fG mA fC mC fA mC fC mA fU mC fU mC (ps) fU (ps) mU | UAAUAGACCACCAUCUCUU |
| 240 | EU164B | [ST23 (ps)]3 ST41 (ps) mA mA mG mA mG mA fU fG fG mU mG mG mU mC mU mA mU (ps) mU (ps) mA | AAGAGAUGGUGGUCUAUUA |
| 241 | EU165A | (vp)-mU fA mA fU mA fG mA fC mC fA mC fC mA fU mC fU mC fU (ps2) mU | UAAUAGACCACCAUCUCUU |
| 242 | EU165B | [ST23]3 ST41 mA (ps2) mA mG mA mG mA fU fG fG mU mG mG mU mC mU mA mU mU (ps2) mA | AAGAGAUGGUGGUCUAUUA |

TABLE 4-continued

Summary sequence table

| SEQ ID NO: | Name (A = 1st strand; B = 2nd strand) | Sequence 5'-3' | Unmodified sequence 5'-3' counterpart |
|---|---|---|---|
| 243 | EU166A | mU (ps) fU (ps) mG fA mA fA mA fG mA fG mC fG mA fA mG fA mC (ps) fA (ps) mA | UUGAAAGAGCGAAGACAA |
| 244 | EU166B | [ST23 (ps)]3 ST41 (ps) mU mU mG mU mC mU fU fC fG mC mU mC mU mU mU mU mC (ps) mA (ps) mA | UUGUCUUCGCUCUUUUCAA |
| 245 | EU167A | (vp)-mU fU mG fA mA fA mA fG mA fG mC fG mA fA mG fA mC (ps) fA (ps) mA | UUGAAAGAGCGAAGACAA |
| 246 | EU167B | [ST23 (ps)]3 ST41 (ps) mU mU mG mU mC mU fU fC fG mC mU mC mU mU mU mU mC (ps) mA (ps) mA | UUGUCUUCGCUCUUUUCAA |
| 247 | EU168A | (vp)-mU fU mG fA mA fA mA fG mA fG mC fG mA fA mG fA mC fA (ps2) mA | UUGAAAGAGCGAAGACAA |
| 248 | EU168B | [ST23]3 ST41 mU (ps2) mU mG mU mC mU fU fC fG mC mU mC mU mU mU mU mC mA (ps2) mA | UUGUCUUCGCUCUUUUCAA |
| 249 | EU169A | mU (ps) fU (ps) mC fG mU fA mU fA mC fA mU fC mC fA mU fC mU (ps) fA (ps) mG | UUCGUAUACAUCCAUCUAG |
| 250 | EU169B | [ST23 (ps)]3 ST41 (ps) mC mU mA mG mA mU fG fG fA mU mG mU mA mU mA mC mG (ps) mA (ps) mA | CUAGAUGGAUGUAUACGAA |
| 251 | EU170A | (vp)-mU fU mC fG mU fA mU fA mC fA mU fC mC fA mU fC mU (ps) fA (ps) mG | UUCGUAUACAUCCAUCUAG |
| 252 | EU170B | [ST23 (ps)]3 ST41 (ps) mC mU mA mG mA mU fG fG fA mU mG mU mA mU mA mC mG (ps) mA (ps) mA | CUAGAUGGAUGUAUACGAA |
| 253 | EU171A | (vp)-mU fU mC fG mU fA mU fA mC fA mU fC mC fA mU fC mU fA (ps2) mG | UUCGUAUACAUCCAUCUAG |
| 254 | EU171B | [ST23]3 ST41 mC (ps2) mU mA mG mA mU fG fG fA mU mG mU mA mU mA mC mG mA (ps2) mA | CUAGAUGGAUGUAUACGAA |
| 255 | EU162Aun | UUAUUCACUUCCAUGCAGC | UUAUUCACUUCCAUGCAGC |
| 256 | EU161B without ligand | mG mC mU mG mC mA fU fG fG mA mA mG mU mG mA mA mU (ps) mA (ps) mU | GCUGCAUGGAAGUGAAUAU |
| 257 | EU163B without ligand | mA mA mG mA mG mA fU fG fG mU mG mG mU mC mU mA mU (ps) mU (ps) mA | AAGAGAUGGUGGUCUAUUA |
| 258 | EU170B without ligand | mC mU mA mG mA mU fG fG fA mU mG mU mA mU mA mC mG (ps) mA (ps) mA | CUAGAUGGAUGUAUACGAA |

We claim:

1. A double-stranded nucleic acid for inhibiting expression of PROS1, wherein the nucleic acid comprises a first strand and a second strand, wherein
the first strand comprises:

(SEQ ID NO 233)
5' mA (ps) fU (ps) mA fU mU fC mA fC mU fU mC fC mA fU mG fC mA (ps) fG (ps) mC 3', wherein m indicates a 2'-O-Methyl modified RNA nucleotide, f indicates a 2' deoxy-2'-Fluoro modified RNA nucleotide, and (ps) indicates a phosphorothioate linkage between adjacent nucleotides.

2. The double-stranded nucleic acid of claim 1, wherein the first strand consists of the sequence of SEQ ID NO 233.

3. The double-stranded nucleic acid of claim 1, wherein the second strand comprises:

(SEQ ID NO 256)
5' mG mC mU mG mC mA fU fG fG mA mA mG mU mG mA mA mU (ps) mA (ps) mU 3'.

4. The double-stranded nucleic acid of claim 1, wherein the second strand consists of the sequence of SEQ ID NO: 256.

5. The double-stranded nucleic acid of claim 1, wherein the first strand comprises the sequence of SEQ ID NO: 233, and the second strand comprises the sequence of SEQ ID NO: 256.

6. The double-stranded nucleic acid of claim 1, wherein the first strand consists of the sequence of SEQ ID NO: 233, and the second strand consists of the sequence of SEQ ID NO: 256.

7. The double-stranded nucleic acid of claim 1, wherein the nucleic acid is conjugated to a ligand.

8. The double stranded nucleic acid of claim 7, wherein the ligand comprises
  (i) one or more N-acetyl galactosamine (GalNAc) moieties, and
  (ii) a linker, wherein the linker conjugates the at least one GalNAc moiety to the nucleic acid.

9. The double-stranded nucleic acid of claim 1, wherein the nucleic acid is conjugated to a ligand comprising a compound of formula (II):

[S—X$^1$—P—X$^2$]$_3$-A-X$^3$-   (II)

wherein:

S represents a saccharide;

X$^1$ represents C$_3$-C$_6$ alkylene or (—CH$_2$—CH$_2$—O)$_m$(—CH$_2$)$_2$— wherein m is 1, 2, or 3;

P is a phosphate or modified phosphate;

X$^2$ is alkylene or an alkylene ether of the formula (—CH$_2$)$_n$—O—CH$_2$— where n=1-6;

A is a branching unit;

X$^3$ represents a bridging unit; and wherein the nucleic acid is conjugated to X$^3$ via a phosphate or modified phosphate.

10. The double-stranded nucleic acid of claim 1, wherein the nucleic acid is conjugated to a ligand, and wherein the ligand has the following structure:

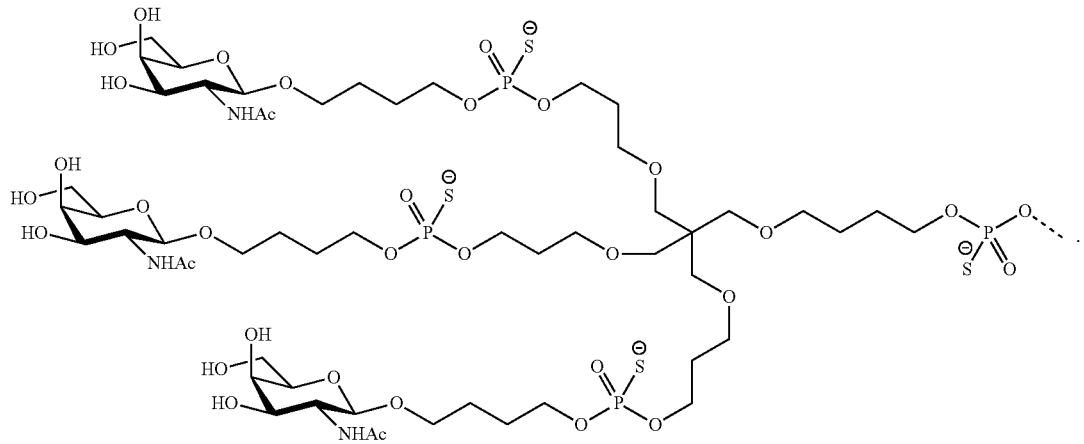

11. The double-stranded nucleic acid of claim 10, wherein the ligand is conjugated to the 5' end of the second strand.

12. The double-stranded nucleic acid of claim 1, wherein

```
- - the first strand comprises:
                                        (SEQ ID NO 233)
5' mA (ps) fU (ps) mA fU mU fC mA fC mU fU mC fC mA fU mG fC mA (ps) fG (ps) mC 3',
``` and
the second strand comprises a ligand,
wherein the ligand has the following structure:

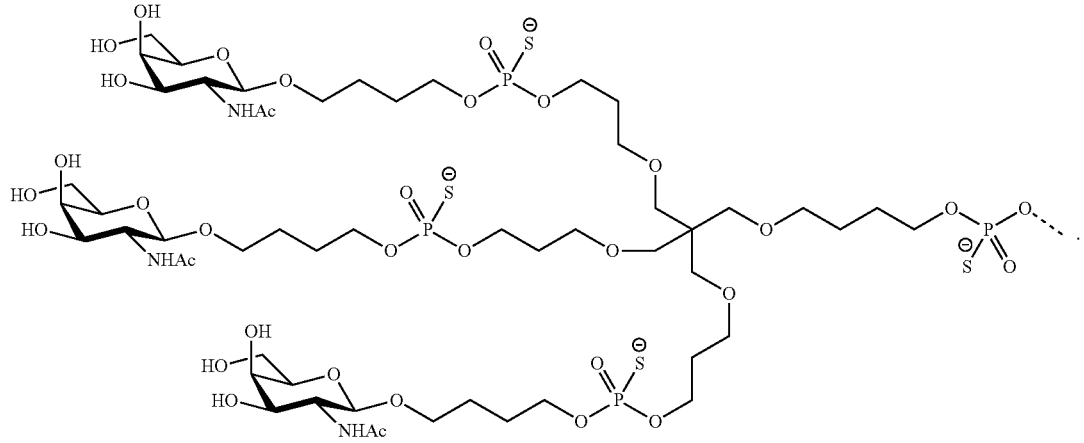

13. The double-stranded nucleic acid of claim 1, wherein the second strand comprises:

```
- the second strand compromises:
                                (SEQ ID NO 234)
5' [ST23 (ps)]3 ST41 (ps) mG mC mU mG mC mA fU fG fG mA mA mG mU mG mA mA mU (ps) mA (ps) mU 3',
```
and wherein [ST23 (ps)]3 ST41 (ps) has the following structure:

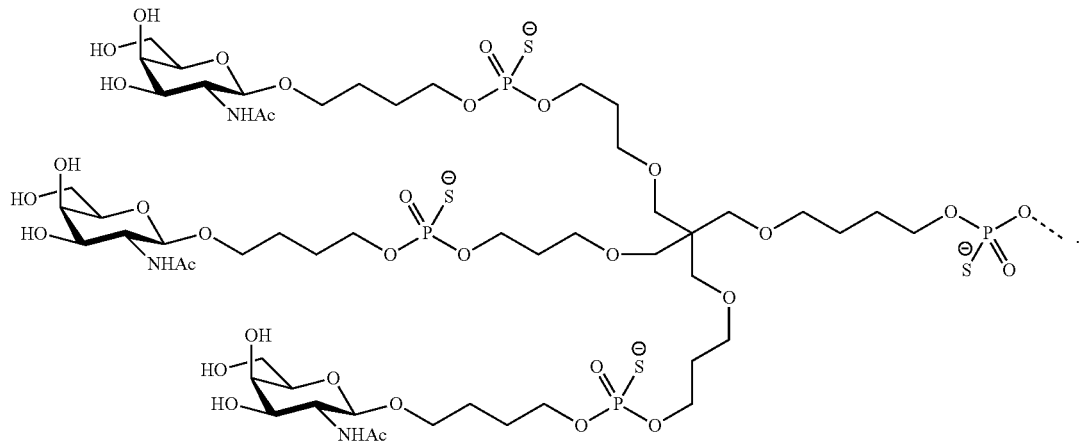

14. The double-stranded nucleic acid of claim 1, wherein

```
- the first strand consists of:
                                (SEQ ID NO 233)
5' mA (ps) fU (ps) mA fU mU fC mA fC mU fU mC
fC mA fU mG fC mA (ps) fG (ps) mC 3',
and
- the second strand consists of:
                                (SEQ ID NO 234)
5' [ST23 (ps)]3 ST41 (ps) mG mC mU mG mC mA fU fG fG mA mA mG mU mG mA mA mU (ps) mA (ps) mU 3',
```
wherein [ST23 (ps)]3 ST41 (ps) has the following structure:

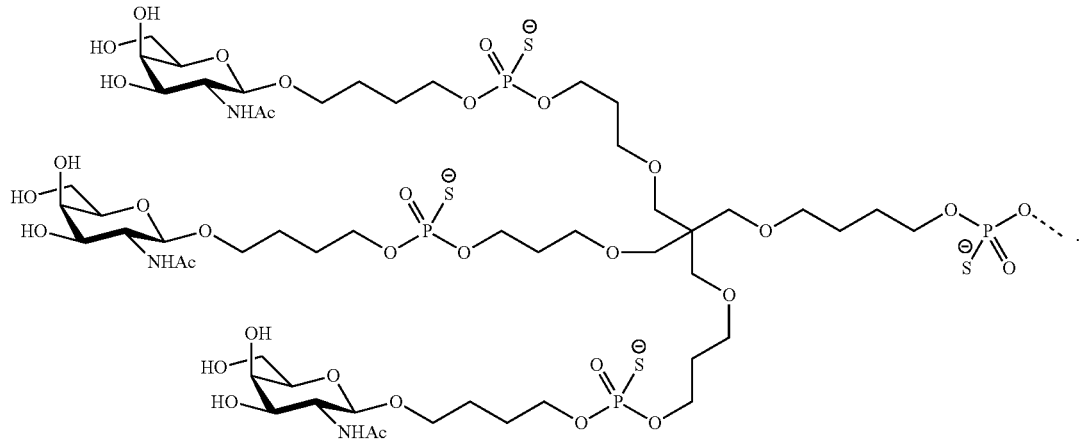

15. The double-stranded nucleic acid of claim 1, wherein the first strand has a terminal 5' (E)-vinylphosphonate nucleotide at its 5' end.

16. A pharmaceutical composition comprising the double-stranded nucleic acid of claim 1, or a pharmaceutically acceptable salt or solvate thereof, and one or more of: a solvent, a delivery vehicle, a physiologically acceptable excipient, a carrier, a salt, a diluent, a buffer, and a preservative.

17. A pharmaceutical composition comprising the double-stranded nucleic acid of claim 12, or a pharmaceutically acceptable salt or solvate thereof, and one or more of: a solvent, a delivery vehicle, a physiologically acceptable excipient, a carrier, a salt, a diluent, a buffer and a preservative.

18. A pharmaceutical composition comprising the double-stranded nucleic acid of claim 13, or a pharmaceutically acceptable salt or solvate thereof, and one or more of: a solvent, a delivery vehicle, a physiologically acceptable excipient, a carrier, a salt, a diluent, a buffer, and a preservative.

19. A pharmaceutical composition comprising the double-stranded nucleic acid of claim 14, or a pharmaceutically acceptable salt or solvate thereof, and one or more of: a solvent, a delivery vehicle, a physiologically acceptable excipient, a carrier, a salt, a diluent, a buffer, and a preservative.

\* \* \* \* \*

SEQUENCE LISTING

```
Sequence total quantity: 258
SEQ ID NO: 1          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 1
tgctttcatt gctttgtcc                                                19

SEQ ID NO: 2          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 2
ggacaaagca atgaaagca                                                19

SEQ ID NO: 3          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 3
ttccacagac accatattc                                                19

SEQ ID NO: 4          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 4
gaatatggtg tctgtggaa                                                19

SEQ ID NO: 5          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 5
tattccagaa gctccttgc                                                19

SEQ ID NO: 6          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 6
gcaaggagct tctggaata                                                19

SEQ ID NO: 7          moltype = RNA   length = 19
FEATURE               Location/Qualifiers
misc_feature          1..19
                      note = siRNA strand
source                1..19
                      mol_type = other RNA
                      organism = synthetic construct
SEQUENCE: 7
tttgtgtcaa ggttcaagg                                                19

SEQ ID NO: 8          moltype = RNA   length = 19
FEATURE               Location/Qualifiers
misc_feature          1..19
                      note = siRNA strand
source                1..19
                      mol_type = other RNA
                      organism = synthetic construct
```

```
SEQUENCE: 8
ccttgaacct tgacacaaa                                                    19

SEQ ID NO: 9              moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 9
attgacacag cttcttagg                                                    19

SEQ ID NO: 10             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 10
cctaagaagc tgtgtcaat                                                    19

SEQ ID NO: 11             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 11
ttctaattct tccacagac                                                    19

SEQ ID NO: 12             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 12
gtctgtggaa gaattagaa                                                    19

SEQ ID NO: 13             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 13
atatccatct tcattgcat                                                    19

SEQ ID NO: 14             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 14
atgcaatgaa gatggatat                                                    19

SEQ ID NO: 15             moltype = RNA  length = 19
FEATURE                   Location/Qualifiers
misc_feature              1..19
                          note = siRNA strand
source                    1..19
                          mol_type = other RNA
                          organism = synthetic construct
SEQUENCE: 15
ttttcaaaga cctccctgg                                                    19

SEQ ID NO: 16             moltype = RNA  length = 19
FEATURE                   Location/Qualifiers
misc_feature              1..19
                          note = siRNA strand
source                    1..19
                          mol_type = other RNA
```

-continued

```
                        organism = synthetic construct
SEQUENCE: 16
ccagggaggt ctttgaaaa                                                    19

SEQ ID NO: 17           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 17
agtttgaatc ctttcttcc                                                    19

SEQ ID NO: 18           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 18
ggaagaaagg attcaaact                                                    19

SEQ ID NO: 19           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 19
tttcattgct ttgtccaag                                                    19

SEQ ID NO: 20           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 20
cttggacaaa gcaatgaaa                                                    19

SEQ ID NO: 21           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 21
cattgctttg tccaagacg                                                    19

SEQ ID NO: 22           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 22
cgtcttggac aaagcaatg                                                    19

SEQ ID NO: 23           moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 23
tatgtttaga aatggcttc                                                    19

SEQ ID NO: 24           moltype = RNA   length = 19
FEATURE                 Location/Qualifiers
misc_feature            1..19
                        note = siRNA strand
source                  1..19
```

```
                        mol_type = other RNA
                        organism = synthetic construct
SEQUENCE: 24
gaagccattt ctaaacata                                                  19

SEQ ID NO: 25           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 25
tgttcttgca cacagctgt                                                  19

SEQ ID NO: 26           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 26
acagctgtgt gcaagaaca                                                  19

SEQ ID NO: 27           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 27
atcttgggca agtttgaat                                                  19

SEQ ID NO: 28           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 28
attcaaactt gcccaagat                                                  19

SEQ ID NO: 29           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 29
aactcttctg atcttgggc                                                  19

SEQ ID NO: 30           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 30
gcccaagatc agaagagtt                                                  19

SEQ ID NO: 31           moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 31
ttcttccaca gacaccata                                                  19

SEQ ID NO: 32           moltype = RNA  length = 19
FEATURE                 Location/Qualifiers
misc_feature            1..19
                        note = siRNA strand
```

```
source                         1..19
                               mol_type = other RNA
                               organism = synthetic construct
SEQUENCE: 32
tatggtgtct gtggaagaa                                                          19

SEQ ID NO: 33                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 33
gtcaggataa gcattagtt                                                          19

SEQ ID NO: 34                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 34
aactaatgct tatcctgac                                                          19

SEQ ID NO: 35                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 35
acagacacca tattccata                                                          19

SEQ ID NO: 36                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 36
tatggaatat ggtgtctgt                                                          19

SEQ ID NO: 37                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 37
tttggataaa aataatccg                                                          19

SEQ ID NO: 38                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 38
cggattattt ttatccaaa                                                          19

SEQ ID NO: 39                  moltype = RNA   length = 19
FEATURE                        Location/Qualifiers
misc_feature                   1..19
                               note = siRNA strand
source                         1..19
                               mol_type = other RNA
                               organism = synthetic construct
SEQUENCE: 39
ctcacaactc ttctgatct                                                          19

SEQ ID NO: 40                  moltype = RNA   length = 19
FEATURE                        Location/Qualifiers
misc_feature                   1..19
```

```
                    note = siRNA strand
source              1..19
                    mol_type = other RNA
                    organism = synthetic construct
SEQUENCE: 40
agatcagaag agttgtgag                                                   19

SEQ ID NO: 41       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 41
gcattcactg gtgtggcac                                                   19

SEQ ID NO: 42       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 42
gtgccacacc agtgaatgc                                                   19

SEQ ID NO: 43       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 43
taggtcagga taagcatta                                                   19

SEQ ID NO: 44       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 44
taatgcttat cctgaccta                                                   19

SEQ ID NO: 45       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 45
agcacacatg ttctcagag                                                   19

SEQ ID NO: 46       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 46
ctctgagaac atgtgtgct                                                   19

SEQ ID NO: 47       moltype = RNA  length = 19
FEATURE             Location/Qualifiers
misc_feature        1..19
                    note = siRNA strand
source              1..19
                    mol_type = other RNA
                    organism = synthetic construct
SEQUENCE: 47
tccacagaca ccatattcc                                                   19

SEQ ID NO: 48       moltype = RNA  length = 19
FEATURE             Location/Qualifiers
```

```
                      -continued
misc_feature          1..19
                      note = siRNA strand
source                1..19
                      mol_type = other RNA
                      organism = synthetic construct
SEQUENCE: 48
ggaatatggt gtctgtgga                                                  19

SEQ ID NO: 49         moltype = RNA   length = 19
FEATURE               Location/Qualifiers
misc_feature          1..19
                      note = siRNA strand
source                1..19
                      mol_type = other RNA
                      organism = synthetic construct
SEQUENCE: 49
tcattcactg gtgtggcac                                                  19

SEQ ID NO: 50         moltype = RNA   length = 19
FEATURE               Location/Qualifiers
misc_feature          1..19
                      note = siRNA strand - modified as per summary sequence
                       table at the endof the description
source                1..19
                      mol_type = other RNA
                      organism = synthetic construct
SEQUENCE: 50
tcgaagtatt ccgcgtacg                                                  19

SEQ ID NO: 51         moltype = RNA   length = 19
FEATURE               Location/Qualifiers
misc_feature          1..19
                      note = siRNA strand - modified as per summary sequence
                       table at the endof the description
source                1..19
                      mol_type = other RNA
                      organism = synthetic construct
SEQUENCE: 51
cgtacgcgga atacttcga                                                  19

SEQ ID NO: 52         moltype = RNA   length = 19
FEATURE               Location/Qualifiers
misc_feature          1..19
                      note = siRNA strand - modified as per summary sequence
                       table at the endof the description
source                1..19
                      mol_type = other RNA
                      organism = synthetic construct
SEQUENCE: 52
tgctttcatt gctttgtcc                                                  19

SEQ ID NO: 53         moltype = RNA   length = 19
FEATURE               Location/Qualifiers
misc_feature          1..19
                      note = siRNA strand - modified as per summary sequence
                       table at the endof the description
source                1..19
                      mol_type = other RNA
                      organism = synthetic construct
SEQUENCE: 53
ggacaaagca atgaaagca                                                  19

SEQ ID NO: 54         moltype = RNA   length = 19
FEATURE               Location/Qualifiers
misc_feature          1..19
                      note = siRNA strand - modified as per summary sequence
                       table at the endof the description
source                1..19
                      mol_type = other RNA
                      organism = synthetic construct
SEQUENCE: 54
ttccacagac accatattc                                                  19

SEQ ID NO: 55         moltype = RNA   length = 19
FEATURE               Location/Qualifiers
misc_feature          1..19
                      note = siRNA strand - modified as per summary sequence
                       table at the endof the description
source                1..19
```

```
                        mol_type = other RNA
                        organism = synthetic construct
SEQUENCE: 55
gaatatggtg tctgtggaa                                                    19

SEQ ID NO: 56           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 56
tattccagaa gctccttgc                                                    19

SEQ ID NO: 57           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 57
gcaaggagct tctggaata                                                    19

SEQ ID NO: 58           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 58
tttgtgtcaa ggttcaagg                                                    19

SEQ ID NO: 59           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 59
ccttgaacct tgacacaaa                                                    19

SEQ ID NO: 60           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 60
attgacacag cttcttagg                                                    19

SEQ ID NO: 61           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 61
cctaagaagc tgtgtcaat                                                    19

SEQ ID NO: 62           moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
```

```
SEQUENCE: 62
ttctaattct tccacagac                                                        19

SEQ ID NO: 63           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 63
gtctgtggaa gaattagaa                                                        19

SEQ ID NO: 64           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 64
atatccatct tcattgcat                                                        19

SEQ ID NO: 65           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 65
atgcaatgaa gatggatat                                                        19

SEQ ID NO: 66           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 66
ttttcaaaga cctccctgg                                                        19

SEQ ID NO: 67           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 67
ccagggaggt ctttgaaaa                                                        19

SEQ ID NO: 68           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 68
agtttgaatc ctttcttcc                                                        19

SEQ ID NO: 69           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 69
ggaagaaagg attcaaact                                                        19
```

-continued

```
SEQ ID NO: 70              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 70
tttcattgct ttgtccaag                                                         19

SEQ ID NO: 71              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 71
cttggacaaa gcaatgaaa                                                         19

SEQ ID NO: 72              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 72
cattgctttg tccaagacg                                                         19

SEQ ID NO: 73              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 73
cgtcttggac aaagcaatg                                                         19

SEQ ID NO: 74              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 74
tatgtttaga aatggcttc                                                         19

SEQ ID NO: 75              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 75
gaagccattt ctaaacata                                                         19

SEQ ID NO: 76              moltype = RNA   length = 19
FEATURE                    Location/Qualifiers
misc_feature               1..19
                           note = siRNA strand - modified as per summary sequence
                           table at the endof the description
source                     1..19
                           mol_type = other RNA
                           organism = synthetic construct
SEQUENCE: 76
tgttcttgca cacagctgt                                                         19

SEQ ID NO: 77              moltype = RNA   length = 19
```

```
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 77
acagctgtgt gcaagaaca                                                  19

SEQ ID NO: 78        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 78
atcttgggca agtttgaat                                                  19

SEQ ID NO: 79        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 79
attcaaactt gcccaagat                                                  19

SEQ ID NO: 80        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 80
aactcttctg atcttgggc                                                  19

SEQ ID NO: 81        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 81
gcccaagatc agaagagtt                                                  19

SEQ ID NO: 82        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 82
ttcttccaca gacaccata                                                  19

SEQ ID NO: 83        moltype = RNA   length = 19
FEATURE              Location/Qualifiers
misc_feature         1..19
                     note = siRNA strand - modified as per summary sequence
                      table at the endof the description
source               1..19
                     mol_type = other RNA
                     organism = synthetic construct
SEQUENCE: 83
tatggtgtct gtggaagaa                                                  19

SEQ ID NO: 84        moltype = RNA   length = 19
FEATURE              Location/Qualifiers
misc_feature         1..19
```

```
                           note = siRNA strand - modified as per summary sequence
                            table at the endof the description
source                     1..19
                           mol_type = other RNA
                           organism = synthetic construct
SEQUENCE: 84
gtcaggataa gcattagtt                                                        19

SEQ ID NO: 85              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 85
aactaatgct tatcctgac                                                        19

SEQ ID NO: 86              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 86
acagacacca tattccata                                                        19

SEQ ID NO: 87              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 87
tatggaatat ggtgtctgt                                                        19

SEQ ID NO: 88              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 88
tttggataaa aataatccg                                                        19

SEQ ID NO: 89              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 89
cggattattt ttatccaaa                                                        19

SEQ ID NO: 90              moltype = RNA  length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 90
ctcacaactc ttctgatct                                                        19

SEQ ID NO: 91              moltype = RNA  length = 19
FEATURE                    Location/Qualifiers
misc_feature               1..19
                           note = siRNA strand - modified as per summary sequence
                            table at the endof the description
```

```
source                  1..19
                        mol_type = other RNA
                        organism = synthetic construct
SEQUENCE: 91
agatcagaag agttgtgag                                                   19

SEQ ID NO: 92           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 92
gcattcactg gtgtggcac                                                   19

SEQ ID NO: 93           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 93
gtgccacacc agtgaatgc                                                   19

SEQ ID NO: 94           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 94
taggtcagga taagcatta                                                   19

SEQ ID NO: 95           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 95
taatgcttat cctgaccta                                                   19

SEQ ID NO: 96           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 96
agcacacatg ttctcagag                                                   19

SEQ ID NO: 97           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 97
ctctgagaac atgtgtgct                                                   19

SEQ ID NO: 98           moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
```

```
                            organism = synthetic construct
SEQUENCE: 98
tccacagaca ccatattcc                                                    19

SEQ ID NO: 99              moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 99
ggaatatggt gtctgtgga                                                    19

SEQ ID NO: 100             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 100
tcgaagtatt ccgcgtacg                                                    19

SEQ ID NO: 101             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 101
cgtacgcgga atacttcga                                                    19

SEQ ID NO: 102             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 102
ttccacagac accatattc                                                    19

SEQ ID NO: 103             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 103
gaatatggtg tctgtggaa                                                    19

SEQ ID NO: 104             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 104
ttctaattct tccacagac                                                    19

SEQ ID NO: 105             moltype = RNA   length = 19
FEATURE                    Location/Qualifiers
misc_feature               1..19
                           note = siRNA strand - modified as per summary sequence
                            table at the endof the description
source                     1..19
                           mol_type = other RNA
                           organism = synthetic construct
SEQUENCE: 105
```

```
gtctgtggaa gaattagaa                                              19

SEQ ID NO: 106         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 106
ttttcaaaga cctccctgg                                              19

SEQ ID NO: 107         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 107
ccagggaggt ctttgaaaa                                              19

SEQ ID NO: 108         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 108
tttcattgct ttgtccaag                                              19

SEQ ID NO: 109         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 109
cttggacaaa gcaatgaaa                                              19

SEQ ID NO: 110         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 110
tgttcttgca cacagctgt                                              19

SEQ ID NO: 111         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 111
acagctgtgt gcaagaaca                                              19

SEQ ID NO: 112         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 112
acagacacca tattccata                                              19
```

```
SEQ ID NO: 113          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 113
tatggaatat ggtgtctgt                                                    19

SEQ ID NO: 114          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 114
tcattcactg gtgtggcac                                                    19

SEQ ID NO: 115          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 115
gtgccacacc agtgaatgc                                                    19

SEQ ID NO: 116          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 116
agcacacatg ttctcagag                                                    19

SEQ ID NO: 117          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 117
ctctgagaac atgtgtgct                                                    19

SEQ ID NO: 118          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 118
tccacagaca ccatattcc                                                    19

SEQ ID NO: 119          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 119
ggaatatggt gtctgtgga                                                    19

SEQ ID NO: 120          moltype = RNA   length = 19
FEATURE                 Location/Qualifiers
```

```
                        misc_feature        1..19
                                            note = siRNA strand - modified as per summary sequence
                                             table at the endof the description
                        source              1..19
                                            mol_type = other RNA
                                            organism = synthetic construct
SEQUENCE: 120
ttccacagac accatattc                                                                    19

SEQ ID NO: 121          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 121
ttctaattct tccacagac                                                                    19

SEQ ID NO: 122          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 122
ttttcaaaga cctccctgg                                                                    19

SEQ ID NO: 123          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 123
tttcattgct ttgtccaag                                                                    19

SEQ ID NO: 124          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 124
tcagacacca tattccata                                                                    19

SEQ ID NO: 125          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 125
ccagggaggt ctttgaaaa                                                                    19

SEQ ID NO: 126          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 126
ttttcaaaga cctccctgg                                                                    19

SEQ ID NO: 127          moltype = RNA   length = 19
FEATURE                 Location/Qualifiers
misc_feature            1..19
                        note = siRNA strand - modified as per summary sequence
```

-continued

```
                        table at the endof the description
source                  1..19
                        mol_type = other RNA
                        organism = synthetic construct
SEQUENCE: 127
ccagggaggt ctttgaaaa                                                         19

SEQ ID NO: 128          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 128
ttttcaaaga cctccctgg                                                         19

SEQ ID NO: 129          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 129
ccagggaggt ctttgaaaa                                                         19

SEQ ID NO: 130          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 130
cttggacaaa gcaatgaaa                                                         19

SEQ ID NO: 131          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 131
tttcattgct ttgtccaag                                                         19

SEQ ID NO: 132          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 132
cttggacaaa gcaatgaaa                                                         19

SEQ ID NO: 133          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 133
cttggacaaa gcaatgaaa                                                         19

SEQ ID NO: 134          moltype = RNA   length = 19
FEATURE                 Location/Qualifiers
misc_feature            1..19
                        note = siRNA strand - modified as per summary sequence
                        table at the endof the description
source                  1..19
```

```
                            mol_type = other RNA
                            organism = synthetic construct
SEQUENCE: 134
cttggacaaa gcaatgaaa                                                      19

SEQ ID NO: 135              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 135
ccagggaggt ctttgaaaa                                                      19

SEQ ID NO: 136              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 136
cttggacaaa gcaatgaaa                                                      19

SEQ ID NO: 137              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 137
tcgaagtatt ccgcgtacg                                                      19

SEQ ID NO: 138              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 138
cgtacgcgga atacttcga                                                      19

SEQ ID NO: 139              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 139
ttttcaaaga cctccctgg                                                      19

SEQ ID NO: 140              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
SEQUENCE: 140
ccagggaggt ctttgaaaa                                                      19

SEQ ID NO: 141              moltype = RNA   length = 19
FEATURE                     Location/Qualifiers
misc_feature                1..19
                            note = siRNA strand - modified as per summary sequence
                            table at the endof the description
source                      1..19
                            mol_type = other RNA
                            organism = synthetic construct
```

```
SEQUENCE: 141
ttataaaagg cattcactg                                                    19

SEQ ID NO: 142         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 142
cagtgaatgc cttttataa                                                    19

SEQ ID NO: 143         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 143
ttttgtaatg tagaccttg                                                    19

SEQ ID NO: 144         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 144
caaggtctac attacaaaa                                                    19

SEQ ID NO: 145         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 145
attaatattc acttccatg                                                    19

SEQ ID NO: 146         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 146
catggaagtg aatattaat                                                    19

SEQ ID NO: 147         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 147
ttgtacttca acaatcaca                                                    19

SEQ ID NO: 148         moltype = RNA  length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 148
tgtgattgtt gaagtacaa                                                    19
```

```
SEQ ID NO: 149          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 149
ctttattgca cagttcttc                                                      19

SEQ ID NO: 150          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 150
gaagaactgt gcaataaag                                                      19

SEQ ID NO: 151          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 151
tatttgaggg atctttgca                                                      19

SEQ ID NO: 152          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 152
tgcaaagatc cctcaaata                                                      19

SEQ ID NO: 153          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 153
atattcactt ccatgcagc                                                      19

SEQ ID NO: 154          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 154
gctgcatgga agtgaatat                                                      19

SEQ ID NO: 155          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 155
agtataatta cacacaagg                                                      19

SEQ ID NO: 156          moltype = RNA  length = 19
```

```
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 156
ccttgtgtgt aattatact                                                          19

SEQ ID NO: 157          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 157
ccttgtgtgt aattatact                                                          19

SEQ ID NO: 158          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 158
aagagatggt ggtctatta                                                          19

SEQ ID NO: 159          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 159
aaatgcatca cagtaccag                                                          19

SEQ ID NO: 160          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 160
ctggtactgt gatgcattt                                                          19

SEQ ID NO: 161          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 161
gtcattttca aagacctcc                                                          19

SEQ ID NO: 162          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 162
ggaggtcttt gaaaatgac                                                          19

SEQ ID NO: 163          moltype = RNA  length = 19
FEATURE                 Location/Qualifiers
misc_feature            1..19
```

-continued

```
                          note = siRNA strand - modified as per summary sequence
                          table at the endof the description
source                    1..19
                          mol_type = other RNA
                          organism = synthetic construct
SEQUENCE: 163
ttgaaaagag cgaagacaa                                                        19

SEQ ID NO: 164            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 164
ttgtcttcgc tcttttcaa                                                        19

SEQ ID NO: 165            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 165
tgtatgttca ttcttaagc                                                        19

SEQ ID NO: 166            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 166
gcttaagaat gaacataca                                                        19

SEQ ID NO: 167            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 167
ttaatgagtt cactttcca                                                        19

SEQ ID NO: 168            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 168
tggaaagtga actcattaa                                                        19

SEQ ID NO: 169            moltype = RNA   length = 19
FEATURE                   Location/Qualifiers
misc_feature              1..19
                          note = siRNA strand - modified as per summary sequence
                          table at the endof the description
source                    1..19
                          mol_type = other RNA
                          organism = synthetic construct
SEQUENCE: 169
ttttacagga acagtggta                                                        19

SEQ ID NO: 170            moltype = RNA   length = 19
FEATURE                   Location/Qualifiers
misc_feature              1..19
                          note = siRNA strand - modified as per summary sequence
                          table at the endof the description
```

```
source                  1..19
                        mol_type = other RNA
                        organism = synthetic construct
SEQUENCE: 170
taccactgtt cctgtaaaa                                                     19

SEQ ID NO: 171          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 171
cattcttaag ctgaacttc                                                     19

SEQ ID NO: 172          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 172
gaagttcagc ttaagaatg                                                     19

SEQ ID NO: 173          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 173
cattattata atctatgtg                                                     19

SEQ ID NO: 174          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 174
cacatagatt ataataatg                                                     19

SEQ ID NO: 175          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 175
cgaatattca aggtcacat                                                     19

SEQ ID NO: 176          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 176
atgtgacctt gaatattcg                                                     19

SEQ ID NO: 177          moltype = RNA   length = 19
FEATURE                 Location/Qualifiers
misc_feature            1..19
                        note = siRNA strand - modified as per summary sequence
                         table at the endof the description
source                  1..19
                        mol_type = other RNA
```

```
                       organism = synthetic construct
SEQUENCE: 177
cactgaatgg aacatctgg                                                    19

SEQ ID NO: 178         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 178
ccagatgttc cattcagtg                                                    19

SEQ ID NO: 179         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 179
tctggaatgg cattgacac                                                    19

SEQ ID NO: 180         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 180
gtgtcaatgc cattccaga                                                    19

SEQ ID NO: 181         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 181
aagtttgcct ctgagacgg                                                    19

SEQ ID NO: 182         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 182
ccgtctcaga ggcaaactt                                                    19

SEQ ID NO: 183         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 183
ttcgtataca tccatctag                                                    19

SEQ ID NO: 184         moltype = RNA   length = 19
FEATURE                Location/Qualifiers
misc_feature           1..19
                       note = siRNA strand - modified as per summary sequence
                       table at the endof the description
source                 1..19
                       mol_type = other RNA
                       organism = synthetic construct
SEQUENCE: 184
```

```
ctagatggat gtatacgaa                                                    19

SEQ ID NO: 185           moltype = RNA   length = 19
FEATURE                  Location/Qualifiers
misc_feature             1..19
                         note = siRNA strand - modified as per summary sequence
                          table at the endof the description
source                   1..19
                         mol_type = other RNA
                         organism = synthetic construct
SEQUENCE: 185
cttagggcct gtatccgat                                                    19

SEQ ID NO: 186           moltype = RNA   length = 19
FEATURE                  Location/Qualifiers
misc_feature             1..19
                         note = siRNA strand - modified as per summary sequence
                          table at the endof the description
source                   1..19
                         mol_type = other RNA
                         organism = synthetic construct
SEQUENCE: 186
atcggataca ggccctaag                                                    19

SEQ ID NO: 187           moltype = RNA   length = 19
FEATURE                  Location/Qualifiers
misc_feature             1..19
                         note = siRNA strand
source                   1..19
                         mol_type = other RNA
                         organism = synthetic construct
SEQUENCE: 187
ttataaagg cattcactg                                                     19

SEQ ID NO: 188           moltype = RNA   length = 19
FEATURE                  Location/Qualifiers
misc_feature             1..19
                         note = siRNA strand
source                   1..19
                         mol_type = other RNA
                         organism = synthetic construct
SEQUENCE: 188
cagtgaatgc cttttataa                                                    19

SEQ ID NO: 189           moltype = RNA   length = 19
FEATURE                  Location/Qualifiers
misc_feature             1..19
                         note = siRNA strand
source                   1..19
                         mol_type = other RNA
                         organism = synthetic construct
SEQUENCE: 189
ttttgtaatg tagaccttg                                                    19

SEQ ID NO: 190           moltype = RNA   length = 19
FEATURE                  Location/Qualifiers
misc_feature             1..19
                         note = siRNA strand
source                   1..19
                         mol_type = other RNA
                         organism = synthetic construct
SEQUENCE: 190
caaggtctac attacaaaa                                                    19

SEQ ID NO: 191           moltype = RNA   length = 19
FEATURE                  Location/Qualifiers
misc_feature             1..19
                         note = siRNA strand
source                   1..19
                         mol_type = other RNA
                         organism = synthetic construct
SEQUENCE: 191
attaatattc acttccatg                                                    19

SEQ ID NO: 192           moltype = RNA   length = 19
FEATURE                  Location/Qualifiers
misc_feature             1..19
                         note = siRNA strand
source                   1..19
```

```
                        mol_type = other RNA
                        organism = synthetic construct
SEQUENCE: 192
catggaagtg aatattaat                                                      19

SEQ ID NO: 193          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 193
ttgtacttca acaatcaca                                                      19

SEQ ID NO: 194          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 194
tgtgattgtt gaagtacaa                                                      19

SEQ ID NO: 195          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 195
ctttattgca cagttcttc                                                      19

SEQ ID NO: 196          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 196
gaagaactgt gcaataaag                                                      19

SEQ ID NO: 197          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 197
tatttgaggg atctttgca                                                      19

SEQ ID NO: 198          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 198
tgcaaagatc cctcaaata                                                      19

SEQ ID NO: 199          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 199
atattcactt ccatgcagc                                                      19

SEQ ID NO: 200          moltype = RNA   length = 19
FEATURE                 Location/Qualifiers
misc_feature            1..19
                        note = siRNA strand
```

```
source                  1..19
                        mol_type = other RNA
                        organism = synthetic construct
SEQUENCE: 200
gctgcatgga agtgaatat                                                  19

SEQ ID NO: 201          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 201
agtataatta cacacaagg                                                  19

SEQ ID NO: 202          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 202
ccttgtgtgt aattatact                                                  19

SEQ ID NO: 203          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 203
taatagacca ccatctctt                                                  19

SEQ ID NO: 204          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 204
aagagatggt ggtctatta                                                  19

SEQ ID NO: 205          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 205
aaatgcatca cagtaccag                                                  19

SEQ ID NO: 206          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 206
ctggtactgt gatgcattt                                                  19

SEQ ID NO: 207          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 207
gtcattttca aagacctcc                                                  19

SEQ ID NO: 208          moltype = RNA  length = 19
FEATURE                 Location/Qualifiers
misc_feature            1..19
```

```
                        note = siRNA strand
source                  1..19
                        mol_type = other RNA
                        organism = synthetic construct
SEQUENCE: 208
ggaggtcttt gaaaatgac                                              19

SEQ ID NO: 209          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 209
ttgaaaagag cgaagacaa                                              19

SEQ ID NO: 210          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 210
ttgtcttcgc tcttttcaa                                              19

SEQ ID NO: 211          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 211
tgtatgttca ttcttaagc                                              19

SEQ ID NO: 212          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 212
gcttaagaat gaacataca                                              19

SEQ ID NO: 213          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 213
ttaatgagtt cactttcca                                              19

SEQ ID NO: 214          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 214
tggaaagtga actcattaa                                              19

SEQ ID NO: 215          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 215
ttttacagga acagtggta                                              19

SEQ ID NO: 216          moltype = RNA   length = 19
FEATURE                 Location/Qualifiers
```

```
                        misc_feature      1..19
                                          note = siRNA strand
                        source            1..19
                                          mol_type = other RNA
                                          organism = synthetic construct
                        SEQUENCE: 216
                        taccactgtt cctgtaaaa                                              19

SEQ ID NO: 217    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 217
                        cattcttaag ctgaacttc                                              19

SEQ ID NO: 218    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 218
                        gaagttcagc ttaagaatg                                              19

SEQ ID NO: 219    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 219
                        cattattata atctatgtg                                              19

SEQ ID NO: 220    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 220
                        cacatagatt ataataatg                                              19

SEQ ID NO: 221    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 221
                        cgaatattca aggtcacat                                              19

SEQ ID NO: 222    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 222
                        atgtgacctt gaatattcg                                              19

SEQ ID NO: 223    moltype = RNA   length = 19
                        FEATURE           Location/Qualifiers
                        misc_feature      1..19
                                          note = siRNA strand
                        source            1..19
                                          mol_type = other RNA
                                          organism = synthetic construct
                        SEQUENCE: 223
                        cactgaatgg aacatctgg                                              19

SEQ ID NO: 224    moltype = RNA   length = 19
```

```
FEATURE            Location/Qualifiers
misc_feature       1..19
                   note = siRNA strand
source             1..19
                   mol_type = other RNA
                   organism = synthetic construct
SEQUENCE: 224
ccagatgttc cattcagtg                                              19

SEQ ID NO: 225     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 225
tctggaatgg cattgacac                                              19

SEQ ID NO: 226     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 226
gtgtcaatgc cattccaga                                              19

SEQ ID NO: 227     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 227
aagtttgcct ctgagacgg                                              19

SEQ ID NO: 228     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 228
ccgtctcaga ggcaaactt                                              19

SEQ ID NO: 229     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 229
ttcgtataca tccatctag                                              19

SEQ ID NO: 230     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 230
ctagatggat gtatacgaa                                              19

SEQ ID NO: 231     moltype = RNA   length = 19
FEATURE            Location/Qualifiers
misc_feature       1..19
                   note = siRNA strand
source             1..19
                   mol_type = other RNA
                   organism = synthetic construct
SEQUENCE: 231
cttagggcct gtatccgat                                              19
```

```
SEQ ID NO: 232          moltype = RNA   length = 19
FEATURE                 Location/Qualifiers
misc_feature            1..19
                        note = siRNA strand
source                  1..19
                        mol_type = other RNA
                        organism = synthetic construct
SEQUENCE: 232
atcggataca ggccctaag                                                      19

SEQ ID NO: 233          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 233
atattcactt ccatgcagc                                                      19

SEQ ID NO: 234          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 234
gctgcatgga agtgaatat                                                      19

SEQ ID NO: 235          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 235
ttattcactt ccatgcagc                                                      19

SEQ ID NO: 236          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 236
gctgcatgga agtgaatat                                                      19

SEQ ID NO: 237          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 237
taatagacca ccatctctt                                                      19

SEQ ID NO: 238          moltype = RNA   length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 238
aagagatggt ggtctatta                                                      19

SEQ ID NO: 239          moltype = RNA   length = 19
FEATURE                 Location/Qualifiers
misc_feature            1..19
```

```
                        note = siRNA strand - modified as per summary sequence
                        table at the endof the description
source                  1..19
                        mol_type = other RNA
                        organism = synthetic construct
SEQUENCE: 239
taatagacca ccatctctt                                                        19

SEQ ID NO: 240          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 240
aagagatggt ggtctatta                                                        19

SEQ ID NO: 241          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 241
taatagacca ccatctctt                                                        19

SEQ ID NO: 242          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 242
aagagatggt ggtctatta                                                        19

SEQ ID NO: 243          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 243
ttgaaaagag cgaagacaa                                                        19

SEQ ID NO: 244          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 244
ttgtcttcgc tcttttcaa                                                        19

SEQ ID NO: 245          moltype = RNA  length = 19
FEATURE                 Location/Qualifiers
misc_feature            1..19
                        note = siRNA strand - modified as per summary sequence
                        table at the endof the description
source                  1..19
                        mol_type = other RNA
                        organism = synthetic construct
SEQUENCE: 245
ttgaaaagag cgaagacaa                                                        19

SEQ ID NO: 246          moltype = RNA  length = 19
FEATURE                 Location/Qualifiers
misc_feature            1..19
                        note = siRNA strand - modified as per summary sequence
                        table at the endof the description
```

```
source                         1..19
                               mol_type = other RNA
                               organism = synthetic construct
SEQUENCE: 246
ttgtcttcgc tcttttcaa                                                    19

SEQ ID NO: 247                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 247
ttgaaaagag cgaagacaa                                                    19

SEQ ID NO: 248                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 248
ttgtcttcgc tcttttcaa                                                    19

SEQ ID NO: 249                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 249
ttcgtataca tccatctag                                                    19

SEQ ID NO: 250                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 250
ctagatggat gtatacgaa                                                    19

SEQ ID NO: 251                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 251
ttcgtataca tccatctag                                                    19

SEQ ID NO: 252                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
                               organism = synthetic construct
SEQUENCE: 252
ctagatggat gtatacgaa                                                    19

SEQ ID NO: 253                 moltype = RNA   length = 19
FEATURE                        Location/Qualifiers
misc_feature                   1..19
                               note = siRNA strand - modified as per summary sequence
                                table at the endof the description
source                         1..19
                               mol_type = other RNA
```

```
                        organism = synthetic construct
SEQUENCE: 253
ttcgtataca tccatctag                                                  19

SEQ ID NO: 254          moltype = RNA  length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 254
ctagatggat gtatacgaa                                                  19

SEQ ID NO: 255          moltype = RNA  length = 19
FEATURE                 Location/Qualifiers
misc_feature            1..19
                        note = siRNA strand
source                  1..19
                        mol_type = other RNA
                        organism = synthetic construct
SEQUENCE: 255
ttattcactt ccatgcagc                                                  19

SEQ ID NO: 256          moltype = RNA  length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 256
gctgcatgga agtgaatat                                                  19

SEQ ID NO: 257          moltype = RNA  length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 257
aagagatggt ggtctatta                                                  19

SEQ ID NO: 258          moltype = RNA  length = 19
FEATURE                 Location/Qualifiers
misc_feature            1..19
                        note = siRNA strand - modified as per summary sequence
                         table at the endof the description
source                  1..19
                        mol_type = other RNA
                        organism = synthetic construct
SEQUENCE: 258
ctagatggat gtatacgaa                                                  19
```